United States Patent
Lee et al.

(10) Patent No.: US 12,284,917 B2
(45) Date of Patent: Apr. 22, 2025

(54) COMPOUND FOR ORGANIC LIGHT-EMITTING DIODE AND ORGANIC LIGHT-EMITTING DIODE COMPRISING SAME

(71) Applicant: SFC CO., LTD., Cheongju-si (KR)

(72) Inventors: Seung-Soo Lee, Cheongju-si (KR); Tae Gyun Lee, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 848 days.

(21) Appl. No.: 17/607,019

(22) PCT Filed: May 21, 2020

(86) PCT No.: PCT/KR2020/006654
§ 371 (c)(1),
(2) Date: Oct. 27, 2021

(87) PCT Pub. No.: WO2020/251183
PCT Pub. Date: Dec. 17, 2020

(65) Prior Publication Data
US 2022/0216431 A1    Jul. 7, 2022

(30) Foreign Application Priority Data
Jun. 10, 2019 (KR) .................. 10-2019-0068201

(51) Int. Cl.
*H01L 51/54* (2006.01)
*H10K 85/60* (2023.01)
*H10K 50/12* (2023.01)
*H10K 71/00* (2023.01)

(52) U.S. Cl.
CPC ....... *H10K 85/6574* (2023.02); *H10K 85/615* (2023.02); *H10K 85/626* (2023.02); *H10K 50/12* (2023.02); *H10K 71/00* (2023.02)

(58) Field of Classification Search
None
See application file for complete search history.

(56) References Cited

U.S. PATENT DOCUMENTS

2017/0018723 A1    1/2017  Cha et al.

FOREIGN PATENT DOCUMENTS

| CN | 106356468 A | 1/2017 |
|---|---|---|
| CN | 106467554 A | 3/2017 |
| CN | 108409761 A | 8/2018 |
| KR | 20090086015 A | 8/2009 |
| KR | 101111406 B1 | 4/2012 |
| KR | 20170009714 A | 1/2017 |
| KR | 20170044001 A | 4/2017 |
| KR | 20180007906 A | 1/2018 |
| KR | 20180077887 A | 7/2018 |
| WO | WO2009069537 A1 | 6/2009 |

OTHER PUBLICATIONS

International Search Report of PCT/KR2020/006654, Sep. 3, 2020, English translation.
The extended European search report of EP 20 82 3636, Mar. 15, 2023.
Hayato Tsuji et al, The hydrogen/deuterium isotope effect of the host material on the lifetime of organic light-emitting diodes, ChemComm, Sep. 15, 2014, vol. 50, pp. 14870-14872, The Royal Society of Chemistry, London, England.

*Primary Examiner* — Andrew K Bohaty
(74) *Attorney, Agent, or Firm* — STIP Law Group, LLC

(57) ABSTRACT

The present disclosure relates to an organic light-emitting compound represented by [Chemical Formula A] and an organic light-emitting diode comprising same.

17 Claims, 1 Drawing Sheet

| 80 |
| :---: |
| 70 |
| 60 |
| 50 |
| 40 |
| 30 |
| 20 |
| 10 |

COMPOUND FOR ORGANIC LIGHT-EMITTING DIODE AND ORGANIC LIGHT-EMITTING DIODE COMPRISING SAME

CROSS-REFERENCE TO RELATED APPLICATIONS

This application is the U.S. National Phase under 35 U.S.C. § 371 of International Application No. PCT/KR2020/006654 filed on May 21, 2020, which in turn claims the benefit of Korean Application No. 10-2019-0068201 filed on Jun. 10, 2019, the disclosures of which are incorporated by reference into the present application.

TECHNICAL FIELD

The present disclosure relates to a compound for an organic light-emitting diode and an organic light-emitting diode comprising same and, more specifically, to a compound for an organic light-emitting diode, and an organic light-emitting diode comprising same, wherein the compound includes a perdeuterated phenyl moiety and an anthracene derivative having a specifically structured substituent attached thereto, which ensure high efficiency and longevity characteristics in the organic light-emitting diode.

BACKGROUND ART

Organic light-emitting diodes, which are self-emitting devices, enjoy advantages including a wide viewing angle, high contrast, fast response time, high luminance, a low driving voltage, a high response speed, and polychromatic properties.

A typical organic light emitting diode includes an anode and a cathode, which face each other, with an organic emission layer for light emission disposed therebetween.

In detail, the organic light-emitting diode may have a structure in which a hole transport layer, a light-emitting layer, an electron transport layer, and a cathode are sequentially formed on an anode. Here, the hole transport layer, the light-emitting layer, and the electron transport layer are each an organic thin film composed of an organic compound.

Having such a structure, the organic light-emitting diode operates according to the following principle. When a voltage is applied between the anode and the cathode, a hole injected from the anode moves toward the light-emitting layer through the hole transport layer while an electron injected from the cathode moves toward the light-emitting layer through the electron transport layer. In the light-emitting layer zone, the carriers such as a hole and an electron recombine to produce an exciton. The exciton returns to the ground state from the excited state, emitting light.

Materials used as organic layers in organic light-emitting diodes may be divided according to functions into luminescent materials and charge transport materials, for example, a hole injection material, a hole transport material, an electron transport material, and an electron injection material. The light-emitting mechanism forms the basis of classification of luminescent materials as fluorescent and phosphorescent materials, which use excitons in singlet and triplet states, respectively.

When a single material is employed as the luminescent material, intermolecular actions cause the maximum luminescence wavelength to shift toward a longer wavelength, resulting in a reduction in color purity and luminous efficiency due to light attenuation. In this regard, a host-dopant system may be used as a luminescent material so as to increase the color purity and the luminous efficiency through energy transfer. This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host moves to the wavelength range of the dopant.

Meanwhile, studies have been conducted to introduce a deuterium-substituted compound as a material in the light emitting layer in order to improve the longevity and stability of the organic light emitting diode.

Compounds substituted with deuterium are known to exhibit differences in thermodynamic behavior from those bonded with hydrogen because the atomic mass of deuterium is twice as great as that of hydrogen, which results in lower zero point energy and lower vibration energy level.

In addition, physicochemical properties involving deuterium, such as chemical bond lengths, etc., appear to be different from those involving hydrogen. In particular, the van der Waals radius of deuterium is smaller than that of hydrogen because of the smaller stretching amplitude of the C-D bond compared to the C—H bond. Generally, the C-D bond is shorter and stronger than the C—H bond. Upon deuterium substitution, the ground state energy is lowered and a short bond length is formed between the carbon atom and the deuterium atom. Accordingly, the molecular hardcore volume becomes smaller, thereby reducing the electron polarizability can be reduced, and the thin film volume can be increased by weakening the intermolecular interaction.

As discussed above, deuterium substitution provides the effect of reducing the crystallinity of the thin film, that is, it makes the thin film amorphous. Generally, a compound having deuterium substitution may be advantageously used to increase the lifespan and driving characteristics of an OLED and further improve the thermal resistance.

With respect to related arts for organic light emitting compounds containing deuterium, reference may be made to Korean Patent Number 10-1111406 (issued Apr. 12, 2012), which discloses a low-voltage driving and long lifespan diode employing a deuterium-substituted, carbazole-containing compound or a mixture of deuterium-substituted compounds and to Korean Patent Number 10-2009-0086015 A (issued Aug. 10, 2009), which discloses the use of an anthracene derivative bearing a deuterium-substituted phenyl group as a host.

In spite of various efforts, including the techniques of the cited documents, made to fabricate organic light emitting diodes exhibiting longevity characteristics, there is a still continuing need for development of a compound, available as a light-emitting layer in an organic light-emitting diode, which has improved long lifespan characteristics and exhibits improved efficiency, and for an organic light-emitting diode using same.

DISCLOSURE

Technical Problem

In order to solve problems encountered in the conventional techniques, an aspect of the present disclosure is to provide an organic light-emitting compound as a host in a light-emitting layer of an organic light-emitting diode, the compound including a perdeuterated phenyl moiety and an anthracene derivative composed of a linker having a specific structure and a dibenzofuran having a specific substituent, whereby improved long lifespan characteristics can be provided, together with high efficiency, for the organic light-emitting diode.

Another aspect of the present disclosure is to provide an organic light-emitting diode comprising the organic light-emitting compound as a host in a light emitting layer thereof.

Technical Problem

Therefore, the present disclosure provides an organic light-emitting compound represented by the following Chemical Formula A:

[Chemical Formula A]

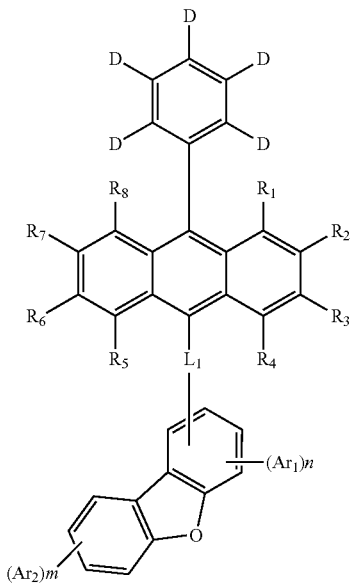

wherein, $R_1$ to $R_8$, which may be same or different, are each independently a hydrogen atom or a deuterium atom, $Ar_1$ and $Ar_2$, which may be same or different, are each independently an at least partially deuterated aryl of 6 to 50 carbon atoms or an at least partially deuterated alkyl of 1 to 30 carbon atoms, n is an integer of 0-3 wherein when n is 2 or larger, the $Ar_1$'s may each be same or different, m is an integer of 0-4 wherein when m is 2 or larger, the $Ar_2$'s may each be same or different, with a proviso that n+m is not 0, the carbon atoms of the aromatic rings in the dibenzofuran moiety may be hydrogenated or deuterated when $Ar_1$ or $Ar_2$ is not bonded thereto, $L_1$ is a linker represented by the following Structural Formula B,

[Structural Formula B]

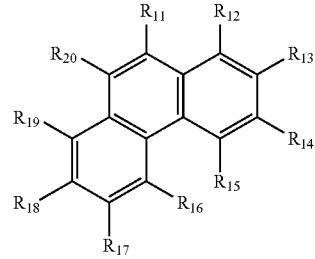

wherein, two of substituents $R_{11}$ to $R_{20}$ are single bonds connected respectively to the anthracenyl moiety and the dibenzofuran moiety in the compound of Chemical Formula A, the remaining eight, other than the two single bonds, among substituents $R_{11}$ to $R_{20}$, may be same or different and are each independently selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted alkylsilyl of 1 to 30 carbon atoms, and a substituted or unsubstituted arylsilyl of 6 to 30 carbon atoms.

In addition, the present disclosure provides an organic light-emitting diode comprising: a first electrode; a second electrode facing the first electrode; and an organic layer interposed between the first electrode and the second electrode, wherein the organic layer contains at least one of the organic light-emitting compounds represented by Chemical Formula A.

Advantageous Effects

When used as a host in a light-emitting layer, the organic light-emitting compound represented by Chemical Formula A according to the present disclosure exhibit longer lifespan properties and higher efficiency than preexisting materials. Thus, the organic light-emitting compound can impart improved properties to organic light-emitting diodes.

DESCRIPTION OF DRAWINGS

FIG. 1 is a schematic view of the structure of an organic light-emitting diode according to an embodiment of the present disclosure.

BEST MODE

Hereinafter, exemplary embodiments which can be easily implemented by those skilled in the art will be described with reference to the accompanying drawing.

In each drawing of the present disclosure, sizes or scales of components may be enlarged or reduced from their actual sizes or scales for better illustration, and known components may not be depicted therein to clearly show features of the present disclosure. Therefore, the present disclosure is not limited to the drawings. When describing the principle of the embodiments of the present disclosure in detail, details of well-known functions and features may be omitted to avoid unnecessarily obscuring the presented embodiments.

In drawings, for convenience of description, sizes of components may be exaggerated for clarity. For example, since sizes and thicknesses of components in drawings are arbitrarily shown for convenience of description, the sizes and thicknesses are not limited thereto. Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between" may be used herein for ease of description to refer to the relative positioning.

Throughout the specification, when a portion may "comprise" or "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an organic light-emitting compound for use as a host in a light emitting layer of an organic light emitting diode, wherein the organic light-emitting compound is based on an anthracene structure to which a perdeuterated phenyl and a substituted or unsubstituted phenanthrene ring introduced as a linker were bonded and wherein the anthracene ring is substituted with only hydrogen or deuterium, except for the perdeuterated phenyl and the linker, whereby high efficiency and more enhanced long lifespan characteristics can be imparted to the organic light emitting diode.

In greater detail, the present disclosure provides an organic light-emitting compound represented by the following Chemical Formula A:

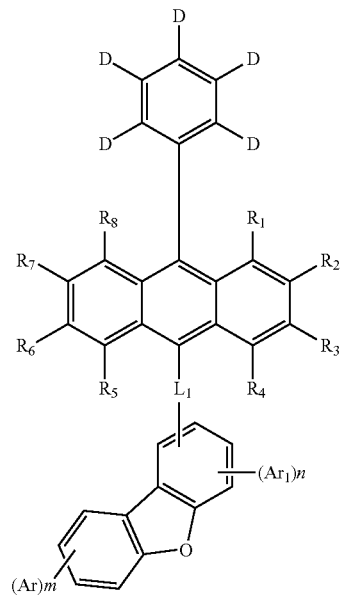

[Chemical Formula A]

wherein, $R_1$ to $R_8$, which may be same or different, are each independently a hydrogen atom or a deuterium atom, $Ar_1$ and $Ar_2$, which may be same or different, are each independently an at least partially deuterated aryl of 6 to 50 carbon atoms or an at least partially deuterated alkyl of 1 to 30 carbon atoms, n is an integer of 0-3 wherein when n is 2 or larger, the $Ar_1$'s may each be same or different, m is an integer of 0-4 wherein when m is 2 or larger, the $Ar_2$'s may each be same or different, with a proviso that n+m is not 0, the carbon atoms of the aromatic rings in the dibenzofuran moiety may be hydrogenated or deuterated when $Ar_1$ or $Ar_2$ is not bonded thereto, $L_1$ is a linker represented by the following Structural Formula

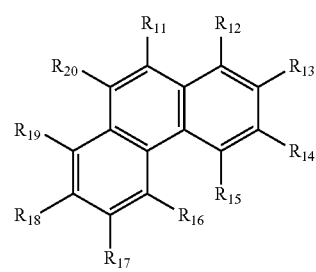

[Structural Formula B]

wherein, two of substituents $R_{11}$ to $R_{20}$ are single bonds connected respectively to the anthracenyl moiety and the dibenzofuran moiety in the compound of Chemical Formula A, the remaining eight, other than the two single bonds, among substituents $R_{11}$ to $R_{20}$, may be same or different and are each independently selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted alkylsilyl of 1 to 30 carbon atoms, and a substituted or unsubstituted arylsilyl of 6 to 30 carbon atoms, wherein the term 'substituted' in the expression "a substituted or unsubstituted" means having at least one substituent selected from the group consisting of a deuterium atom, a cyano, a halogen, a nitro, an alkyl of 1 to 24 carbon atoms, a cycloalkyl of 3 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms, an alkoxy of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system including a 5- to 7-membered ring, and preferably a 5- to 6-membered ring. Further, the aromatic system may include a fused ring that is formed by adjacent substituents on the aryl radical.

Examples of the aryl include phenyl, naphthyl, biphenyl, terphenyl, anthryl, indenyl, fluorenyl, phenanthryl, triperylenyl, pyrenyl, perylenyl, chrysenyl, naphthacenyl, and fluoranthenyl, but are not limited thereto.

At least one hydrogen atom of the aryl may be substituted by a deuterium atom, a halogen atom, a hydroxy, a nitro, a cyano, a silyl, an amino (—NH$_2$, —NH(R), —N(R') (R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The heteroaryl substituent used in the compound of the present disclosure refers to a hetero aromatic radical of 2 to 24 carbon atoms bearing 1 to 4 heteroatoms selected from among N, O, P, Se, Te, Si, Ge, and S. In the aromatic radical, two or more rings may be fused. One or more hydrogen atoms on the heteroaryl may be substituted by the same substituents as on the aryl.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the alkoxy substituent useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

As used herein, the term "at least partially deuterated" means that when there are two or more hydrogen atoms bonded to one or more carbon atoms, at least one hydrogen atom (H) is substituted by a deuterium atom (D). For instance, "an at least partially deuterated aryl of 6 to 50 carbon atoms" means an aryl of 6 to 50 carbon atoms in which at least one hydrogen atom (H) bonded directly to the carbon atoms in the aryl radical is substituted by a deuterium atom (D).

The organic light-emitting compound represented by Chemical Formula A according to the present disclosure is structurally characterized in that: the anthracene ring moiety has a perdeuterated phenyl on the carbon atom at position 10 thereof and a substituted or unsubstituted phenanthrene moiety, represented by the following Structural Formula B, as a linker L$_1$ on the carbon atom at position 9:

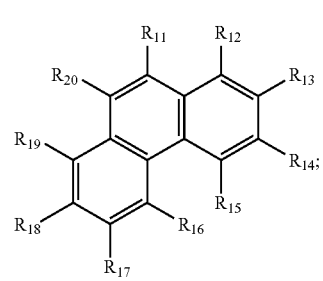

[Structural Formula B]

only hydrogen or deuterium is positioned on all the carbon members in the anthracene ring, except for the carbons bonded to the perdeuterated phenyl moiety and the linkder (L$_1$); and the linker (L$_1$) is bonded to one carbon member of the aromatic rings in the dibenzofuran moiety where the aromatic rings, whether or not the linker is bonded thereto, may have as a substituent(s) at least one, particularly one to three at least partially deuterated or unsubstituted aryl radicals of 6 to 50 carbon atoms, particularly one to three at least partially deuterated or unsubstituted alkyl radicals of 1 to 30 carbon atoms. More particularly, such one or two aryl or alkyl radicals may be bonded to the aromatic ring carbon atoms of the dibenzofuran ring moiety. When used as a material for a light-emitting layer in an organic light-emitting diode, the organic light-emitting compound of the present disclosure, having the structural characteristics, can impart sure longevity and improved efficiency to the organic light-emitting diode.

In the organic light-emitting compound represented by Chemical Formula A according to an embodiment of the present disclosure, n may be 0 and m may be 1 or 2; or n may be 1 or 2 and m may be 0. In this case, the substituent $Ar_1$ or $Ar_2$ is bonded to only one of the two aromatic rings in the dibenzofuran moiety, with the number of the substituents amounting to 1 or 2.

In the organic light-emitting compound represented by Chemical Formula A according to an embodiment of the present disclosure, the substituents $Ar_1$ and $Ar_2$, which may be same or different, are each independently "an at least partially deuterated or unsubstituted aryl of 6 to 50 carbon atoms", or "an at least partially deuterated or unsubstituted alkyl of 1 to 30 carbon atoms". In a particular embodiment, the substituents $Ar_1$ and $Ar_2$, which may be same or different, are each independently "an at least partially deuterated or unsubstituted aryl of 6 to 50 carbon atoms". In a more particular embodiment, the substituents $Ar_1$ and $Ar_2$, which may be same or different, are each independently "an at least partially deuterated or unsubstituted aryl of 6 to 20 carbon atoms, and further particularly, a perdeuterated aryl of 6 to 20 carbon atoms.

As for the "at least partially deuterated aryl of 6 to 20 carbon atoms" in the present disclosure, the substituents $Ar_1$ and $Ar_2$, which may be same or different, may each be independently selected from among "an at least partially deuterated phenyl", "an at least partially deuterated naphthyl", "an at least partially deuterated phenanthrenyl", and "an at least partially deuterated biphenyl" and more particularly from among "a perdeuterated phenyl", "a perdeuterated naphthyl", "a perdeuterated phenanthrenyl", and "a perdeuterated biphenyl".

In the organic light-emitting compound represented by Chemical Formula A according to an embodiment of the present disclosure, the remaining eight, other than the two single bonds, among substituents $R_{11}$ to $R_{20}$ in the linker represented by Structural Formula B, may be same or different and are each independently a hydrogen atom or a deuterium atom.

In an embodiment, the two single bonds of Structural Formula B, connected respectively to the anthracenyl moiety and the dibenzofuran moiety in the organic light-emitting compound represented by Chemical Formula A according to the present disclosure may each be selected from among $R_{11}$, $R_{14}$, $R_{15}$, $R_{17}$, and $R_{18}$, and particularly from among $R_{11}$, $R_{14}$, and $R_{18}$; or from among $R_{11}$ and $R_{17}$.

In addition, when the two single bonds of Structural Formula B, connected respectively to the anthracenyl moiety and the dibenzofuran moiety in the organic light-emitting compound represented by Chemical Formula A according to the present disclosure are each selected from among $R_{11}$, $R_{14}$, $R_{15}$, $R_{17}$, and $R_{18}$, the substituent $R_{11}$ in Structural Formula B may be a single bond connected to the anthracenyl moiety in the compound represented by Chemical Formula A and one of the substituents $R_{14}$ and $R_{18}$ may be a single bond connected to the dibenzofuran moiety in the compound represented by Chemical Formula A.

When the two single bonds of Structural Formula B, connected respectively to the anthracenyl moiety and the dibenzofuran moiety in the compound represented by Chemical Formula A according to the present disclosure are each selected from among $R_{11}$, $R_{14}$, $R_{15}$, $R_{17}$, and $R_{18}$, the substituent $R_{15}$ may be a single bond connected to the anthracenyl moiety in the compound represented by Chemical Formula A and the substituent $R_{15}$ may be a single bond connected to the dibenzofuran moiety in the compound represented by Chemical Formula A, or the substituent $R_{17}$ may be a single bond connected to the anthracenyl moiety in the compound represented by Chemical Formula A and the substituent may be a single bond connected to the dibenzofuran moiety in the compound represented by Chemical Formula A When the two single bonds of Structural Formula B, connected respectively to the anthracenyl moiety and the dibenzofuran moiety in the compound represented by Chemical Formula A according to the present disclosure are each selected from among $R_{11}$, $R_{14}$, $R_{15}$, $R_{17}$, and $R_{18}$, the substituent $R_{18}$ may be a single bond connected to the anthracenyl moiety in the compound represented by Chemical Formula A and the substituent $R_{11}$ may be a single bond connected to the dibenzofuran moiety in the compound represented by Chemical Formula A.

In addition, the compound represented by Chemical Formula A according to the present disclosure may be an organic light-emitting compound represented by the following Chemical Formula A-1 or Chemical Formula A-2, which accounts for preferable connection structures between the dibenzofuran moiety and the linker $L_1$:

[Chemical Formula A-1]

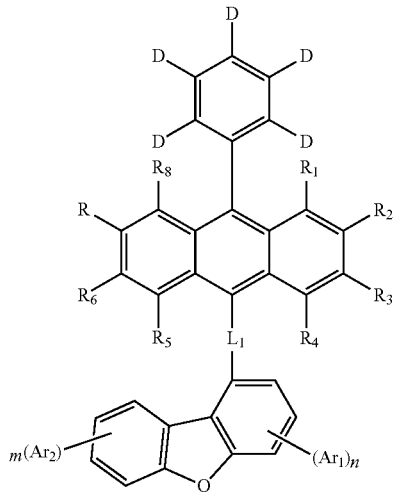

[Chemical Formula A-2]

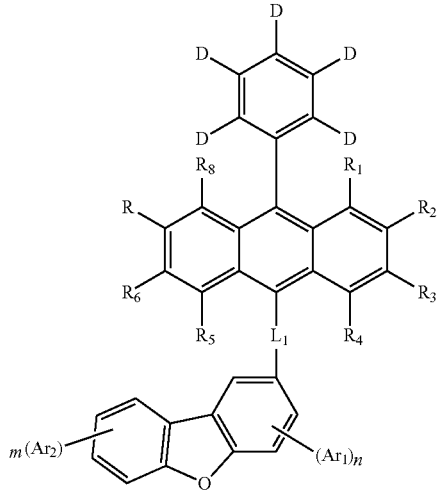

wherein $R_1$ to $R_8$, $L_1$, $Ar_1$, $Ar_2$, m, and n are as defined in Chemical Formula A.
Concrete examples of the organic light-emitting compound represented by Chemical Formula A include, but are not limited to, <Compound 1> to <Compound 35>:
<Compound 1>
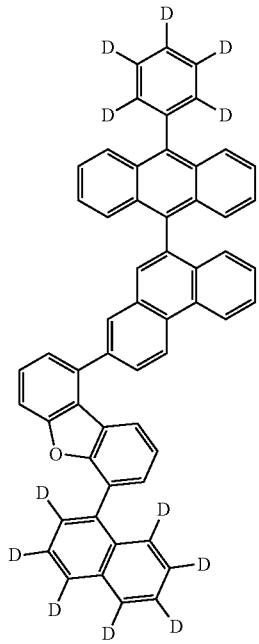
<Compound 2>
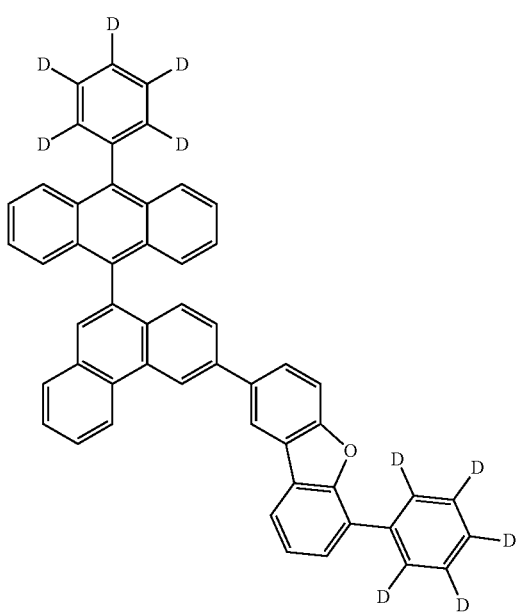
<Compound 3>
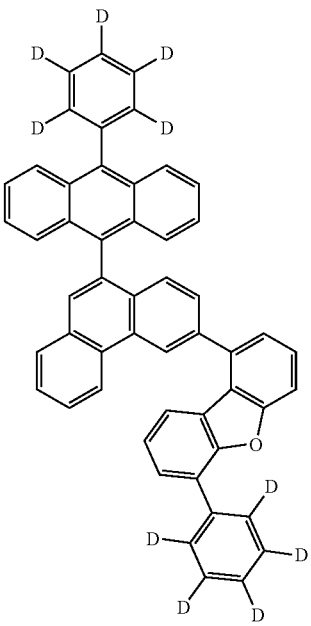
<Compound 4>
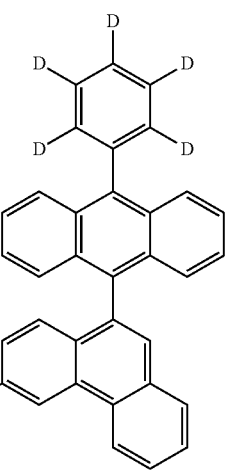

<Compound 5>
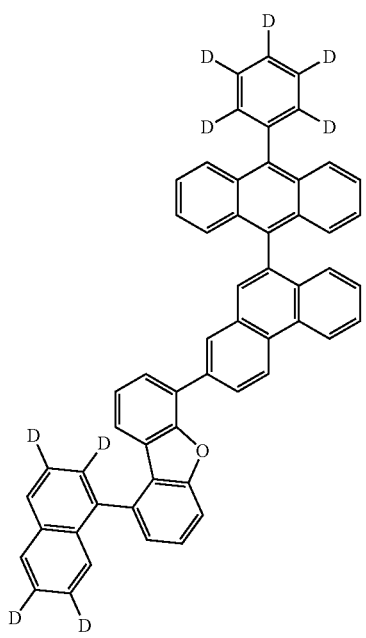
<Compound 6>
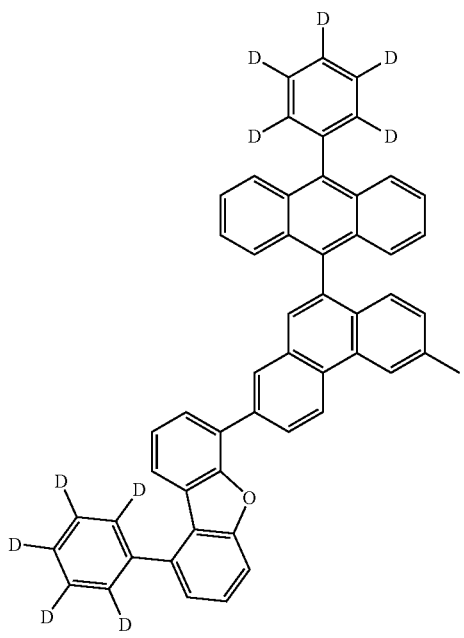
<Compound 7>
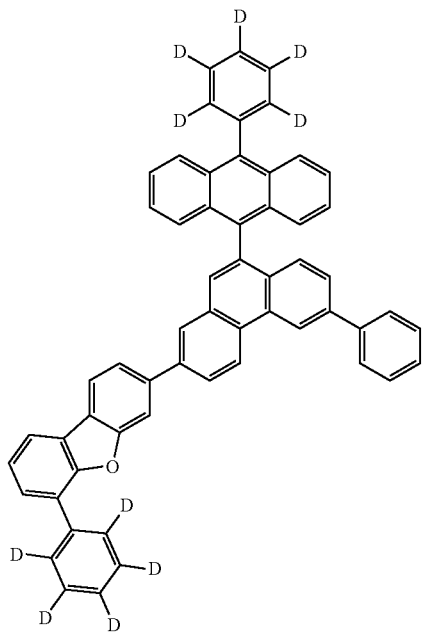
<Compound 8>
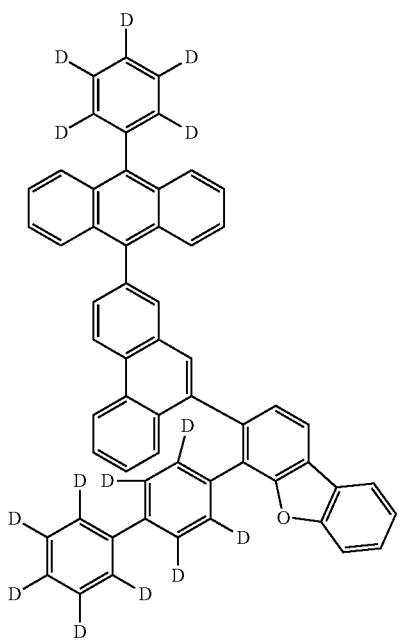

<Compound 9>
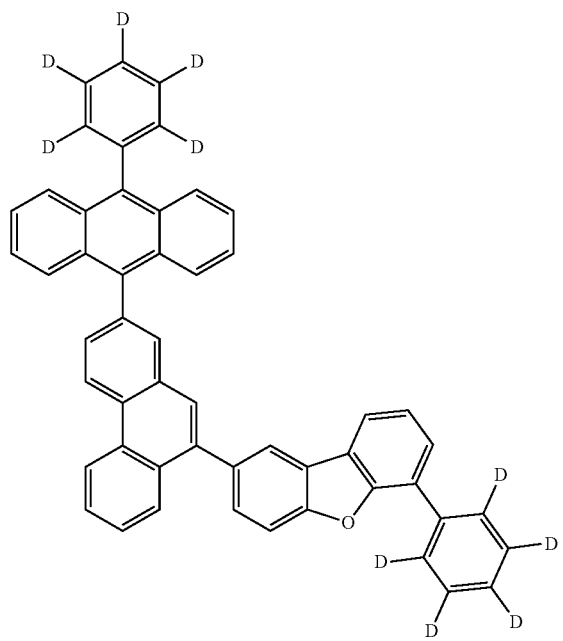
<Compound 10>
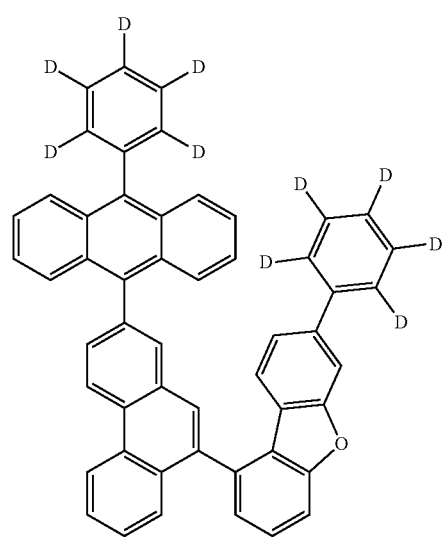
<Compound 11>
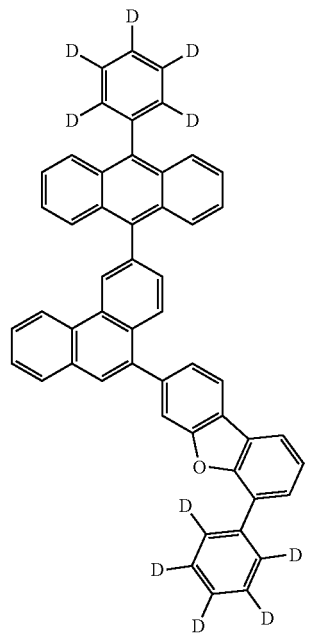
<Compound 12>
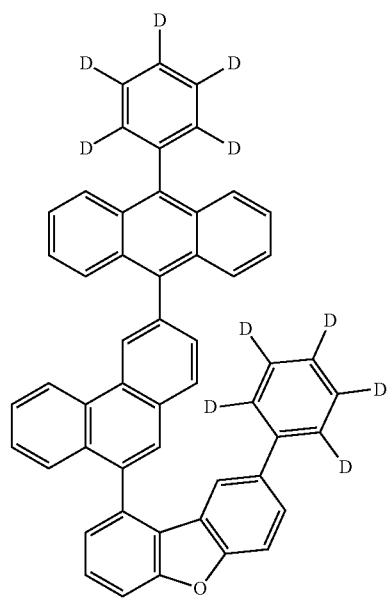

<Compound 13>
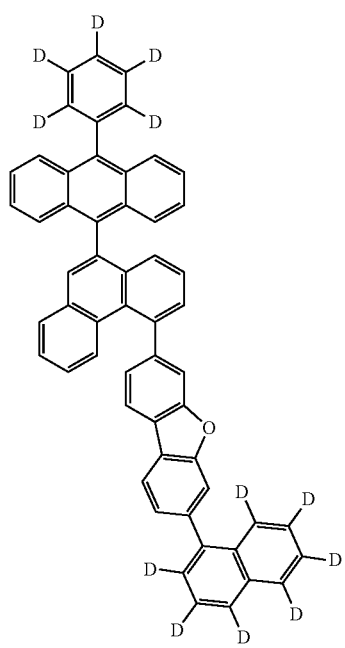
<Compound 14>
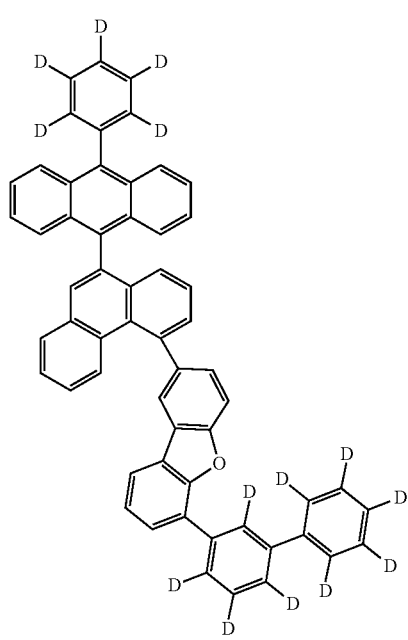
<Compound 15>
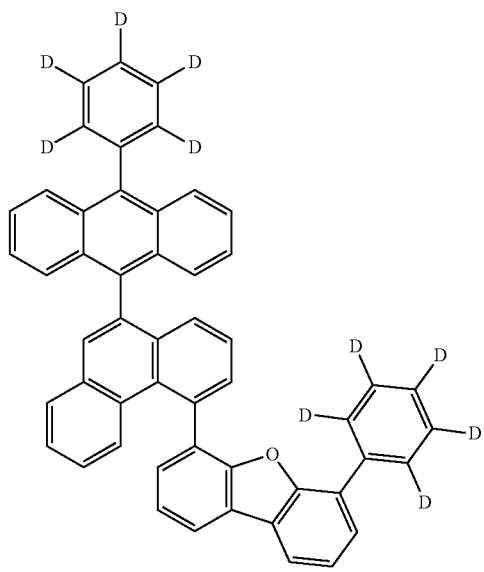
<Compound 16>
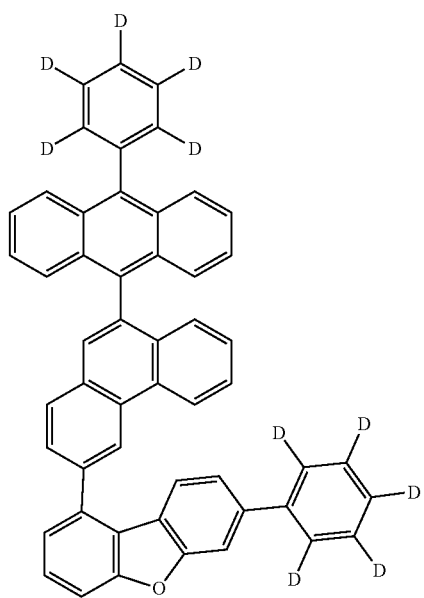

<Compound 17>
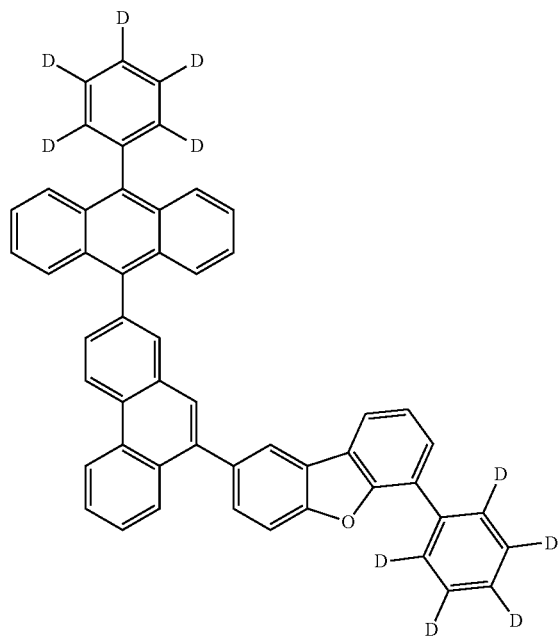
<Compound 18>
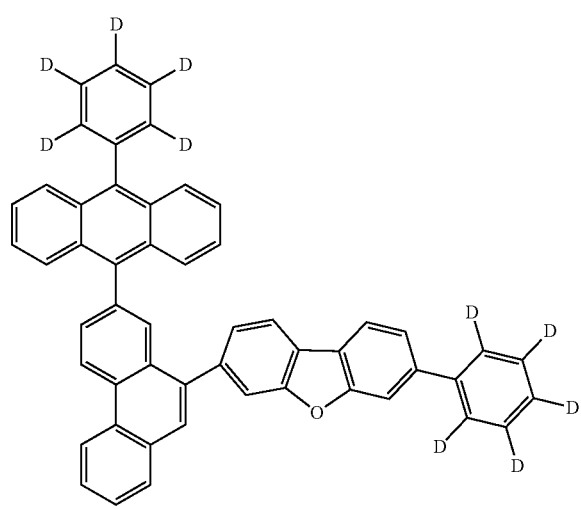
<Compound 19>
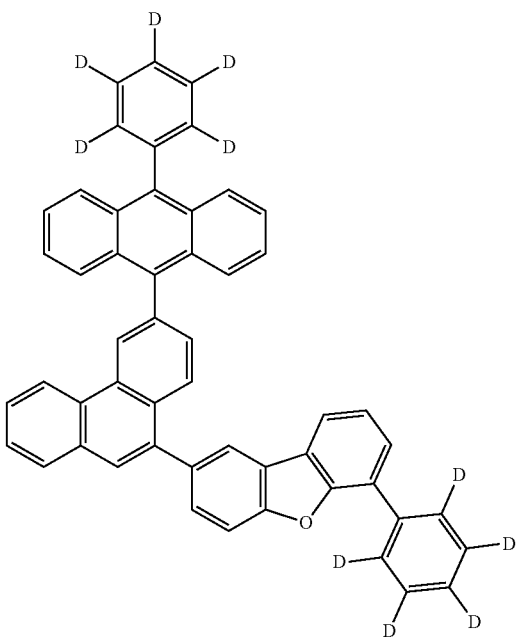
<Compound 20>

<Compound 21>
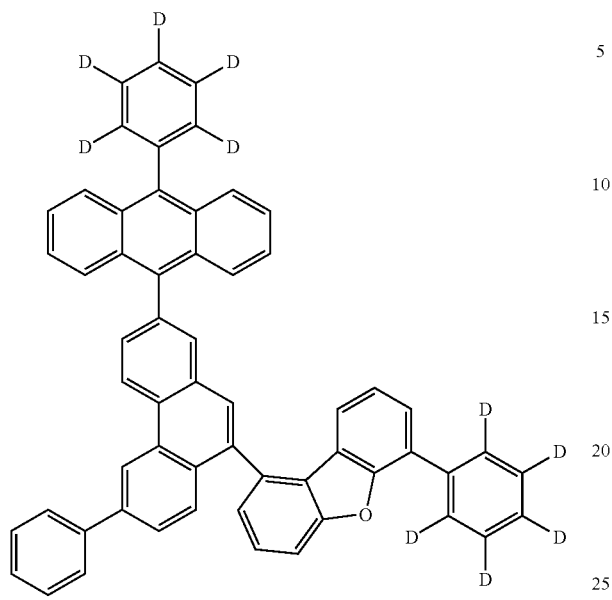
<Compound 22>
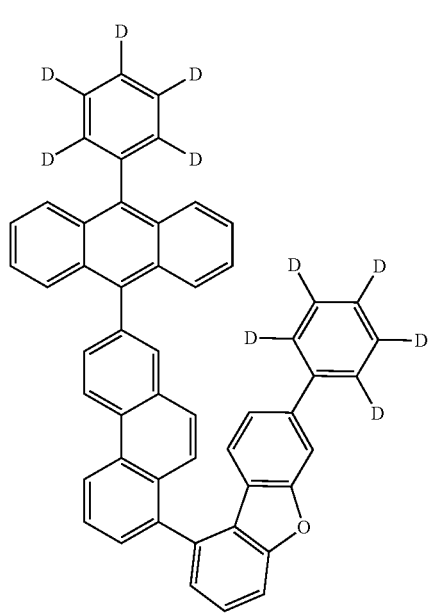
<Compound 23>
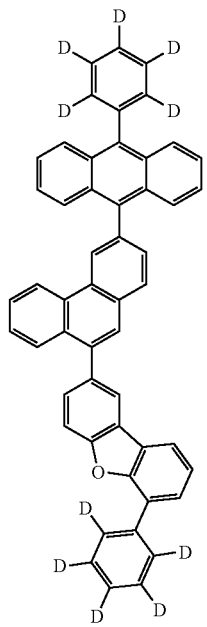
<Compound 24>
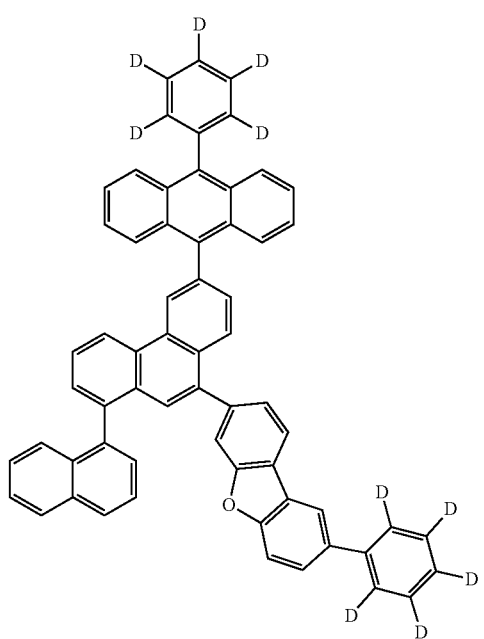

<Compound 25>
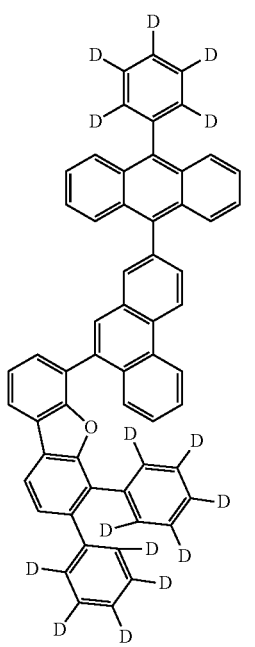
<Compound 27>
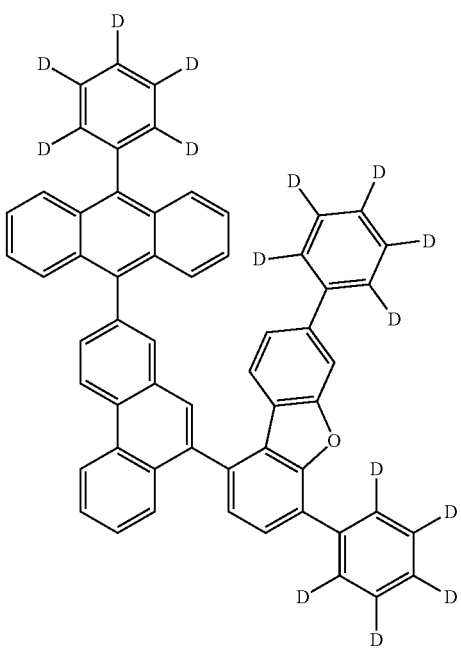
<Compound 26>
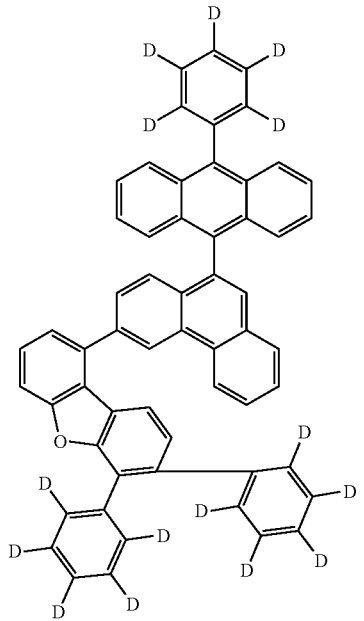
<Compound 28>
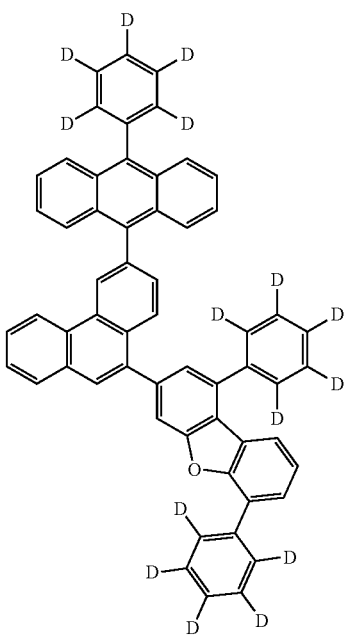

<Compound 29>
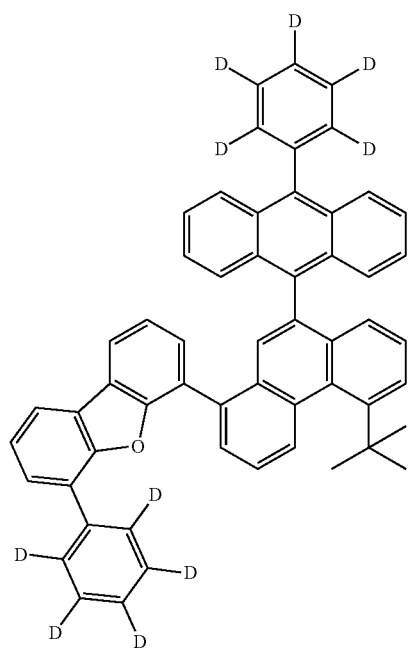
<Compound 30>
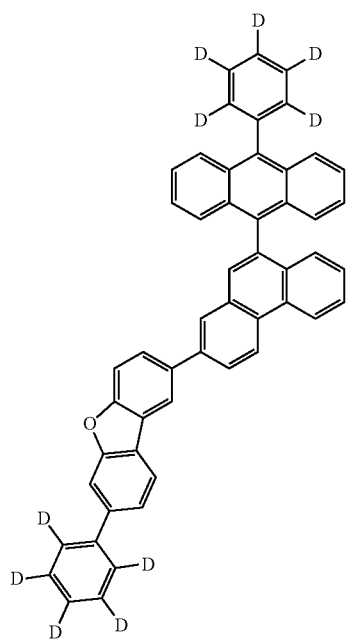
<Compound 31>
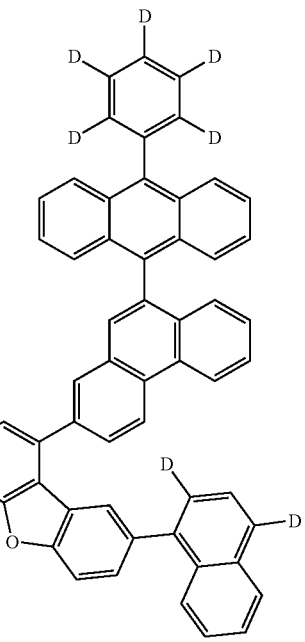
<Compound 32>
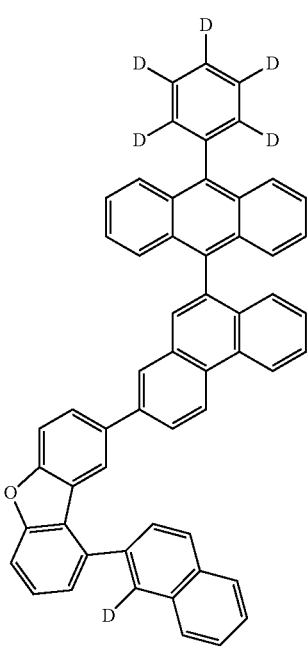

<Compound 33>

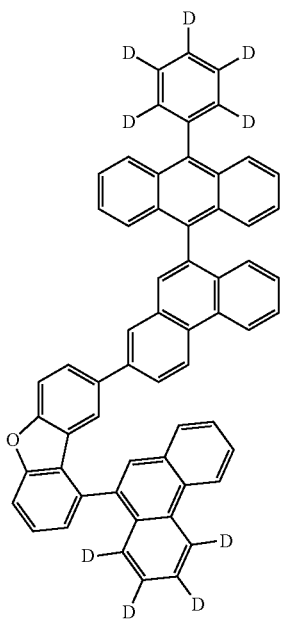

<Compound 34>

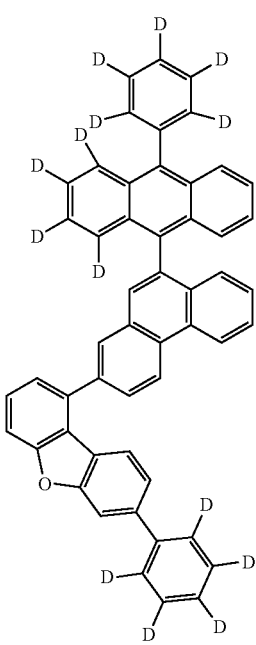

<Compound 35>

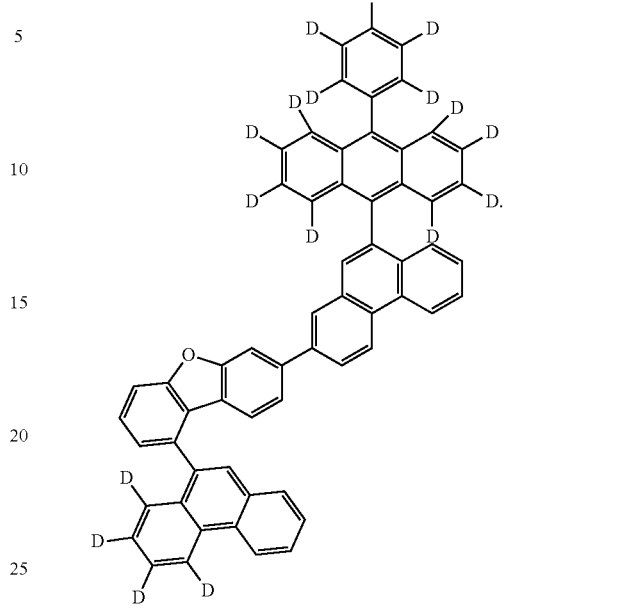

In another aspect, the present disclosure provides an organic light-emitting diode comprising at least one of the organic light-emitting compound represented by Chemical Formula A.

In detail, the organic light-emitting diode may comprise: a first electrode; a second electrode facing the first electrode; and an organic layer disposed between the first electrode and the second electrode, wherein the organic layer includes the organic light-emitting compound of the present disclosure.

In this regard, the organic layer within the organic light-emitting diode may further comprise at least one of a hole injection layer, a hole transport layer, a functional layer capable of both hole injection and hole transport, a light-emitting layer, an electron transport layer, and an electron injection layer.

Moreover, the organic layer interposed between the first electrode and the second electrode is a light-emitting layer wherein the light emitting layer may contain a host and a dopant, with the organic light-emitting compound serving as the host.

FIG. 1 is a schematic view of the structure of an organic light-emitting diode according to the present disclosure.

As shown in FIG. 1, the organic light-emitting diode according to an embodiment of the present disclosure comprises an anode (20), a hole transport layer (40), an organic light-emitting layer (50), an electron transport layer (60), and a cathode (80), and optionally a hole injection layer (30) and an electron injection layer (70). In addition, one or two intermediate layers may be further formed in the organic light-emitting diode.

Here, the organic light-emitting compound represented by Chemical Formula A can be used as a host in the light emitting layer.

Reference is made to FIG. 1 with regard to the organic light-emitting diode of the present disclosure and the fabrication thereof. First, a substrate (10) is coated with an anode electrode material to form an anode (20). So long as it is used in a typical organic electroluminescence device, any substrate may be used as the substrate (10). Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode (20) by thermal deposition in a vacuum or by spin coating to form a hole injection layer (30). Subsequently, thermal deposition in a vacuum or by spin coating may also be conducted to form a hole transport layer (40) with a hole transport layer material on the hole injection layer (30).

No particular limitations are imparted to the hole injection layer material, as long as it is one that is typically used in the art. For example, mention may be made of 2-TNATA [4,4',4''-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine], but the present disclosure is not limited thereby.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD), and N,N'-di(naphthalen-1-yl)-N,N'-diphenyl-benzidine (a-NPD).

Then, an organic light-emitting layer (50) containing a host and a dopant is deposited on the hole transport layer (40) by deposition in a vacuum or by spin coating. In some embodiments of the present disclosure, the light-emitting layer particularly ranges in thickness from 50 to 2,000 Å. Here, an electron density control layer (not shown) may be further formed on the organic light-emitting layer (50), as necessary.

On the other hand, the light emitting layer may contain a dopant material as well as the host including the organic light emitting compound according to the present disclosure. In the case where the light-emitting layer contains a host and a dopant, the content of the dopant may range from about 0.01 to 20 parts by weight, based on 100 parts by weight of the host, but is not limited thereto.

In addition, the anthracene derivative represented by Chemical Formula A may be used as a host, alone, or in combination with a well-known host.

When used in combination with a well-known host, an available host may be at least one of the compounds represented by Chemical Formula C, below:

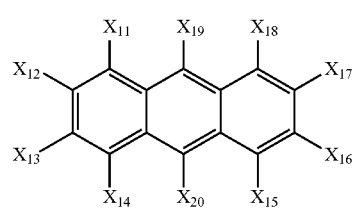

[Chemical Formula C]

wherein, $X_{11}$ to $X_{20}$, which may be same or different, are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 5 to 50 carbon atoms, a substituted or unsubstituted heteroaryl of 3 to 50 carbon atoms bearing O, N, or S as a heteroatom, a substituted or unsubstituted silicone, a substituted or unsubstituted boron, a substituted or unsubstituted silane, a carbonyl, a phosphoryl, an amino, a nitrile, a halogen, an amide, and an ester, wherein adjacent radicals may form an aliphatic, an aromatic, an aliphatic hetero, or an aromatic hetero fused ring.

More particularly, concrete examples of the host compound represented by Chemical Formula C include, but are not limited to, compounds of [Chemical Formula H 1] to [Chemical Formula H 196]:

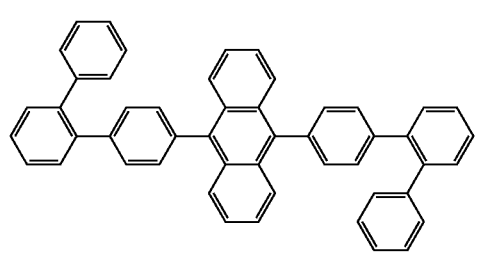

[H 1]

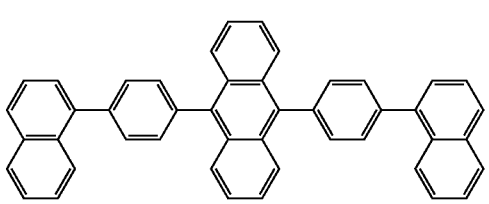

[H 2]

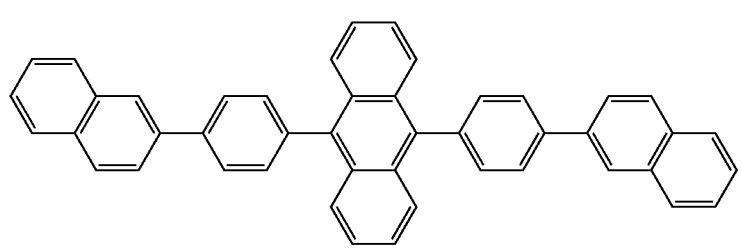

[H 3]

[H 4]
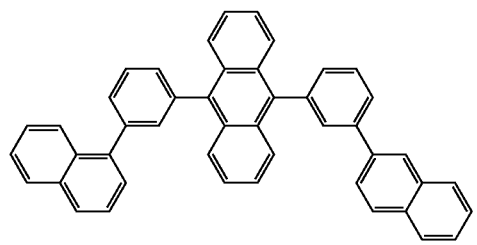
[H 5]
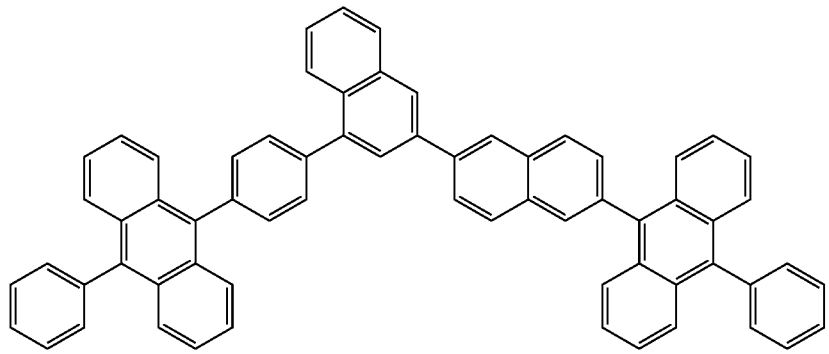
[H 6]
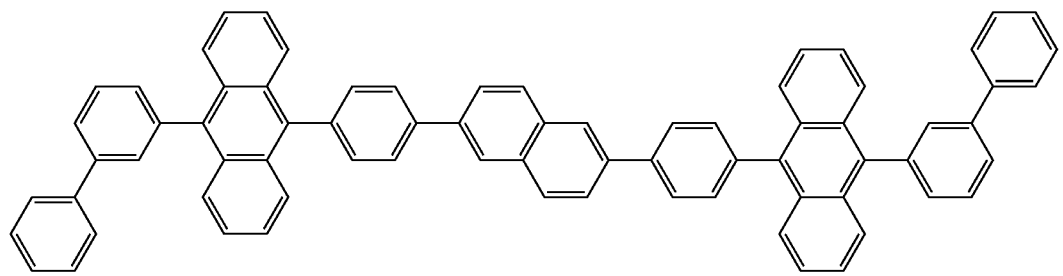
[H 7]
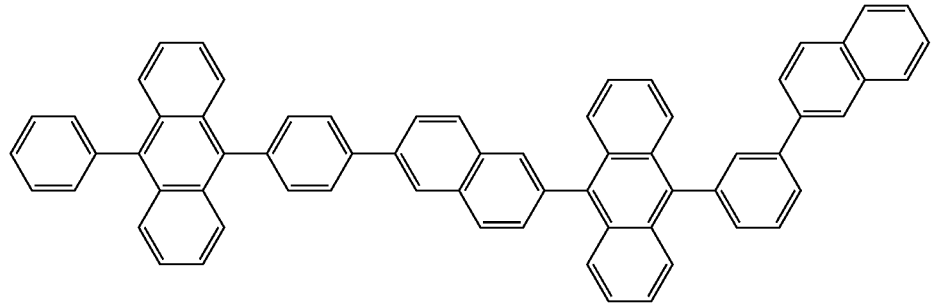
[H 8]
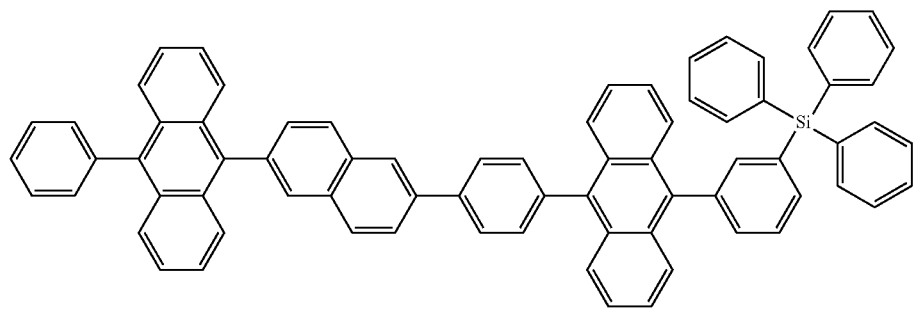

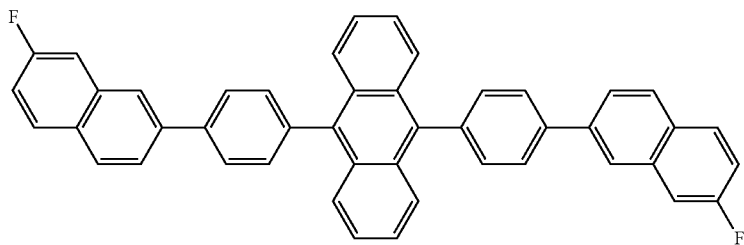
[H 9]
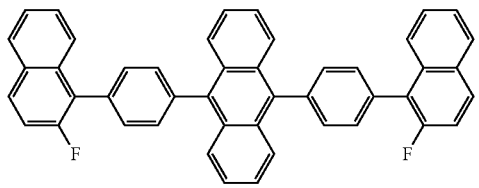
[H 10]
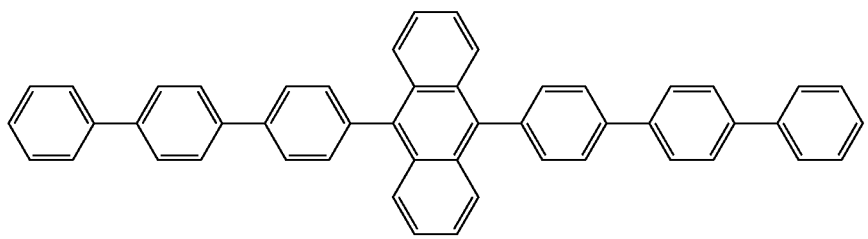
[H 11]
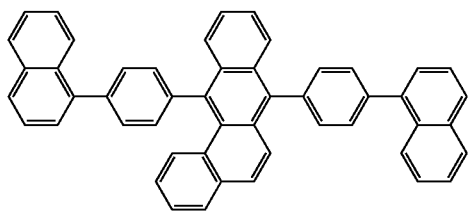
[H 12]
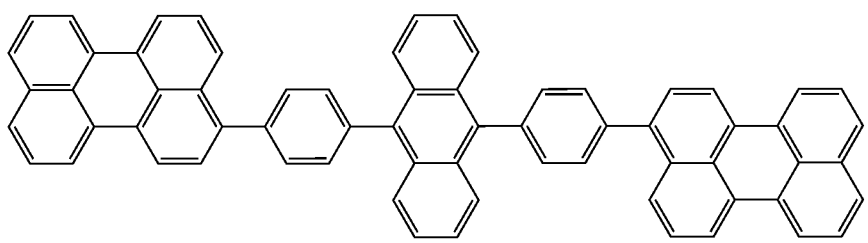
[H 13]
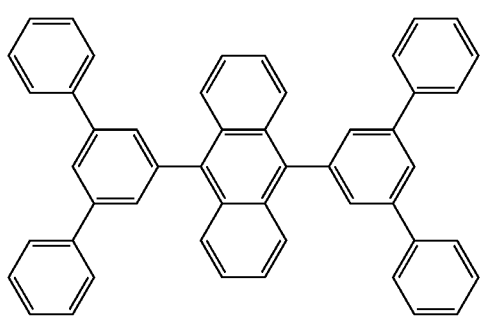
[H 14]
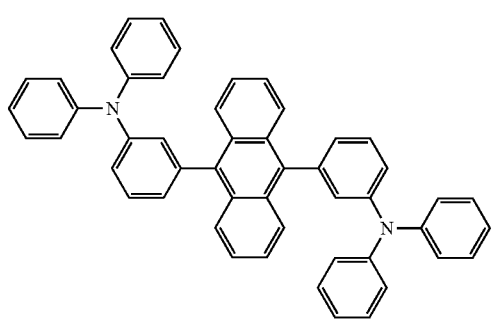
[H 15]

[H 16]
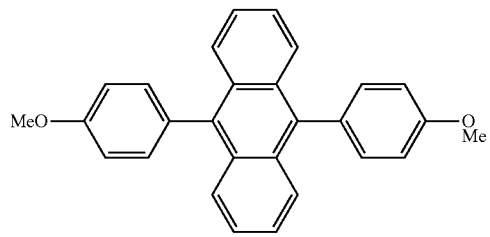
[H 17]
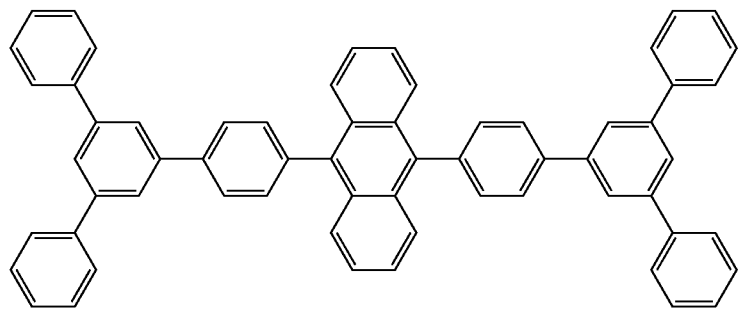
[H 18]
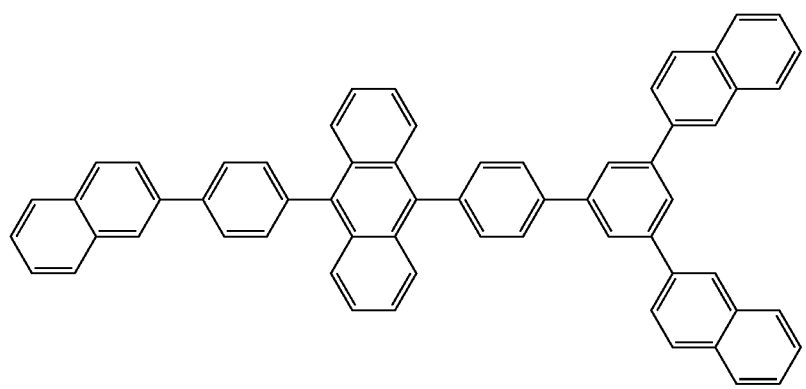
[H 19]
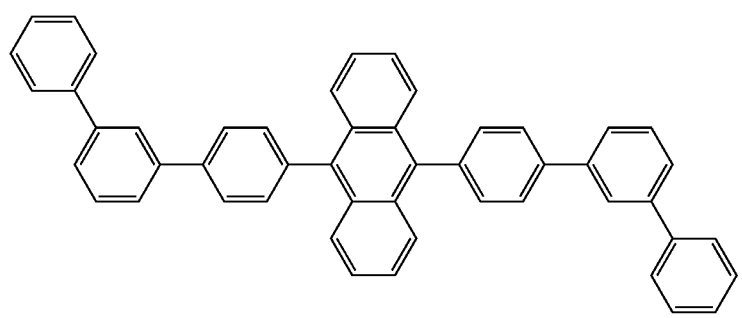
[H 20]
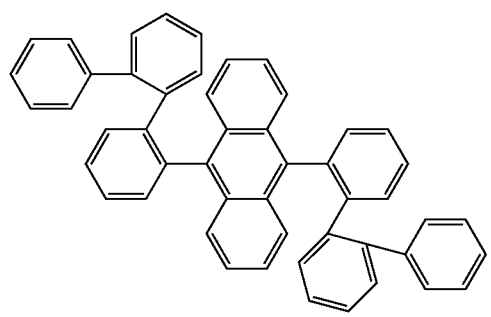
[H 21]
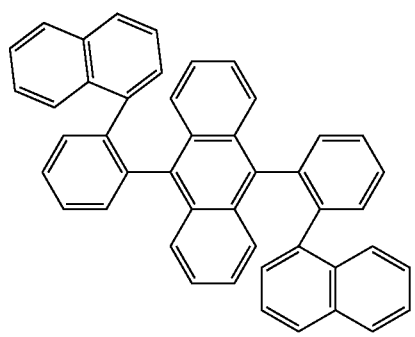

-continued
[H 22]
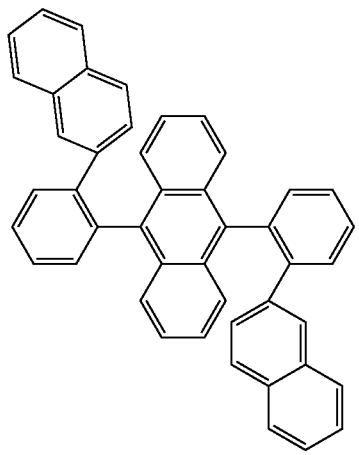
[H 23]
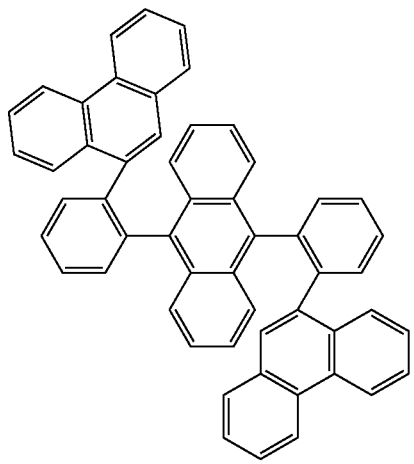
[H 24]
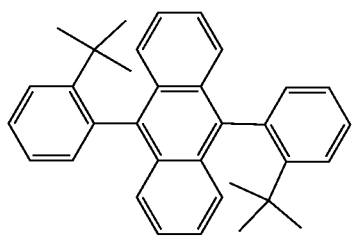
[H 25]
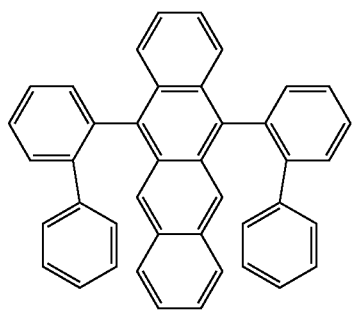
[H 26]
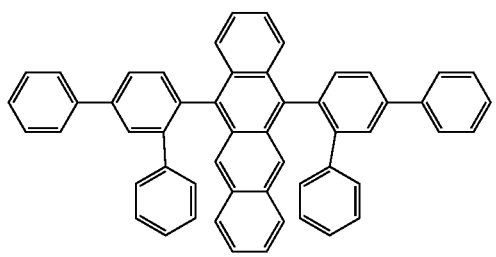
[H 27]
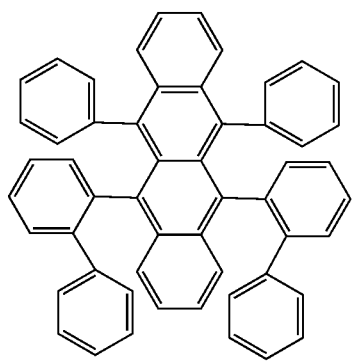
[H 28]
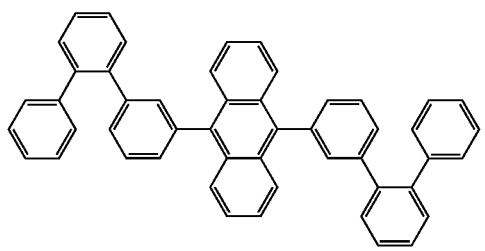
[H 29]
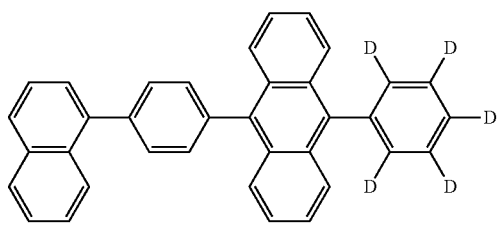

-continued
[H 30]
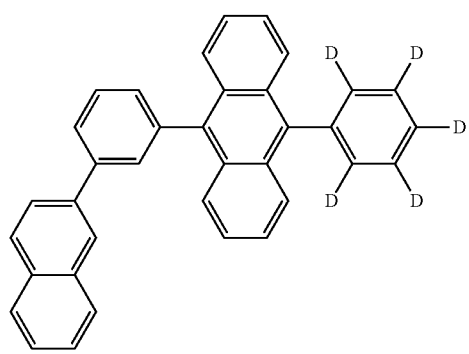
[H 31]
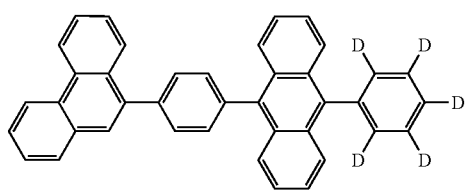
[H 32]
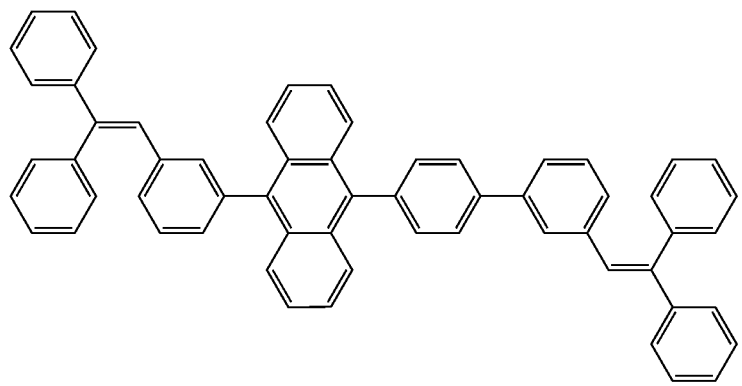
[H 33]
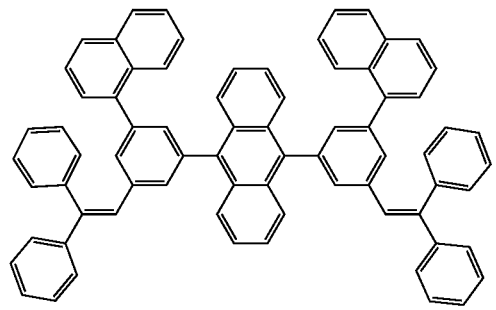
[H 34]
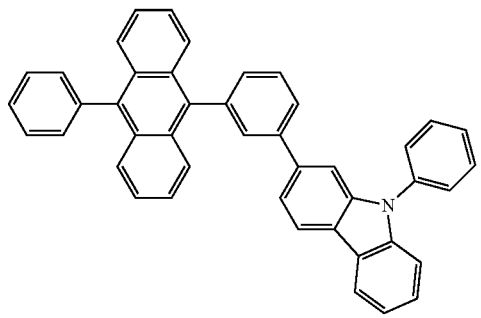
[H 35]
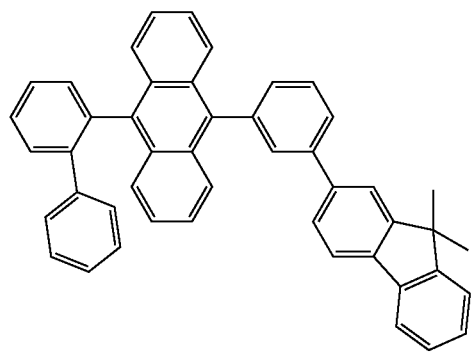
[H 36]
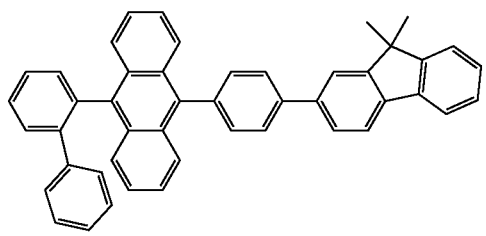

-continued
[H 37]
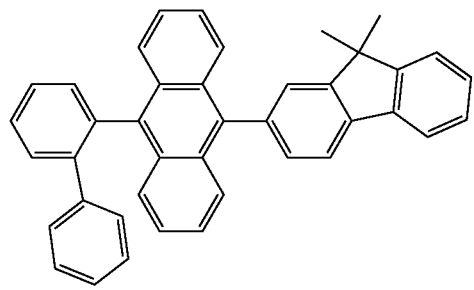
[H 38]
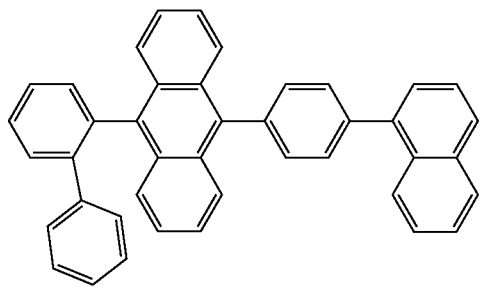
[H 39]
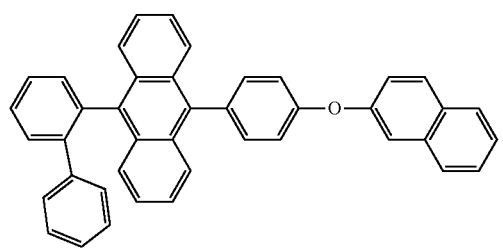
[H 40]
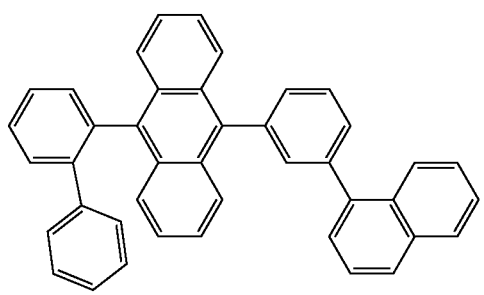
[H 41]
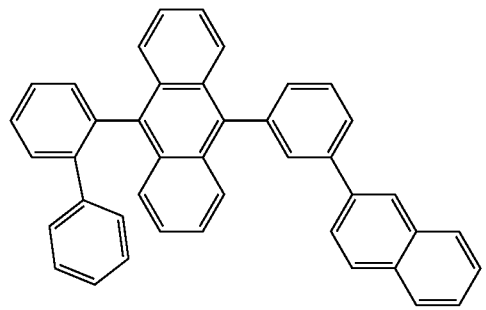
[H 42]
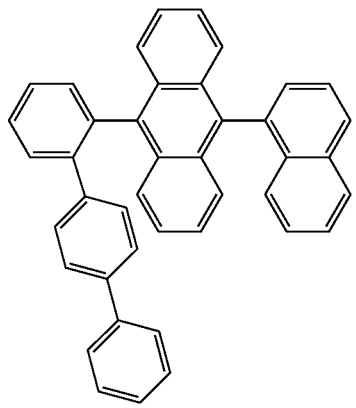
[H 43]
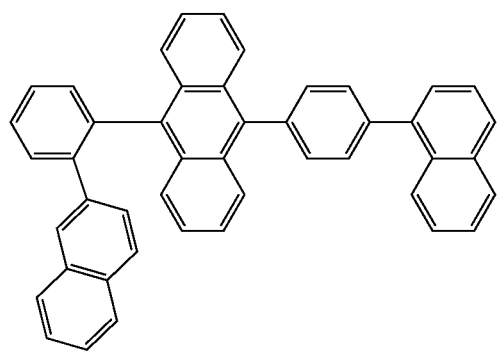

-continued
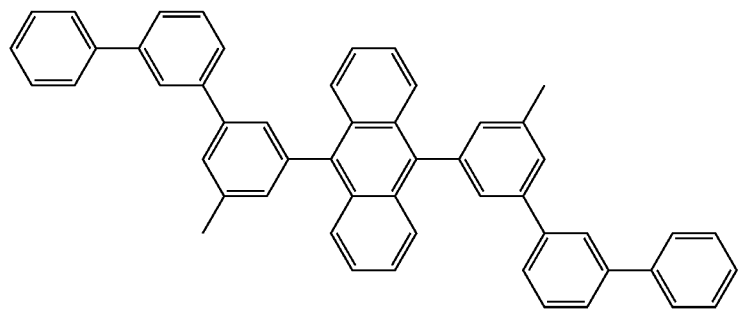
[H 44]
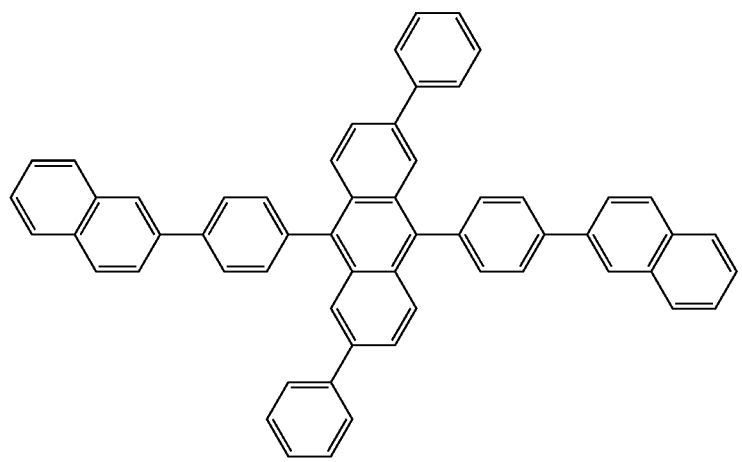
[H 45]
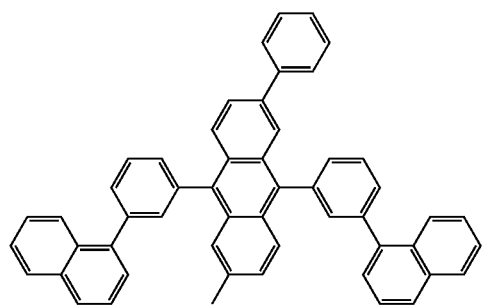
[H 46]
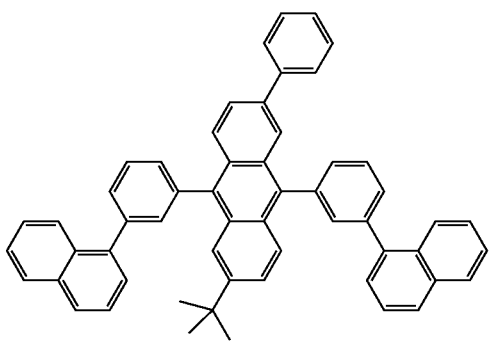
[H 47]
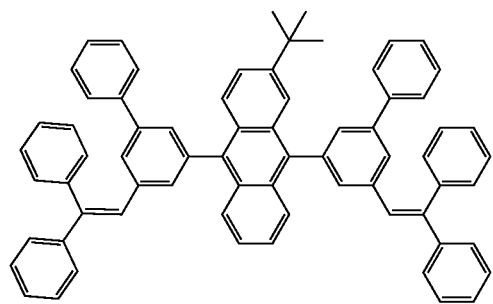
[H 48]

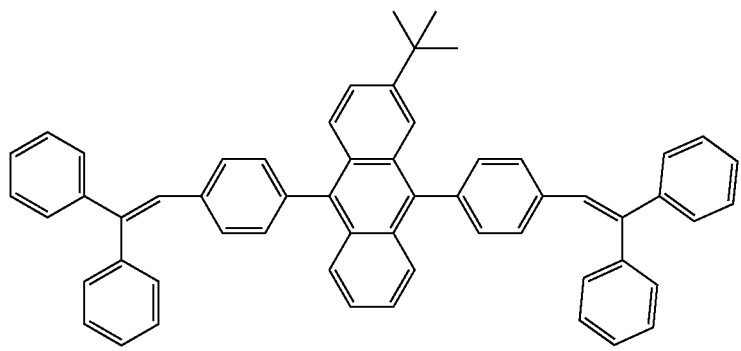
[H 49]
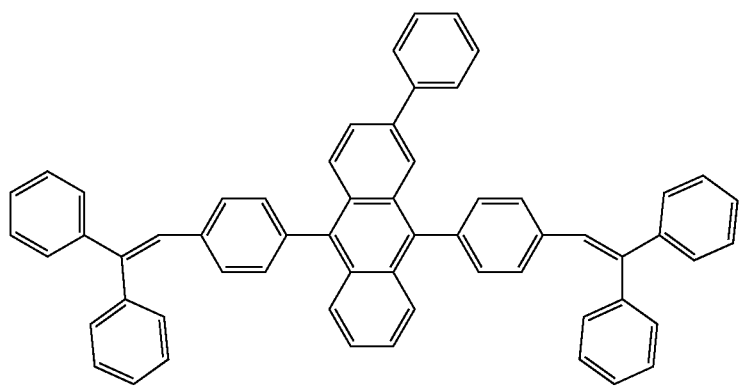
[H 50]
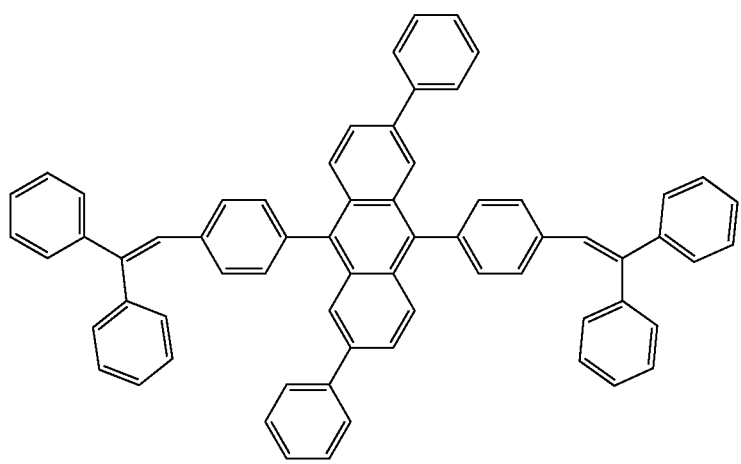
[H 51]
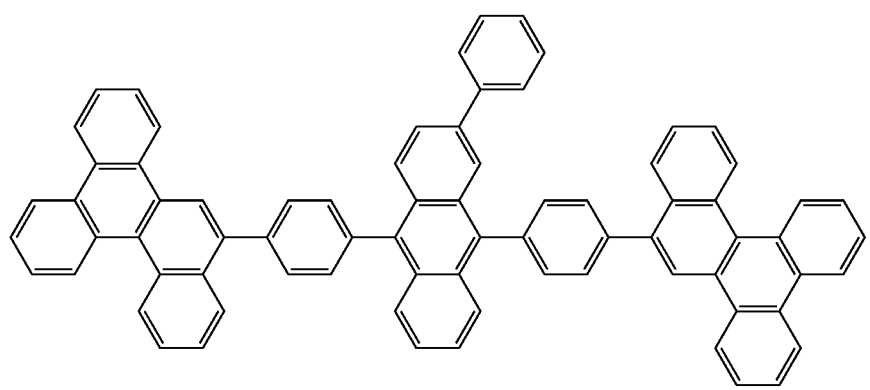
[H 52]

-continued
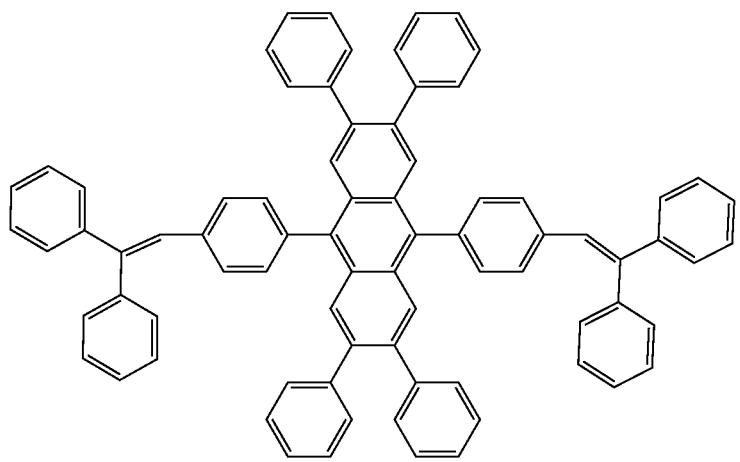
[H 53]
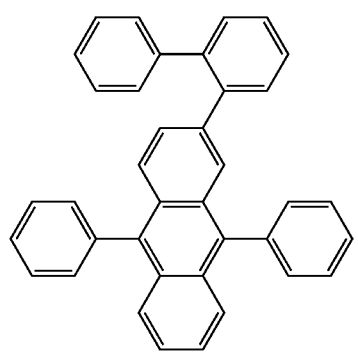
[H 54]
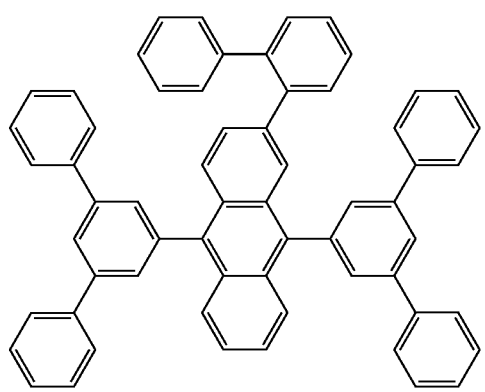
[H 55]
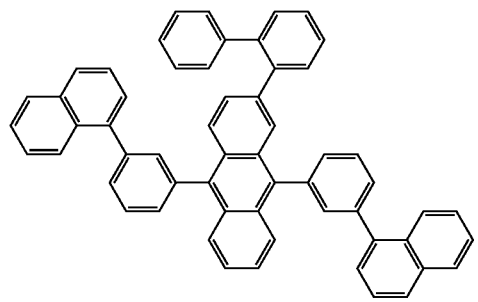
[H 56]
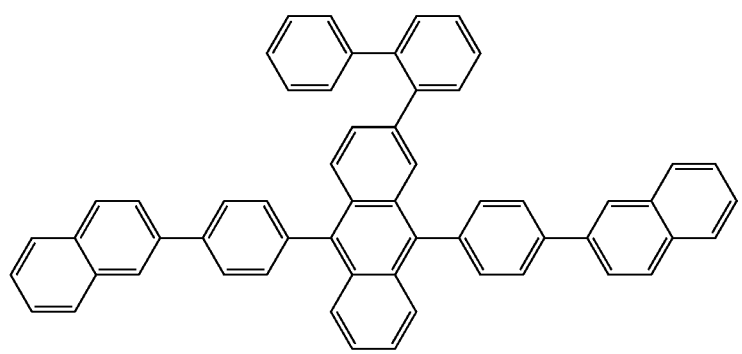
[H 57]

[H 58]
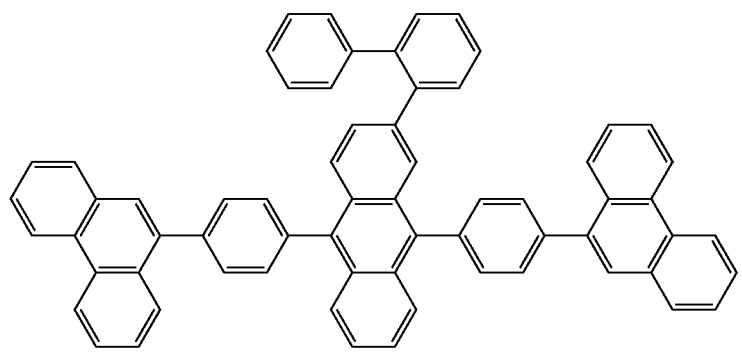
[H 59]
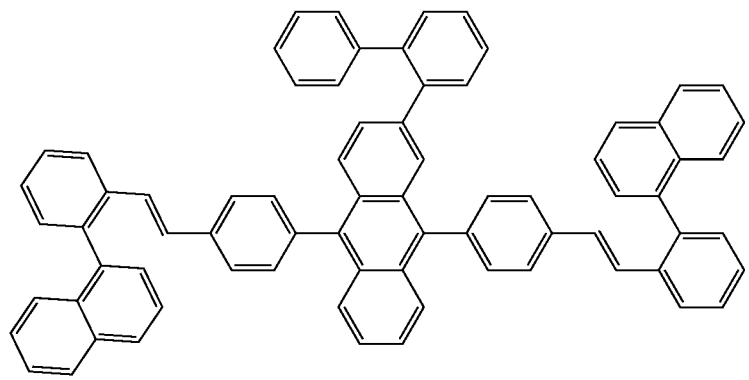
[H 60]
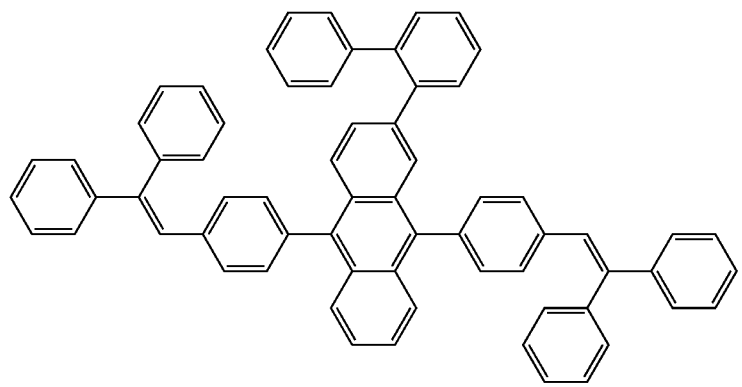
[H 61]
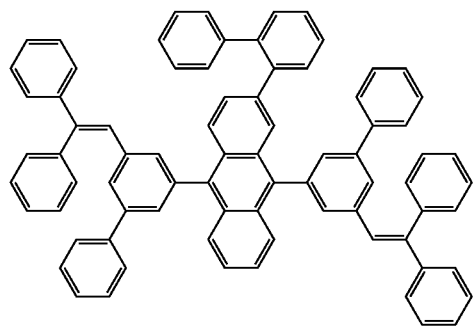
[H 62]
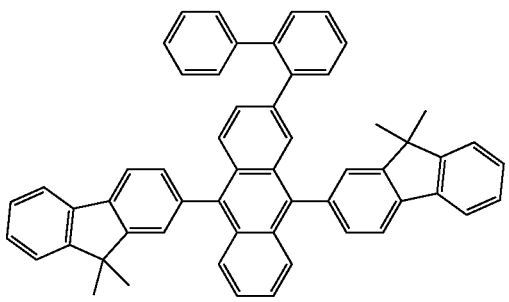

-continued
[H 63]
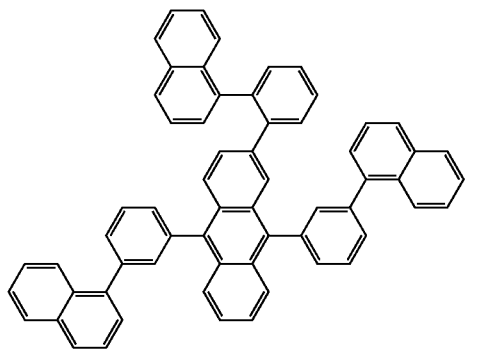
[H 64]
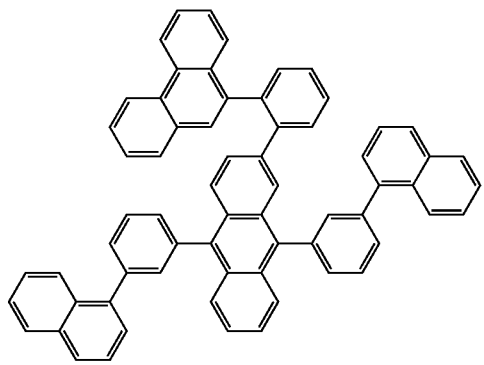
[H 65]
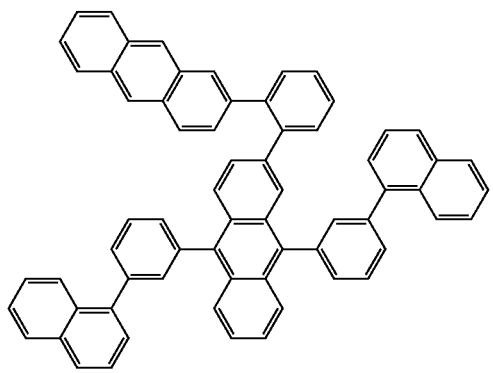
[H 66]
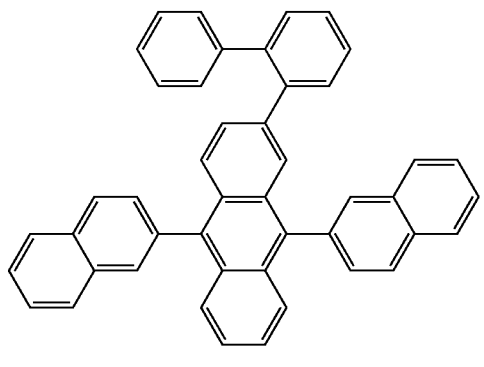
[H 67]
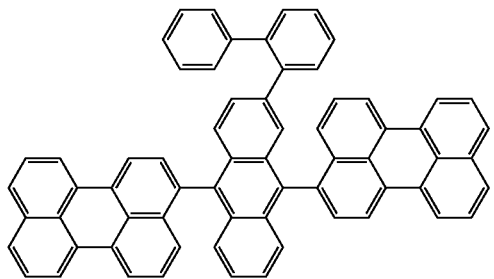
[H 68]
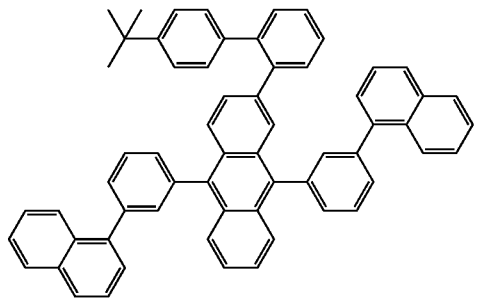
[H 69]
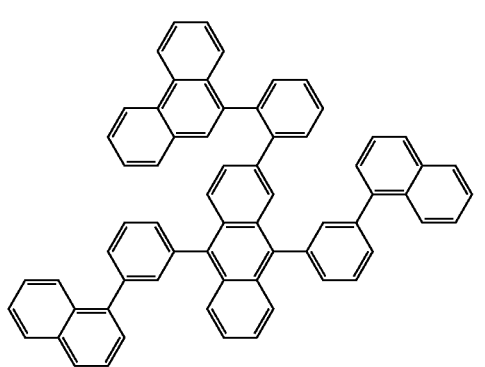
[H 70]
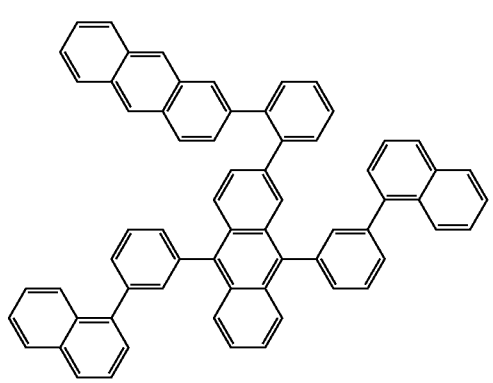

[H 71]
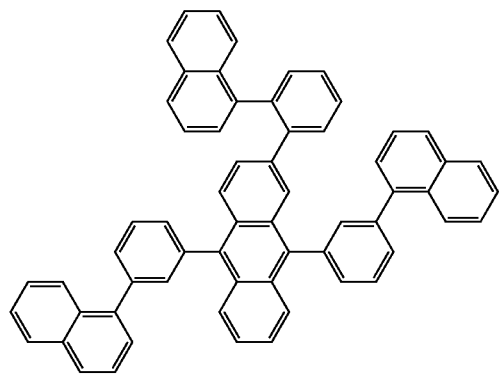
[H 72]
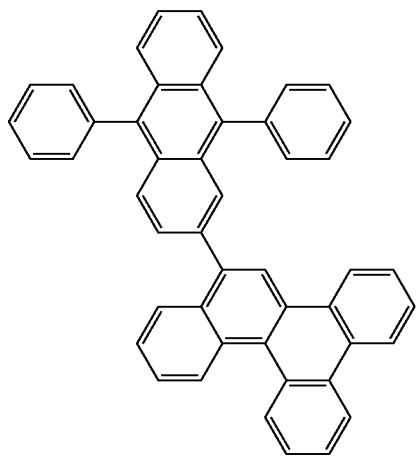
[H 73]
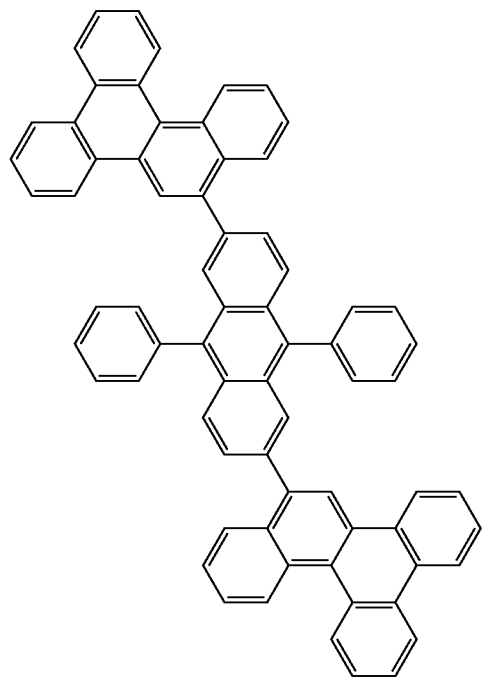
[H 74]
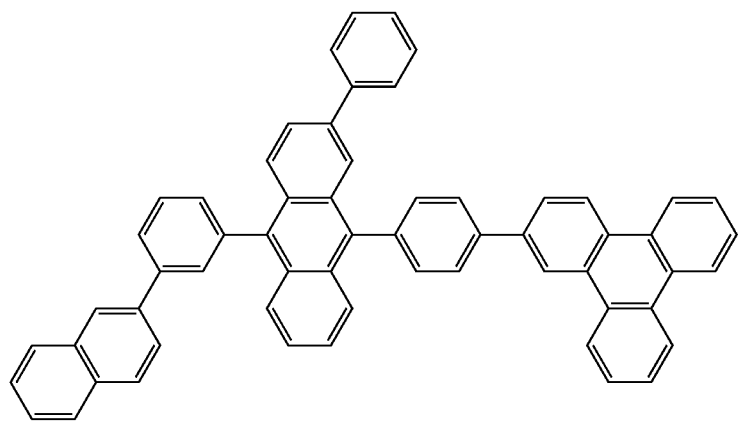

-continued
[H 75]
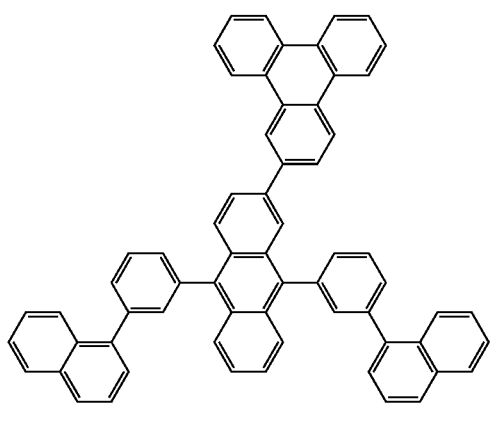
[H 76]
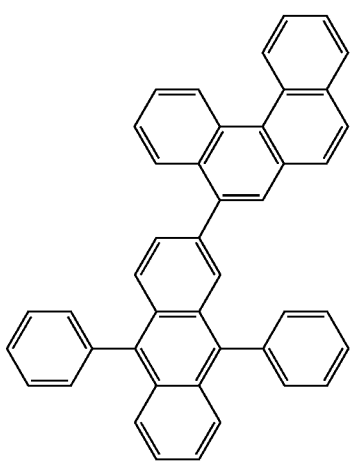
[H 77]
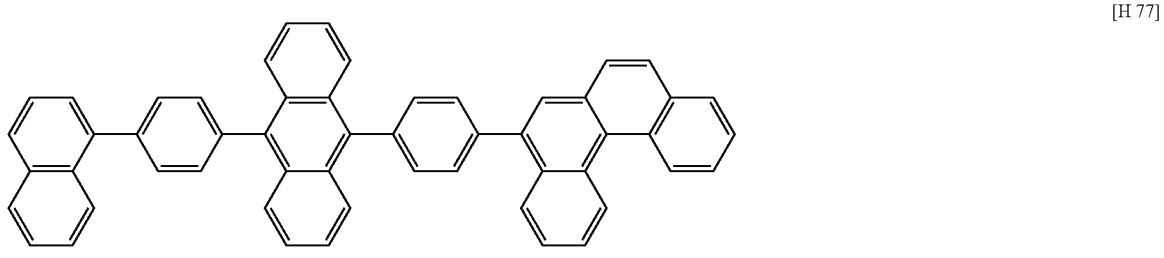
[H 78]
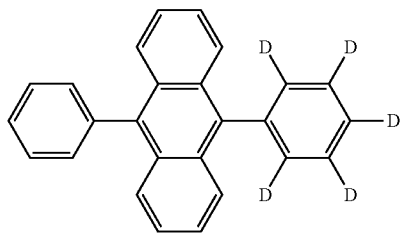
[H 79]
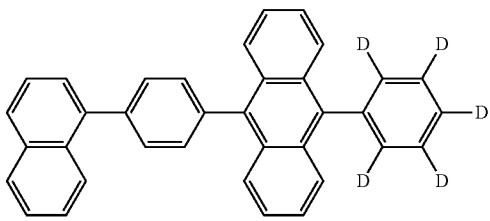
[H 80]
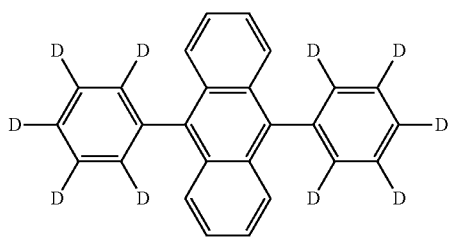
[H 81]
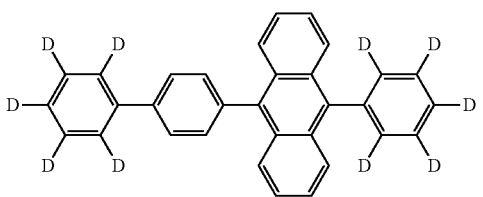
[H 82]
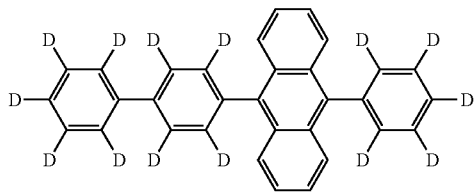
[H 83]
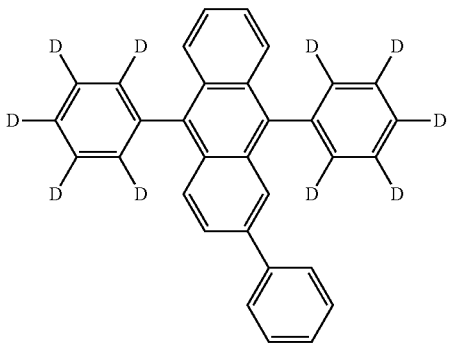

[H 84]
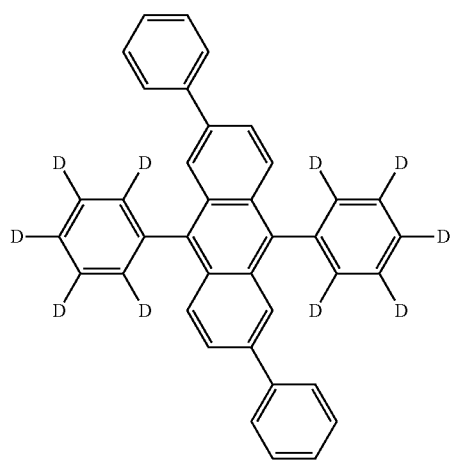
[H 85]
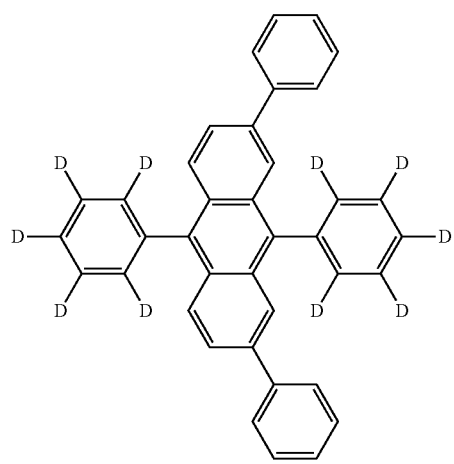
[H 86]
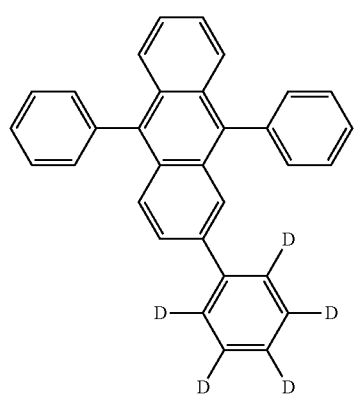
[H 87]
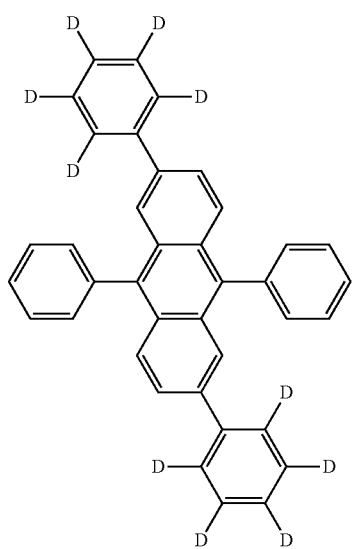
[H 88]
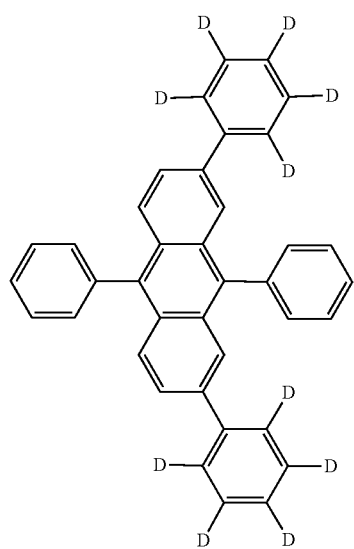
[H 89]
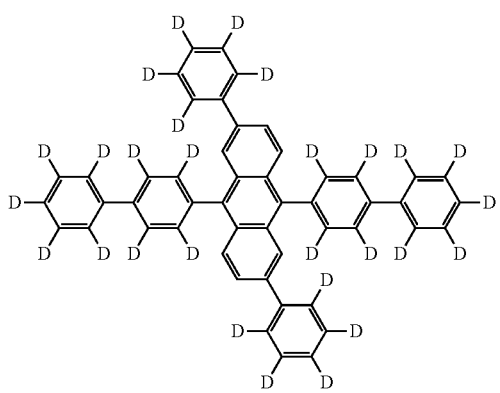

-continued
[H 90]
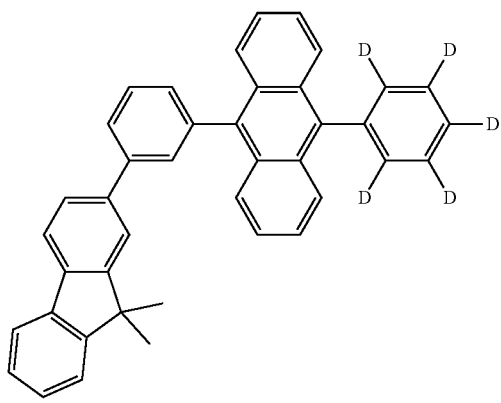
[H 91]
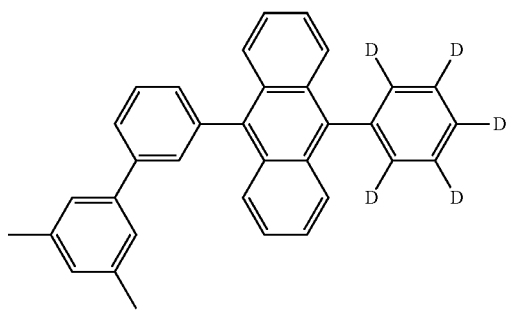
[H 92]
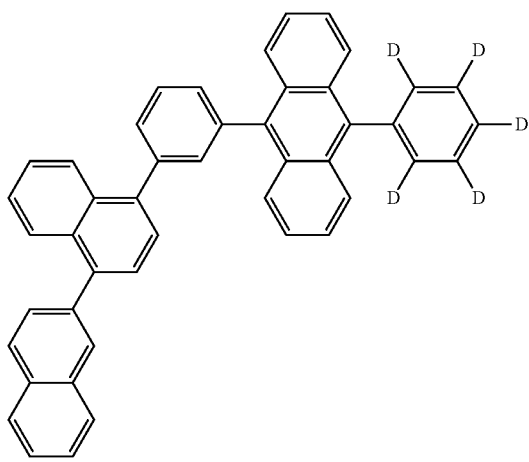
[H 93]
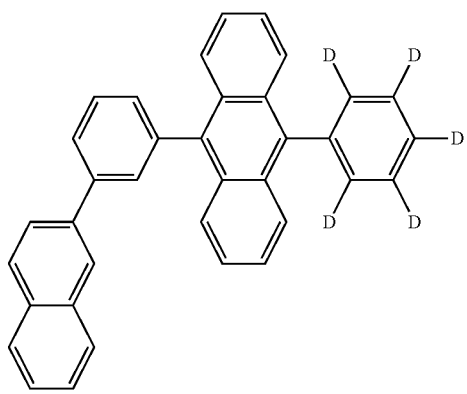
[H 94]
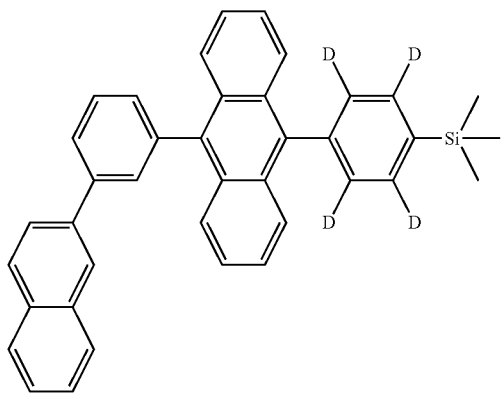
[H 95]
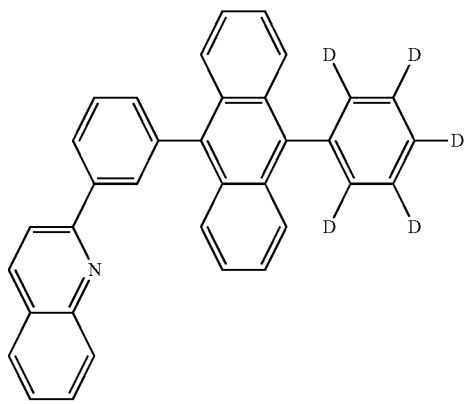

[H 96]
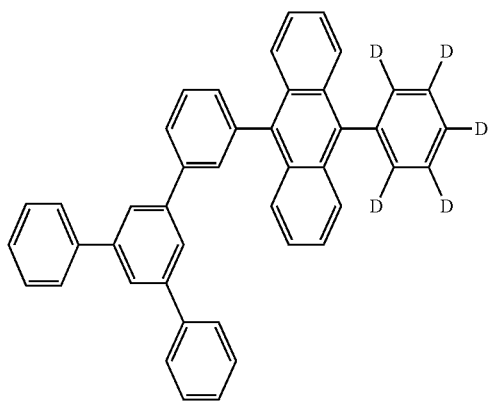
[H 97]
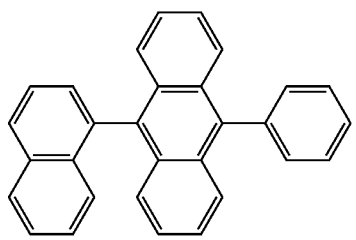
[H 98]
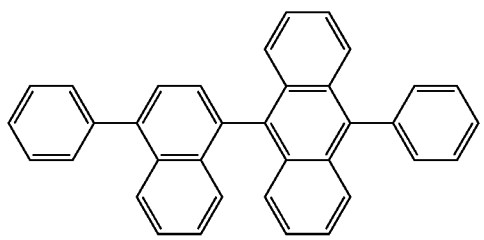
[H 99]
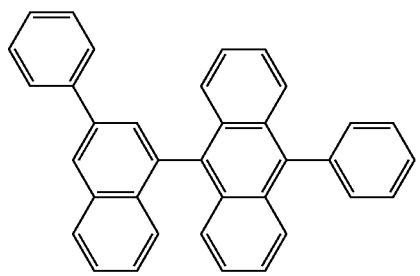
[H 100]
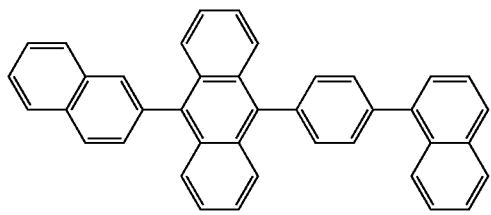
[H 101]
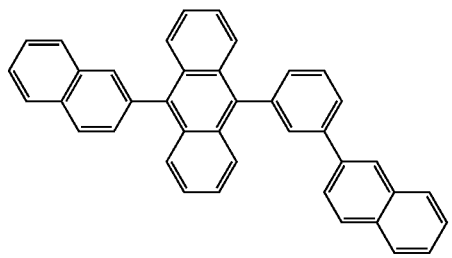
[H 102]
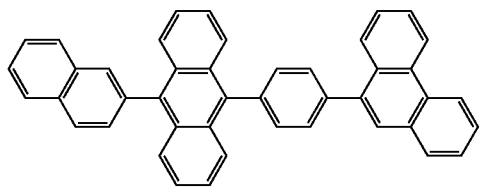
[H 103]
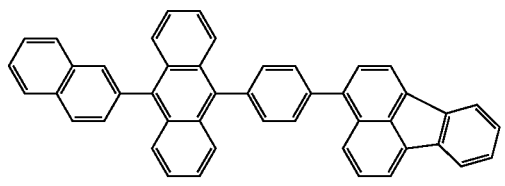
[H 104]
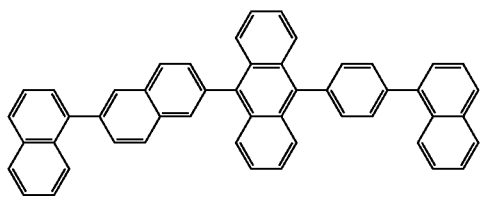
[H 105]
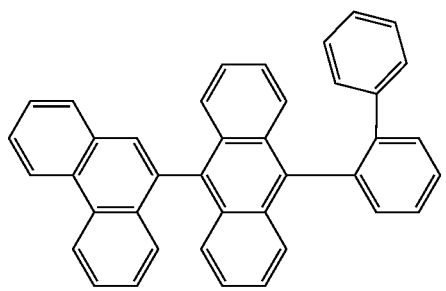

-continued
[H 106]
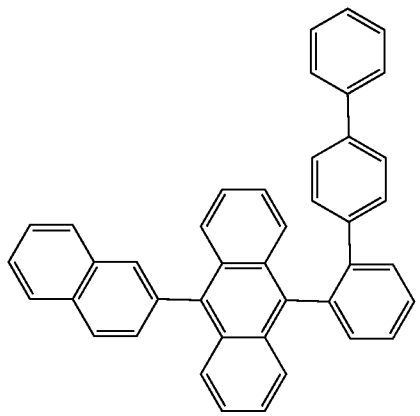
[H 107]
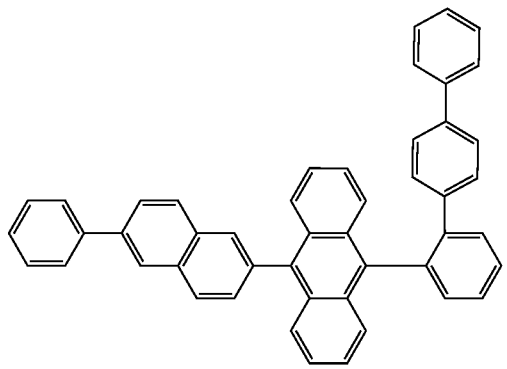
[H 108]
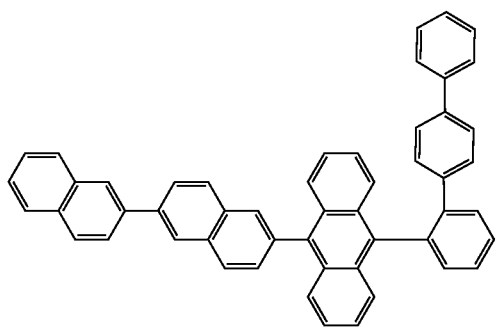
-continued
[H 111]
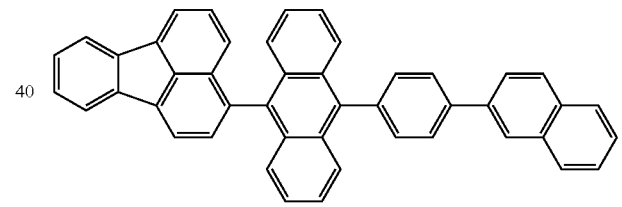
[H 109]
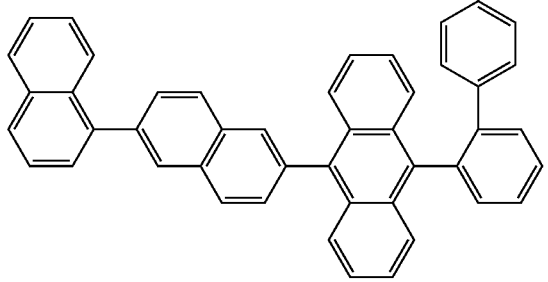
[H 112]
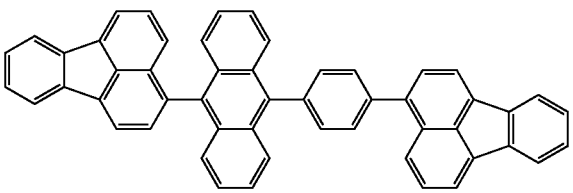
[H 113]
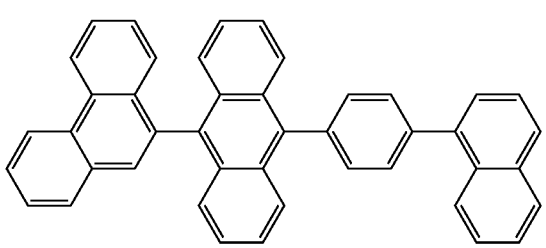
[H 110]
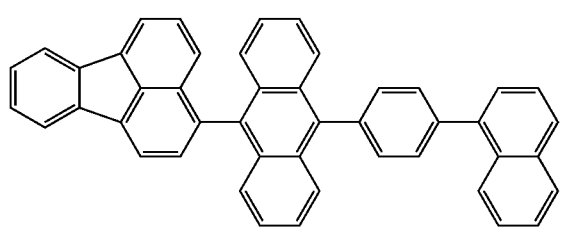

[H 114]
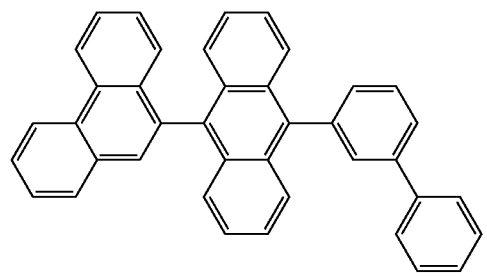
[H 115]
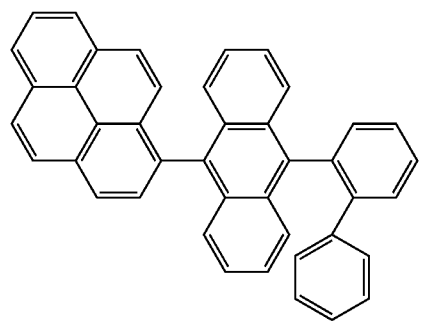
[H 116]
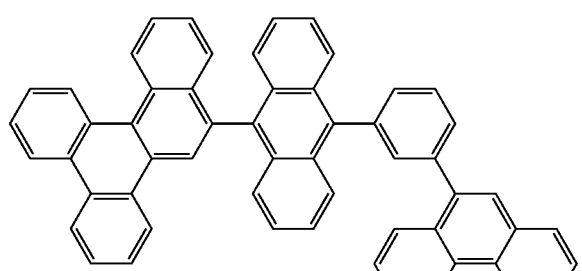
[H 117]
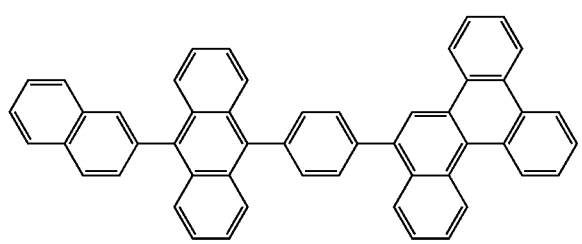
[H 118]
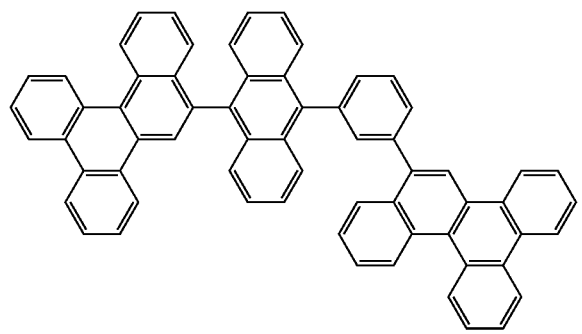
[H 119]
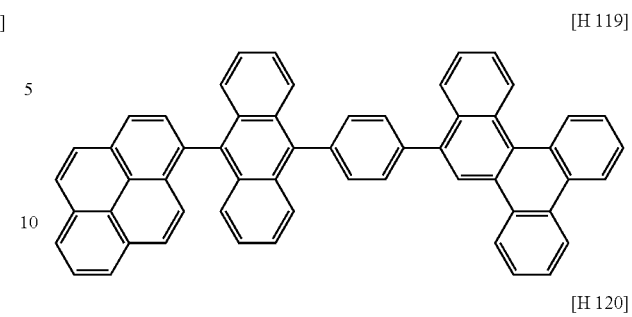
[H 120]
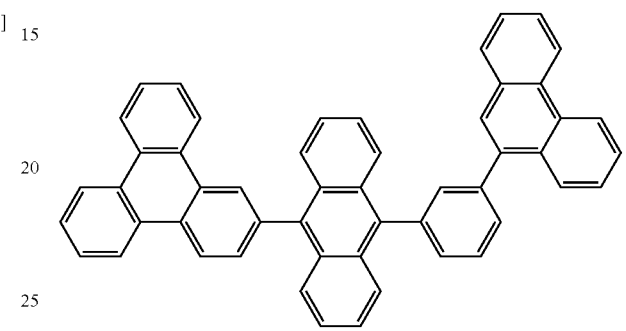
[H 121]
[H 122]
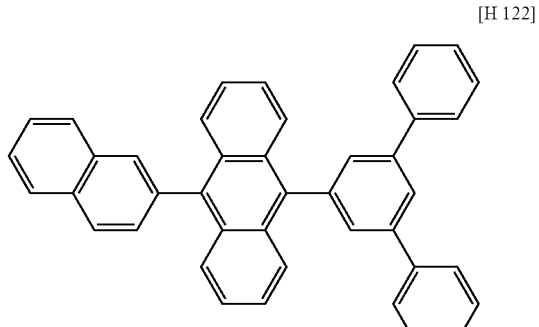

[H 123]
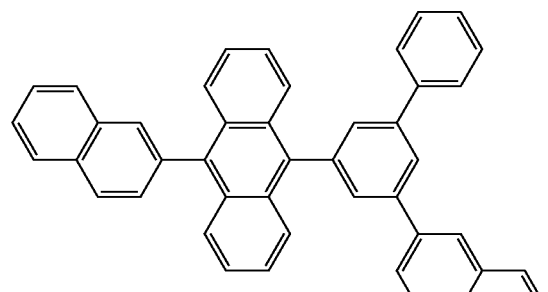
[H 124]
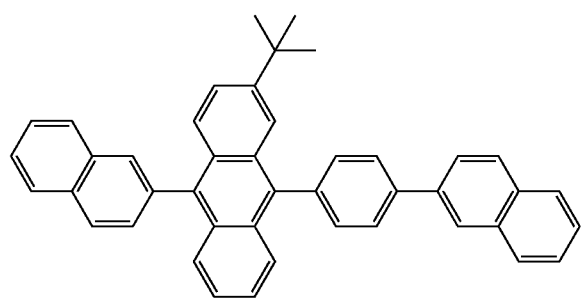
[H 125]
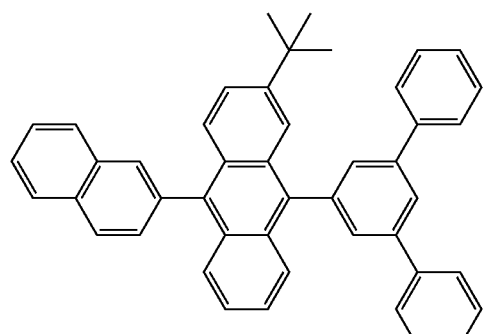
[H 126]
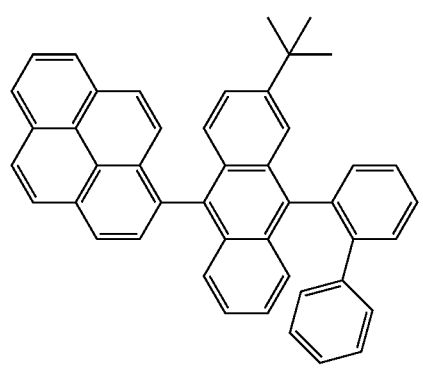
[H 127]
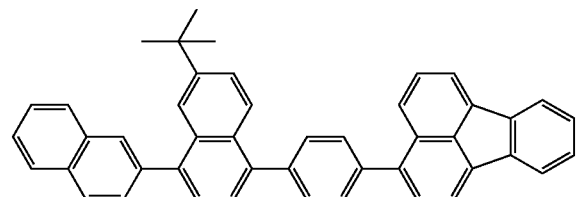
[H 128]
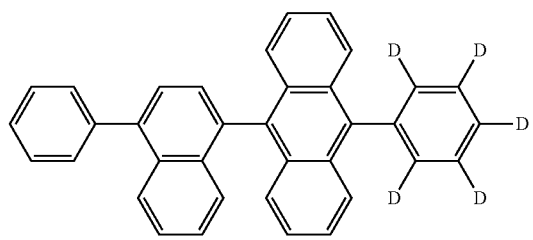
[H 129]
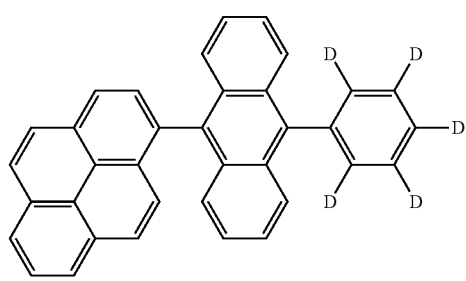
[H 130]
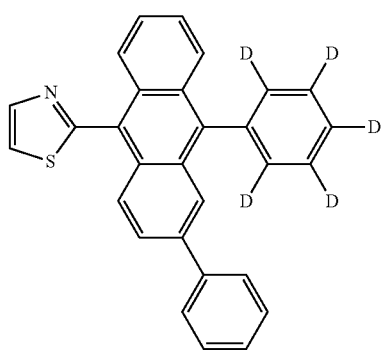
[H 131]
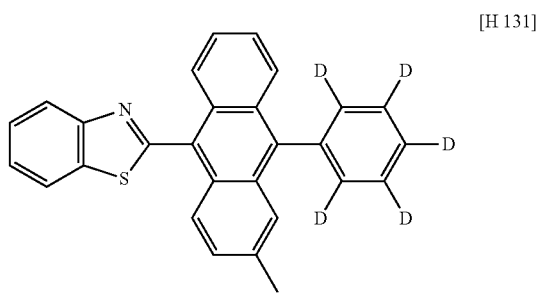

[H 132]
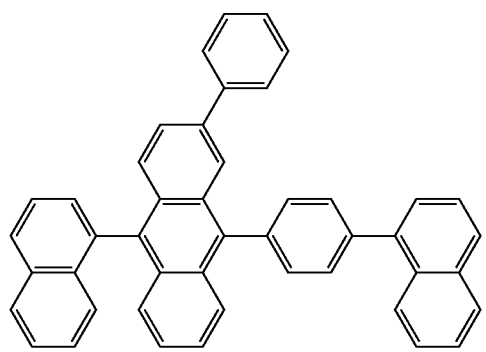
[H 133]
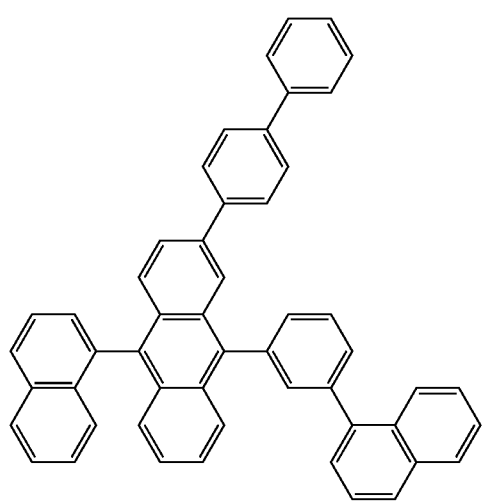
[H 134]
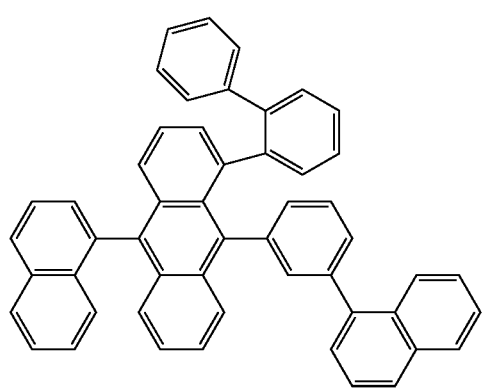
[H 135]
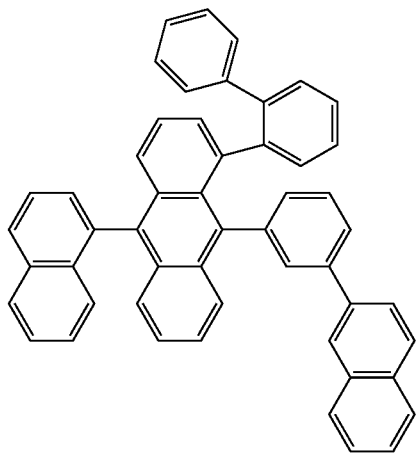
[H 136]
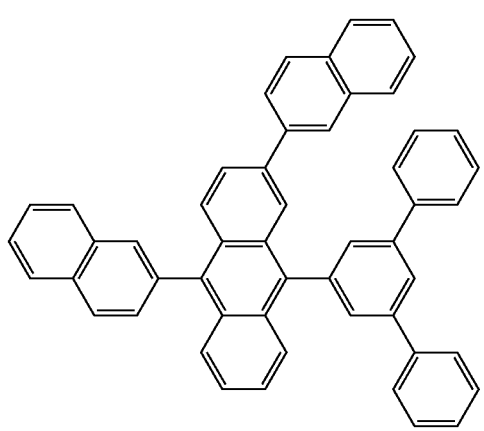
[H 137]
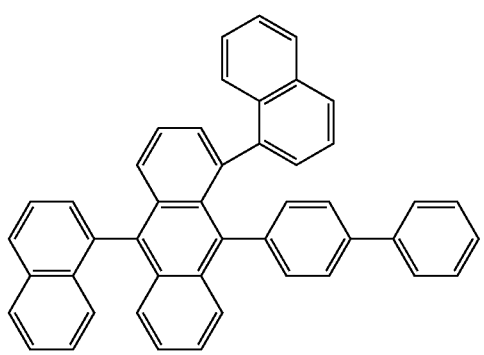

[H 138]
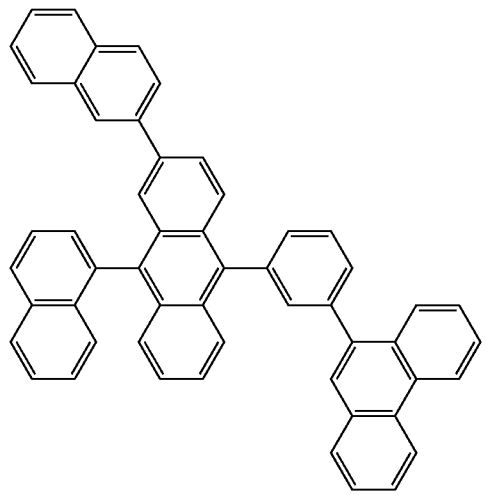
[H 139]
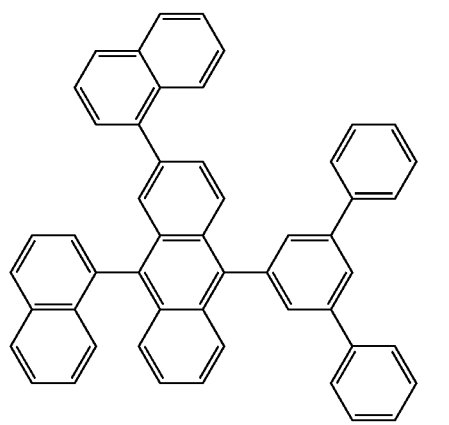
[H 140]
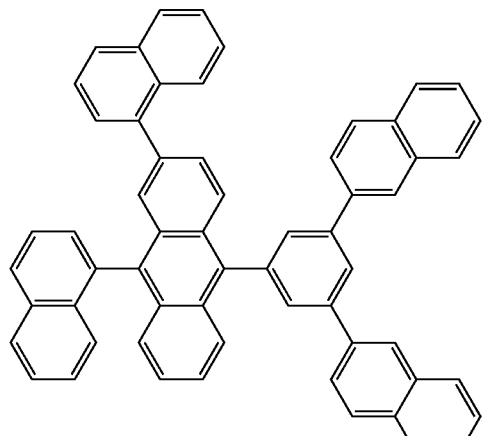
[H 141]
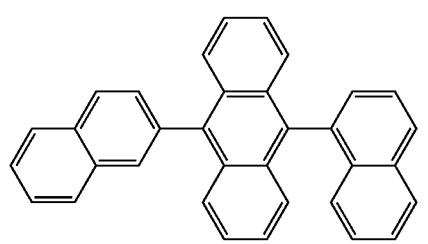
[H 142]
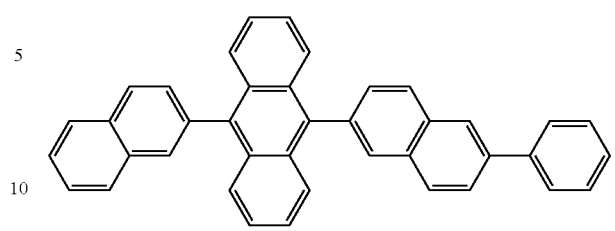
[H 143]
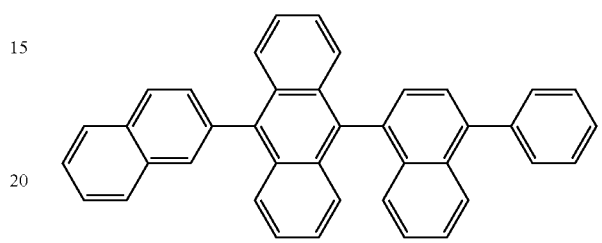
[H 144]
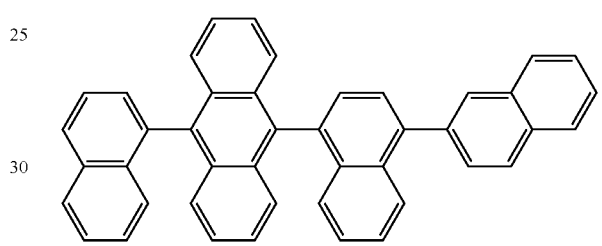
[H 145]
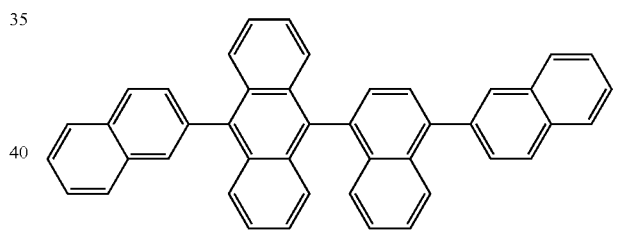
[H 146]
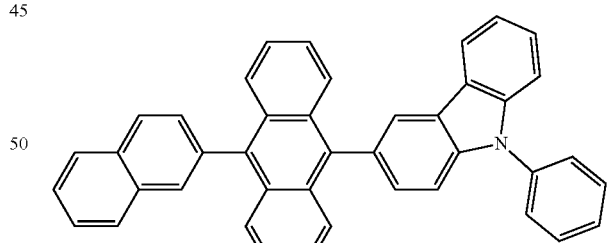
[H 147]
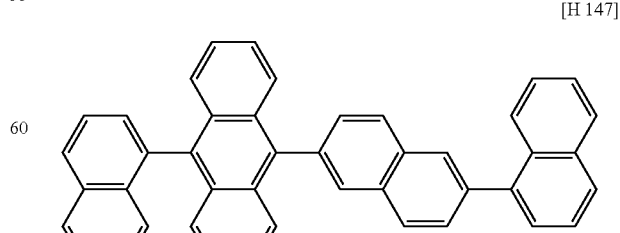

[H 148]
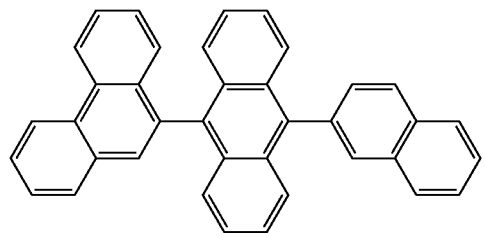
[H 149]
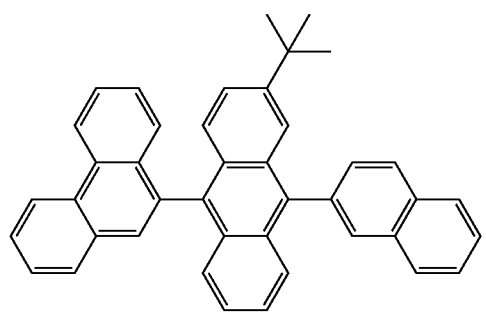
[H 150]
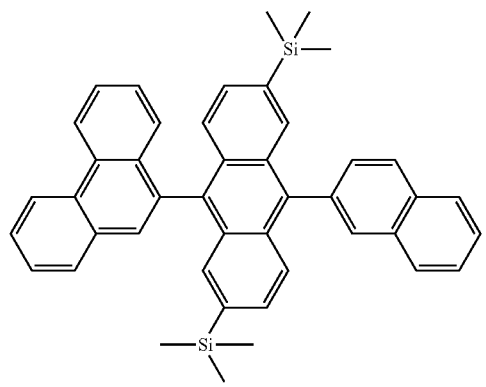
[H 151]
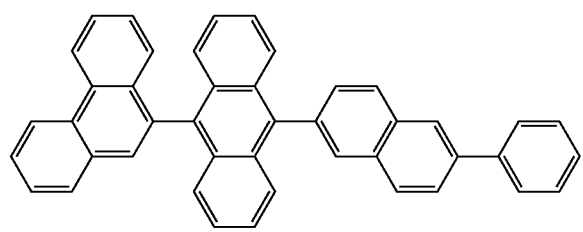
[H 152]
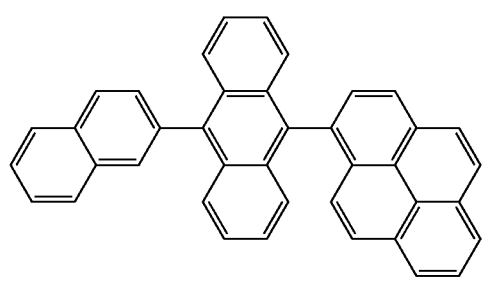
[H 153]
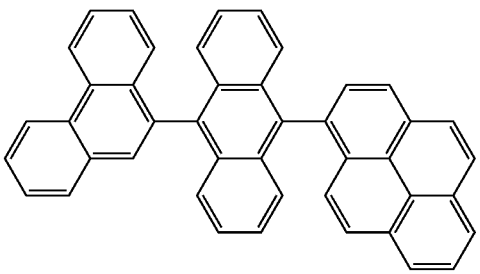
[H 154]
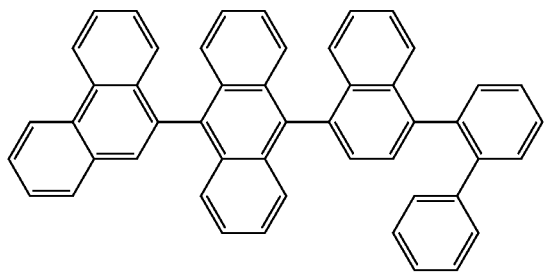
[H 155]
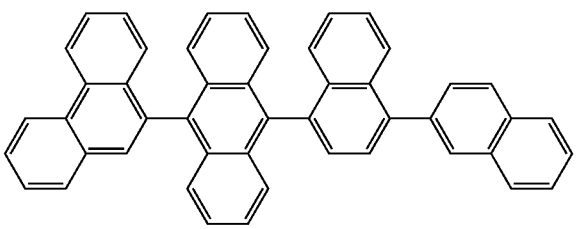
[H 156]
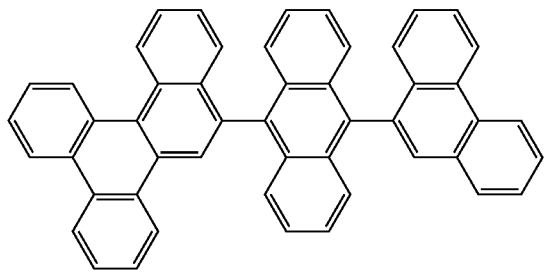
[H 157]
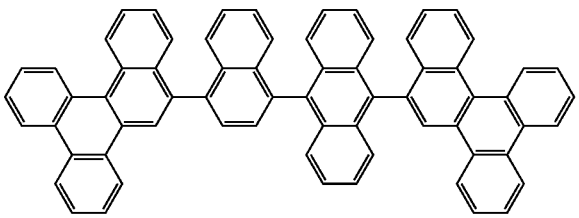

[H 158]
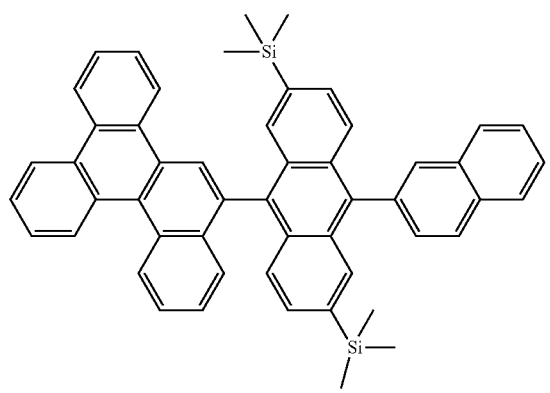
[H 159]
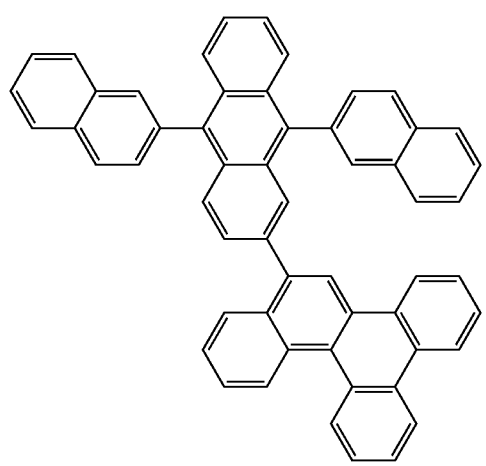
[H 160]
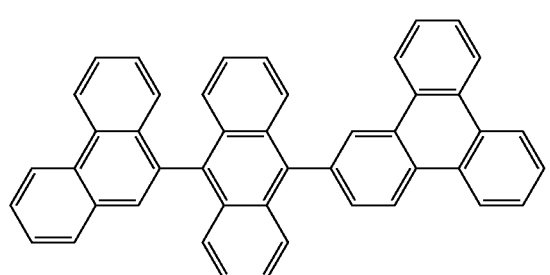
[H 161]
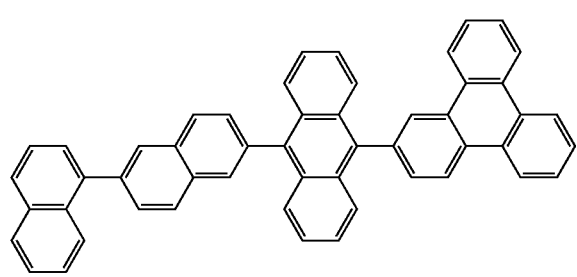
[H 162]
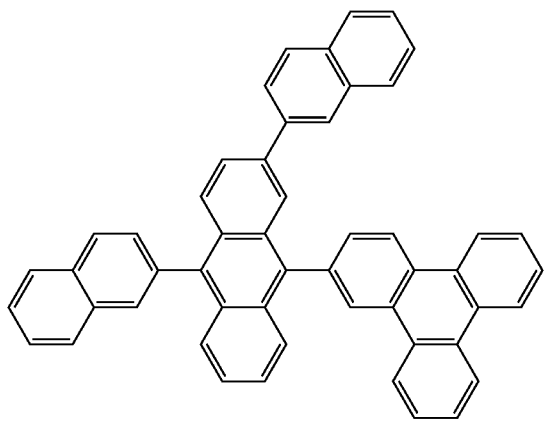
[H 163]
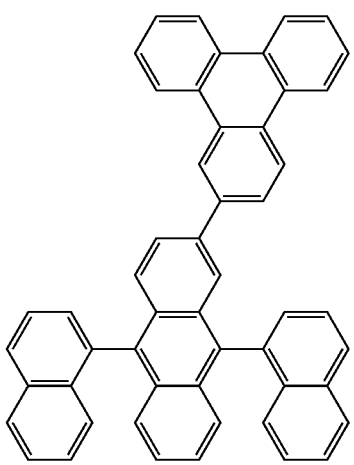
[H 164]
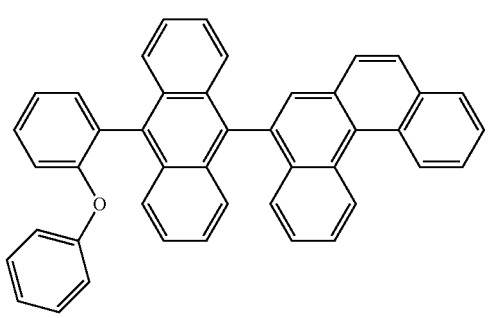
[H 165]
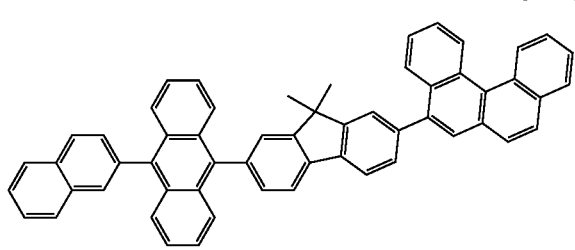

[H 166]
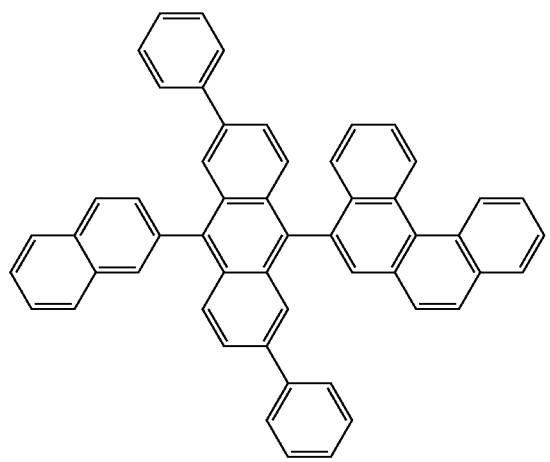
[H 167]
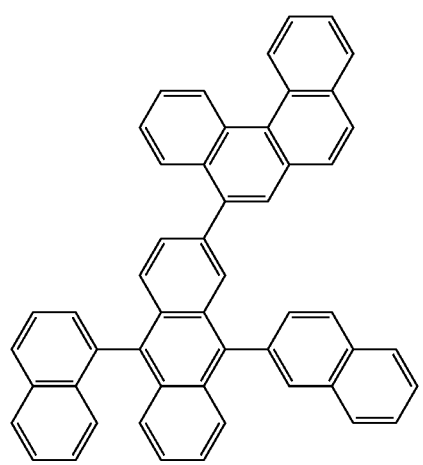
[H 168]
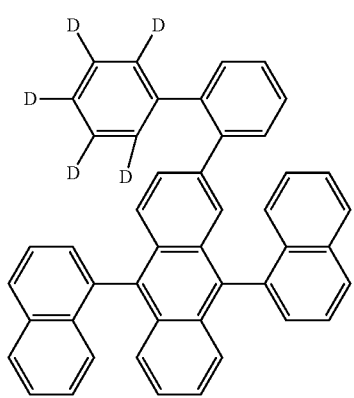
[H 169]
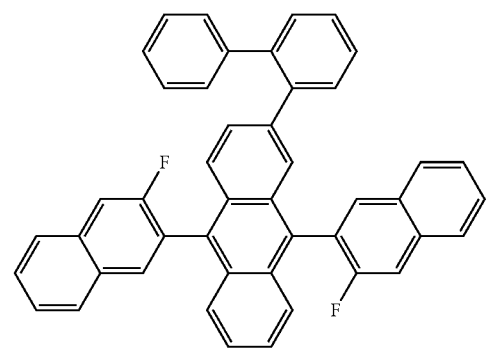
[H 170]
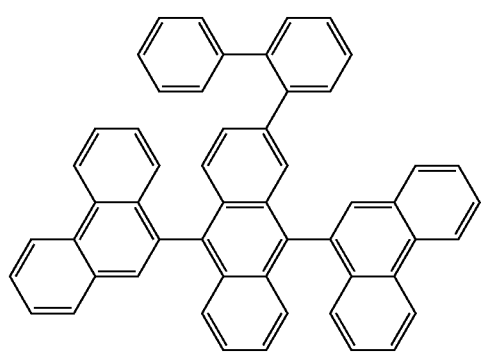
[H 171]
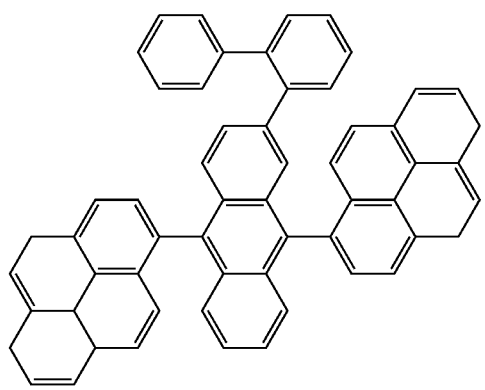
[H 172]
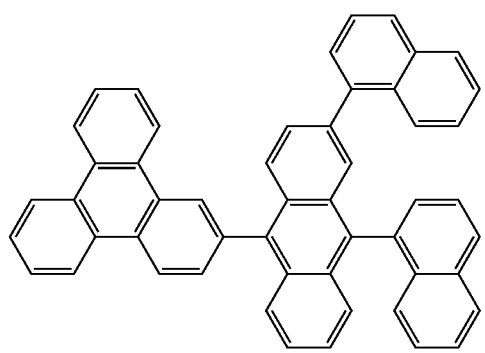

[H 173]
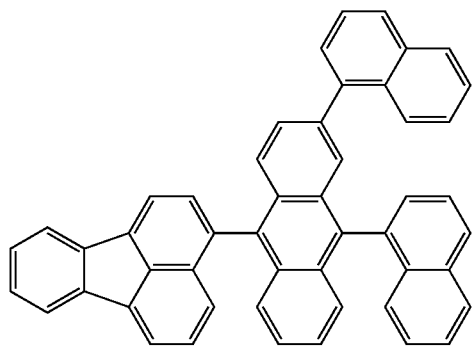
[H 174]
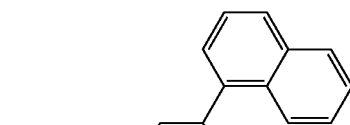
[H 175]
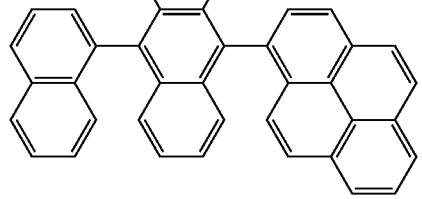
[H 176]
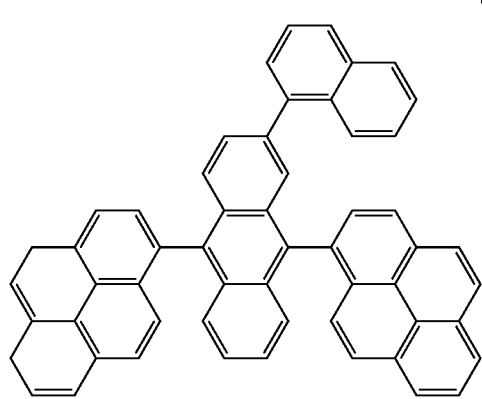
[H 177]
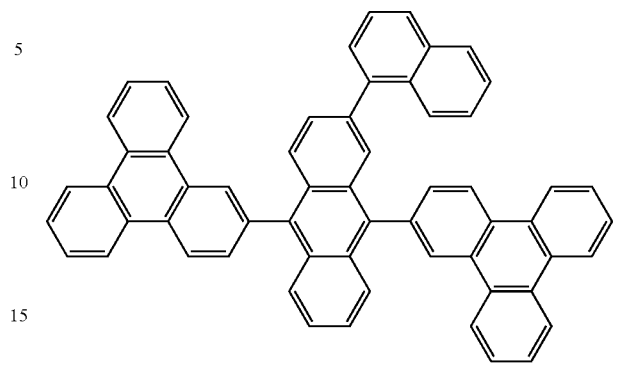
[H 178]
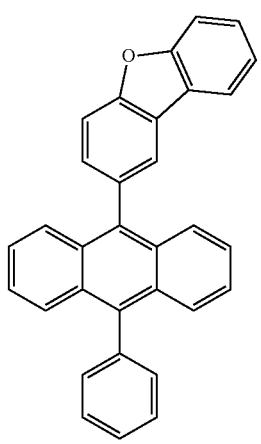
[H 179]
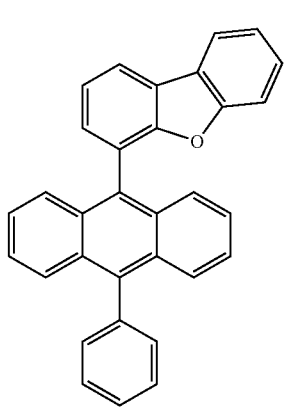

[H 180]
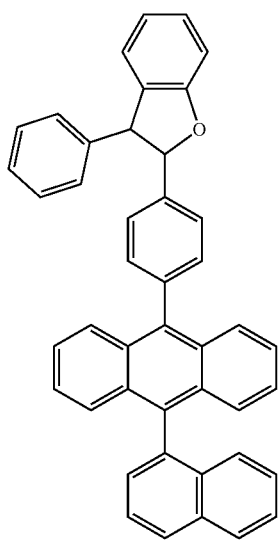
[H 181]
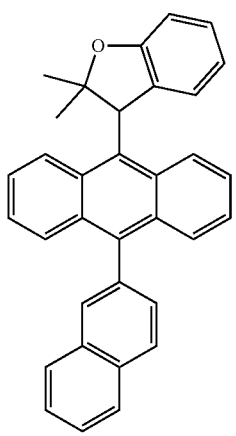
[H 182]
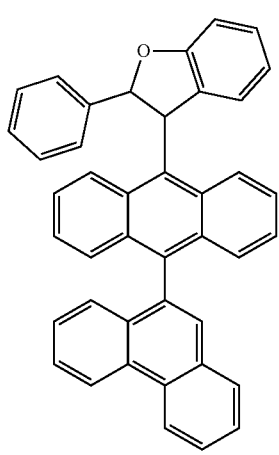
[H 183]
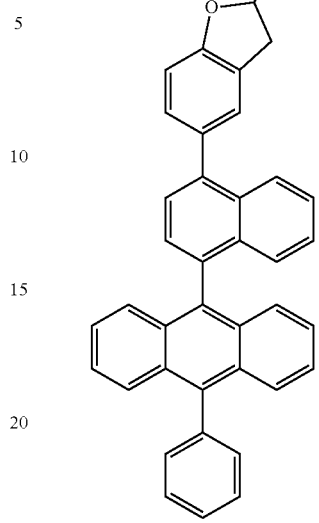
[H 184]
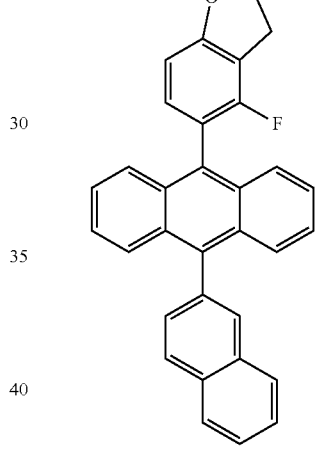
[H 185]
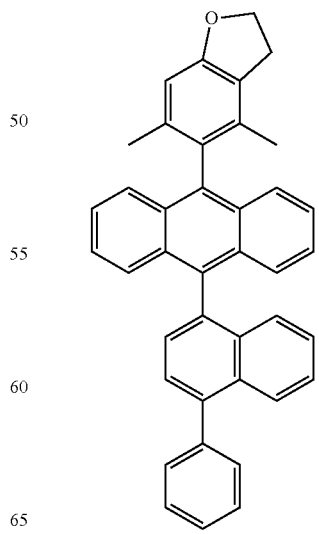

[H 186]
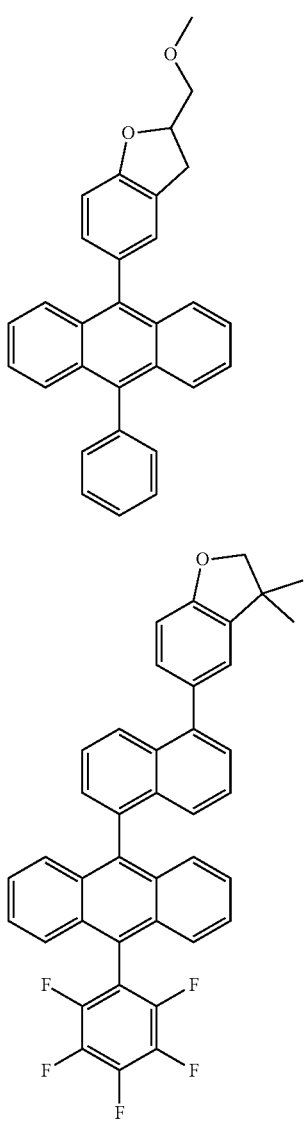
[H 187]
[H 188]
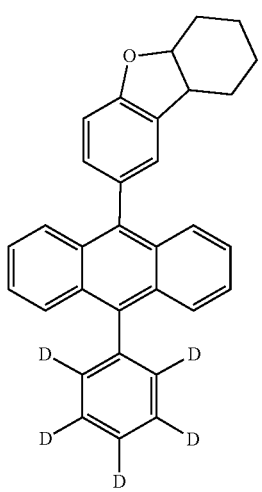
[H 189]
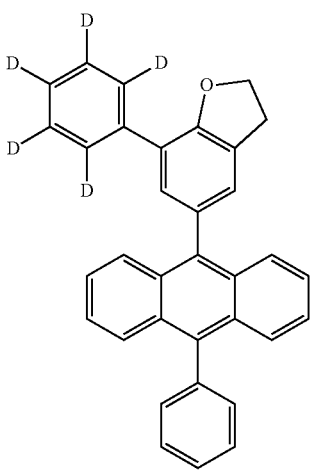
[H 190]
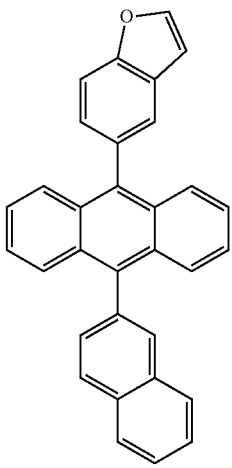
[H 191]
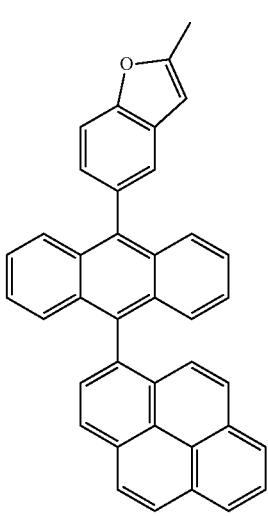

[H 192] 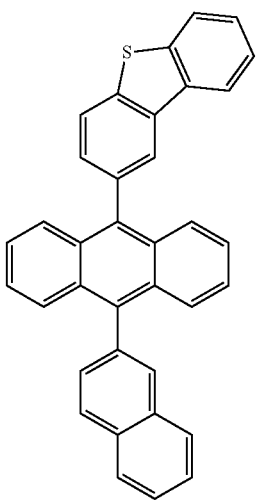
[H 193] 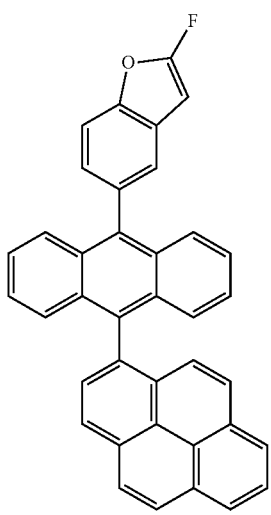
[H 195] 
[H 196] 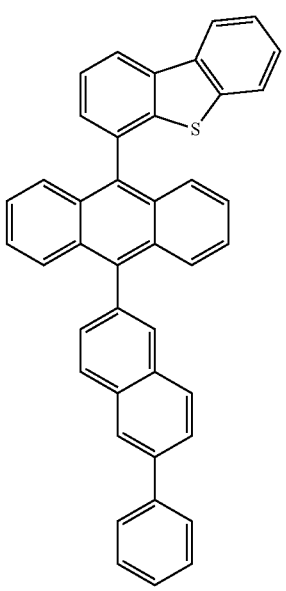
[H 194] 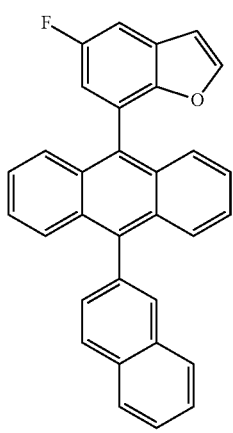
In addition, the light-emitting layer of the present disclosure may contain as a dopant compound at least one of the compounds represented by the following Chemical Formula D1 to Chemical Formula D7:
[Chemical Formula D1]
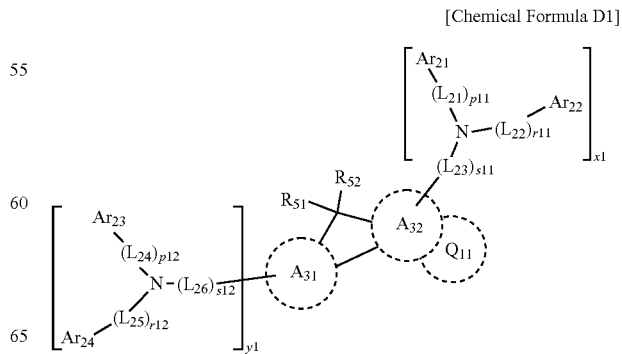

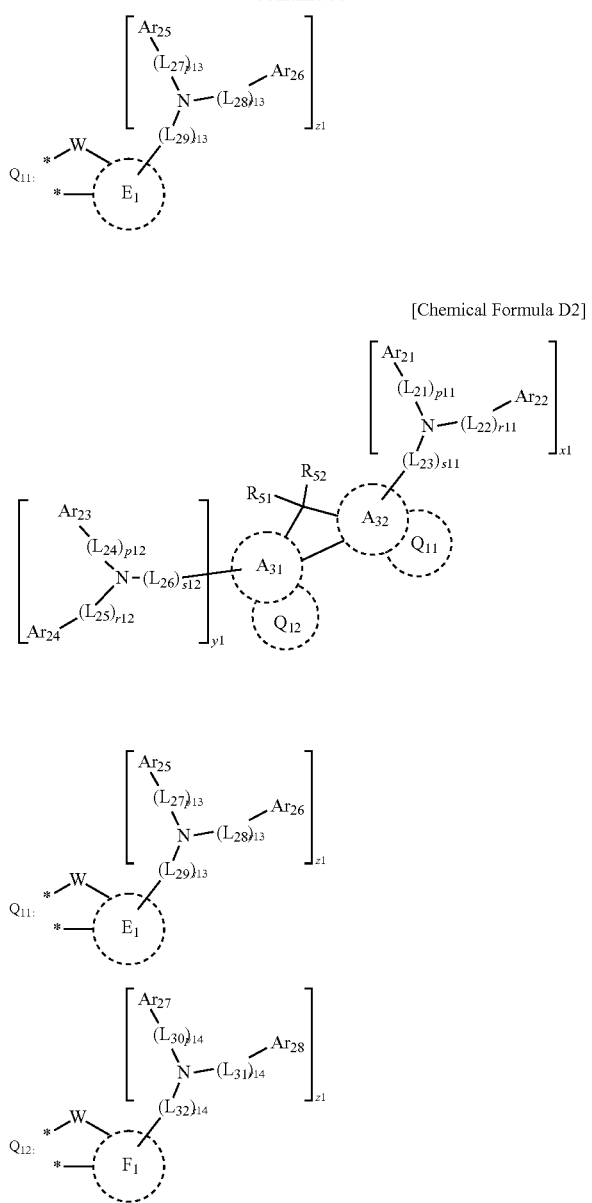

[Chemical Formula D2]

wherein,
$A_{31}$, $A_{32}$, $E_1$ and $F_1$ may be same or different, are each independently a substituted or unsubstituted aromatic hydrocarbon ring of 6 to 50 carbon atoms, or a substituted or unsubstituted aromatic heterocyclic of 2 to 40 carbon atoms wherein two adjacent carbon atoms of the aromatic ring $A_{31}$ and two adjacent carbon atoms of the aromatic ring $A_{32}$ form a 5-membered fused ring together with a carbon atom to which substituents $R_{51}$ and $R_{52}$ are bonded;

linkers $L_{21}$ to $L_{32}$, which may be same or different, are each independently selected from a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is any one selected from N—$R_{53}$, $CR_{54}R_{55}$, $SiR_{56}R_{57}$, $GeR_{58}R_{59}$, O, S, and Se;

$R_{51}$ to $R_{59}$, and $Ar_{21}$ to $Ar_{28}$, which may be the same or different, are each independently any one of selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_{51}$ and $R_{52}$ together may form a mono- or polycyclic aliphatic or aromatic ring that may be a heterocyclic ring bearing a heteroatom selected from N, O, P, Si, S, Ge, Se, and Te as a ring member;

p11 to p14, r11 to r14, and s11 to s14 are each independently an integer of 1 to 3, wherein when any of them is 2 or greater, the corresponding $L_{21}$ to $L_{32}$ may be same or different, x1 is an integer of 1 or 2, and y1 and z1 may be same or different and are each independently an integer of 0 to 3;

$Ar_{21}$ may form a ring with $Ar_{22}$, $Ar_{23}$ may form a ring with $Ar_{24}$, $Ar_{25}$ may form a ring with $Ar_{26}$, and $Ar_{27}$ may form a ring with $Ar_{28}$;

two adjacent carbon atoms of the $A_{32}$ ring moiety of Chemical Formula D1 may occupy respective positions * of Structural Formula $Q_{11}$ to form a fused ring; and two adjacent carbon atoms of the $A_{31}$ ring moiety of Chemical Formula D2 may occupy respective positions * of structural Formula $Q_{12}$ to form a fused ring, and two adjacent carbon atoms of the $A_{32}$ ring moiety of Chemical Formula D2 may occupy respective positions * of Structural Formula $Q_{11}$ to form a fuse ring;

[Chemical Formula D3]

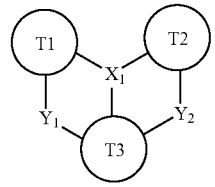

wherein, $X_1$ is any one selected from among B, P, and P=O, $T_1$ to $T_3$, which are same or different, are each independently a substituted or unsubstituted aromatic hydrocarbon ring of 6 to 50 carbon atoms, or a substituted or unsubstituted heteroaromatic ring of 2 to 40 carbon atoms;

$Y_1$ is any one selected from among N—$R_{61}$, $CR_{62}R_{63}$, O, S, and $SiR_{64}R_{65}$;

$Y_2$ is any one selected from among N—$R_{66}$, $CR_{67}R_{68}$, O, S, $SiR_{69}R_{70}$ wherein $R_{61}$ to $R_{70}$, which may be same or different, are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen and wherein at least one of $R_{61}$ to $R_{70}$ may be connected to at least one of $T_1$ to $T_3$ to form an additional mono- or polycyclic aliphatic or aromatic ring;

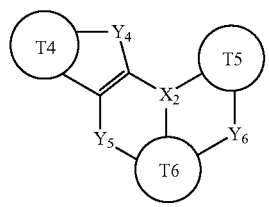

[Chemical Formula D4]

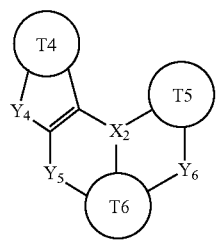

[Chemical Formula D5]

wherein, $X_2$ is any one selected from among B, P, and P=O, $T_4$ to $T_6$ are as defined for $T_1$ to $T_3$ in Chemical Formula D3, $Y_4$ to $Y_6$ are as defined for $Y_1$ to $Y_2$ in Chemical Formula D3;

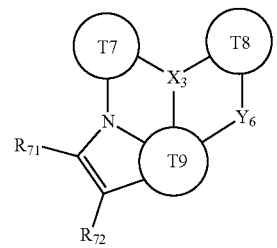

[Chemical Formula D6]

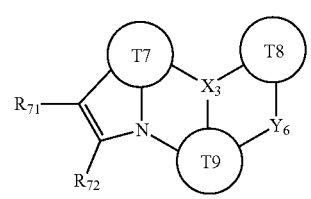

[Chemical Formula D7]

$X_3$ is any one selected from among B, P, and P=O, $T_7$ to $T_9$ are as defined for $T_1$ to $T_3$ in Chemical Formula D3, $Y_6$ is as defined for $Y_1$ to $Y_2$ in Chemical Formula D3, $R_{71}$ to $R_{72}$, which are same or different, are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen, wherein $R_{71}$ and $R_{72}$ may be connected to each other to form an additional mono- or polycyclic aliphatic or aromatic ring or connected to T7 or T9 ring moiety to form an additional mono- or polycyclic aliphatic or aromatic ring, wherein the term 'substituted' in the expression "a substituted or unsubstituted" means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Among the dopant compounds according to the present disclosure, the boron compound represented by Chemical Formulas D3 to D7 may have on the aromatic hydrocarbon rings or heteroaromatic rings of $T_1$ to $T_9$ a substituent selected from a deuterium atom, an alkyl of 1 to 24 carbon atoms, an aryl of 6 to 24 carbon atoms, an alkylamino of 1 to 24 carbon atoms, and an arylamino of 6 to 24 carbon atoms wherein the alkyl radicals or the aryl radicals in the alkylamino of 1 to 24 carbon atoms and the arylamino of 6 to 24 carbon atoms on the rings may be linked to each other, and particularly a substituent selected from an alkyl of 1 to 12 carbon atoms, an aryl of 6 to 18 carbon atoms, an alkylamino of 1 to 12 carbon atoms, and an arylamino of 6 to 18 carbon atoms wherein the alkyl radicals or aryl radicals in the alkylamino of 1 to 12 carbon atoms and the arylamino of 6 to 18 carbon atoms on the rings may be linked to each other.

In addition, concrete examples of the dopant compound used for the light-emitting layer, represented by one of Chemical Formulas D1 and D2, include compounds represented by the following d1 to d239:

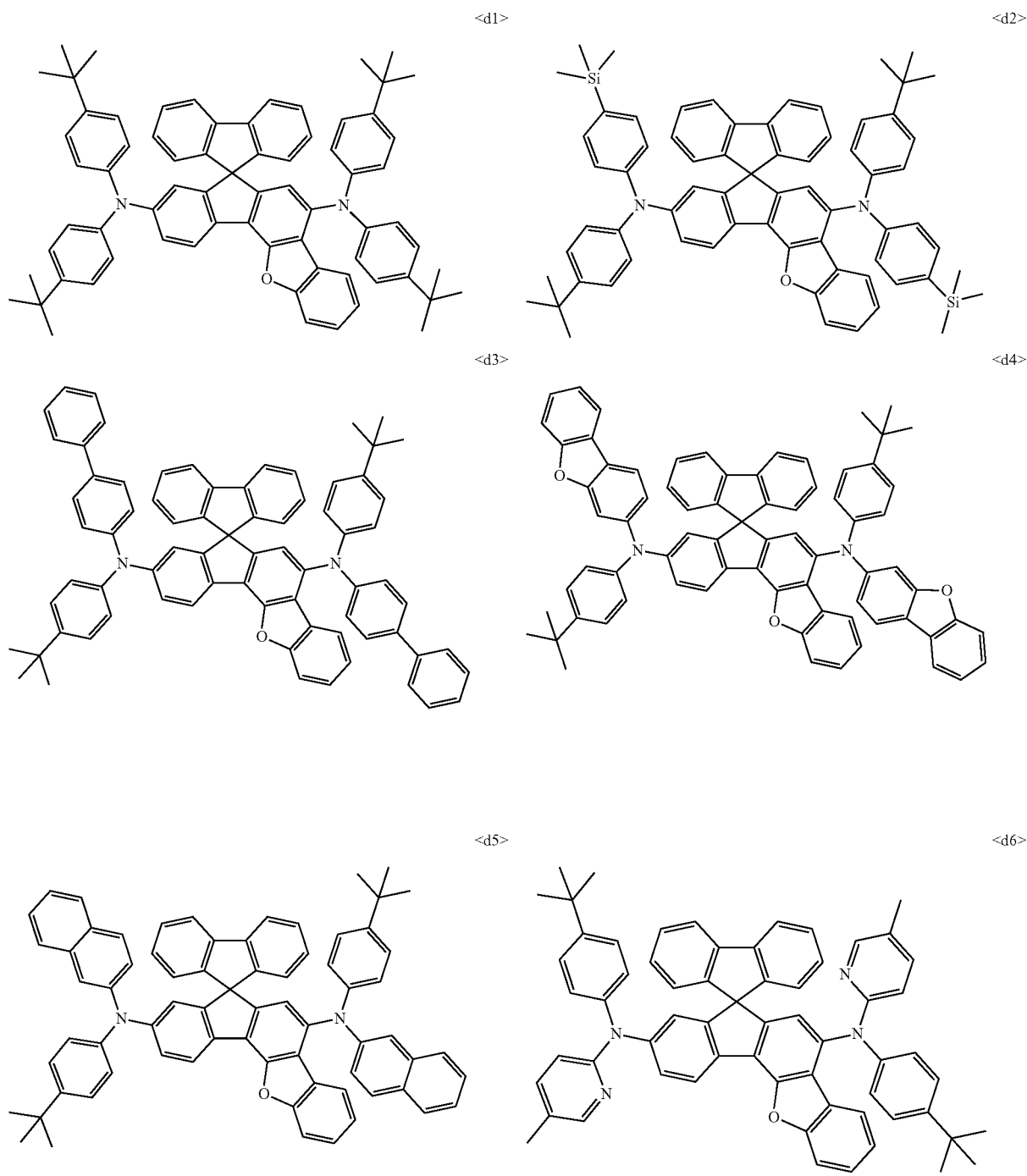

-continued
<d7>
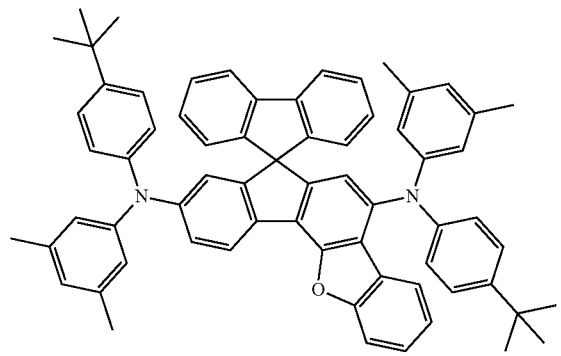
<d8>
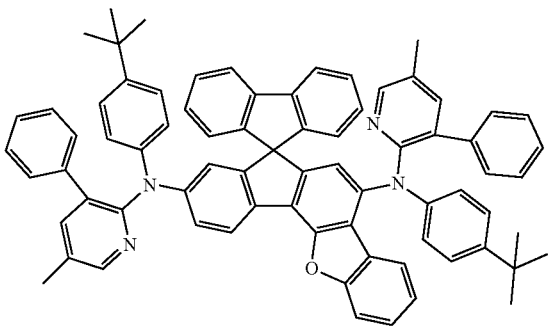
<d9>
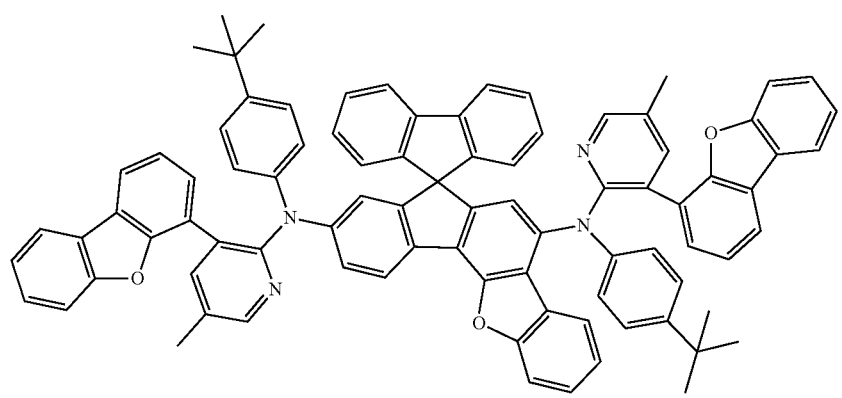
<d10>
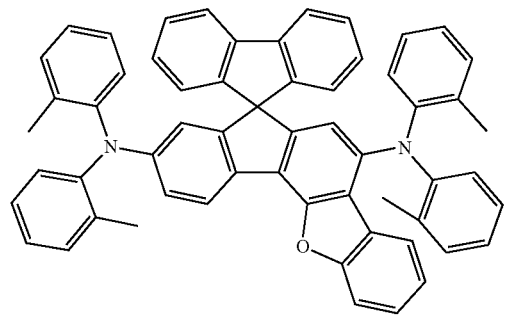
<d11>
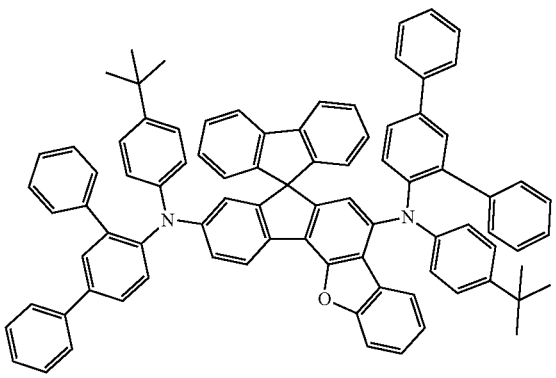
<d12>
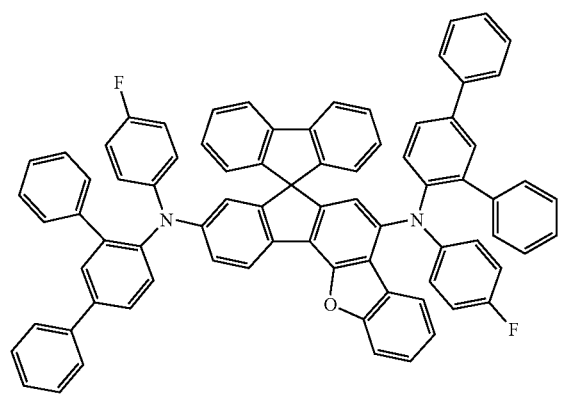
<d13>
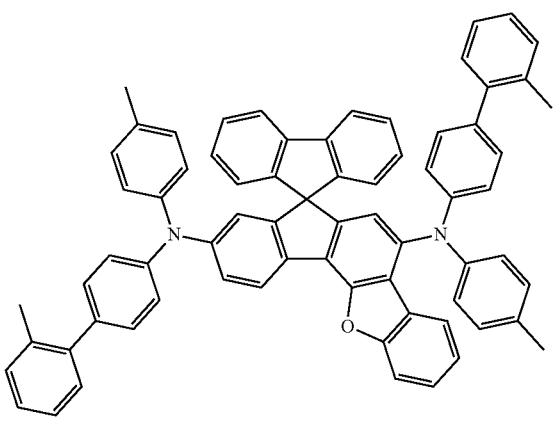

-continued
<d14>
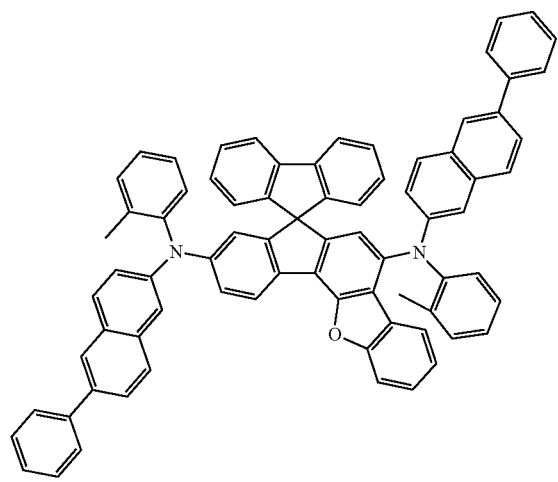
<d15>
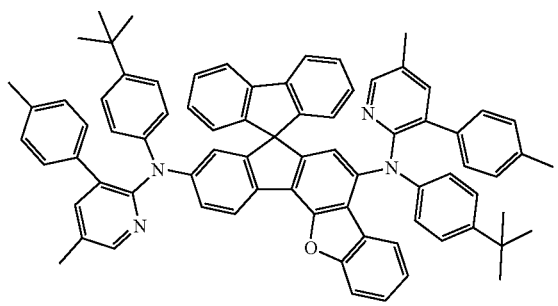
<d16>
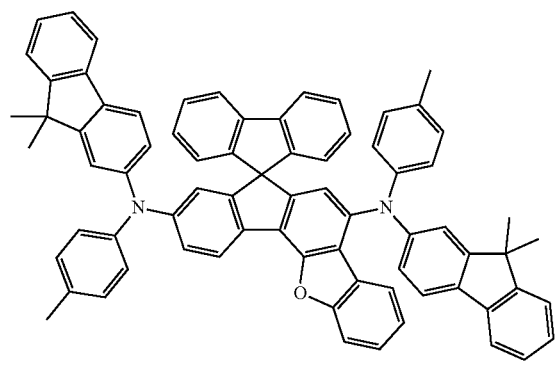
<d17>
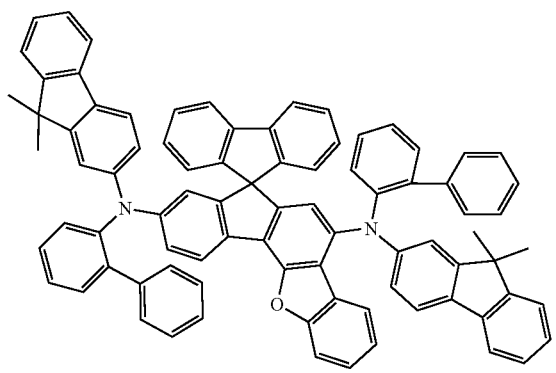
<d18>
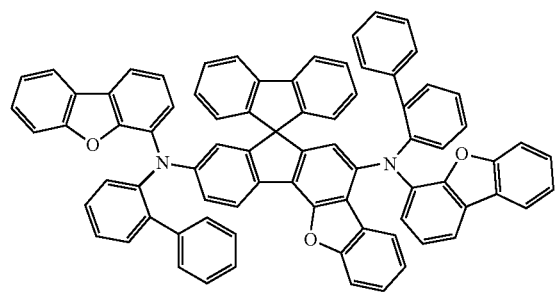
<d19>
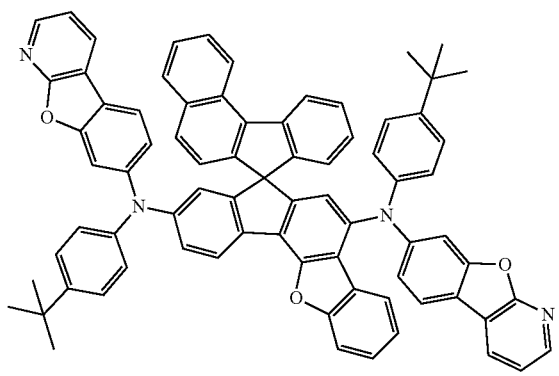

-continued
<d20>
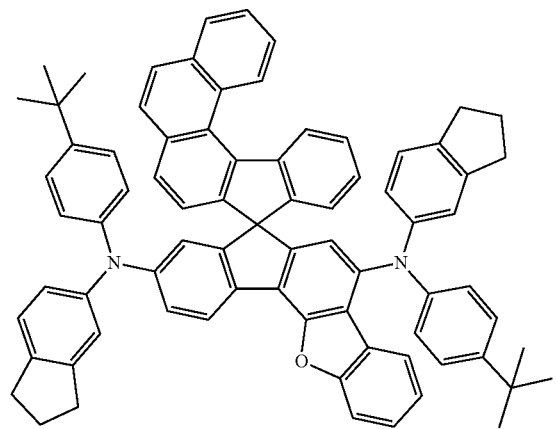
<d21>
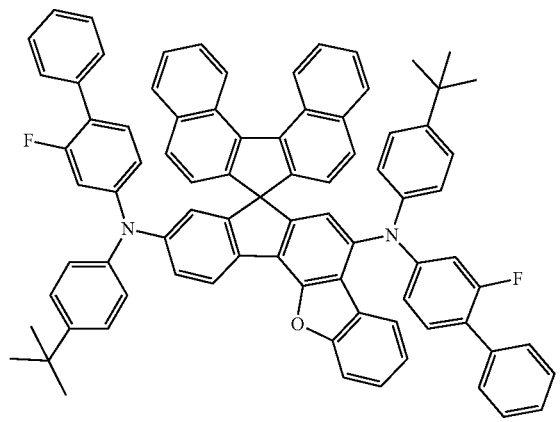
<d22>
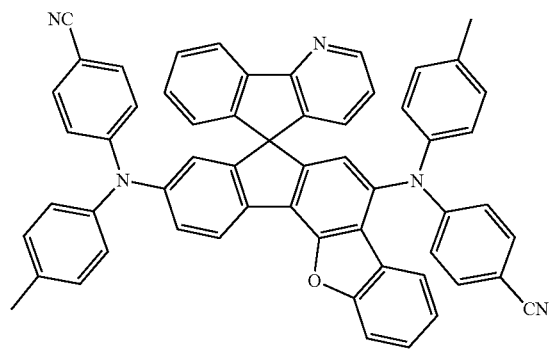
<d23>
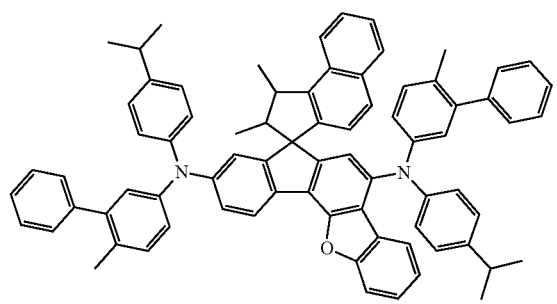
<d24>
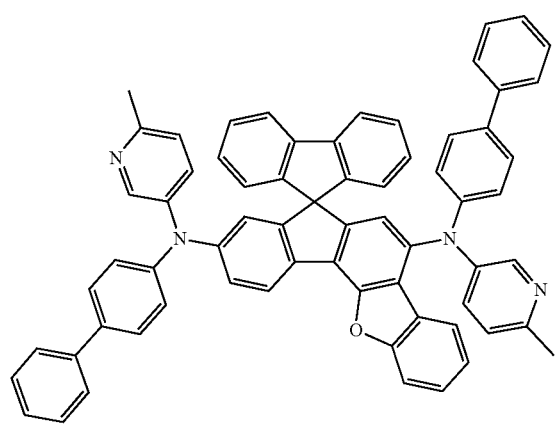
<d25>
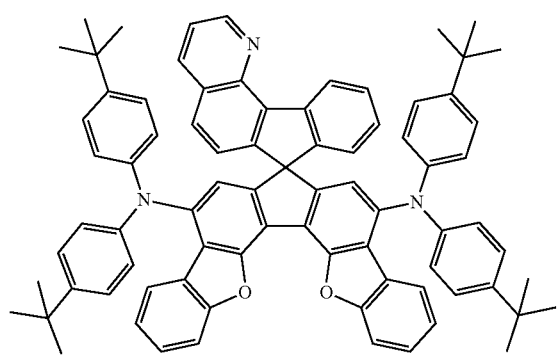

-continued
<d26>
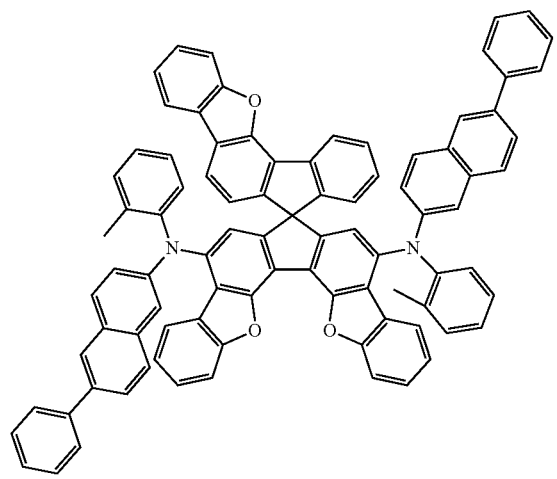
<d27>
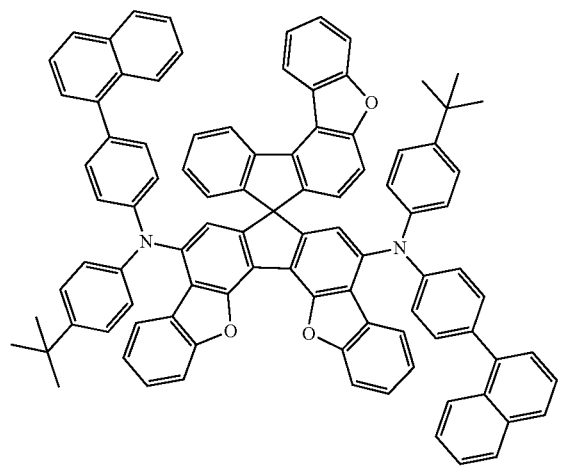
<d28>
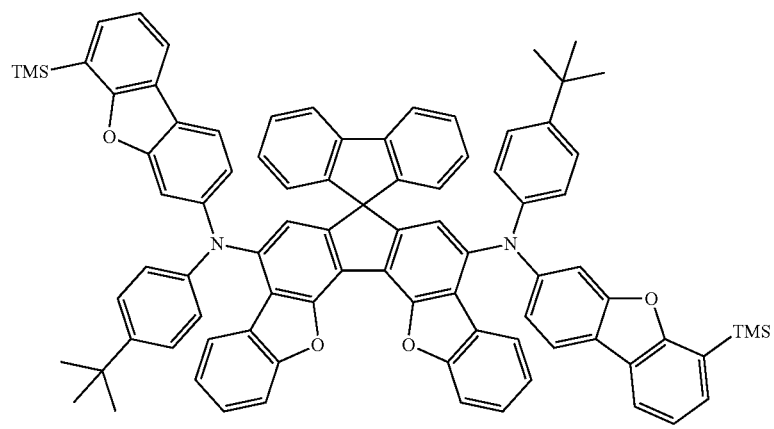
<d29>
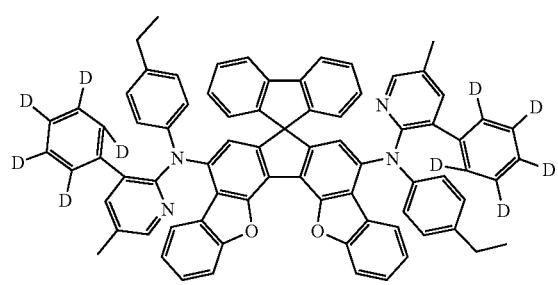
<d30>
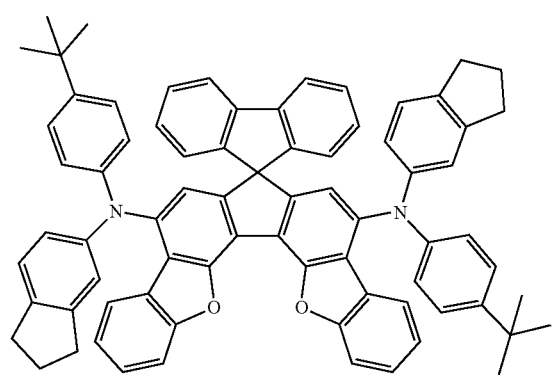

<d31>
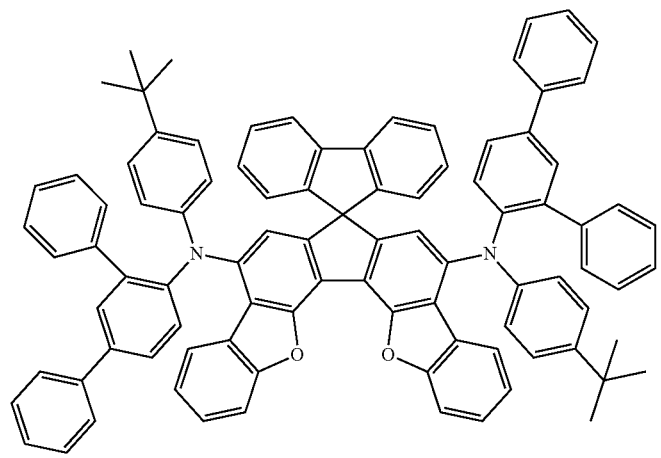
<d32>
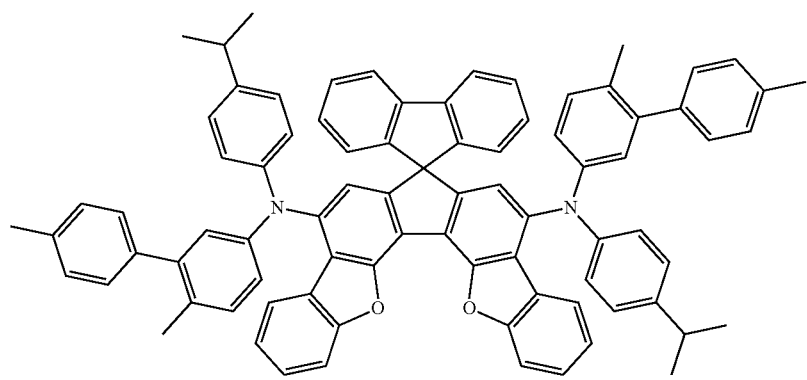
<d33>
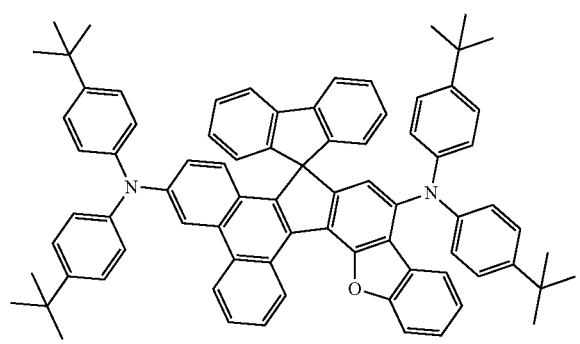
<d34>
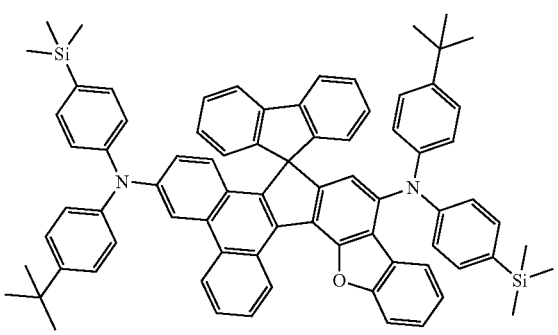

-continued
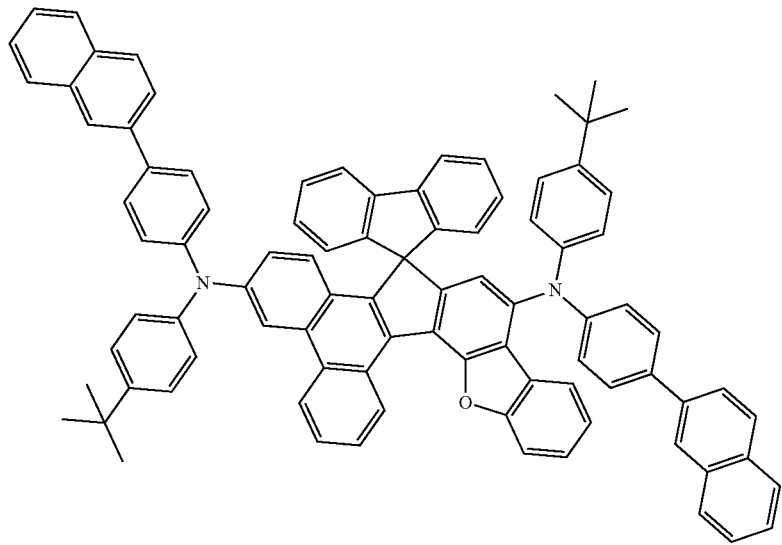
<d 35>
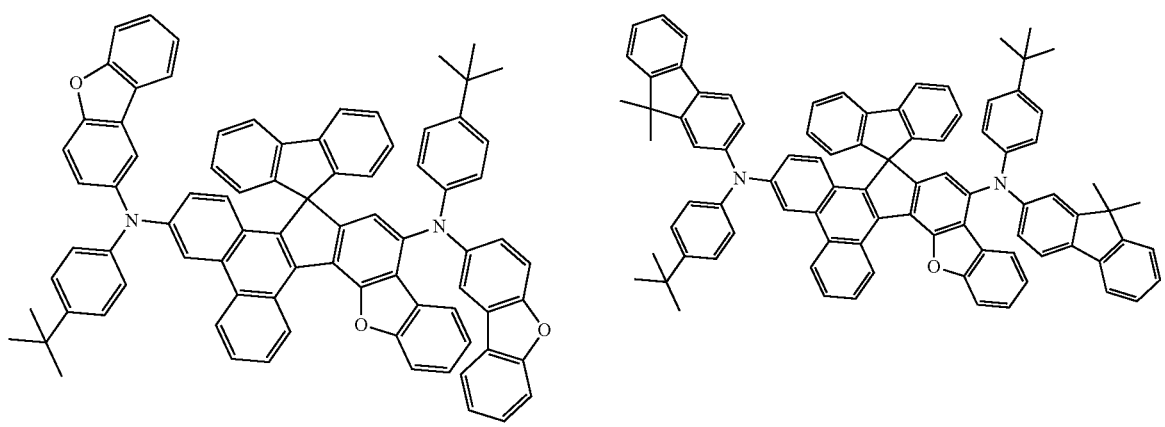
<d 36>       <d 37>
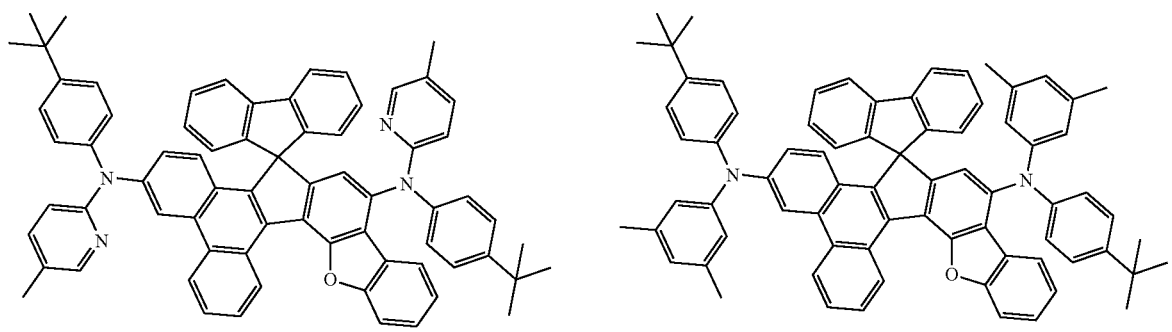
<d 38>       <d 39>

-continued
<d 40>
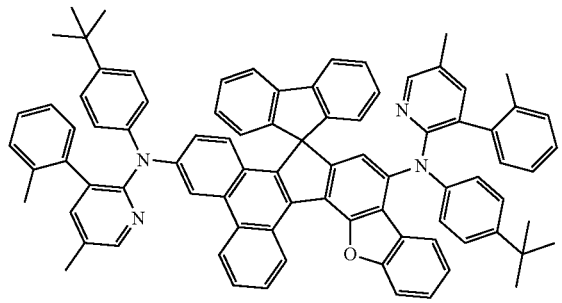
<d 41>
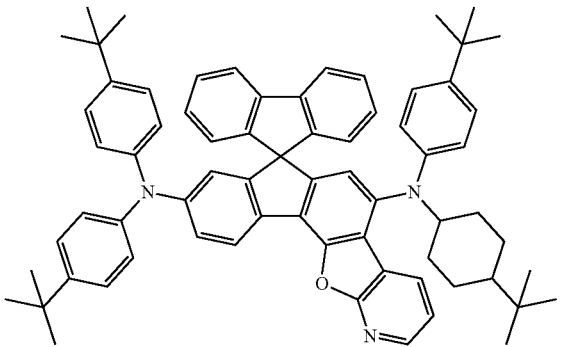
<d 42>
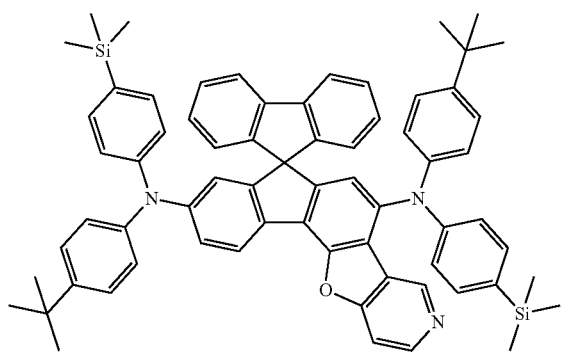
<d 43>
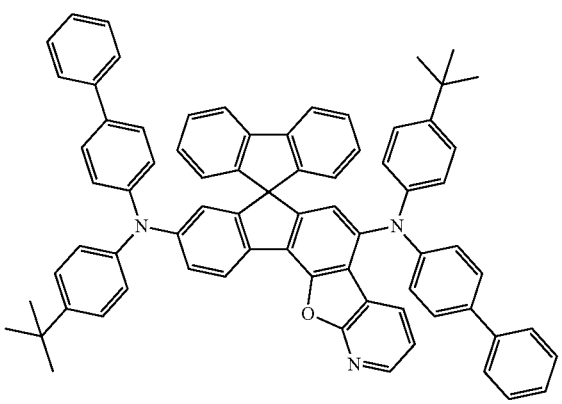
<d 44>
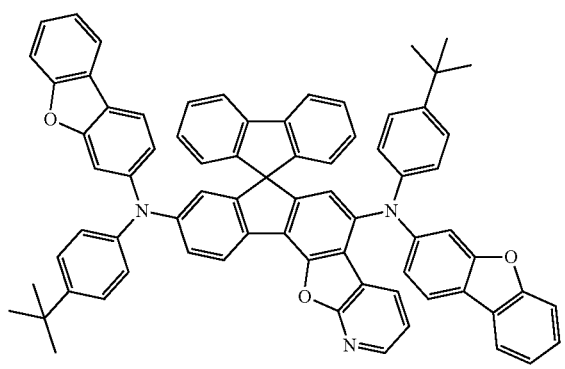
<d 45>
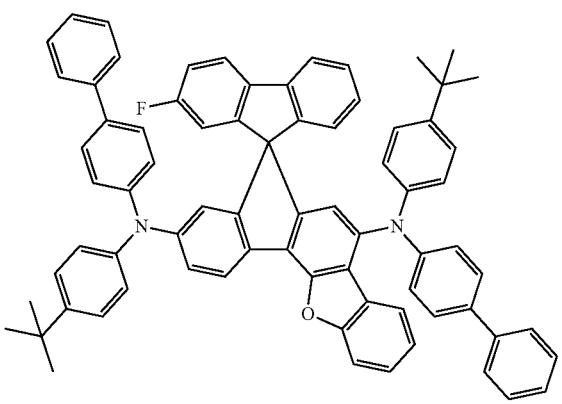
<d 46>
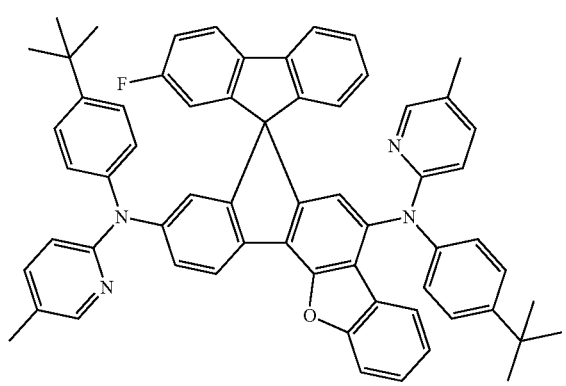
<d 47>
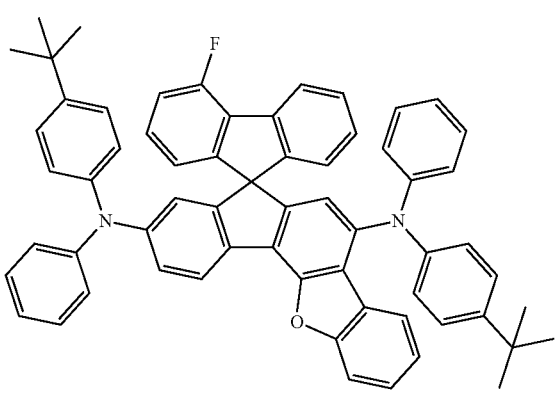

-continued
<d 48>
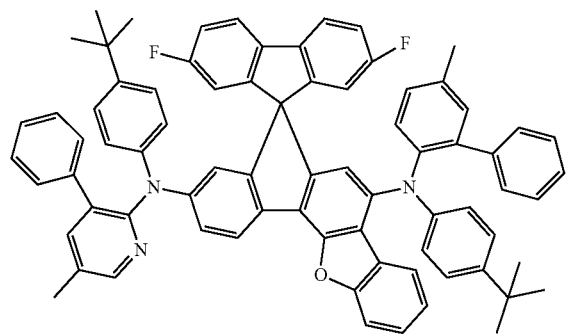
<d 49>
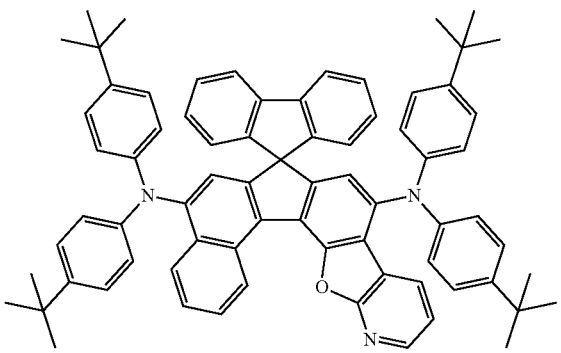
<d 50>
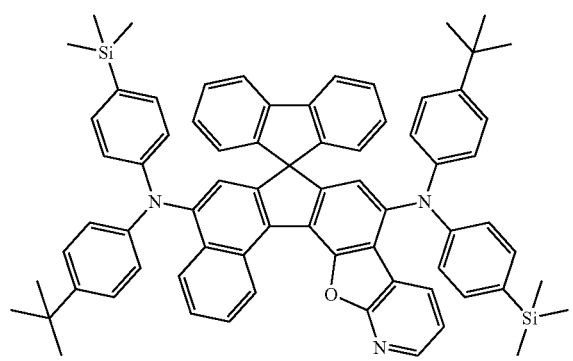
<d 51>
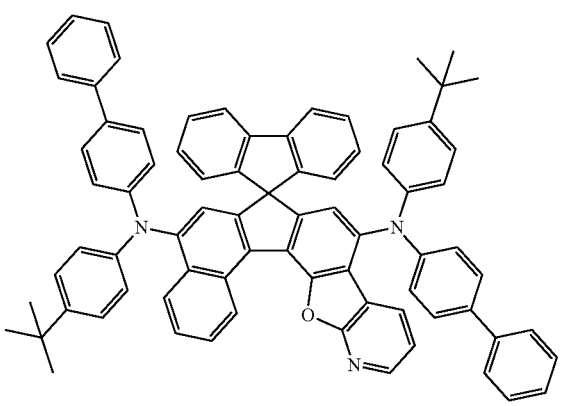
<d 52>
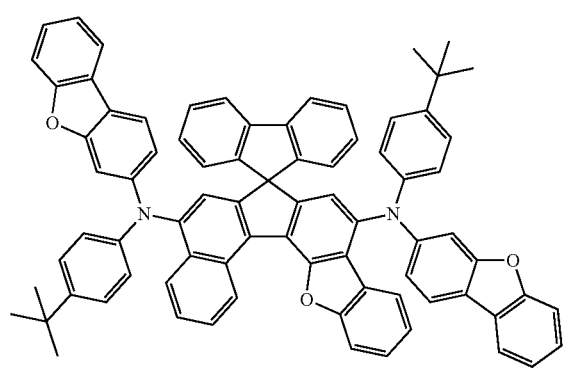
<d 53>
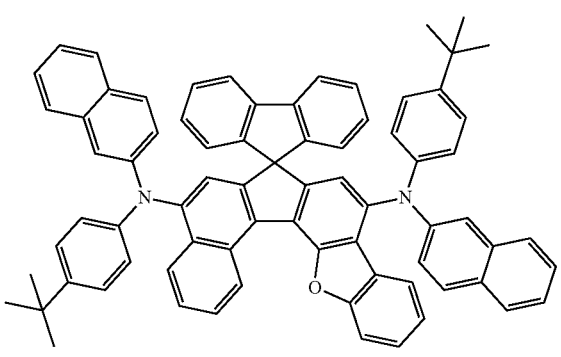
<d 54>
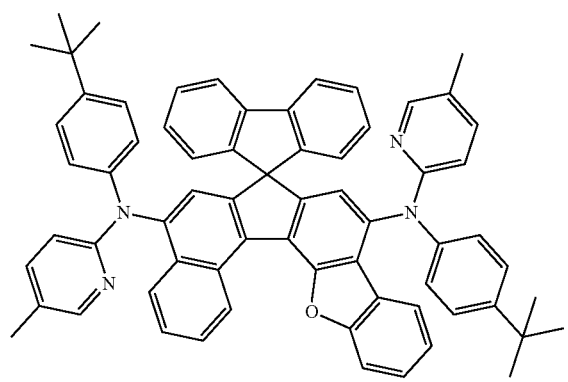
<d 55>
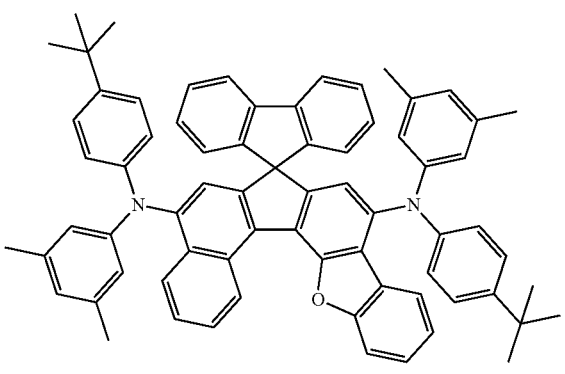

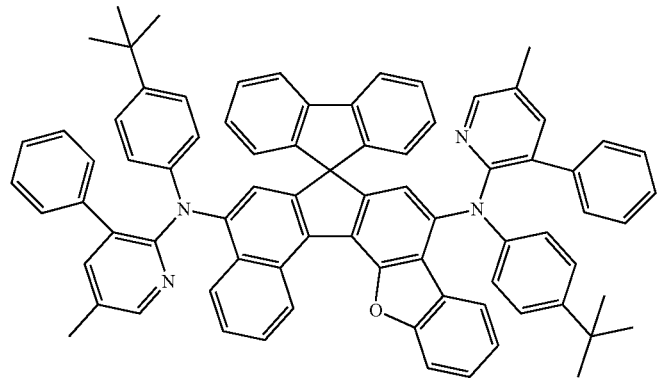
<d 56>
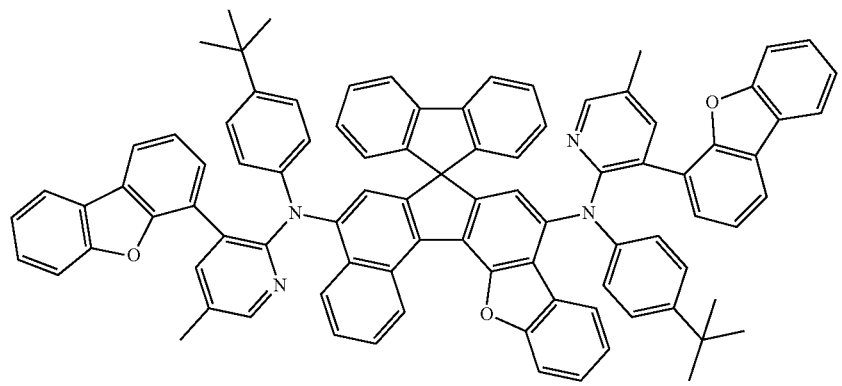
<d 57>
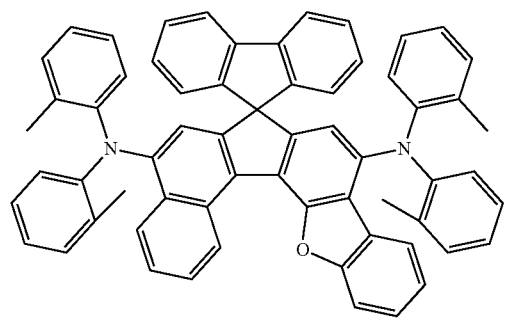
<d 58>
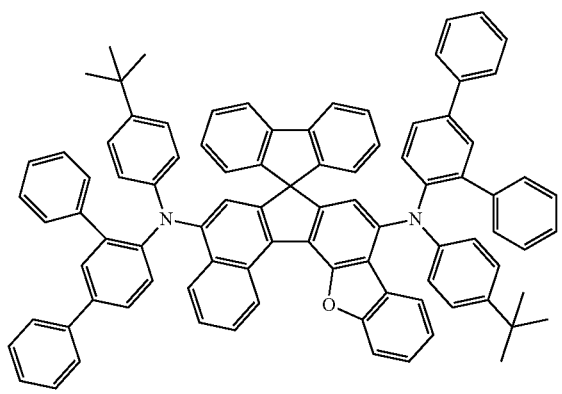
<d 59>
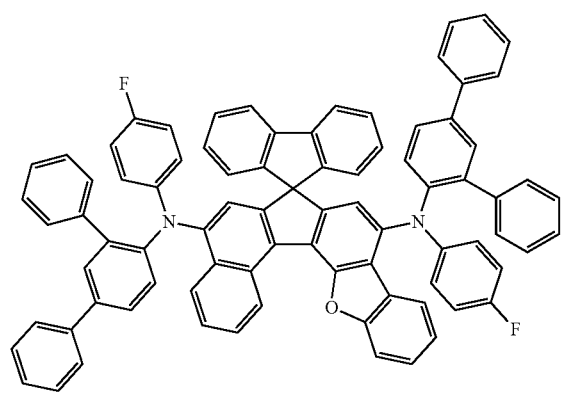
<d 60>
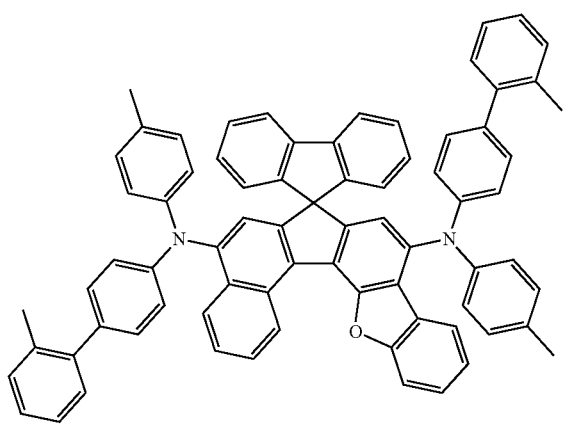
<d 61>

<d 62>
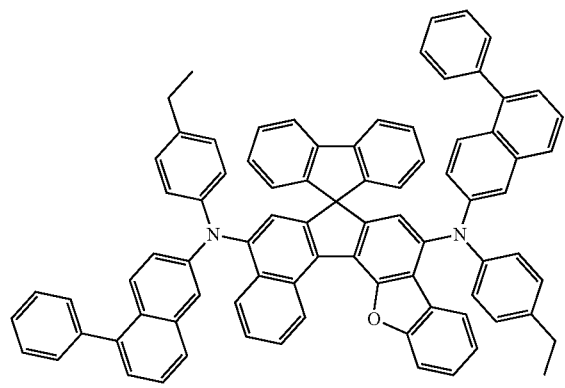
<d 63>
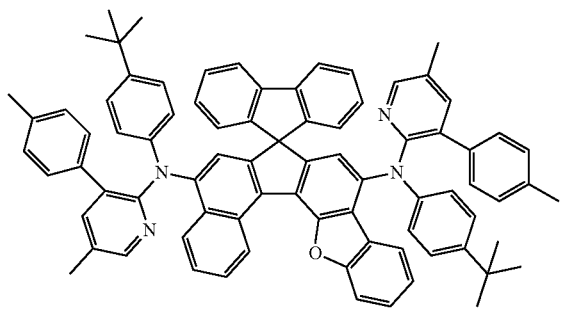
<d 64>
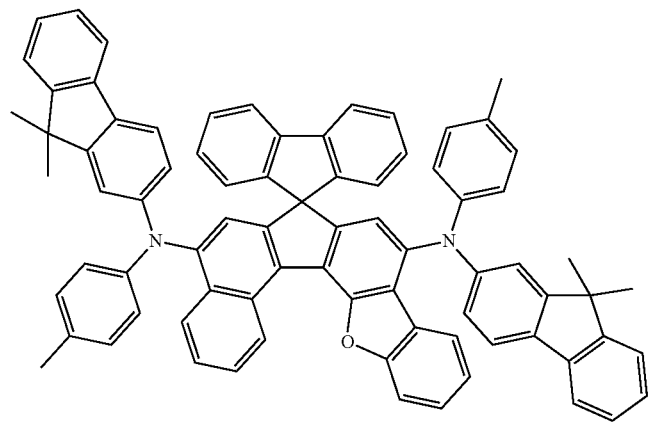
<d 65>
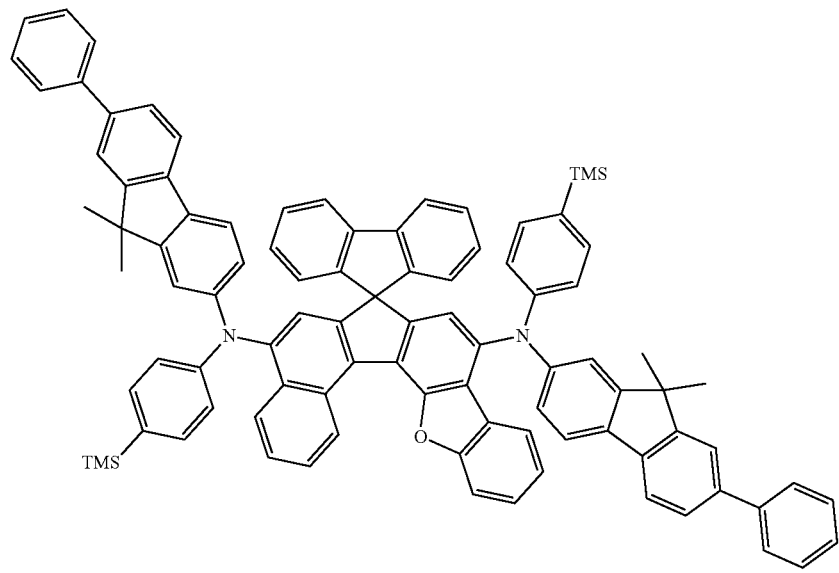

-continued
<d 66>
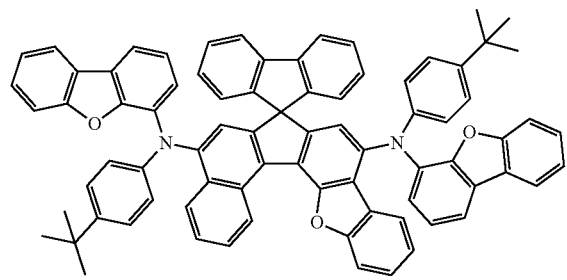
<d 67>
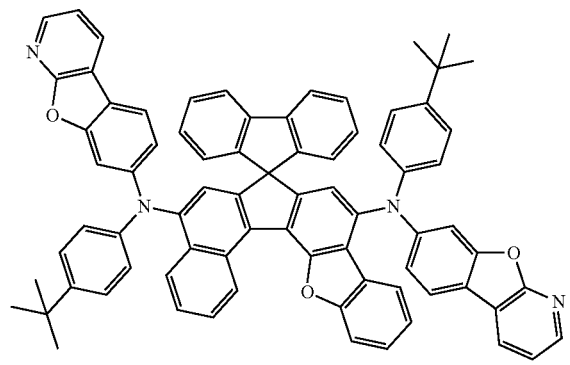
<d 68>
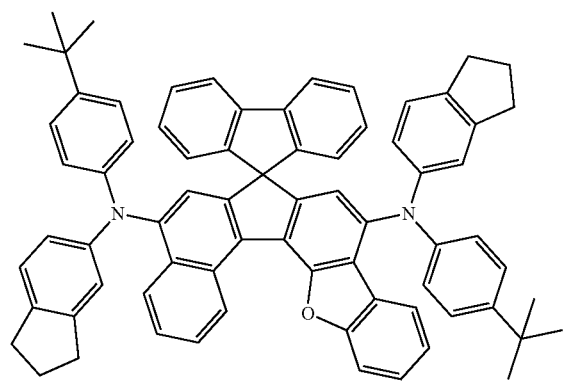
<d 69>
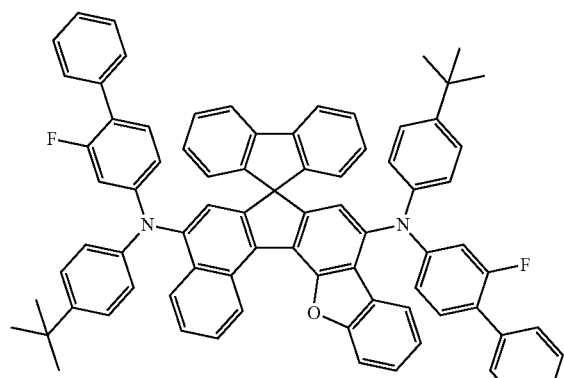
<d 70>
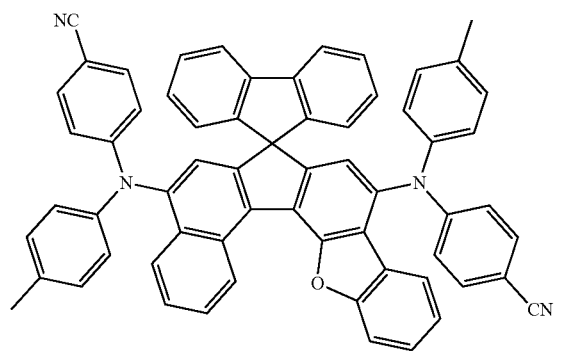
<d 71>
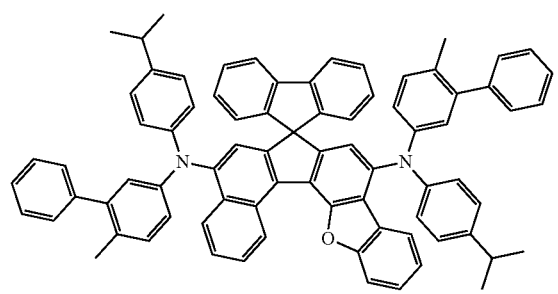
<d 72>
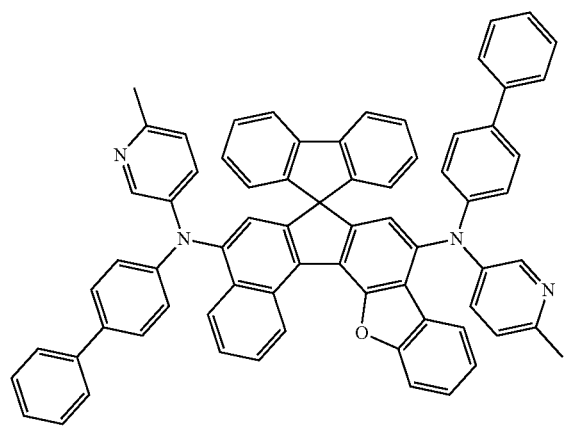

<d 73> 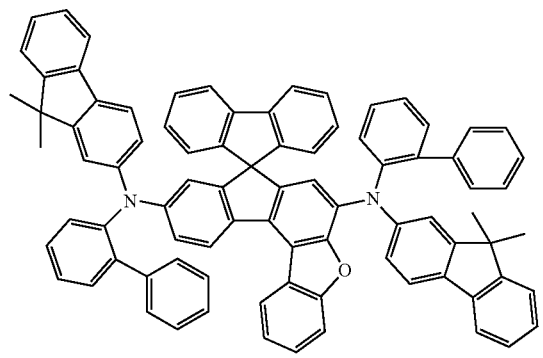
<d 74> 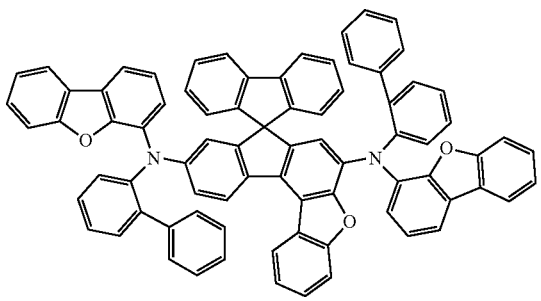
<d 75> 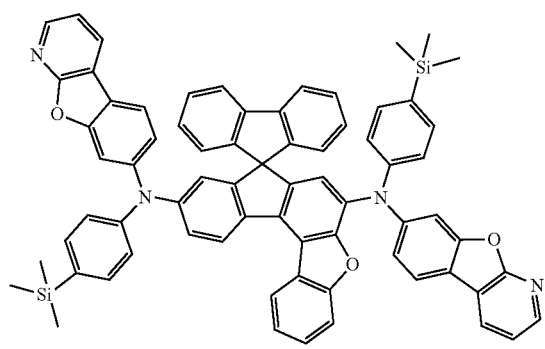
<d 76> 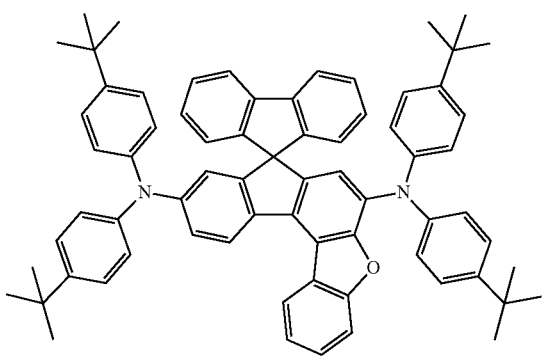
<d 77> 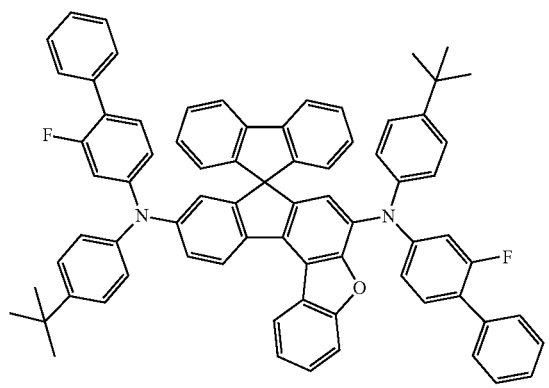
<d 78> 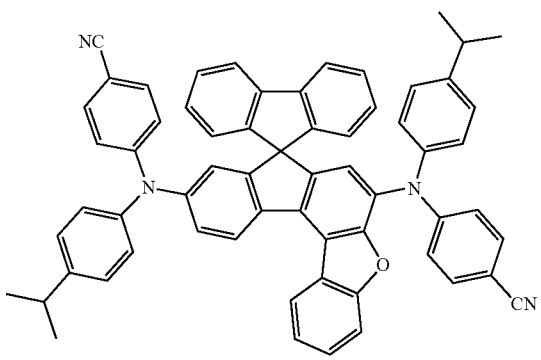
<d 79> 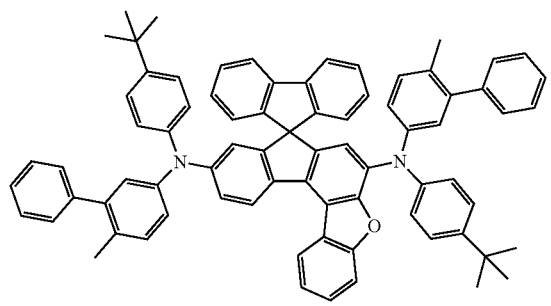
<d 80> 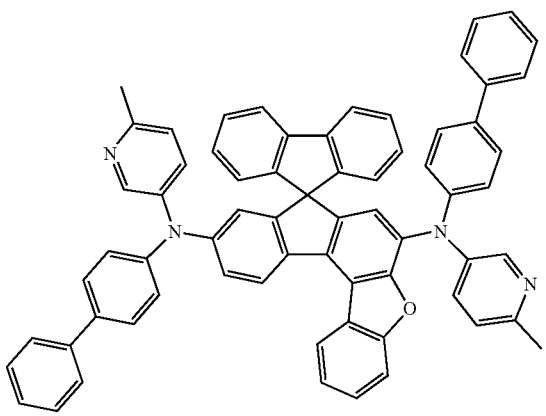

-continued
<d 81>
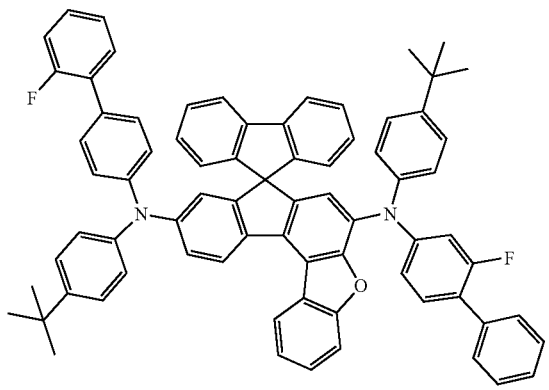
<d 82>
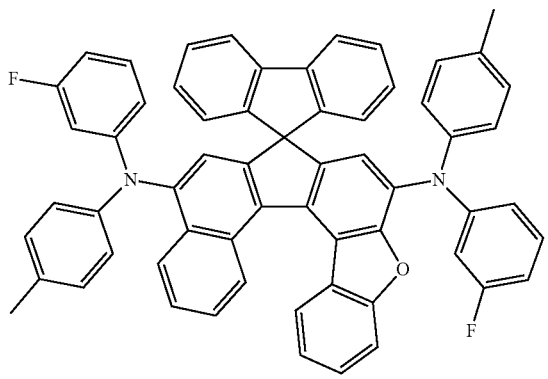
<d 83>
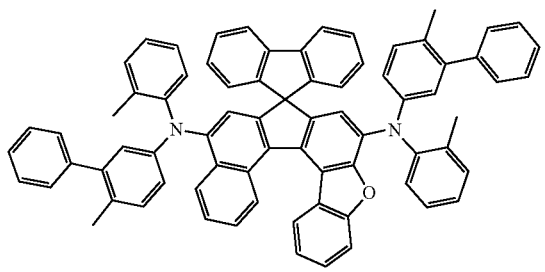
<d 84>
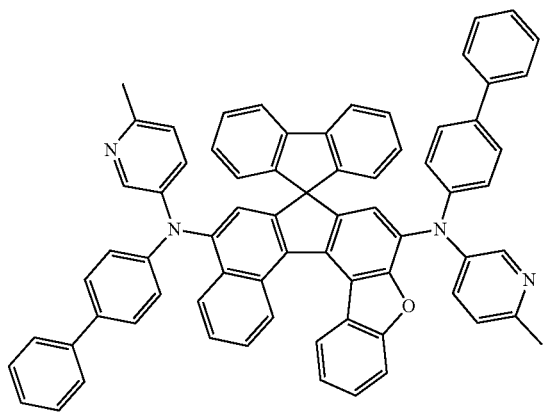
<d 85>
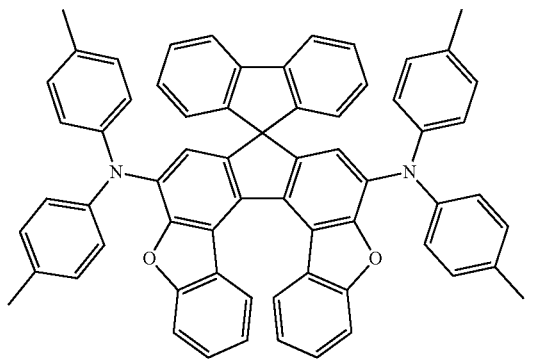
<d 86>
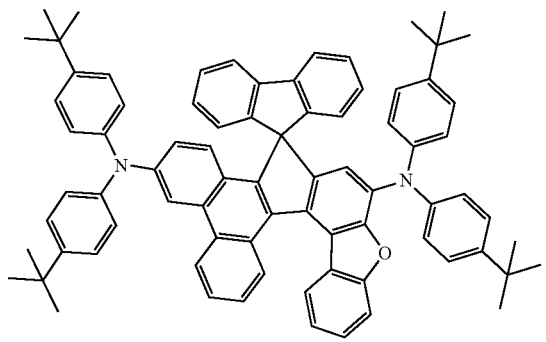
<d 87>
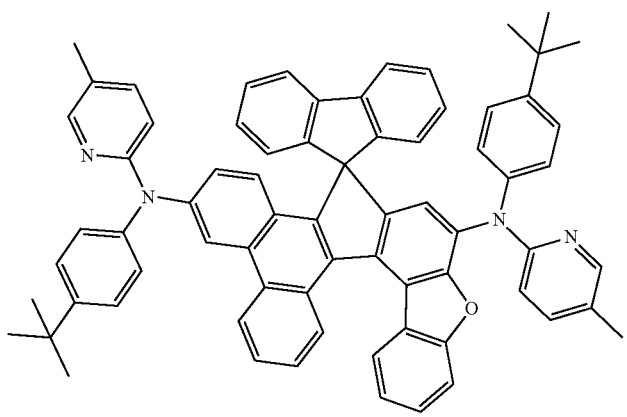

-continued
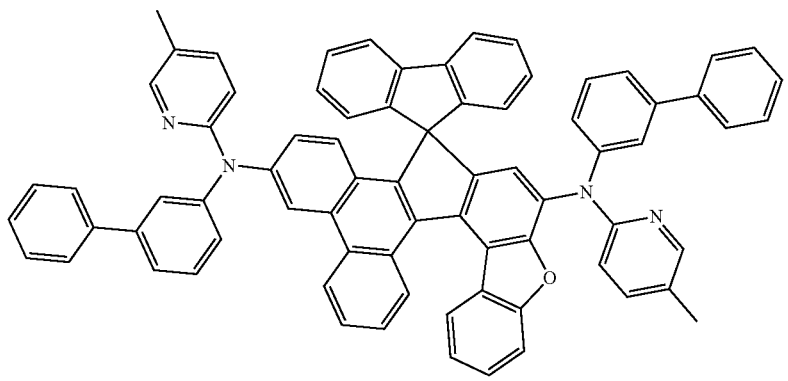
<d 88>
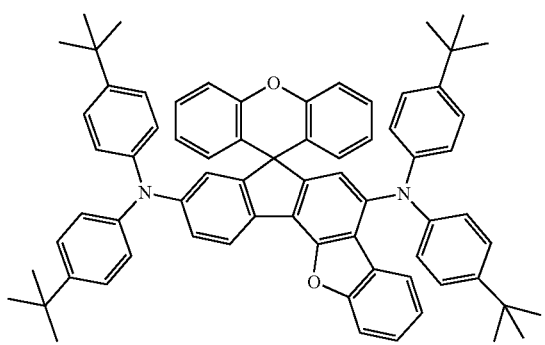
<d 89>
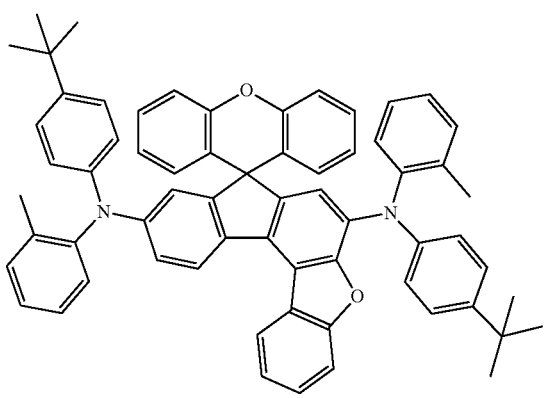
<d 90>
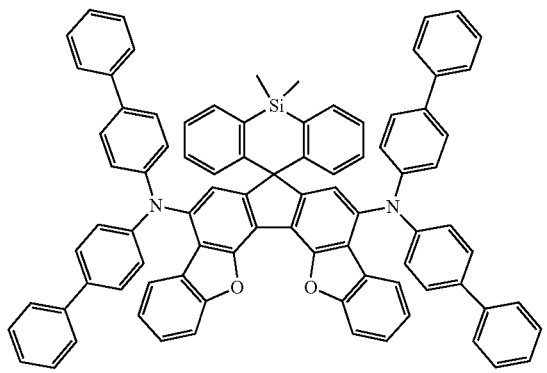
<d 91>
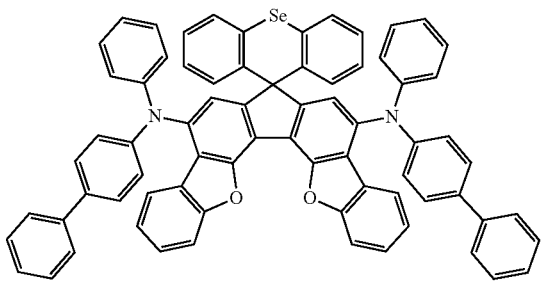
<d 92>
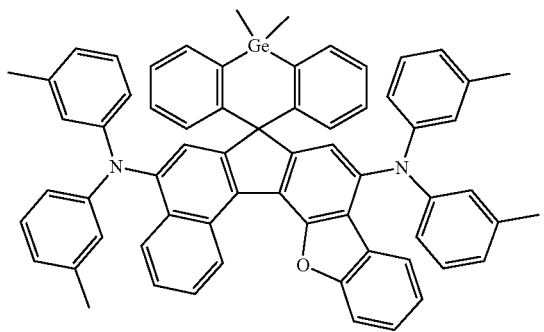
<d 93>
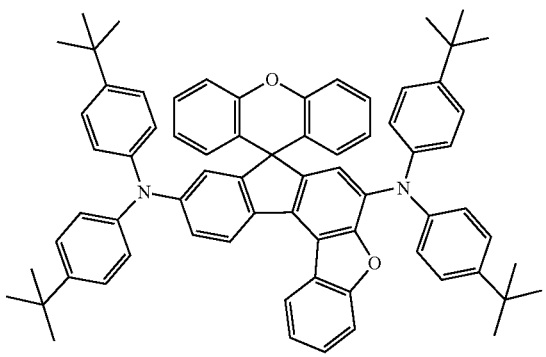
<d 94>

-continued
<d 95>
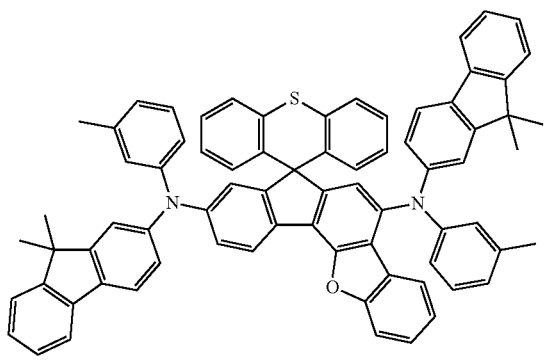
<d 96>
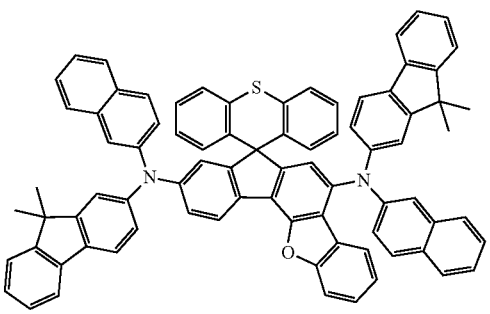
<d 97>
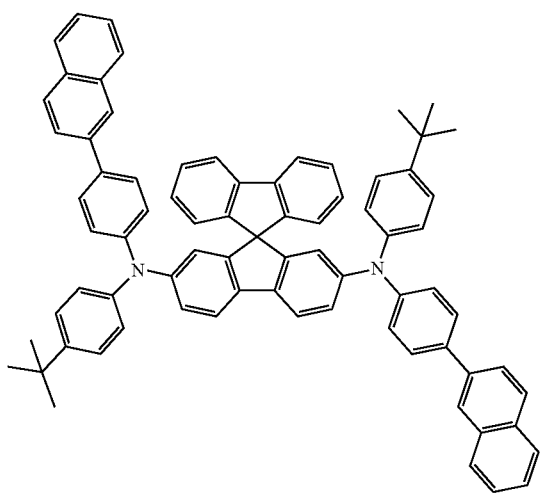
<d 98>
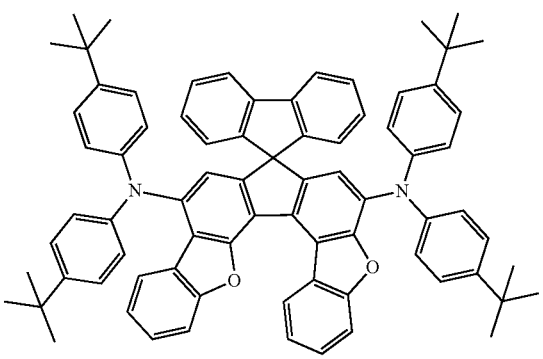
<d 99>
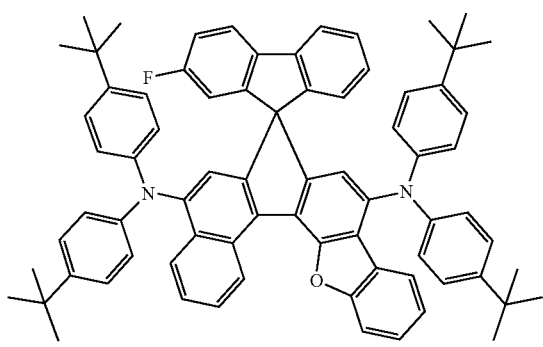
<d 100>
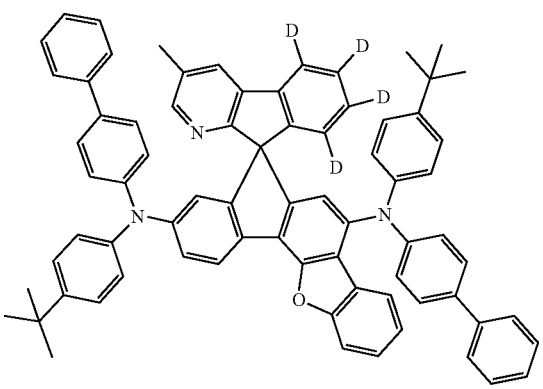

-continued
<d 101>
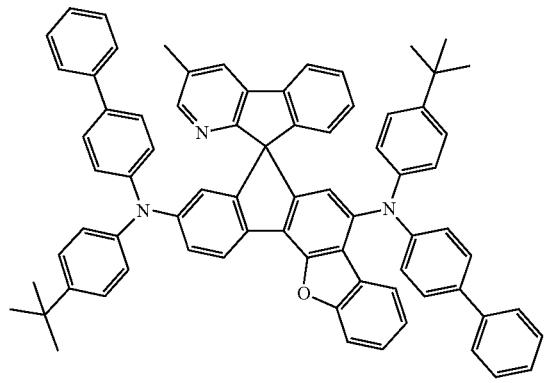
<d 102>
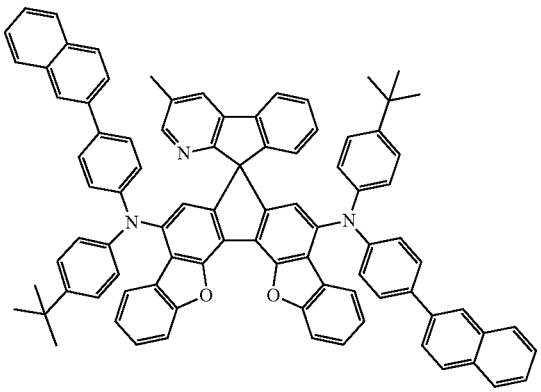
<d 103>
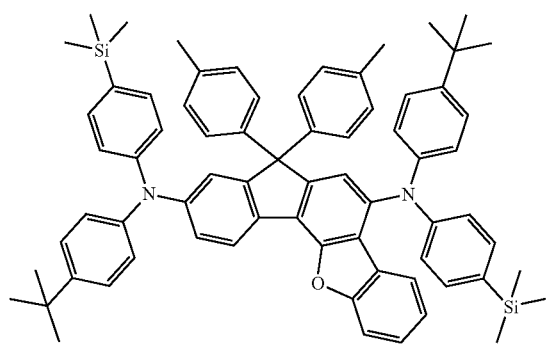
<d 104>
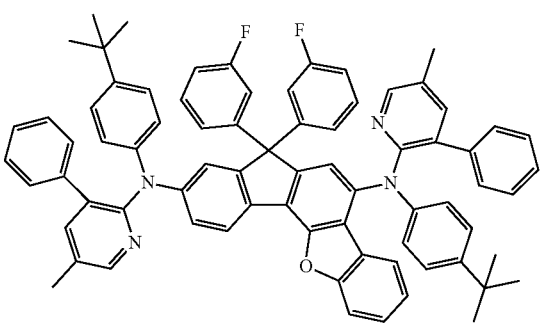
<d 105>
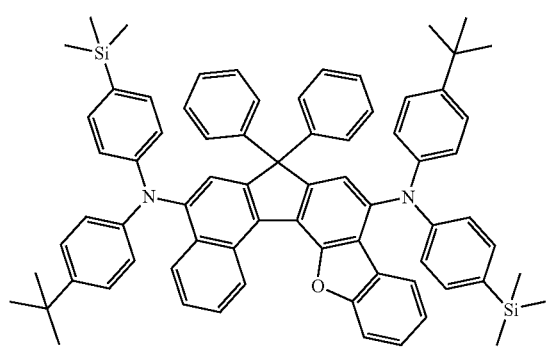
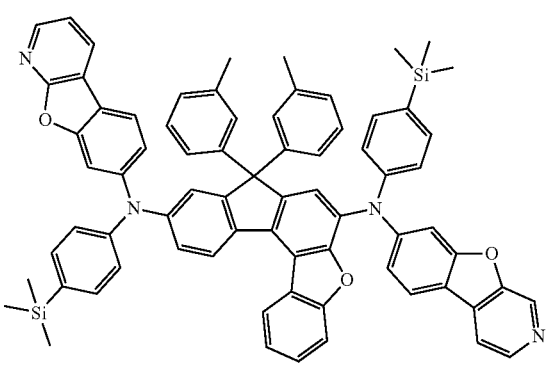
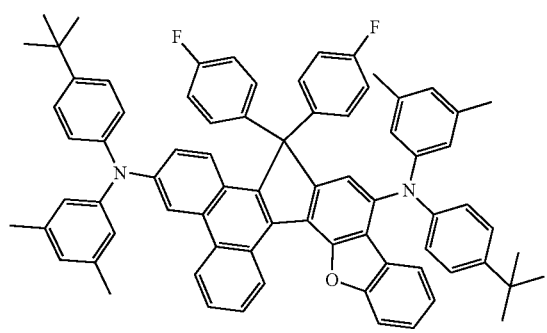
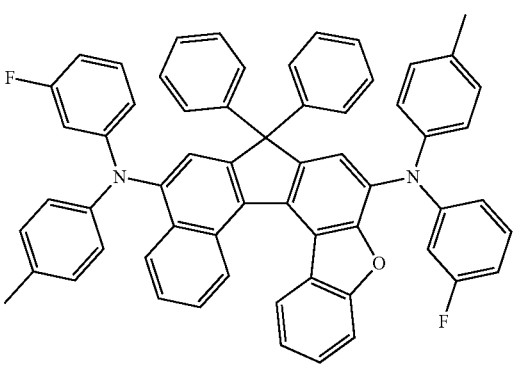

-continued
<d109>
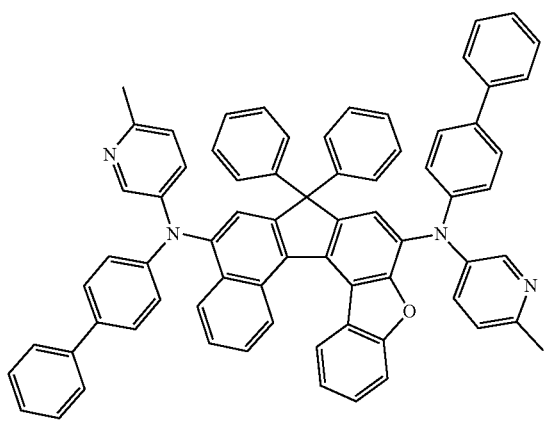
<d110>
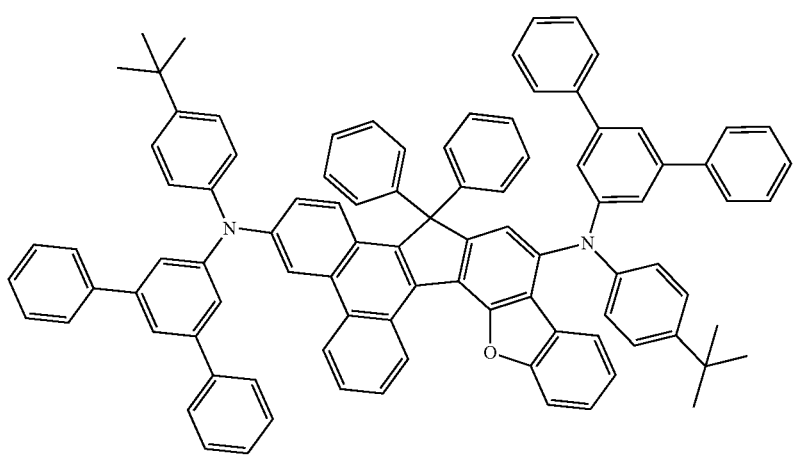
<d111>
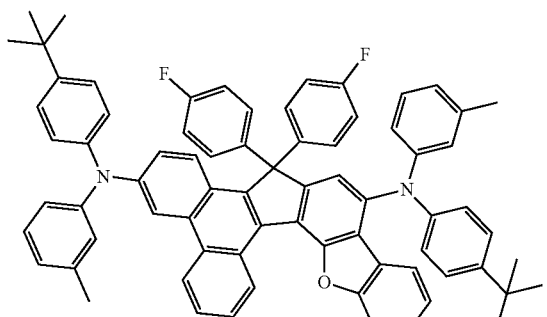
<d112>
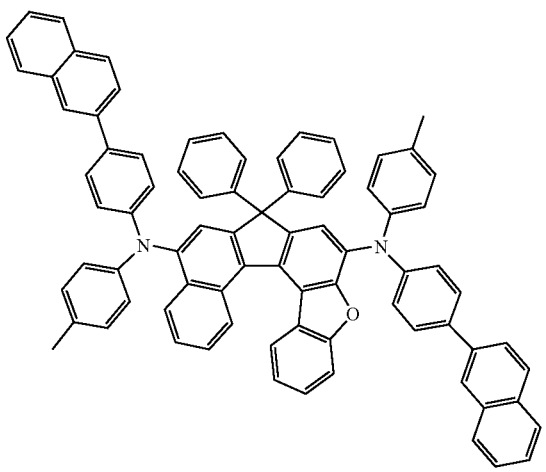

-continued
<d 113>
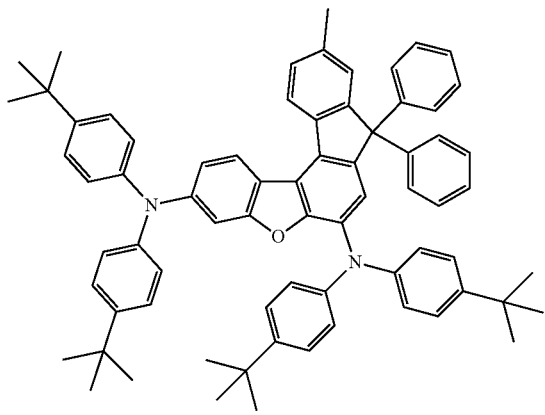
<d 114>
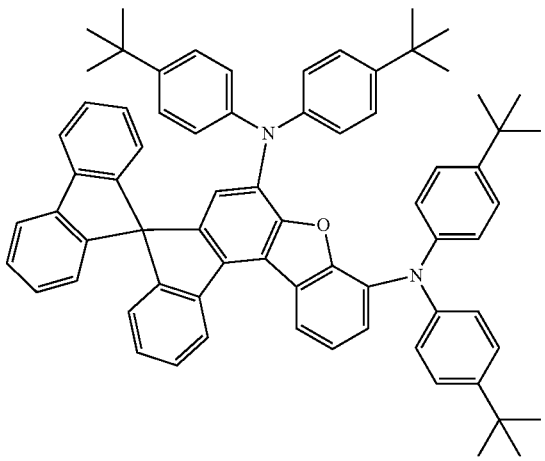
<d 115>
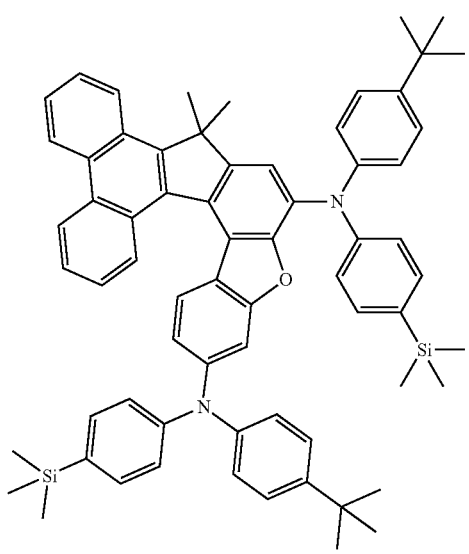
<d 116>
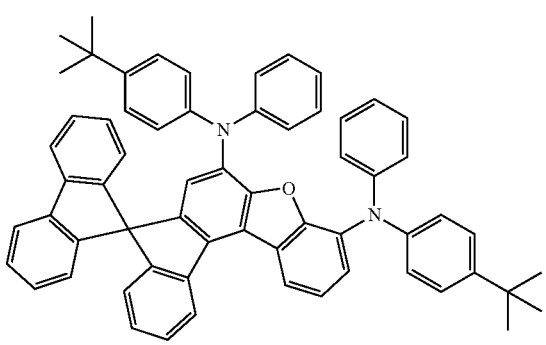
<d 117>
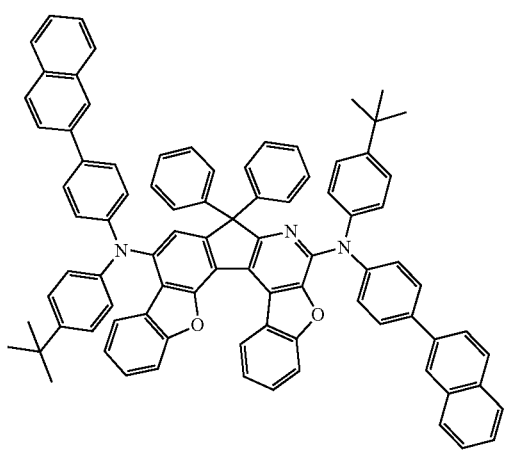
<d 118>
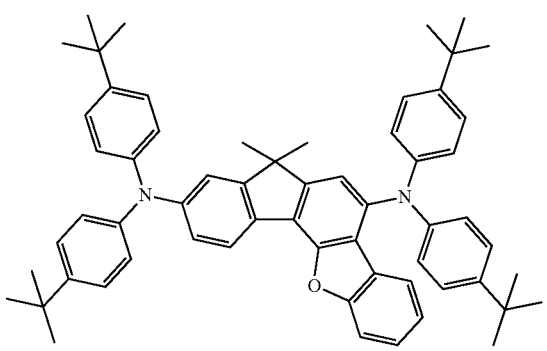

-continued
<d 119>
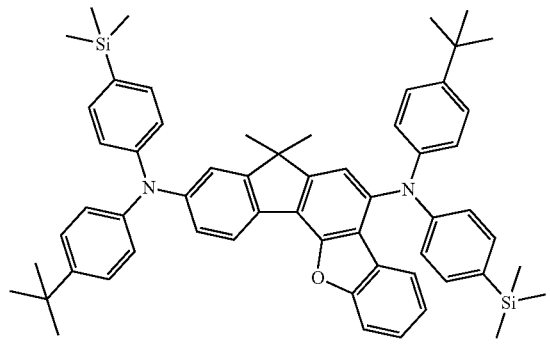
<d 120>
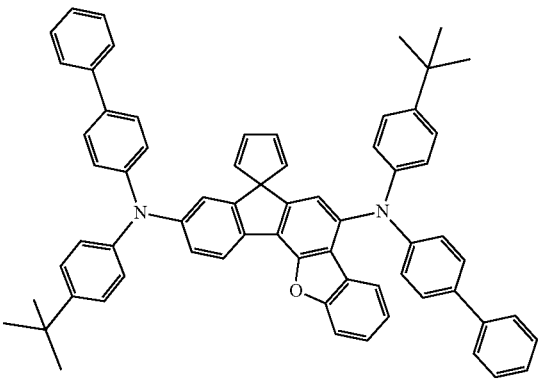
-continued
<d 121>
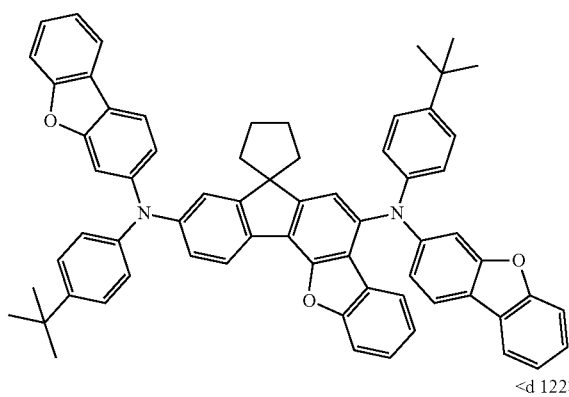
<d 124>
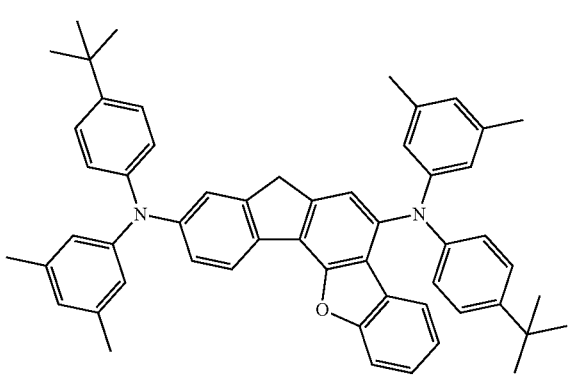
<d 122>
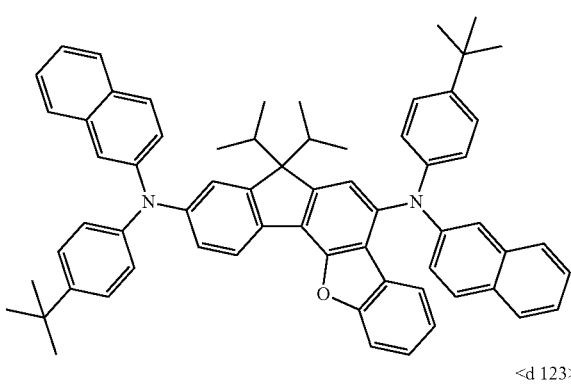
<d 125>
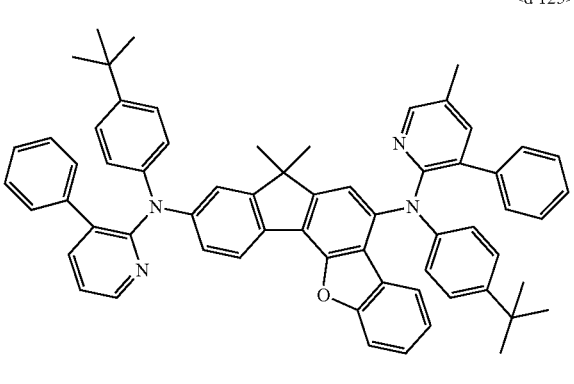
<d 123>
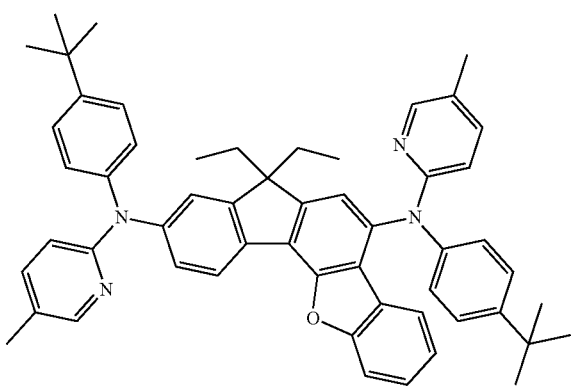
<d 126>
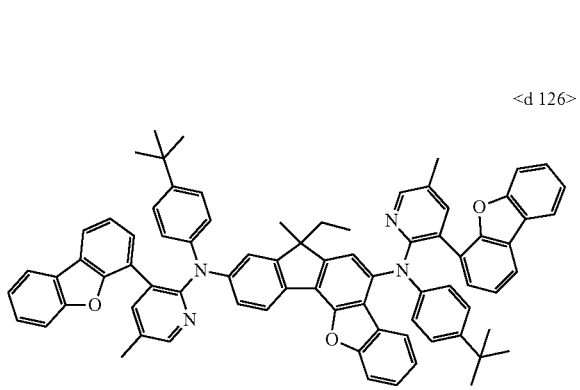

<d 127>
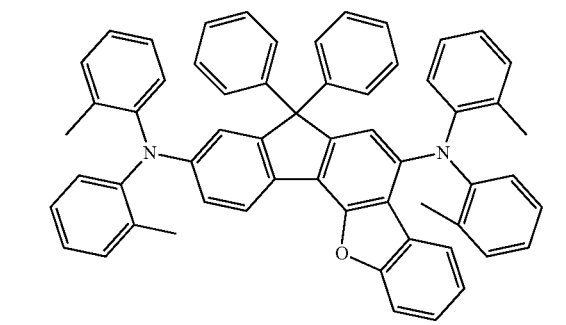
<d 128>
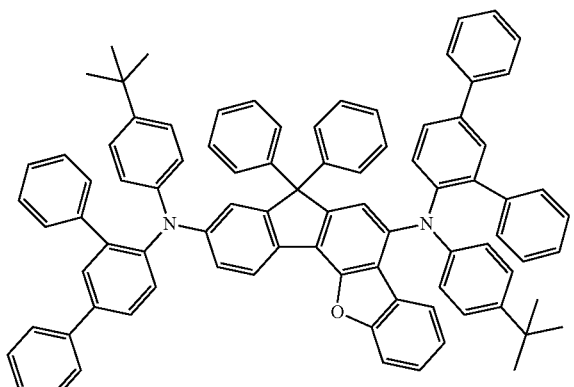
<d 129>
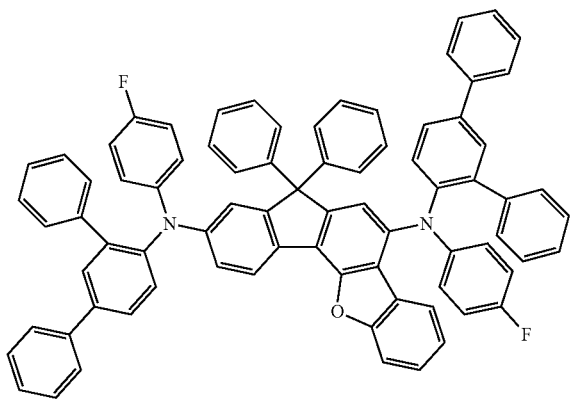
<d 130>
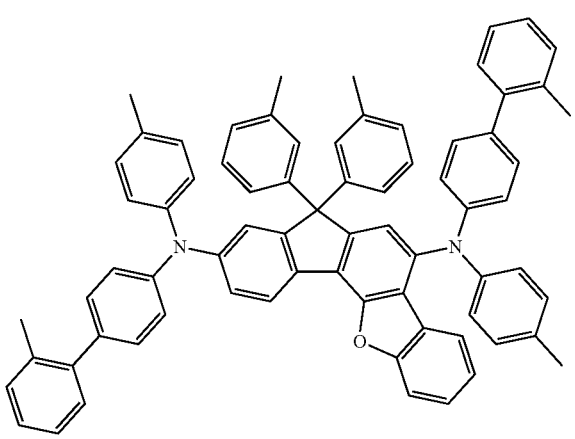
<d 131>
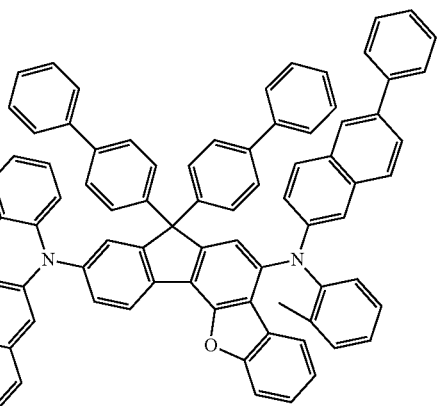
<d 132>
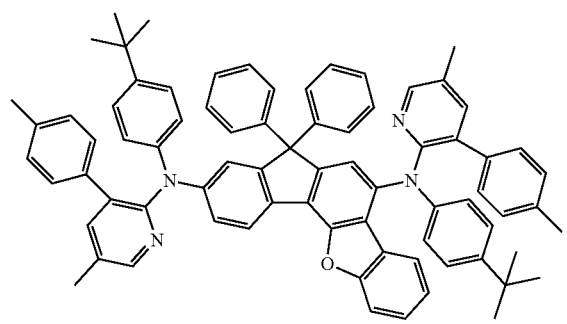
<d 133>
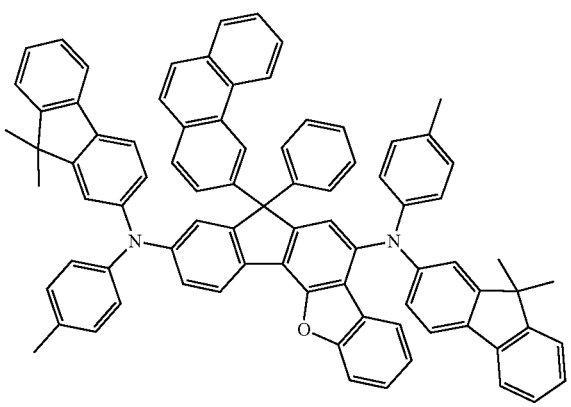

<d134>
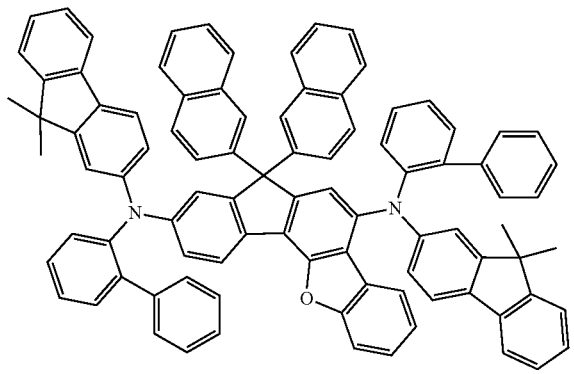
<d135>
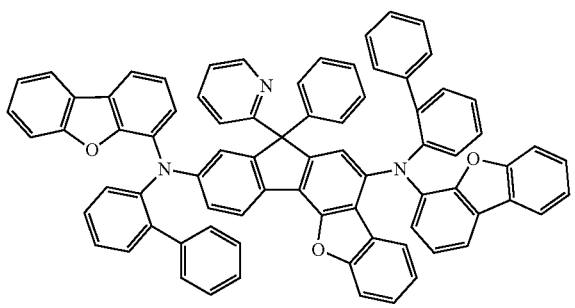
<d136>
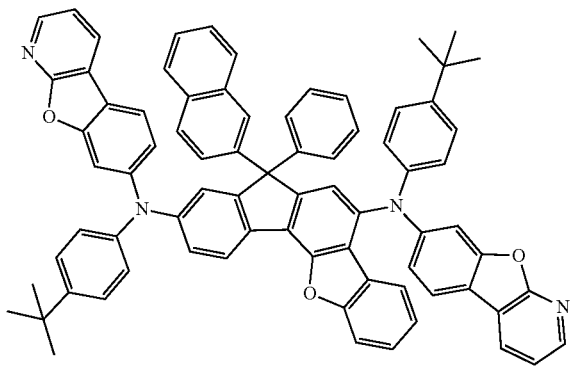
<d137>
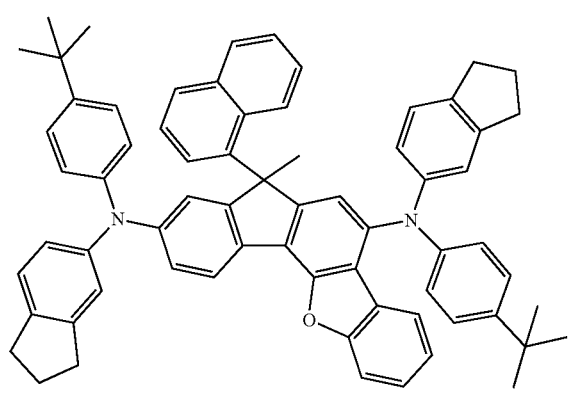
<d138>
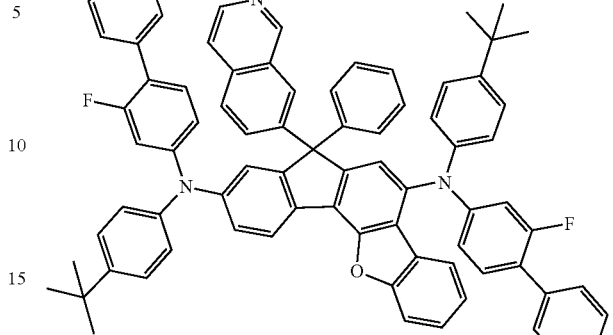
<d139>
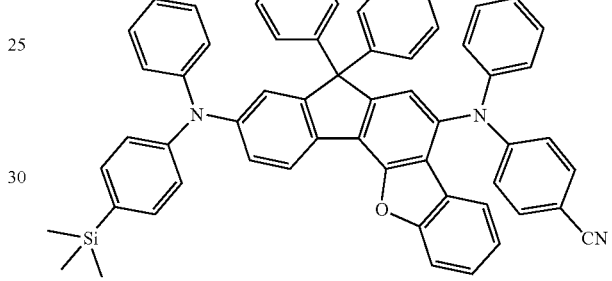
<d140>
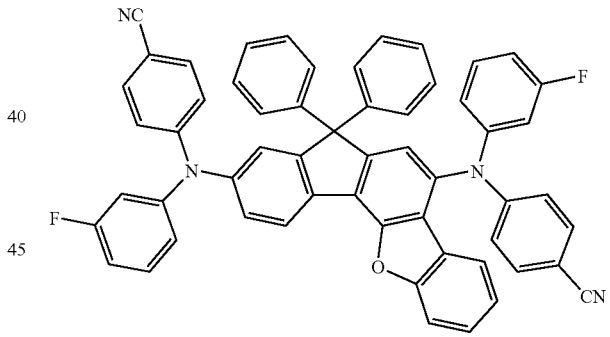
<d141>
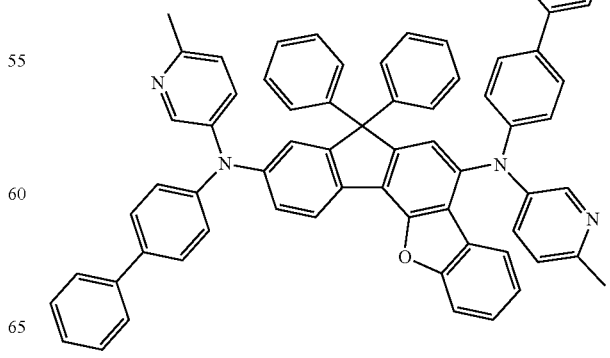

<d 142>
<d 143>
<d 144>
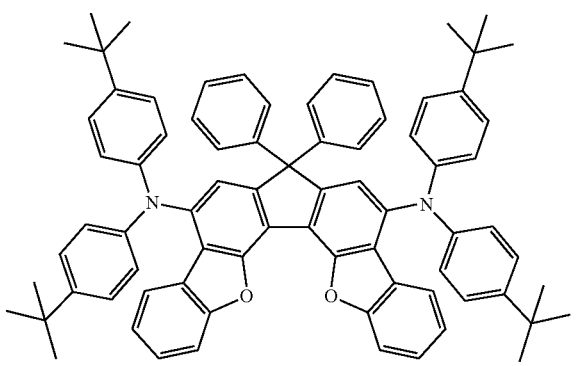
<d 145>
<d 146>
<d 147>
<d 148>
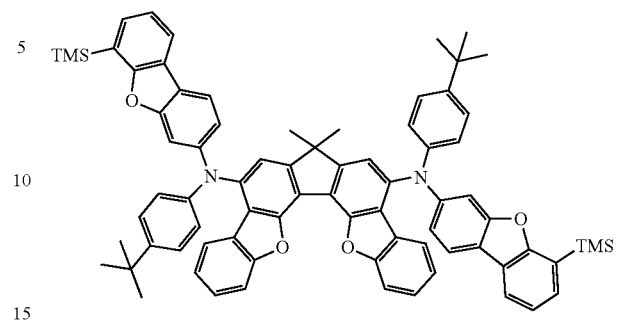
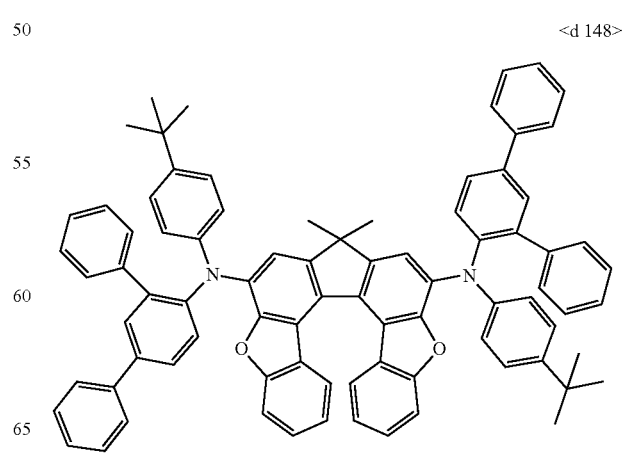

<d 149>
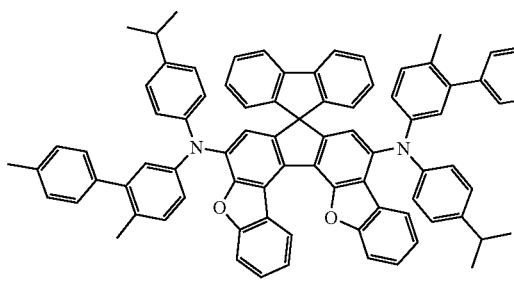
<d 150>
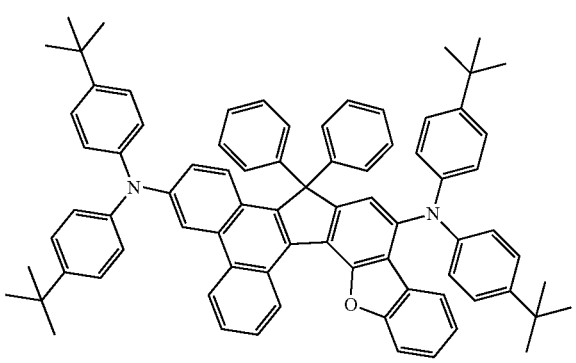
<d 151>
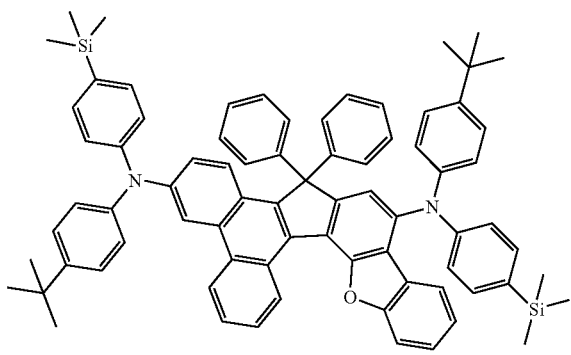
<d 152>
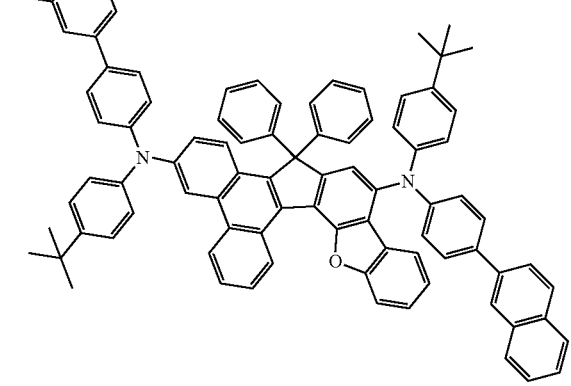
<d 153>
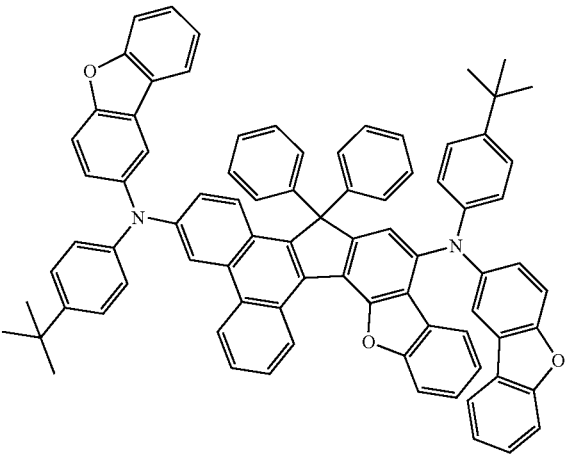
<d 154>
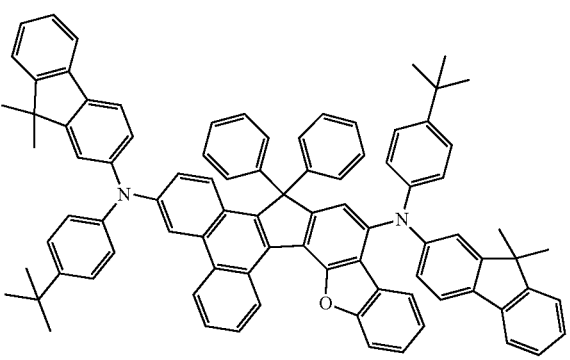
<d 155>
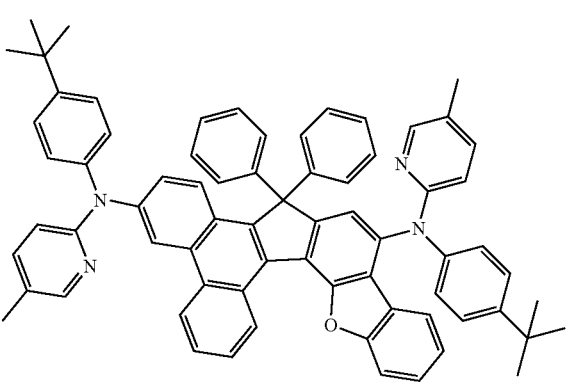
<d 156>
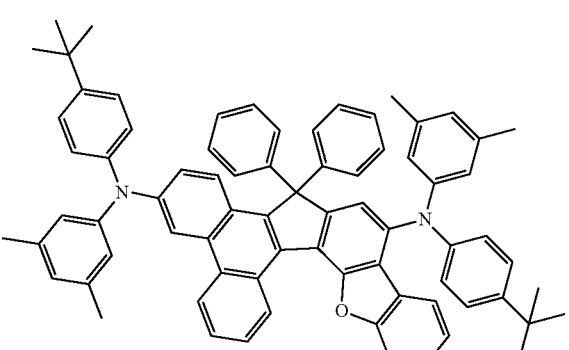

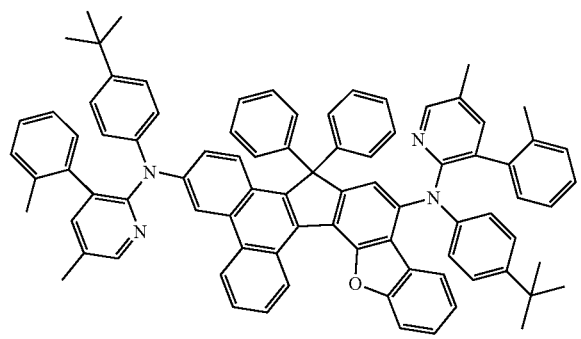
<d 157>
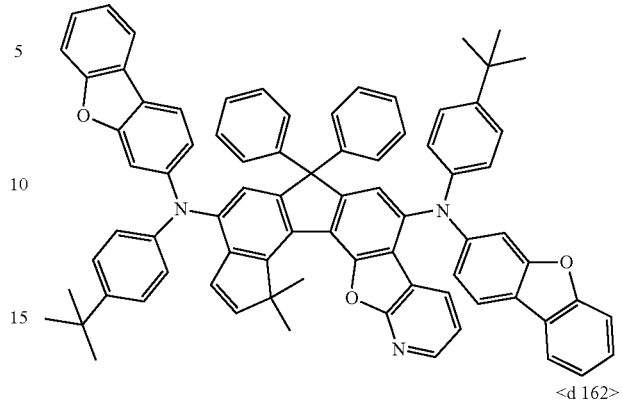
<d 161>
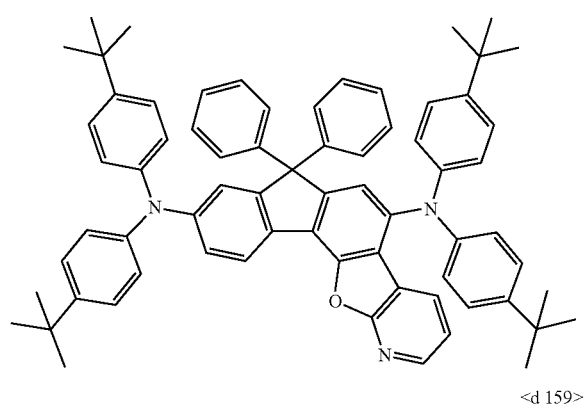
<d 158>
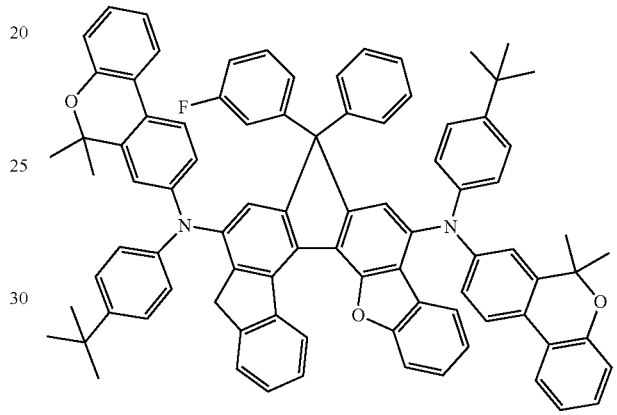
<d 162>
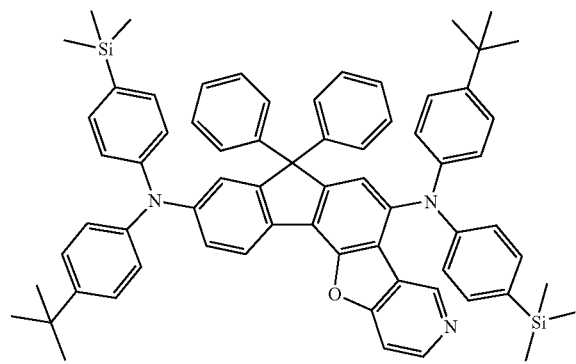
<d 159>
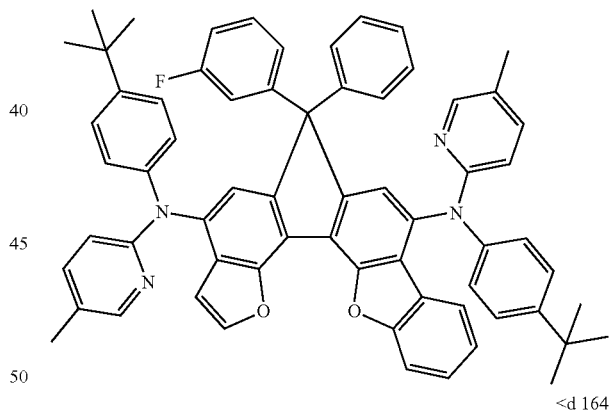
<d 163>
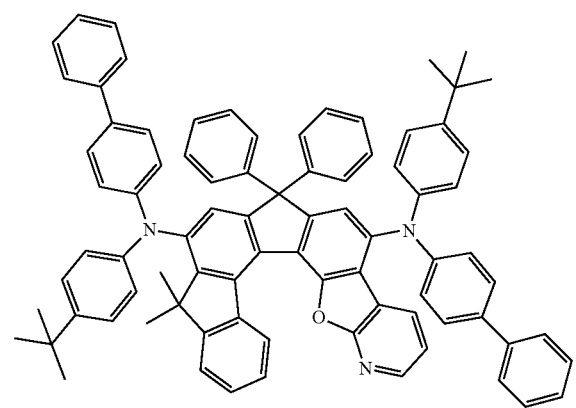
<d 160>
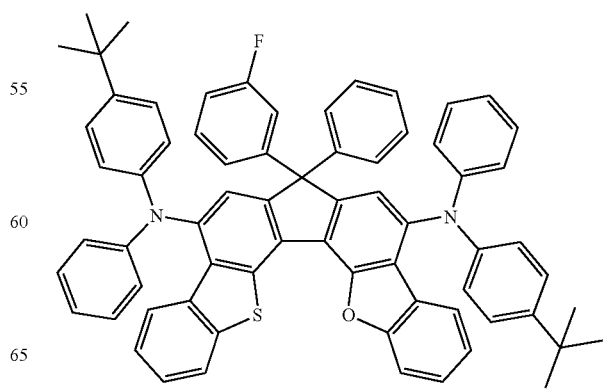
<d 164>

<d 165>
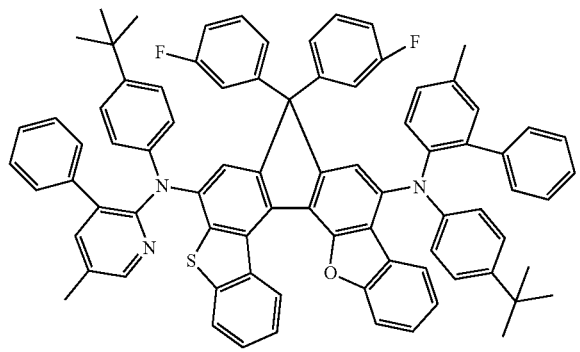
<d 166>
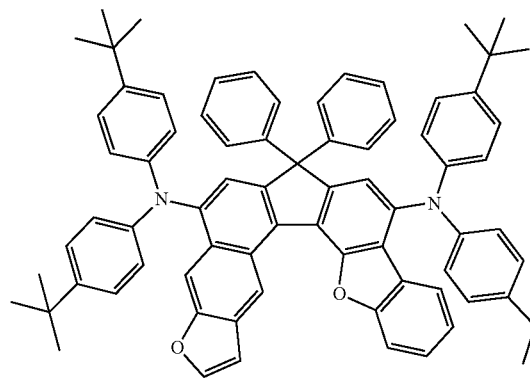
<d 167>
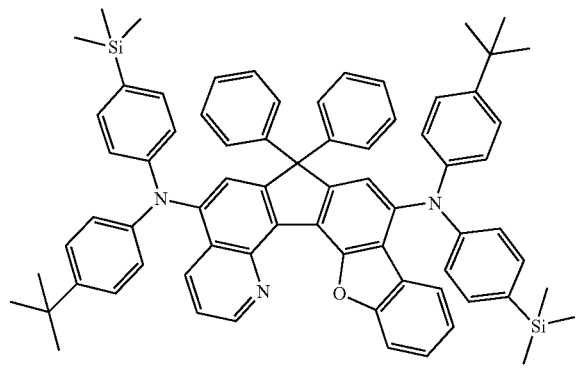
<d 168>
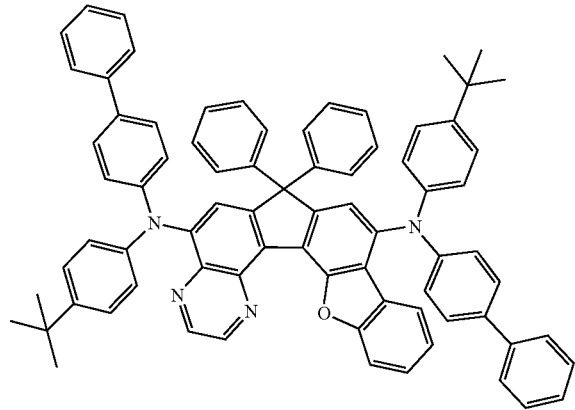
<d 169>
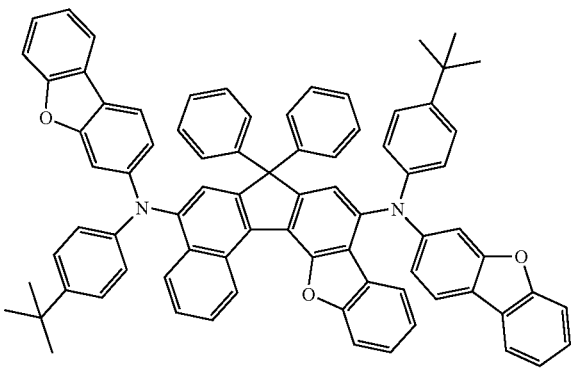
<d 170>
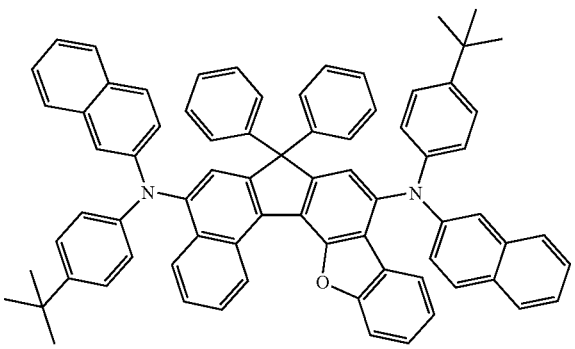
<d 171>
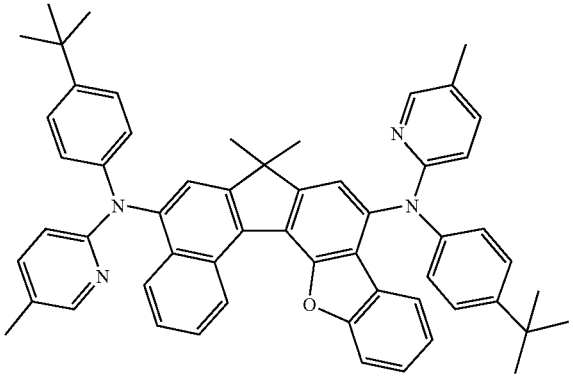
<d 172>
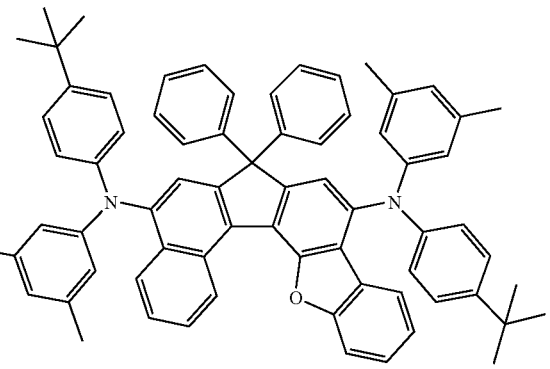

-continued
<d 173>
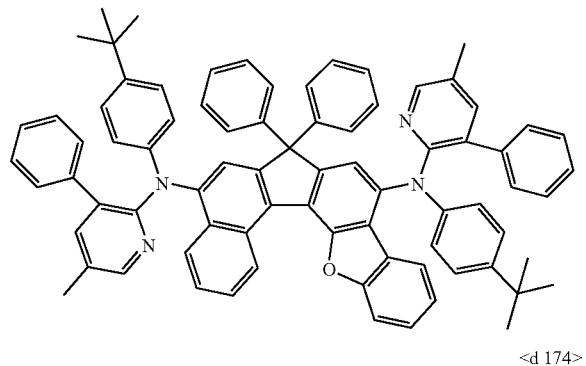
<d 174>
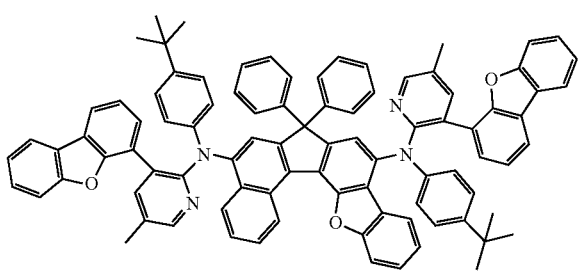
<d 175>
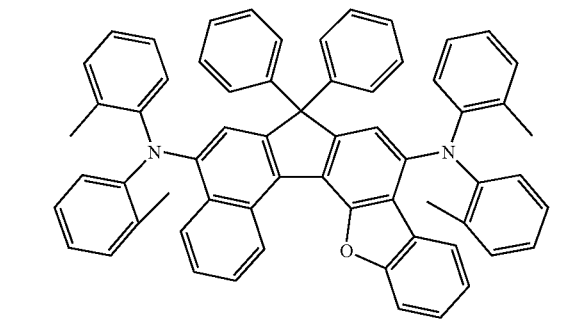
<d 176>
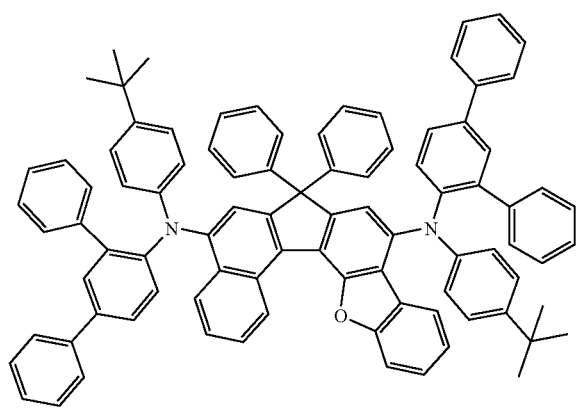
<d 177>
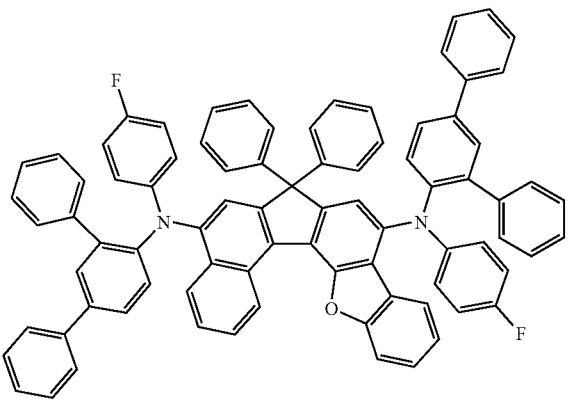
<d 178>
<d 179>
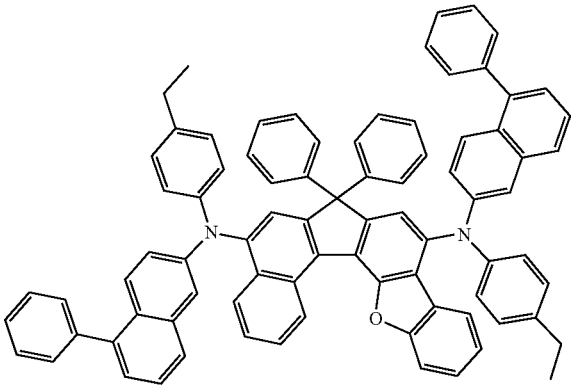
<d 180>
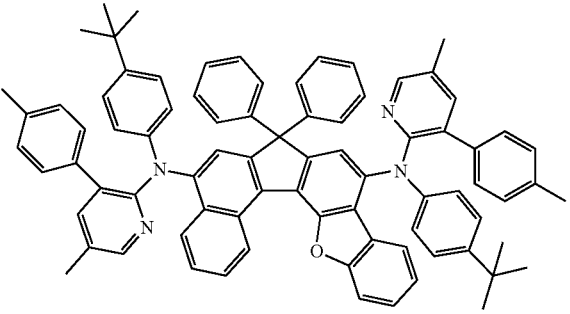

<d 181>
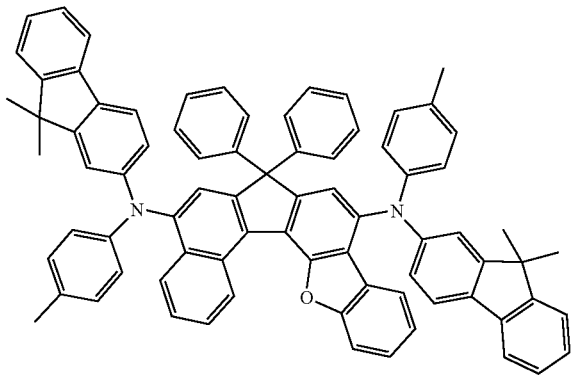
<d 182>
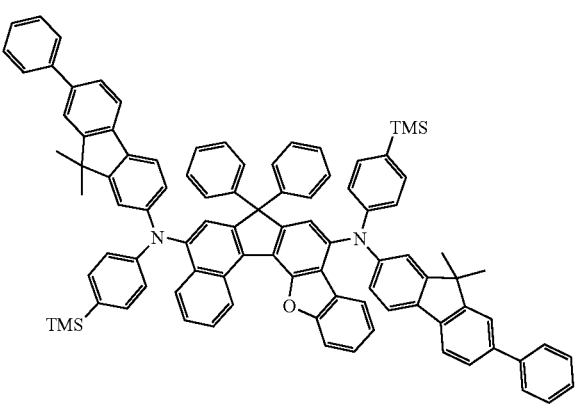
<d 183>
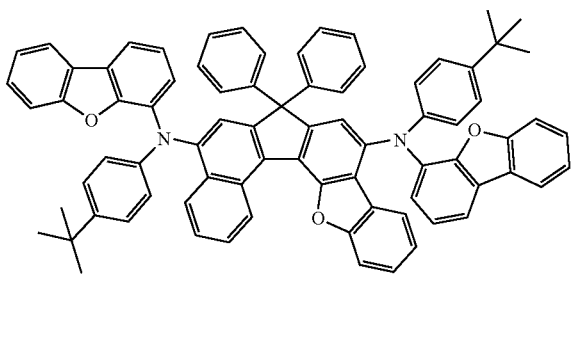
<d 184>
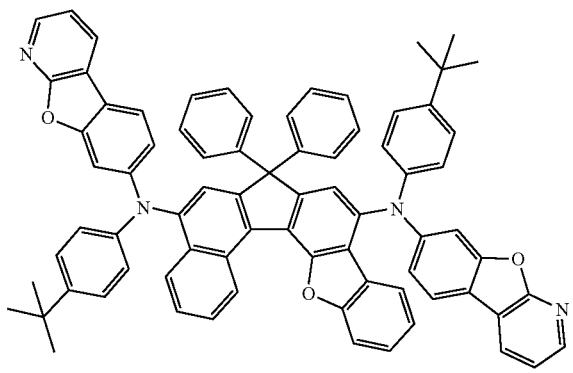
<d 185>
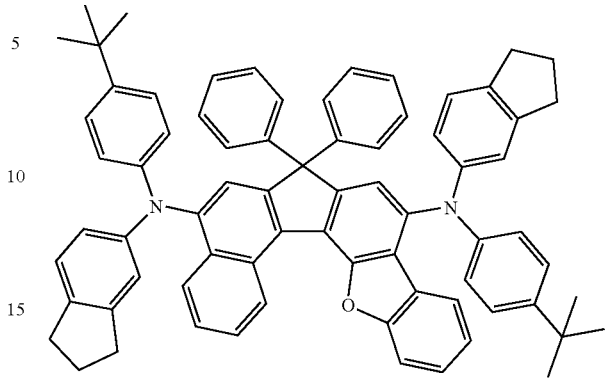
<d 186>
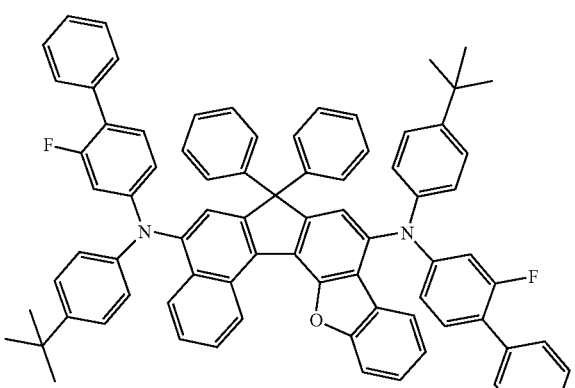
<d 187>
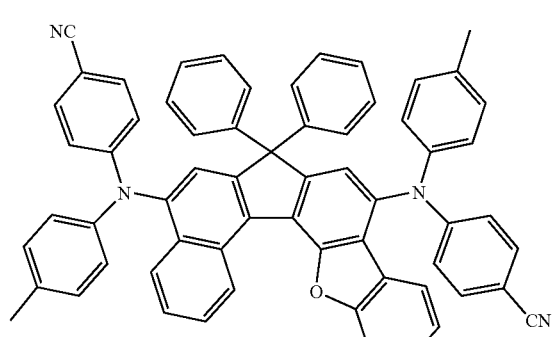
<d 188>
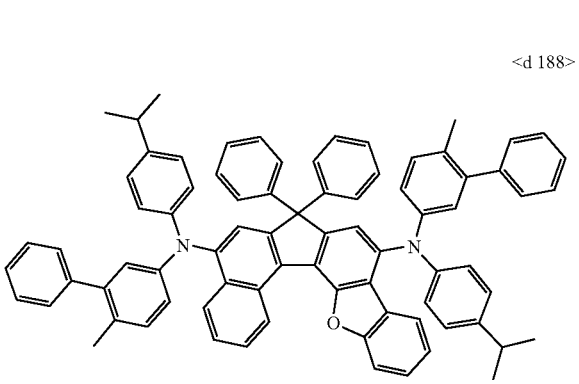

<d189>
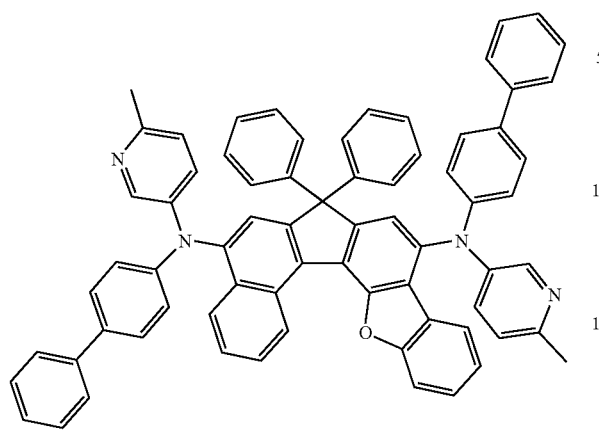
<d190>
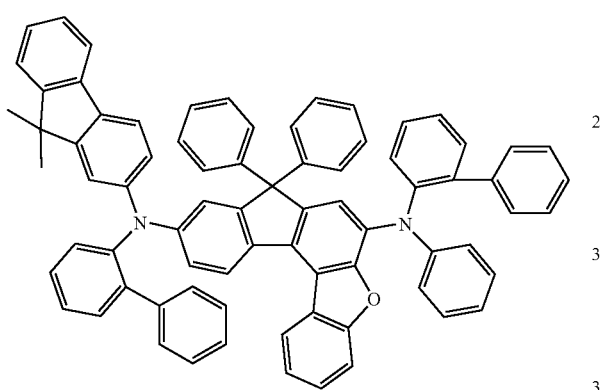
<d191>
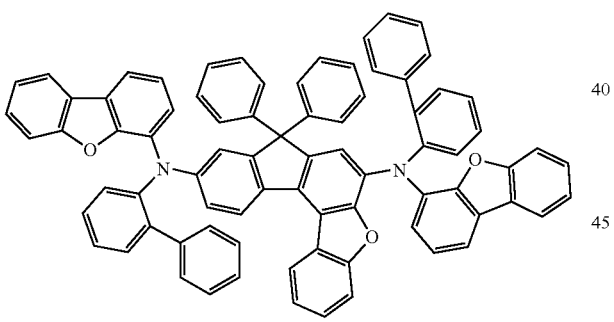
<d192>
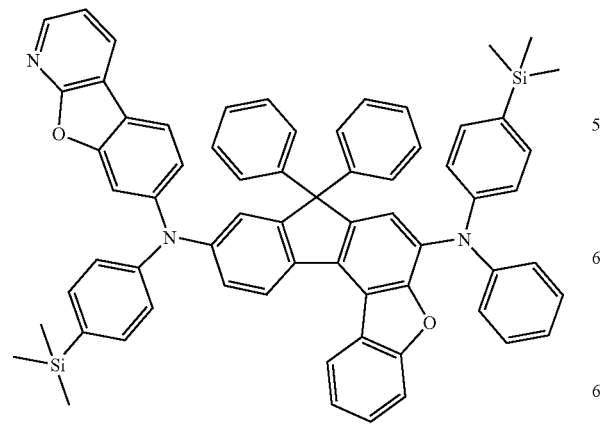
<d193>
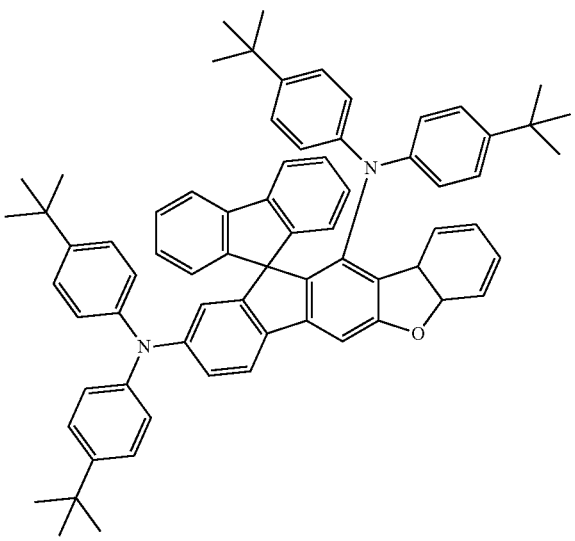
<d194>
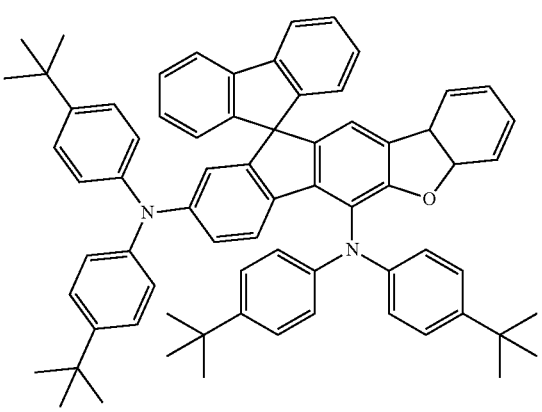
<d195>
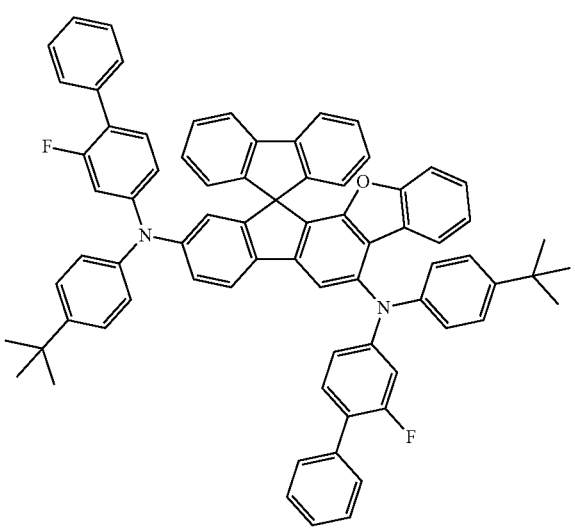

<d 196>
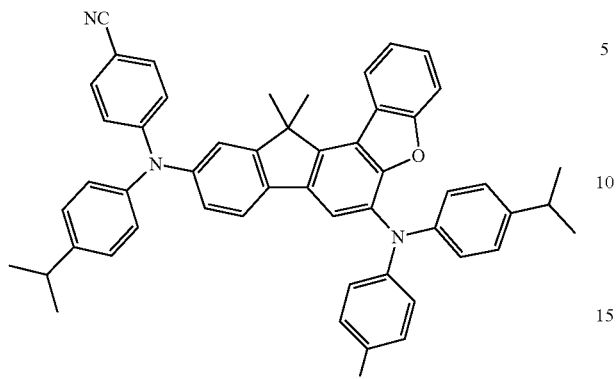
<d 197>
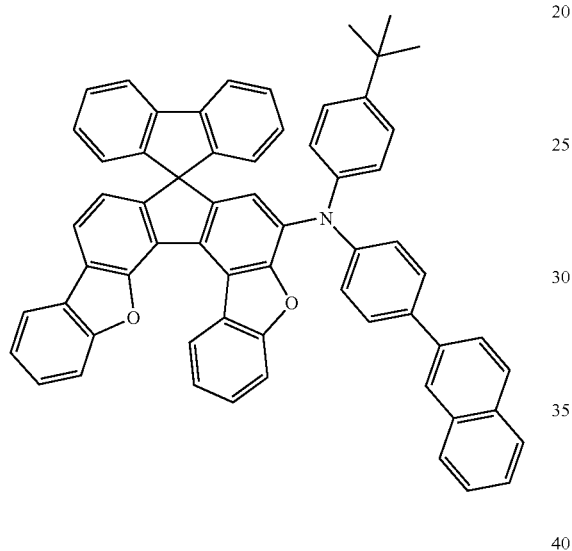
<d 198>
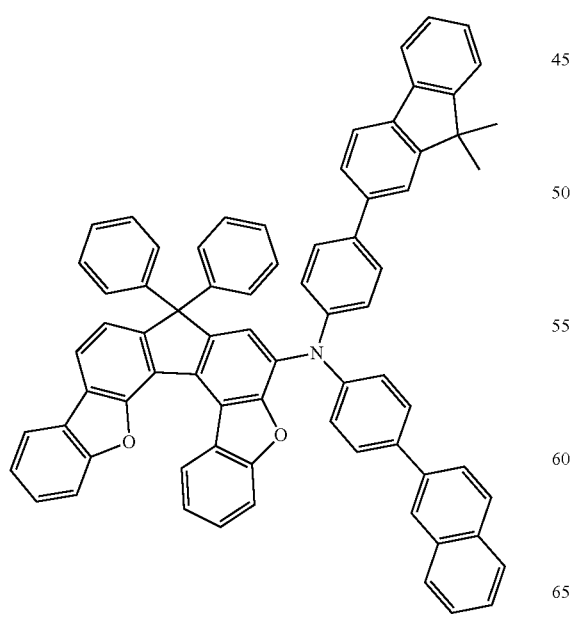
<d 199>
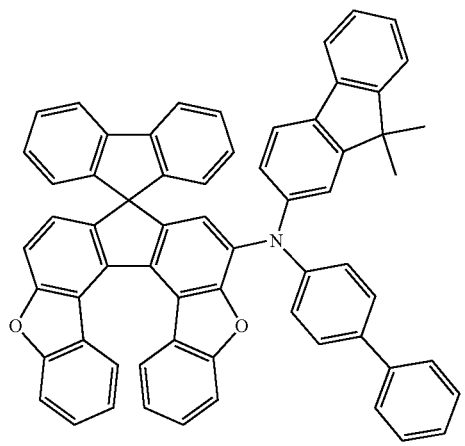
<d 200>
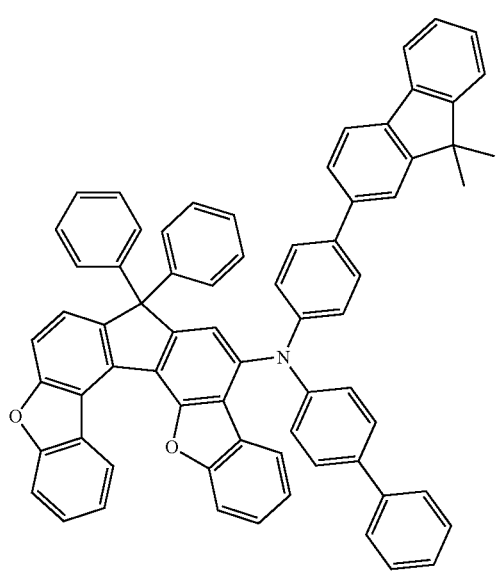

-continued
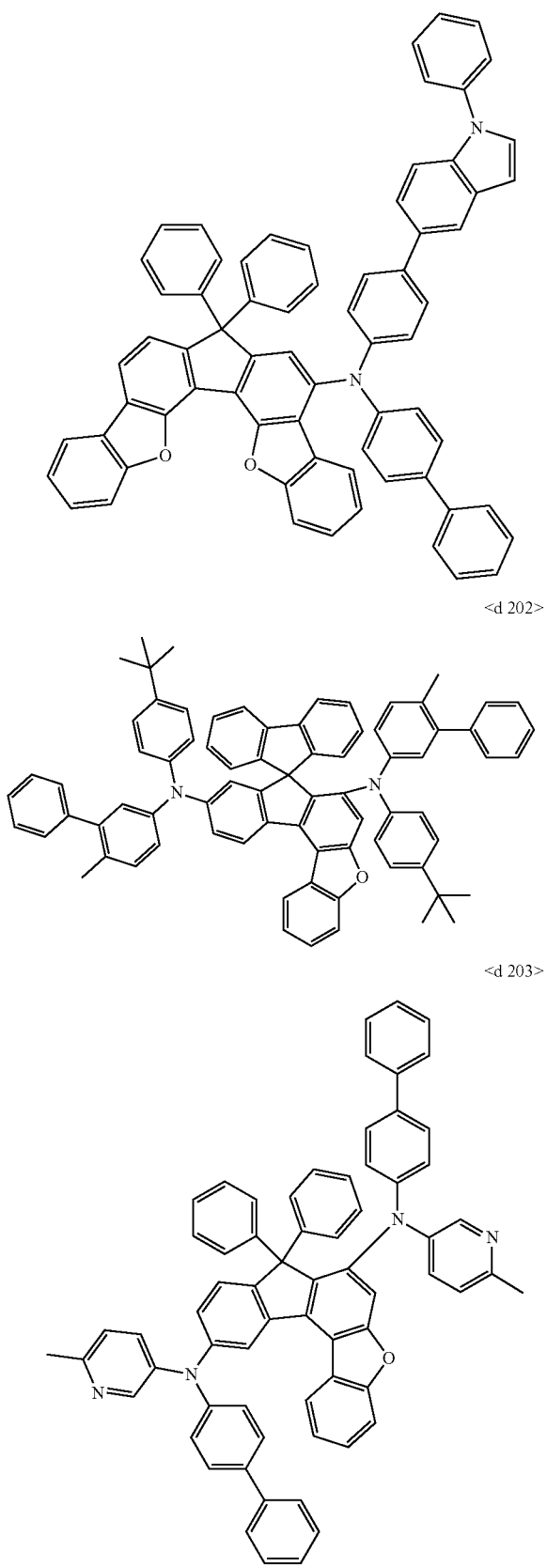
-continued
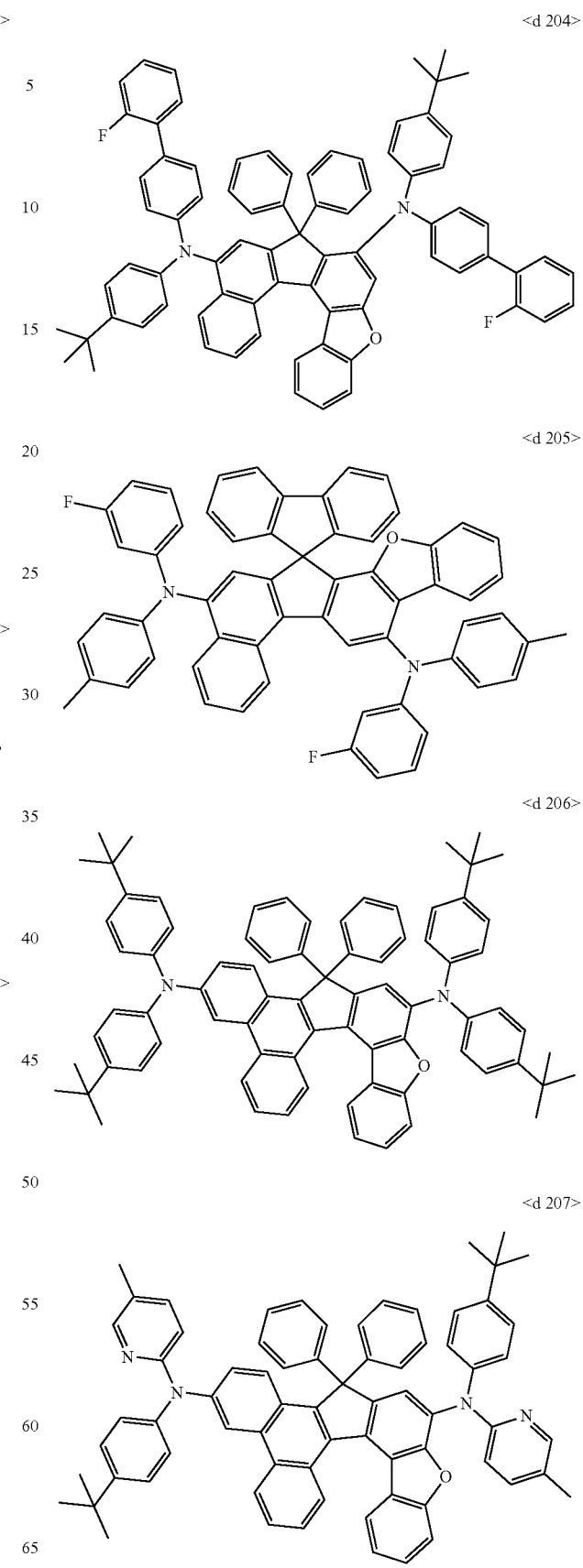

<d 208>
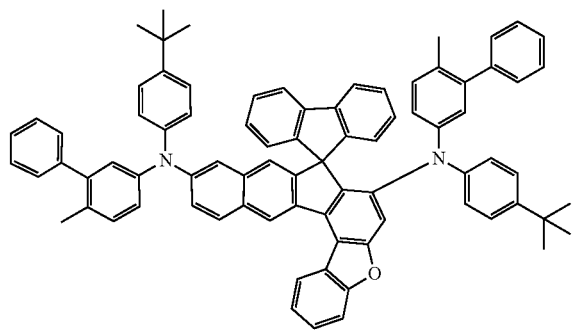
<d 209>
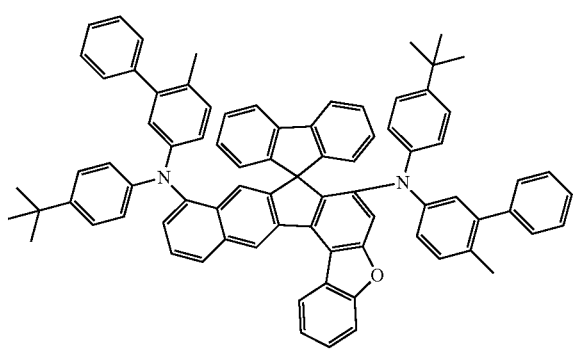
<d 210>
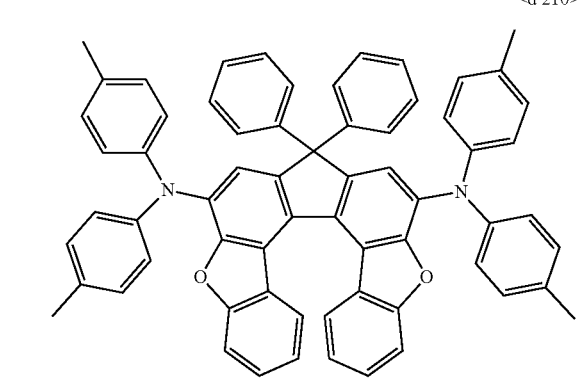
<d 211>
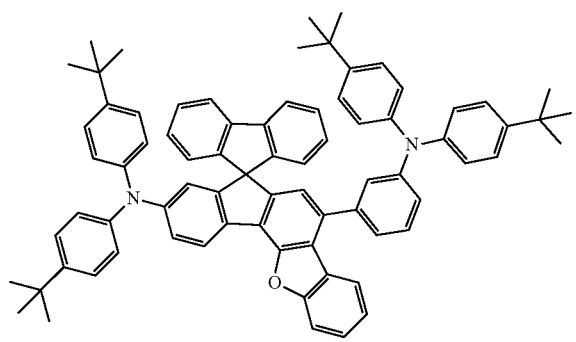
<d 212>
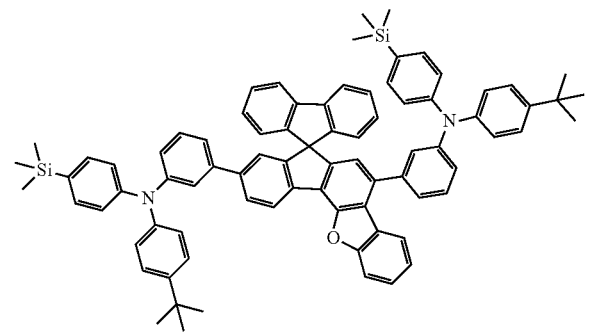
<d 213>
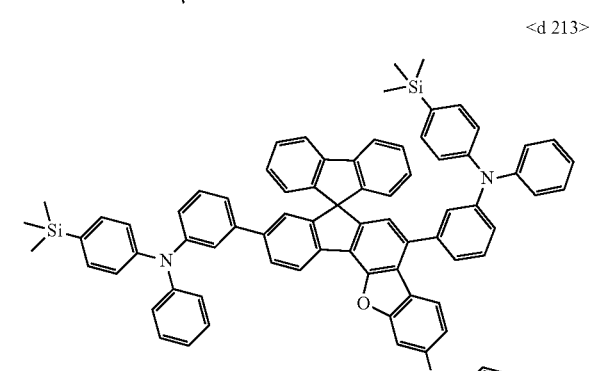
<d 214>
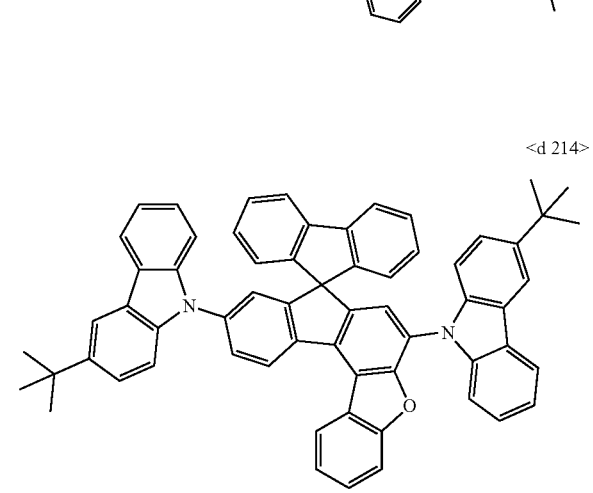
<d 215>
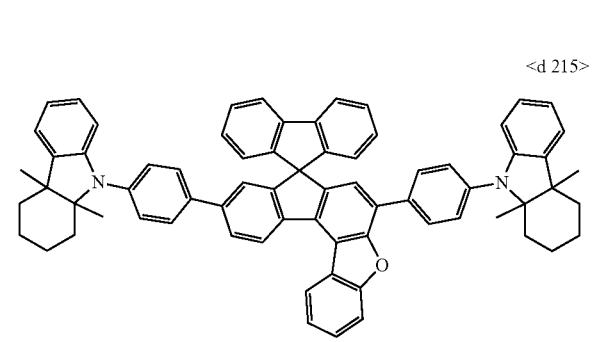

-continued
<d 216>
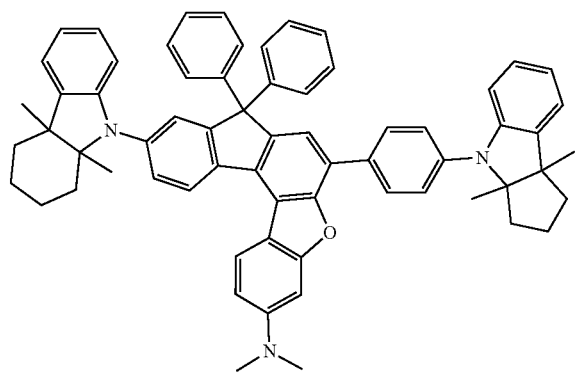
<d 217>
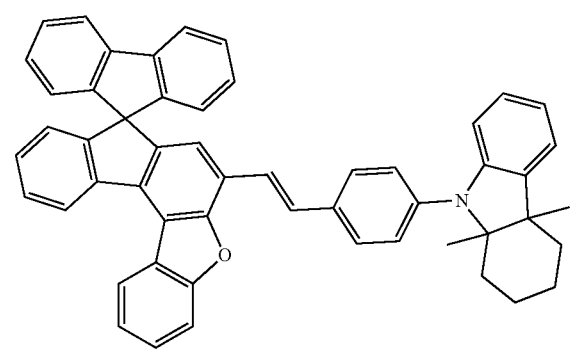
<d 218>
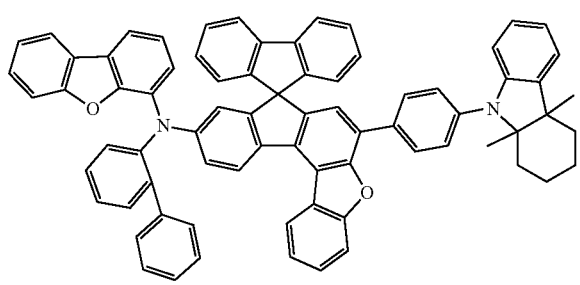
<d 219>
-continued
<d 220>
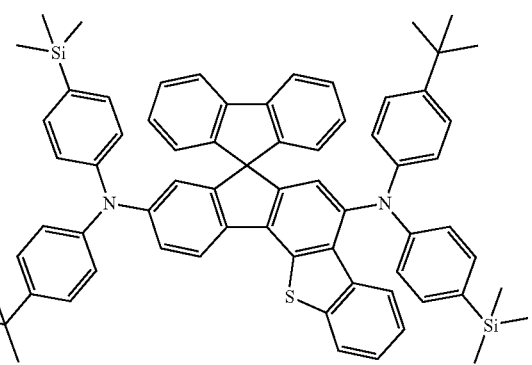
<d 221>
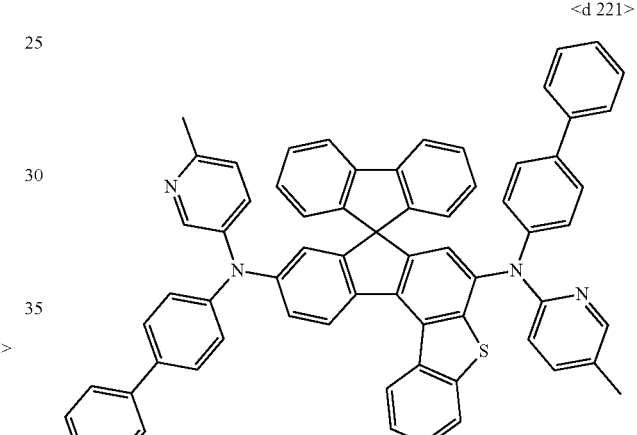
<d 222>
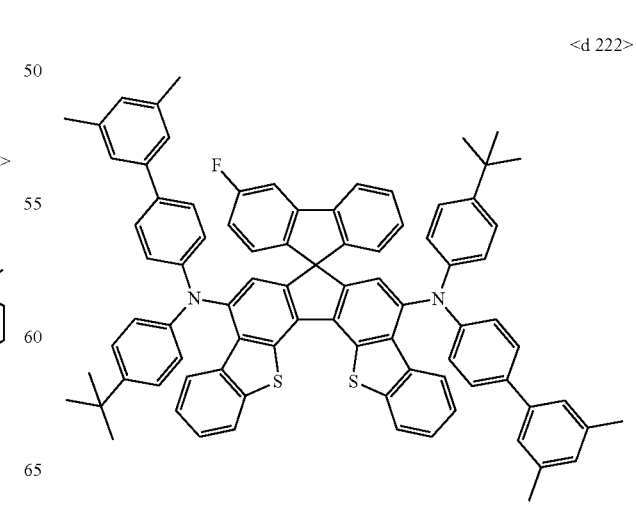

<d 223>
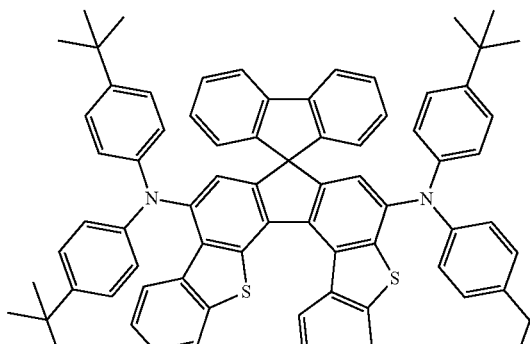
<d 224>
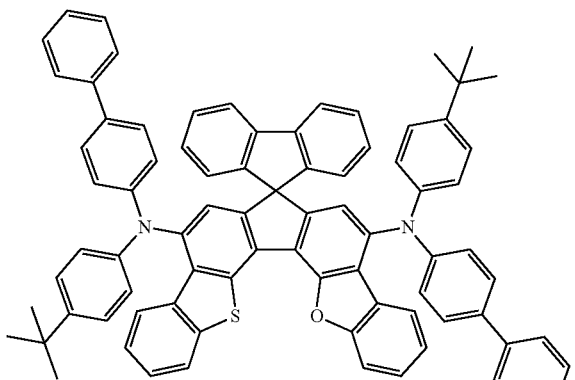
<d 225>
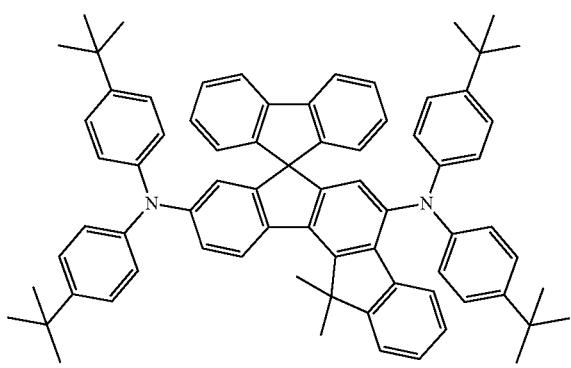
<d 226>
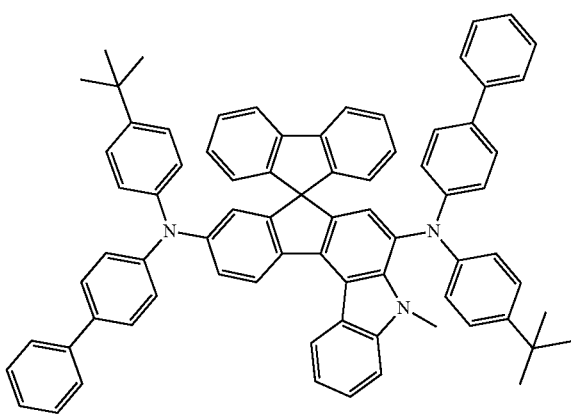
<d 227>
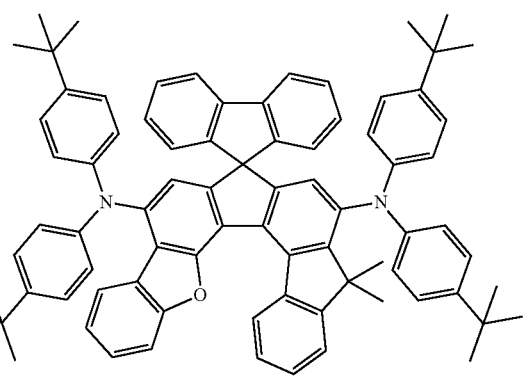
<d 228>
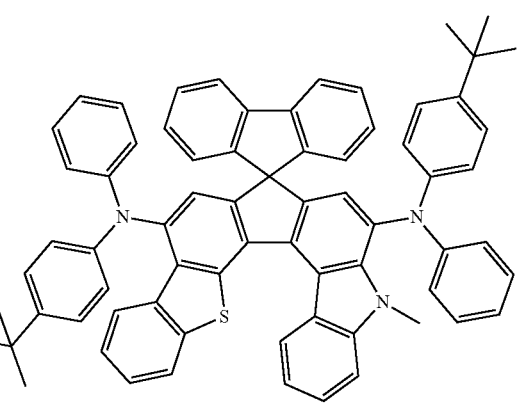
<d 229>
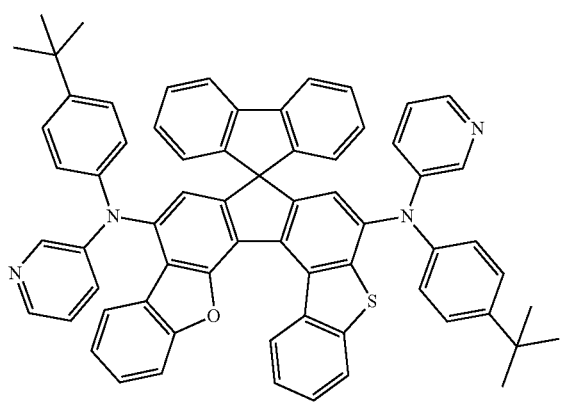

<d 230>
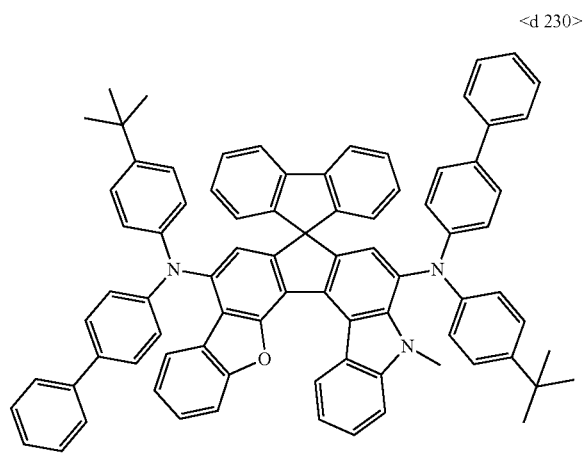
<d 231>
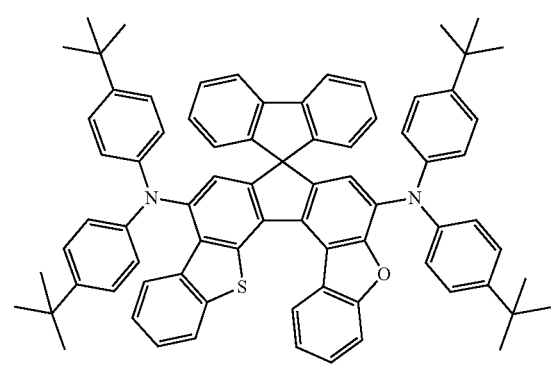
<d 232>
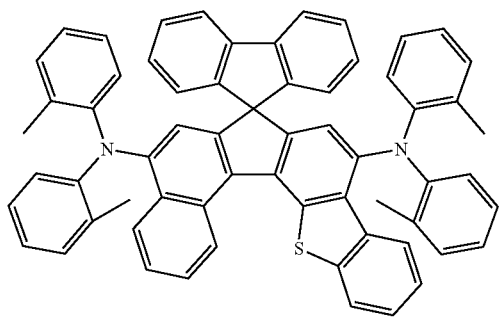
<d 233>
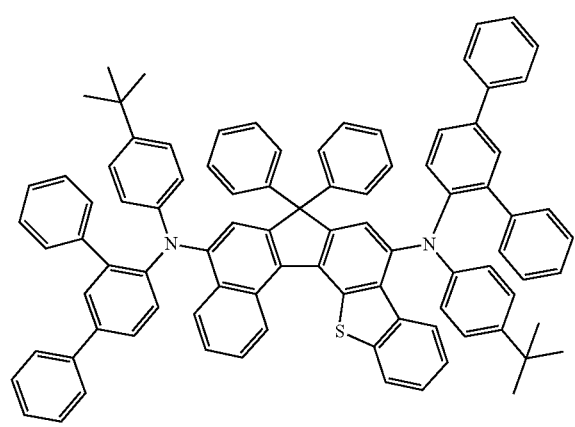
<d 234>
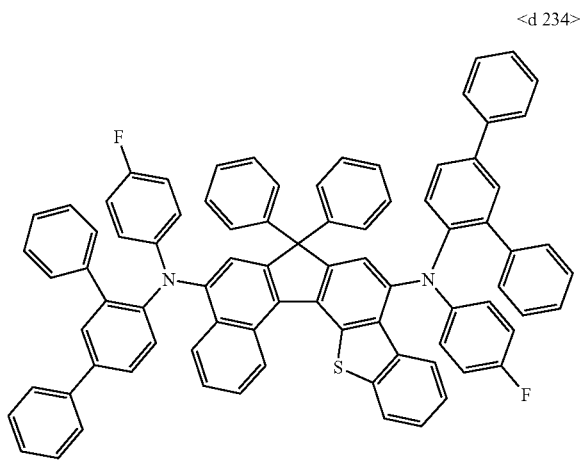
<d 235>
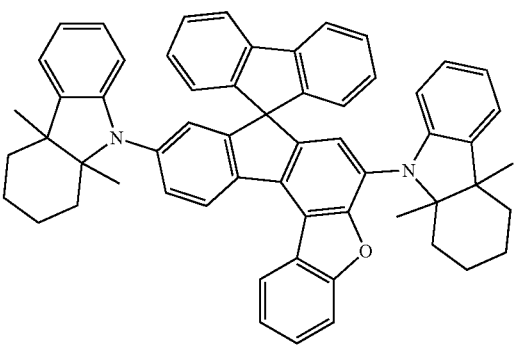
<d 236>
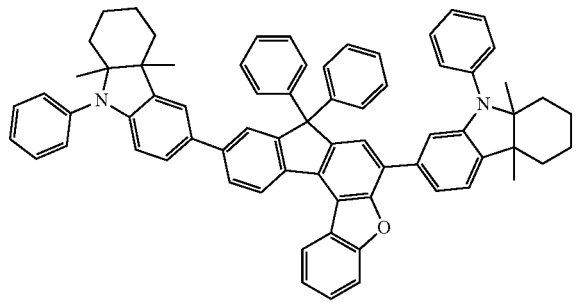
<d 237>
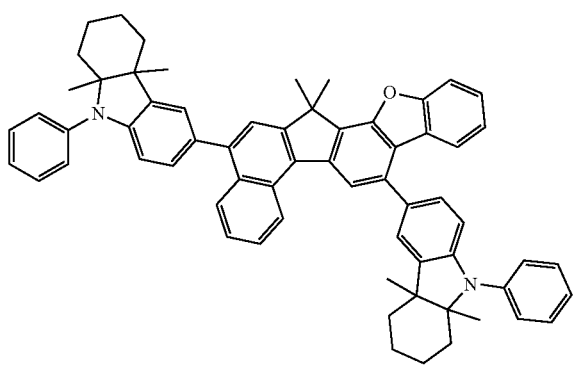

<d 238>
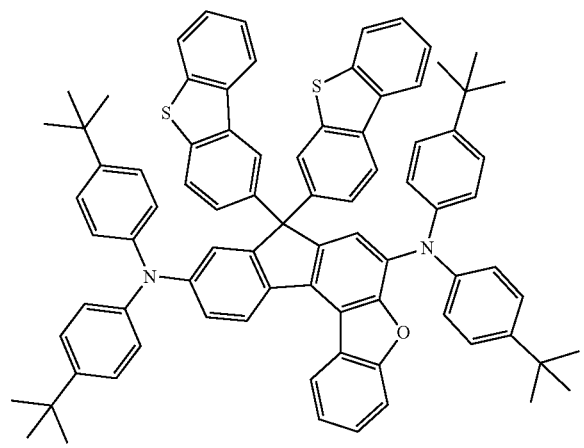
<d 239>
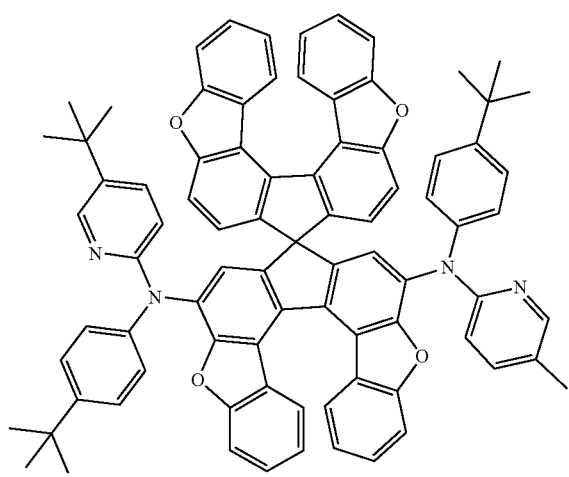
In addition, the compound represented by Chemical Formula D3 may be any one selected from the following <D 101> to <D 130>:
<D 101>
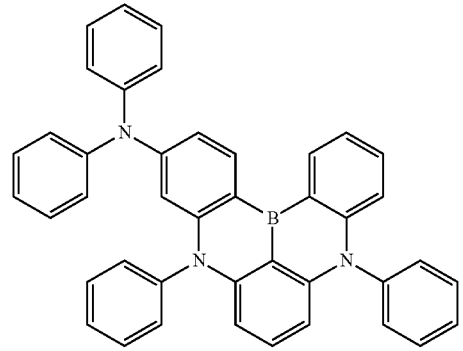
<D 102>
<D 103>
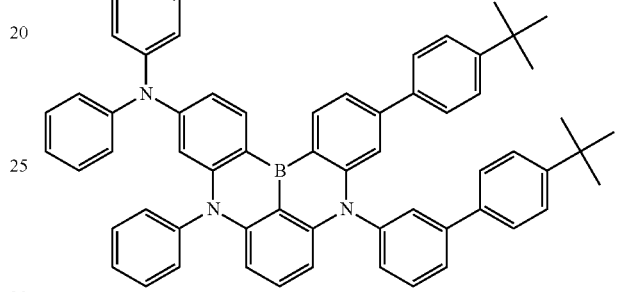
<D 104>
<D 105>
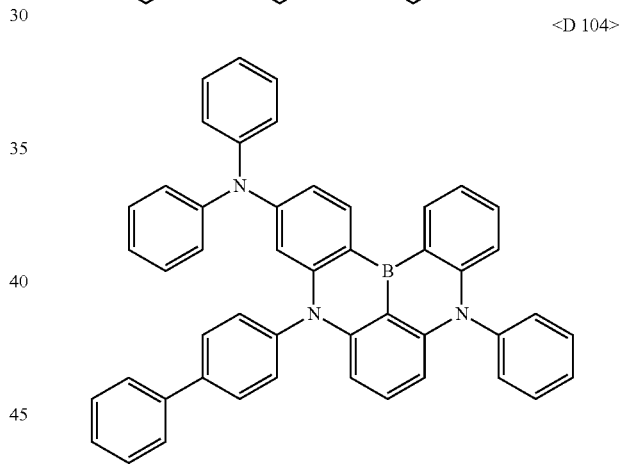
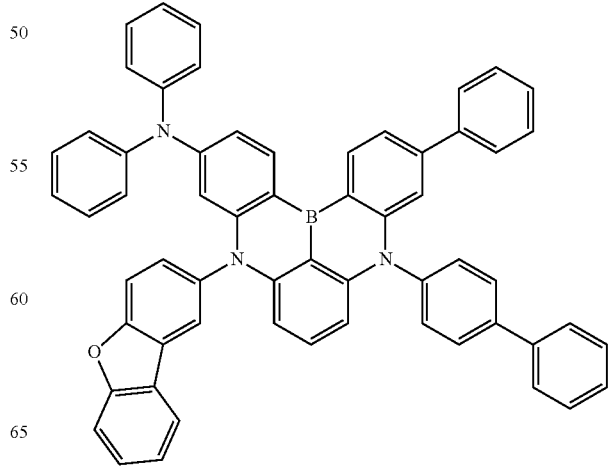

<D 106>
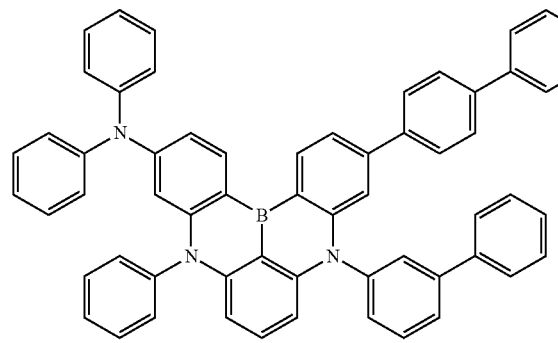
<D 107>
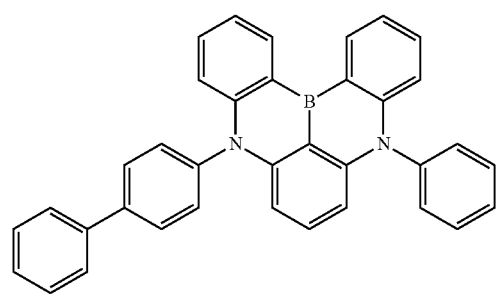
<D 108>
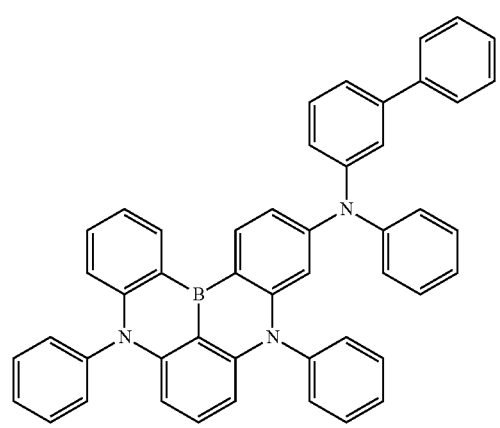
<D 109>
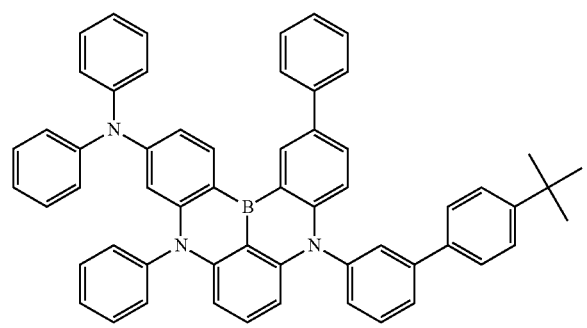
<D 110>
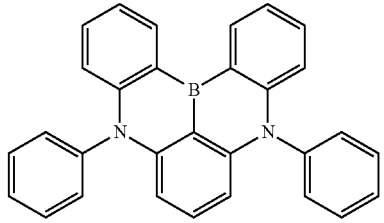
<D 111>
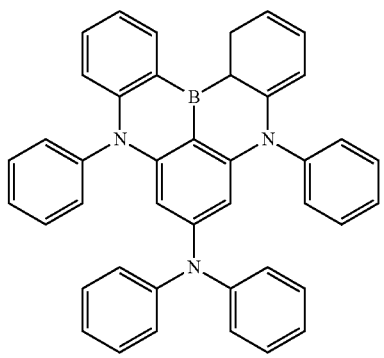
<D 112>
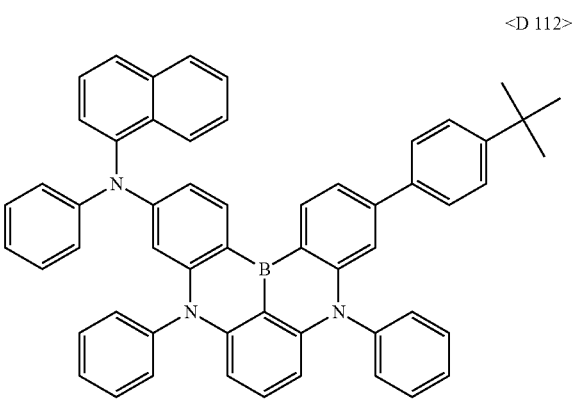
<D 113>
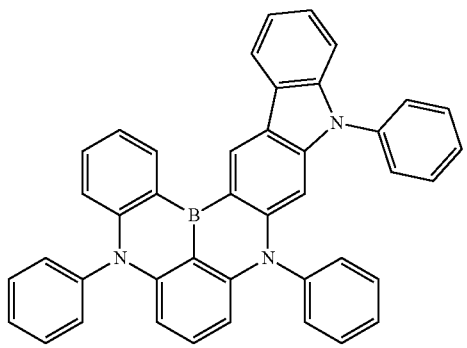

<D 114>
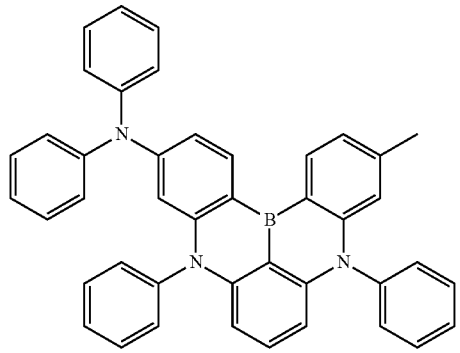
<D 115>
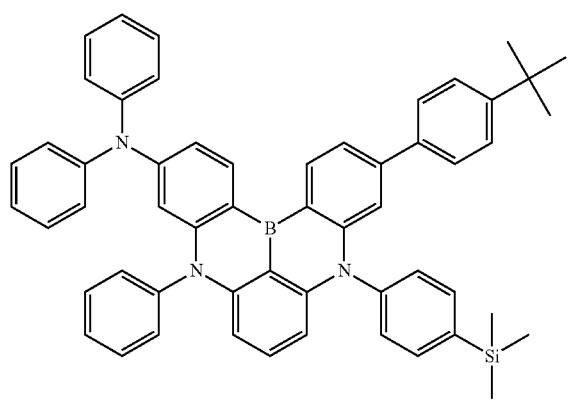
<D 116>
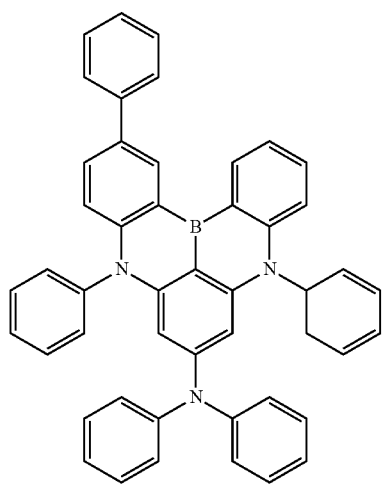
<D 117>
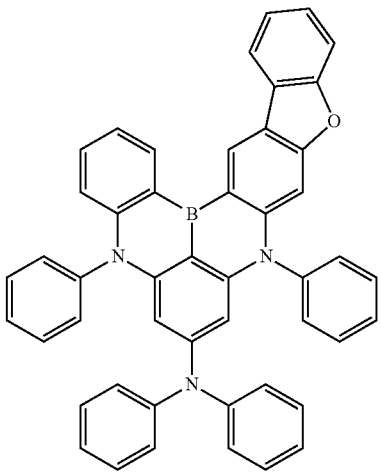
<D 118>
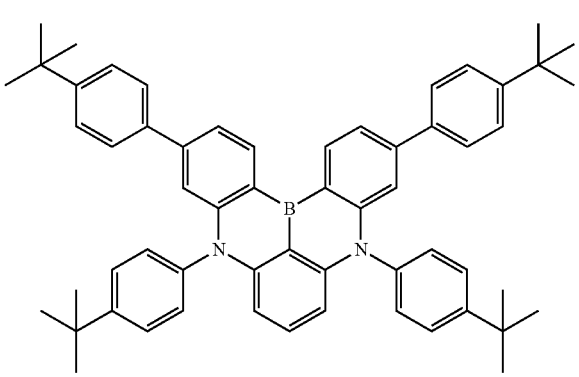
<D 119>
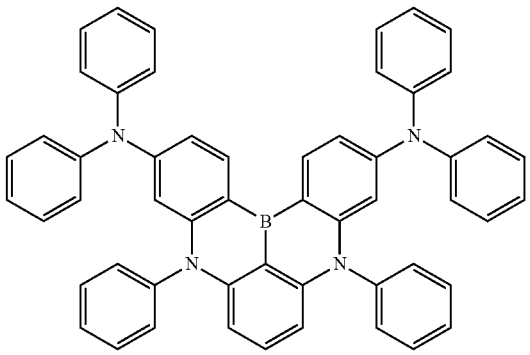

<D120>
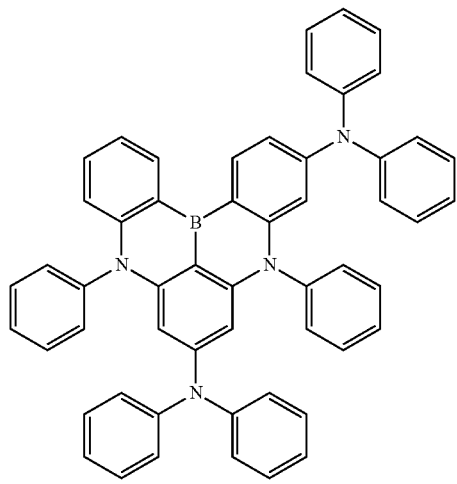
<D121>
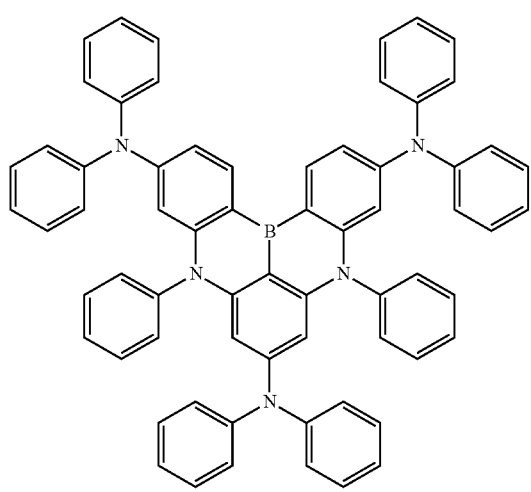
<D122>
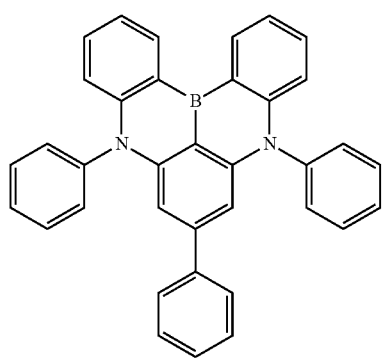
<D123>
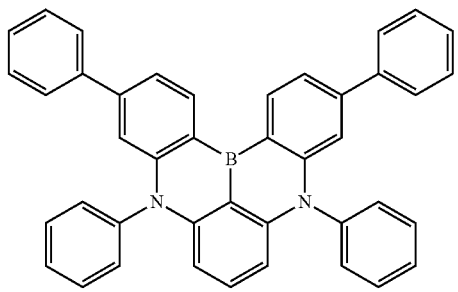
<D124>
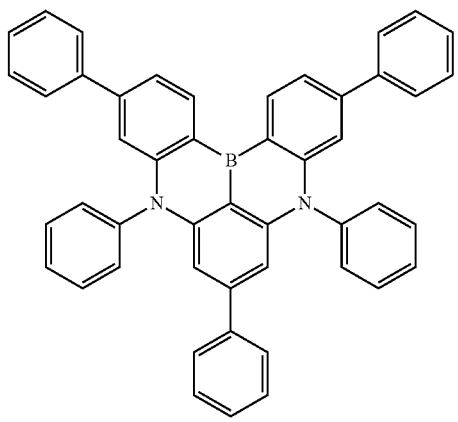
<D125>
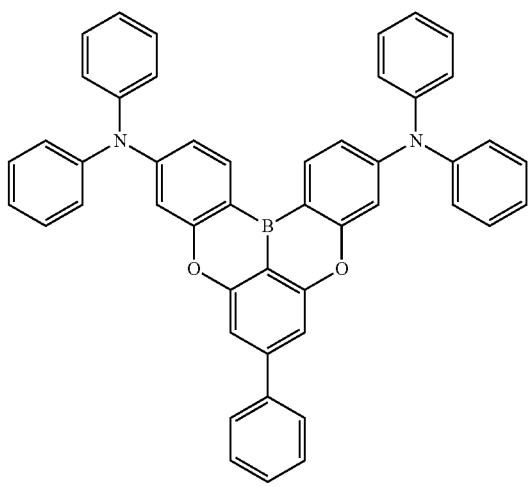

<D 126>
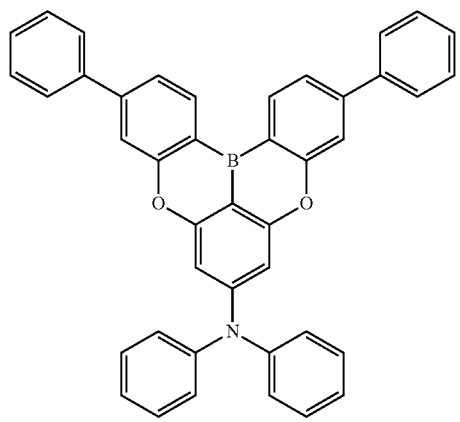
<D 127>
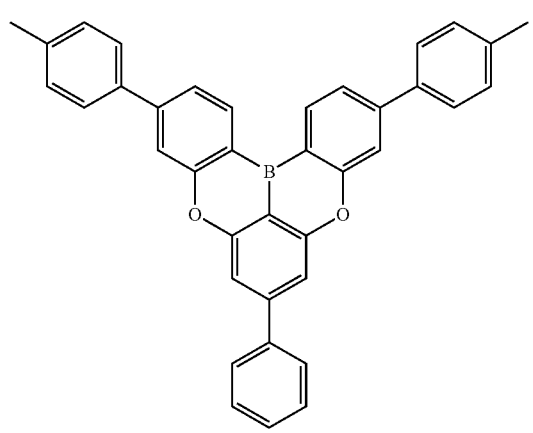
<D 128>
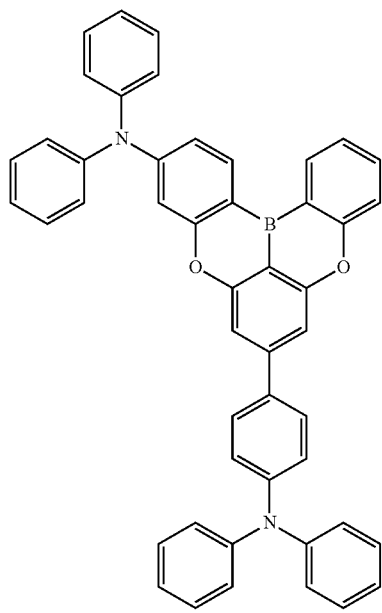
<D 129>
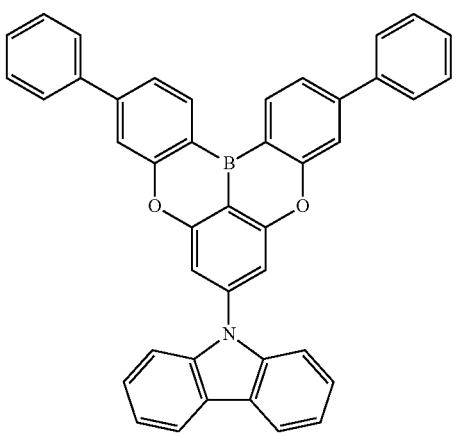
<D 130>
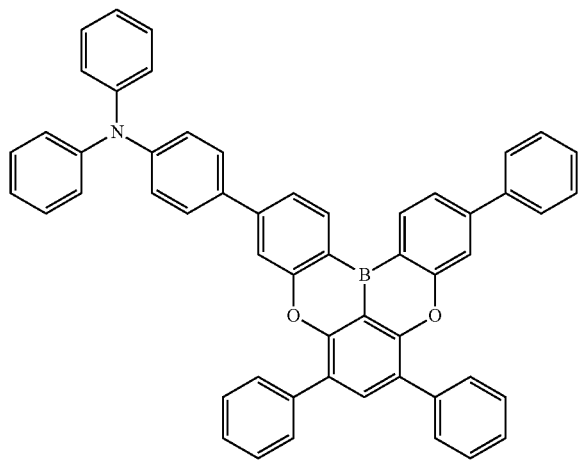
In addition, the compounds represented by Chemical Formulas D4 and D5 may each be any one selected from the following <D 201> to <D 280>:
[D 201]
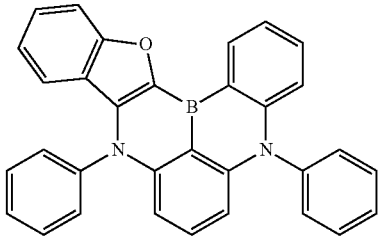
[D 202]
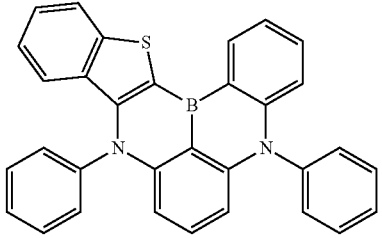

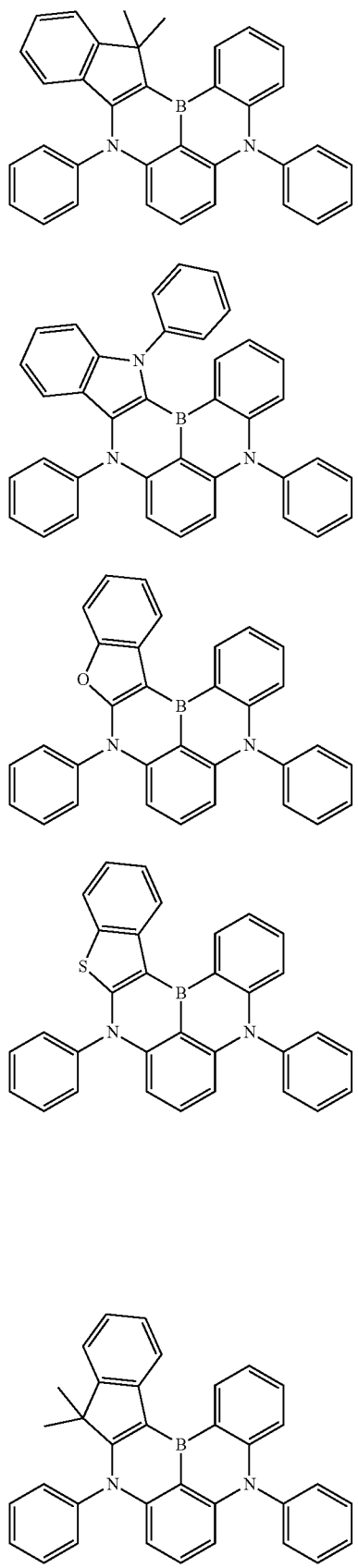
[D 203]
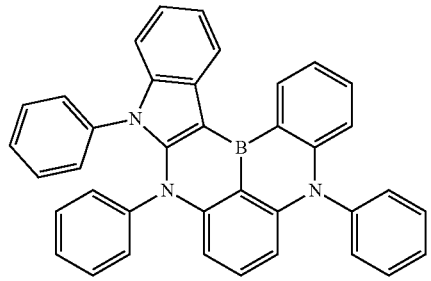
[D 204]
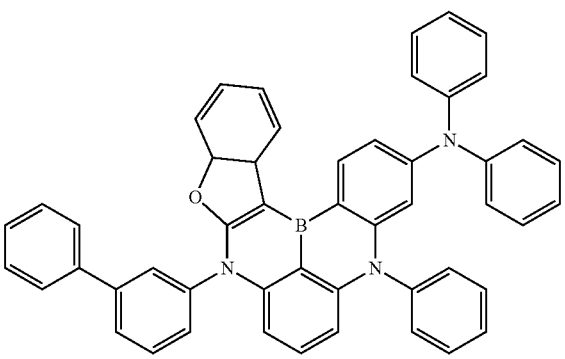
[D 205]
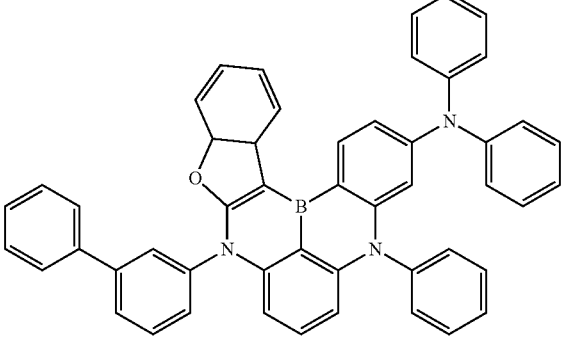
[D 206]
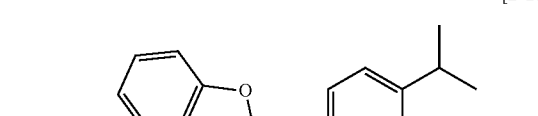
[D 207]
[D 208]
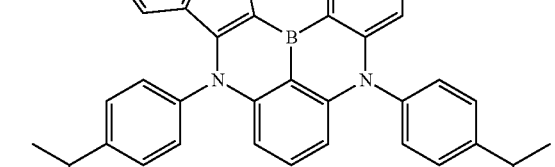
[D 209]
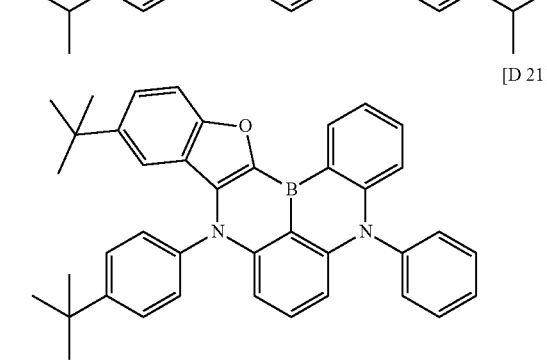
[D 210]
[D 211]
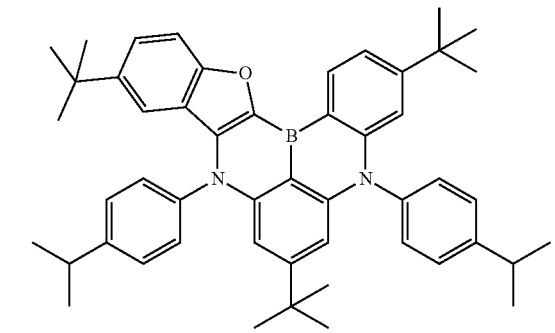
[D 212]

[D 213]
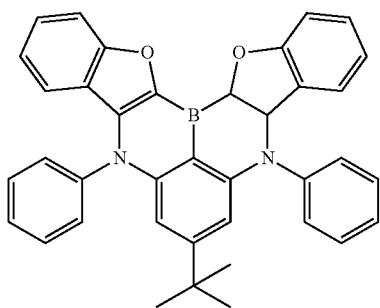
[D 214]
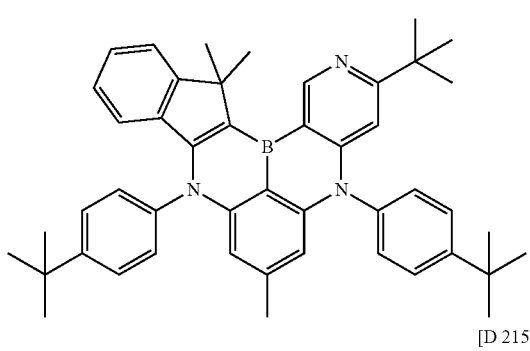
[D 215]
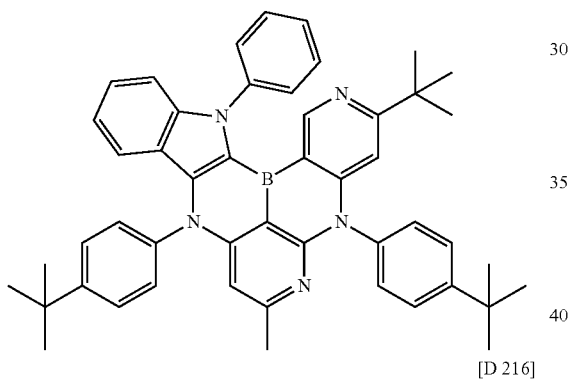
[D 216]
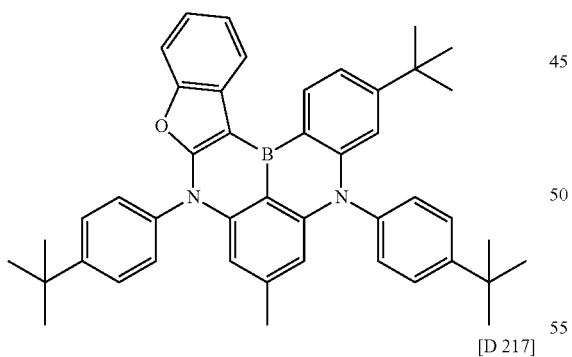
[D 217]
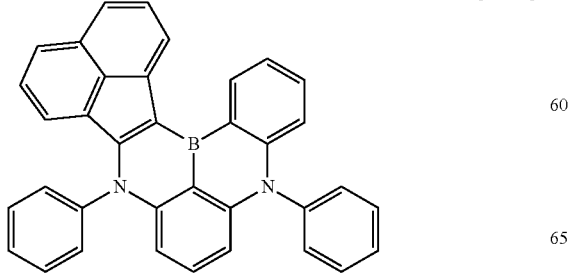
[D 218]
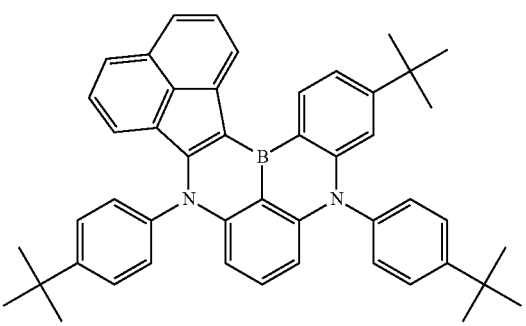
[D 219]
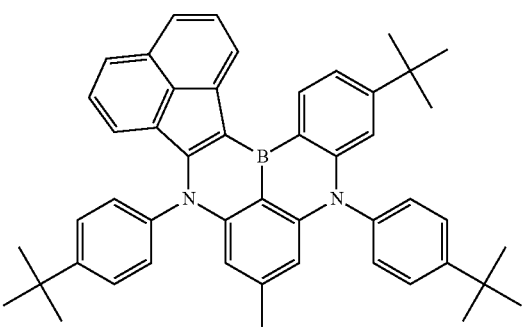
[D 220]
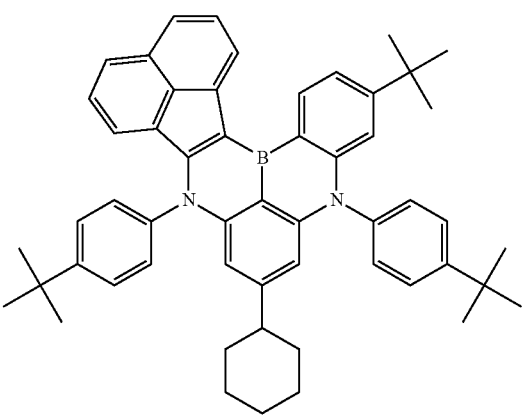
[D 221]
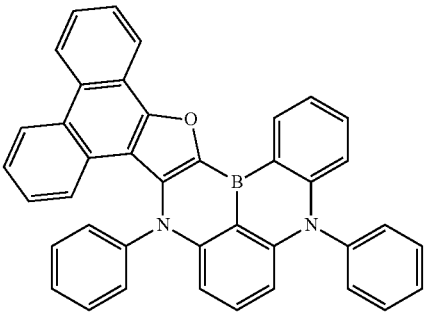

[D 222]
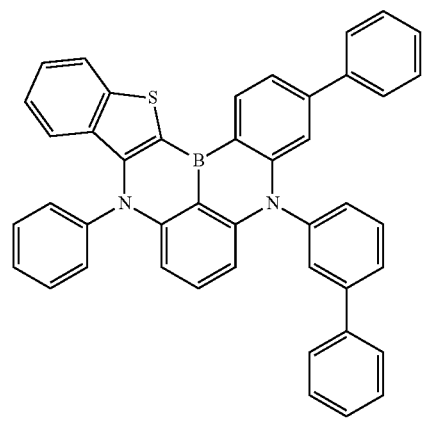
[D 223]
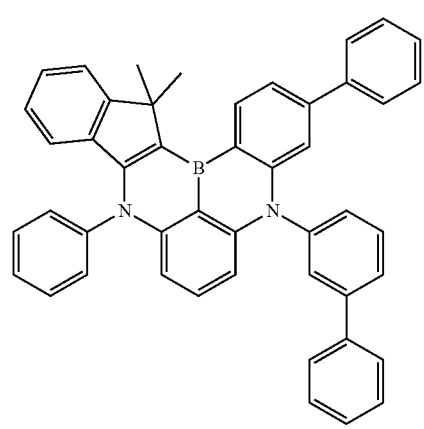
[D 224]
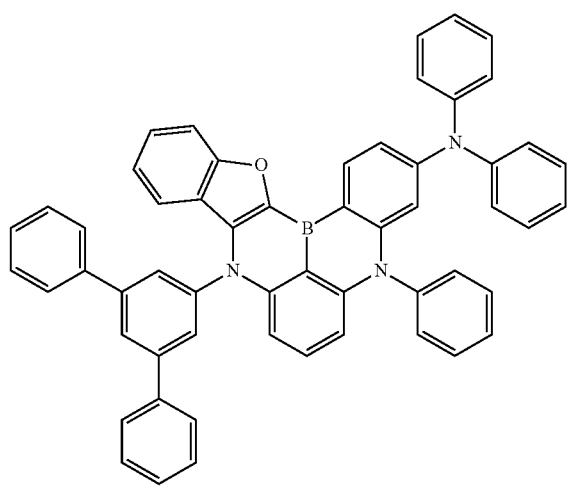
[D 225]
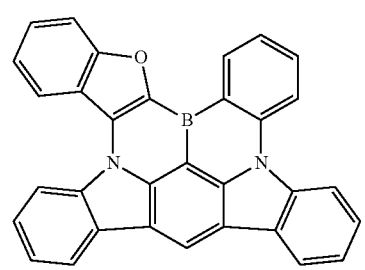
[D 226]
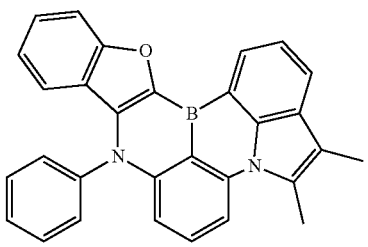
[D 227]
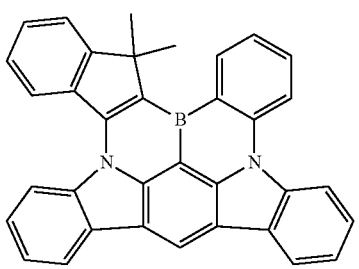
[D 228]
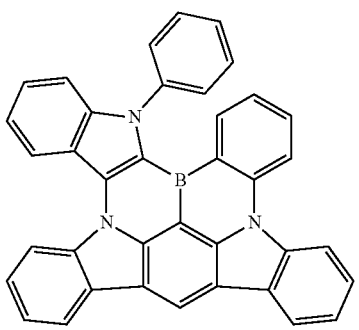
[D 229]
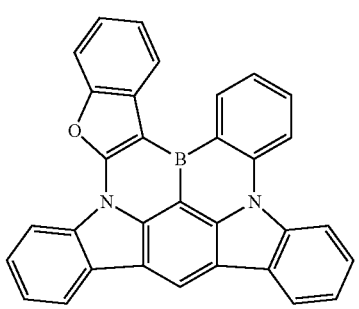
[D 230]
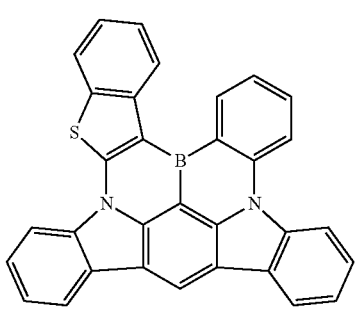

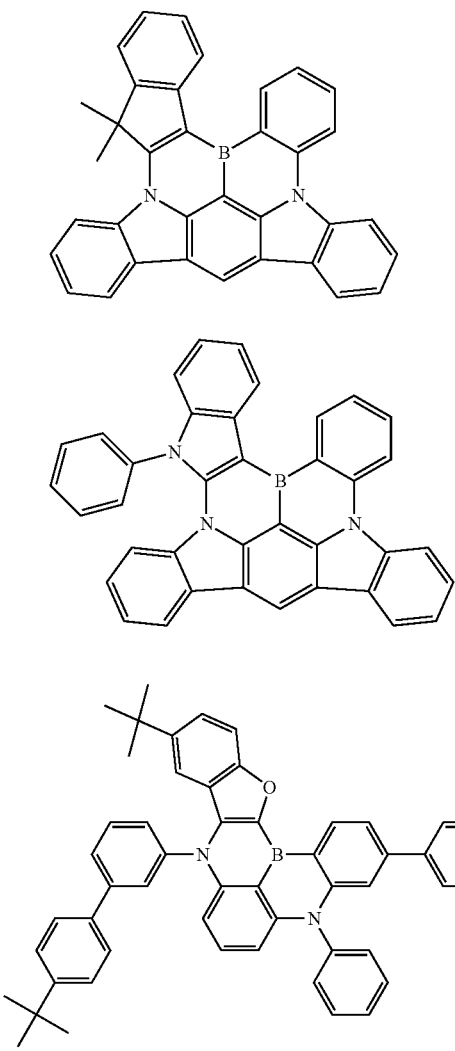
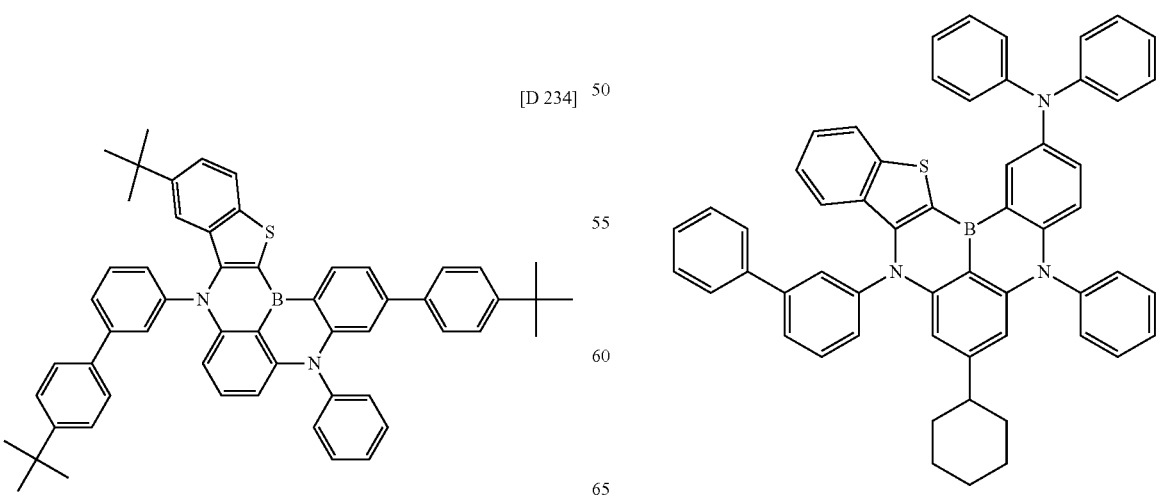

[D 238]
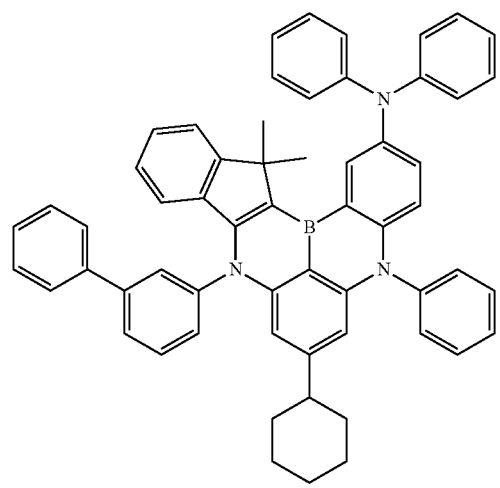
[D 239]
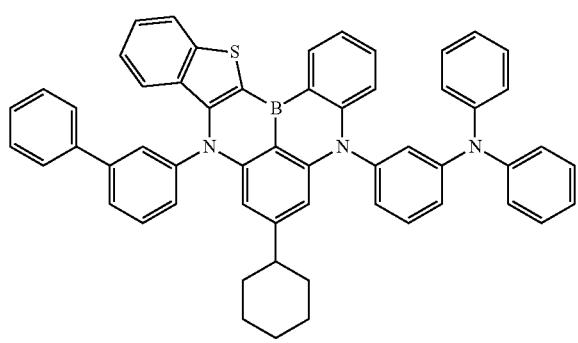
[D 240]
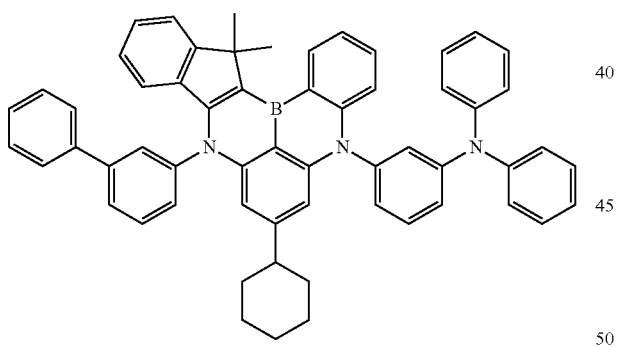
[D 241]
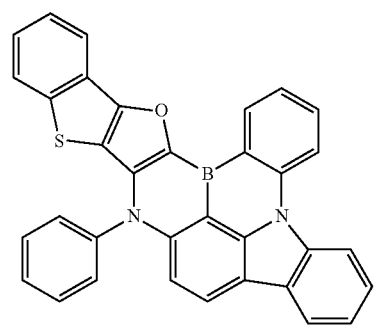
[D 242]
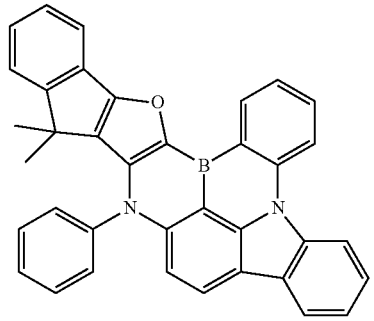
[D 243]
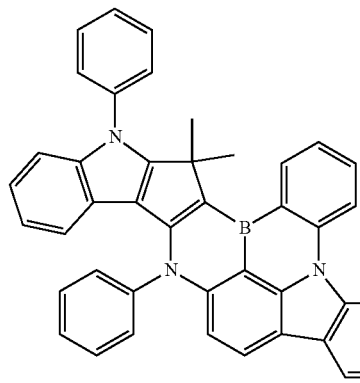
[D 244]
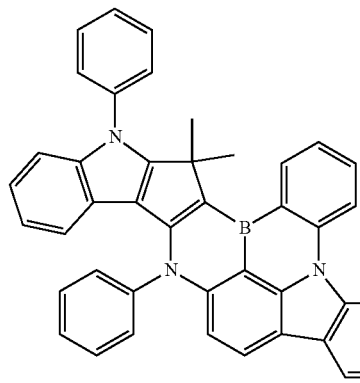
[D 245]
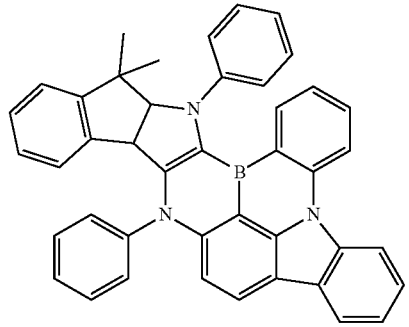
[D 246]
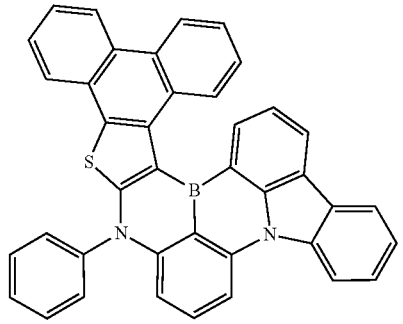

-continued
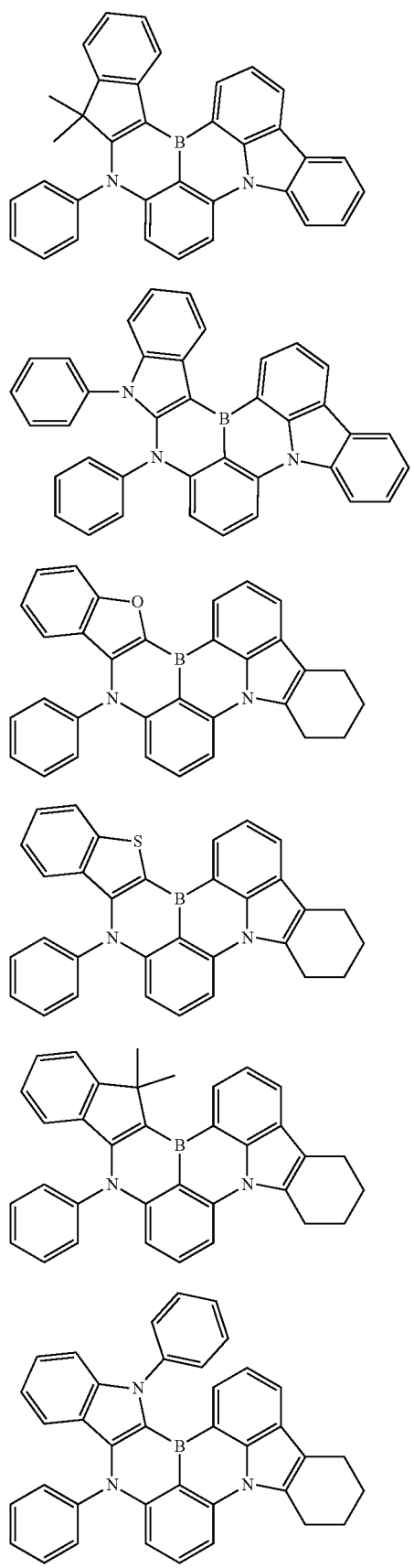
[D 247]
[D 248]
[D 249]
[D 250]
[D 251]
[D 252]
-continued
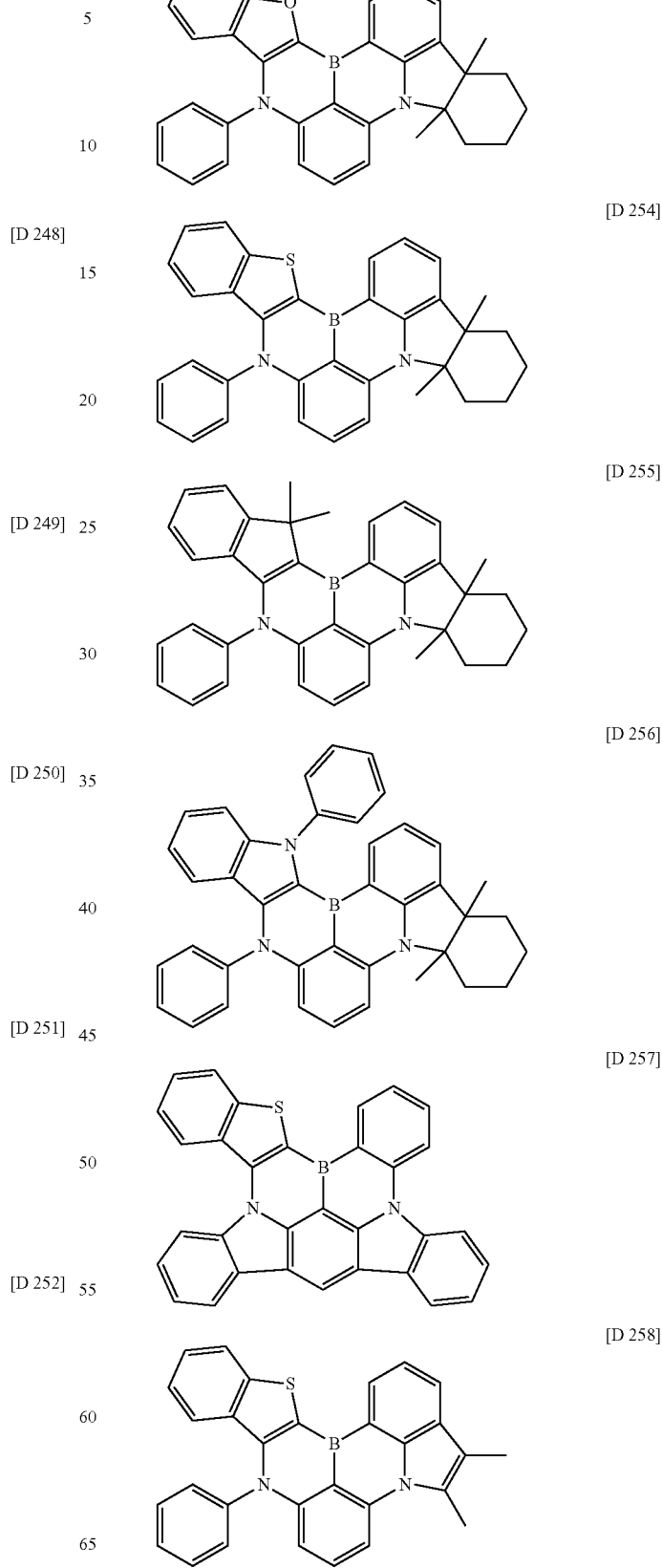
[D 253]
[D 254]
[D 255]
[D 256]
[D 257]
[D 258]

-continued
[D 259]
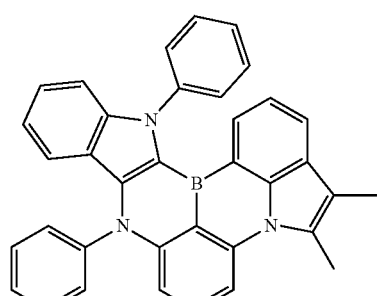
[D 260]
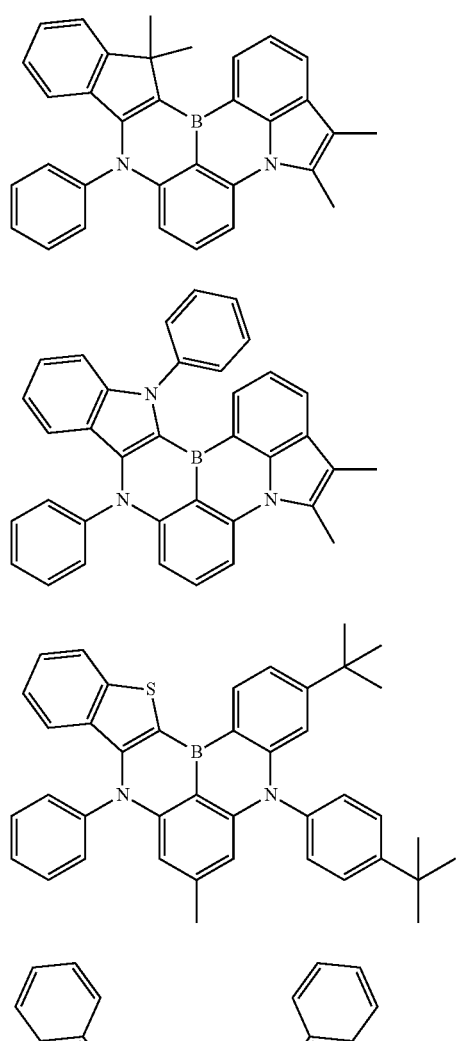
[D 261]
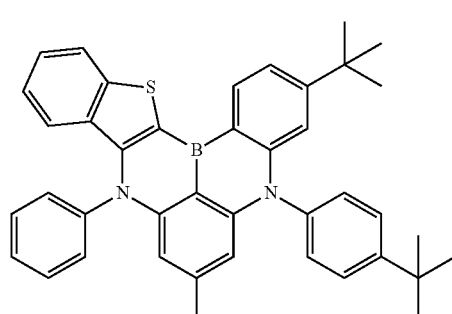
[D 262]
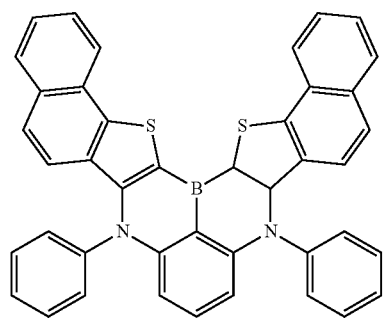
[D 263]
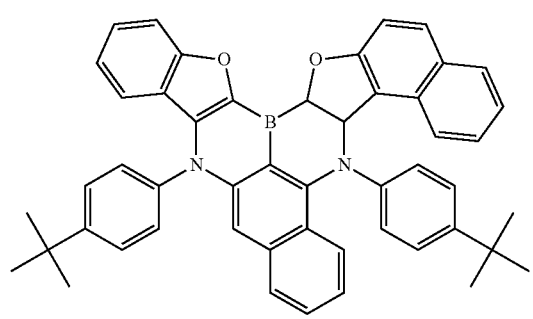
-continued
[D 264]
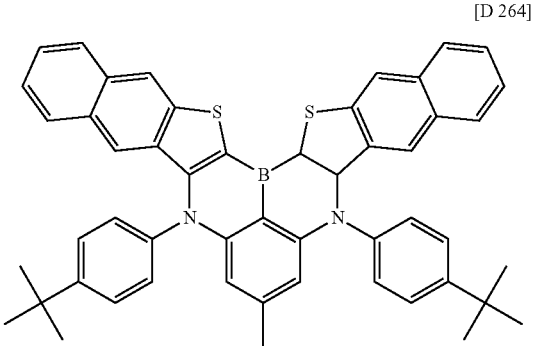
[D 265]
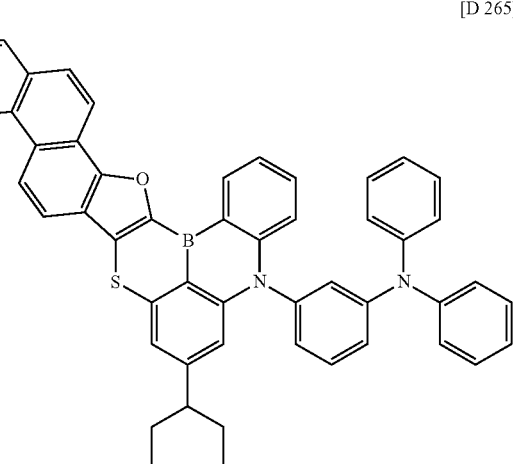
[D 266]
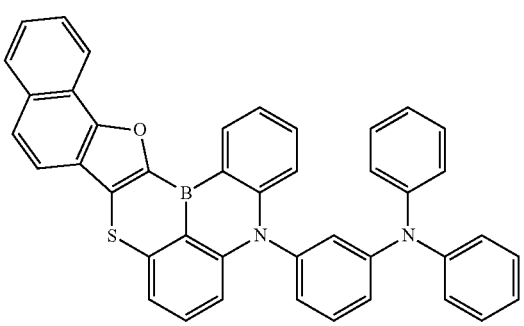
[D 267]
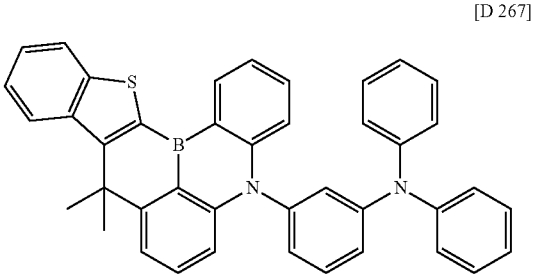

[D 268]
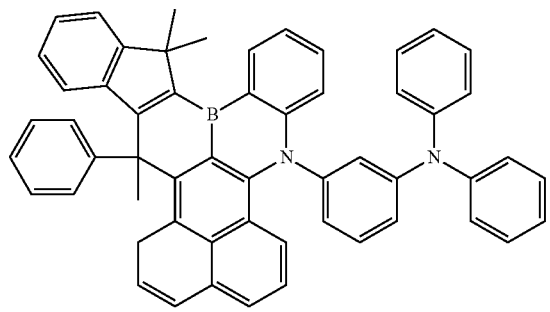
[D 269]
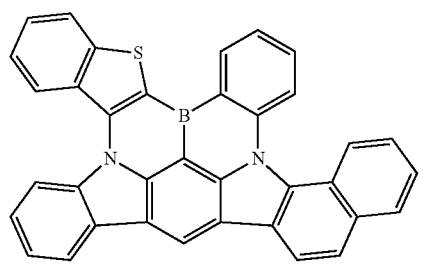
[D 270]
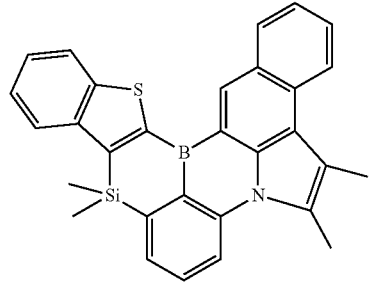
[D 271]
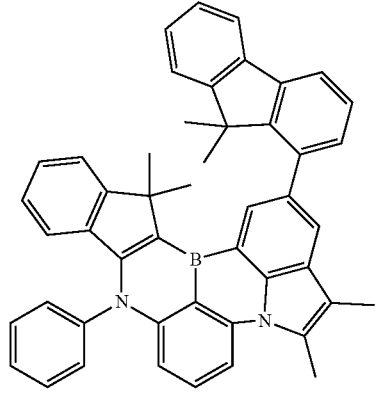
[D 272]
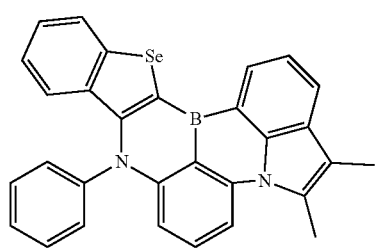
[D 273]
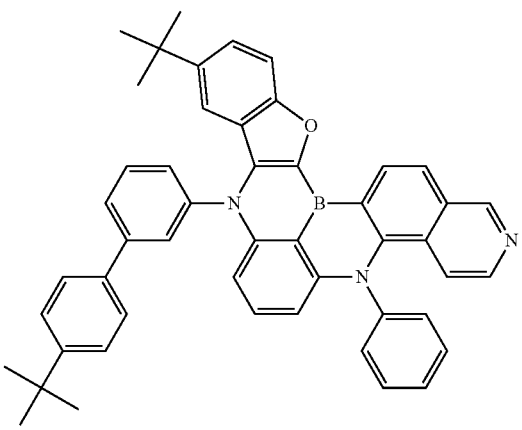
[D 274]
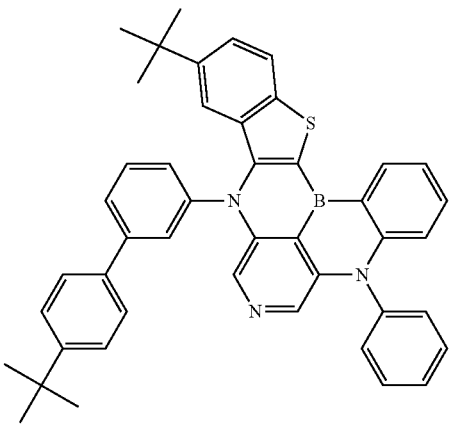
[D 275]
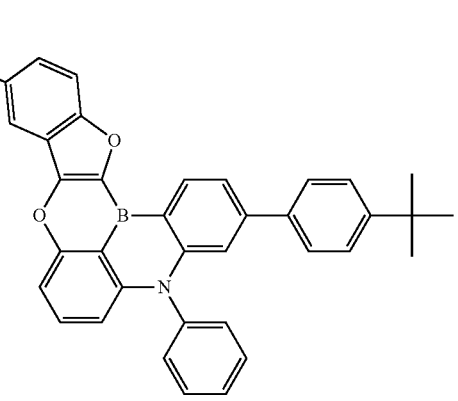

[D 276]
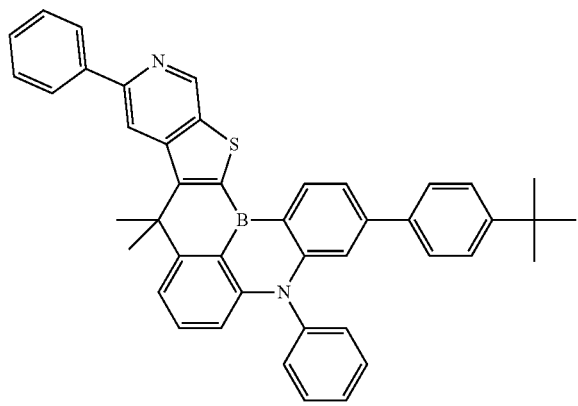
[D 277]
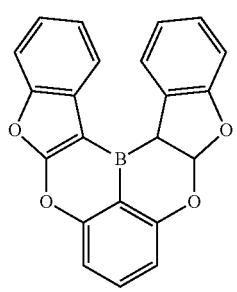
[D 278]
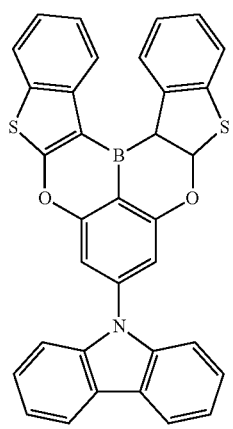
[D 279]
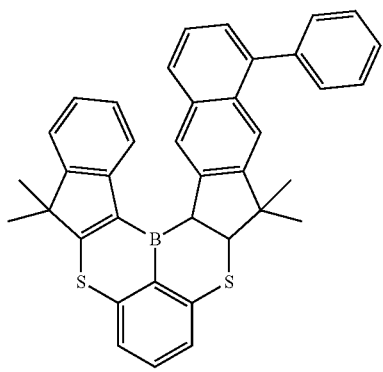
[D 280]
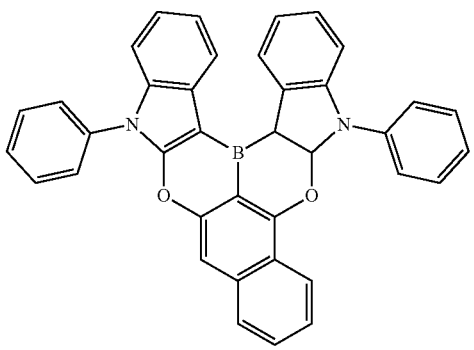
In addition, the compounds represented by Chemical Formulas D6 and D7 may each be any one selected from the following <D 301> to <D 387>:
<D 301>
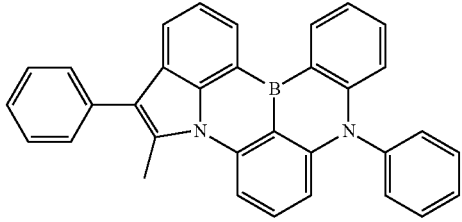
<D 302>
<D 303>
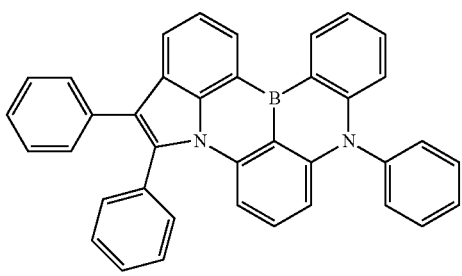
<D 304>
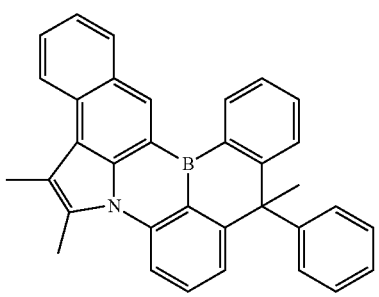

<D 305>
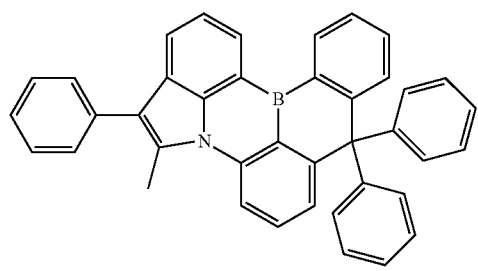
<D 306>
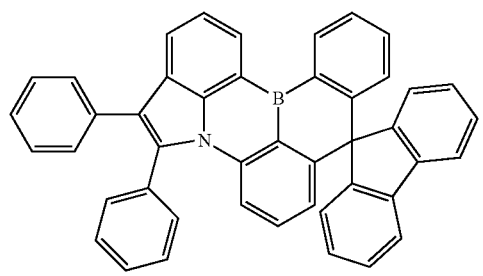
<D 307>
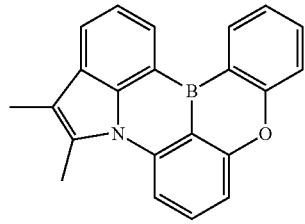
<D 308>
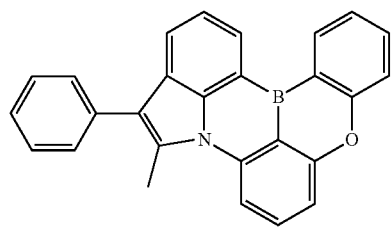
<D 309>
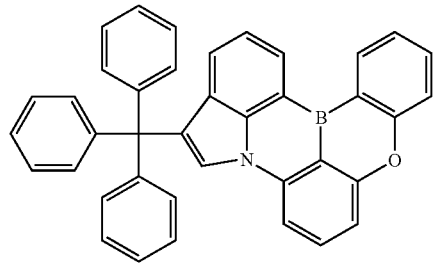
<D 310>
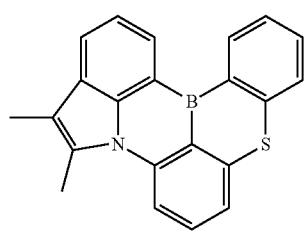
<D 311>
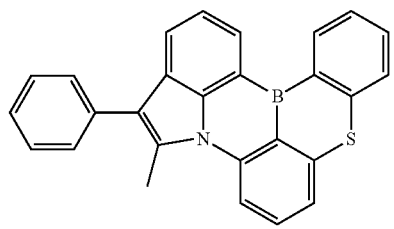
<D 312>
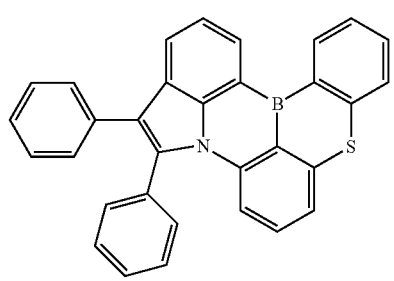
<D 313>
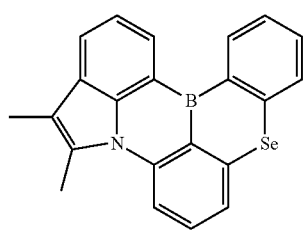
<D 314>
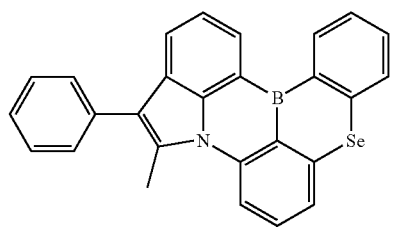
<D 315>
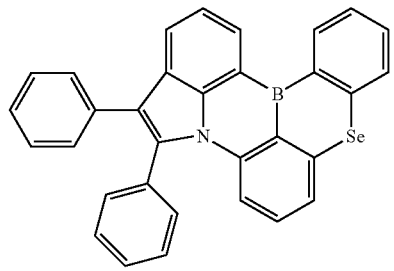
<D 316>
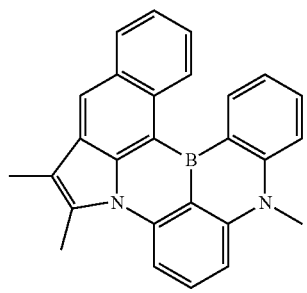

<D 317>
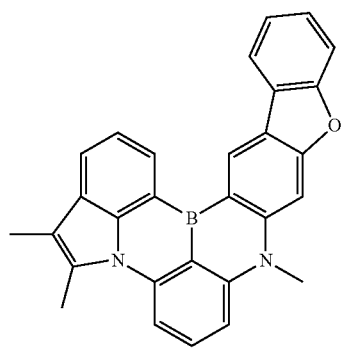
<D 318>
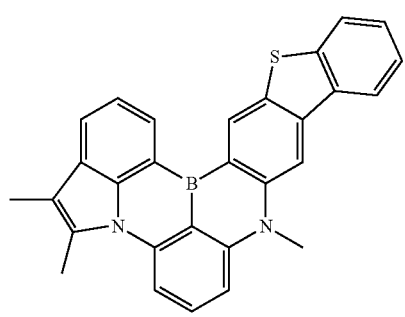
<D 319>
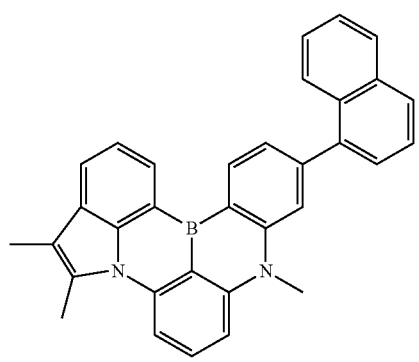
<D 320>
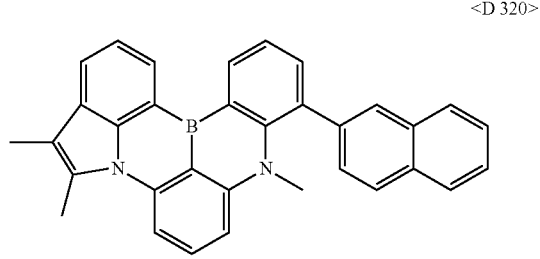
<D 321>
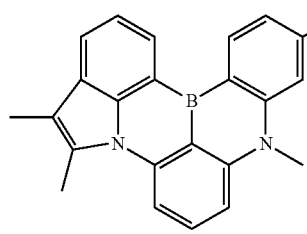
<D 322>
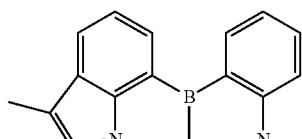
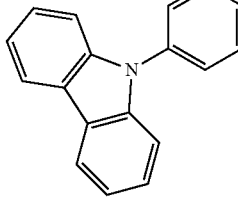
<D 323>
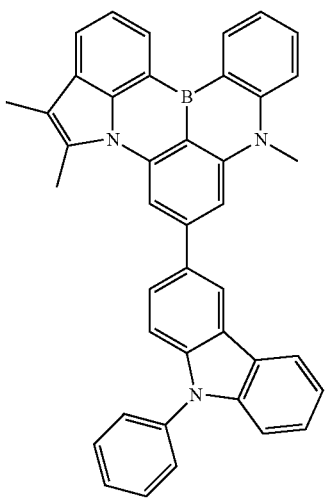
<D 324>
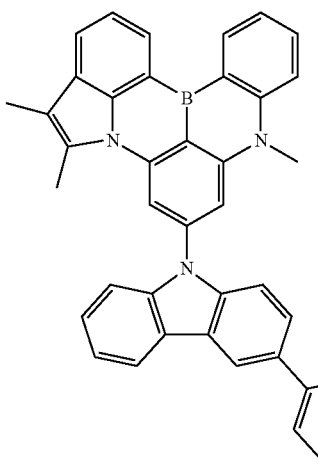

<D 325>
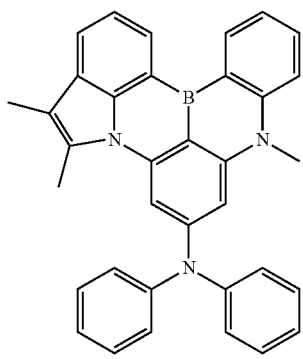
<D 326>
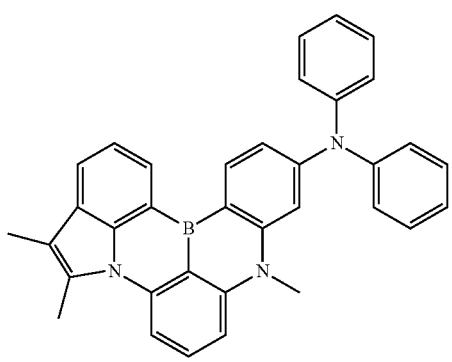
<D 327>
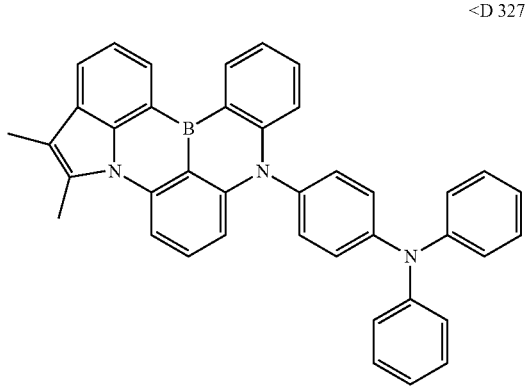
<D 328>
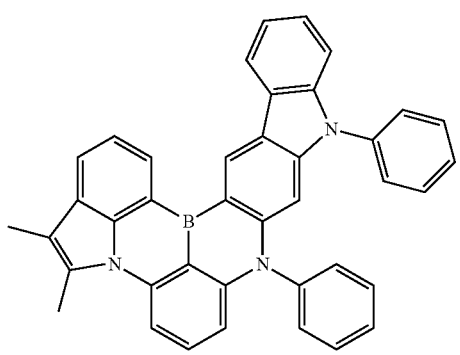
<D 329>
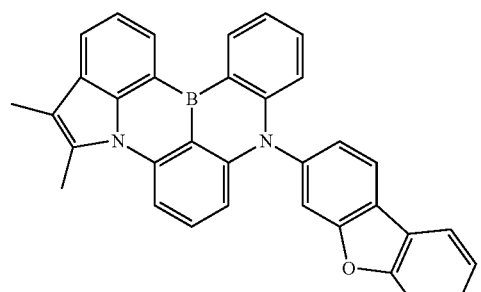
<D 330>
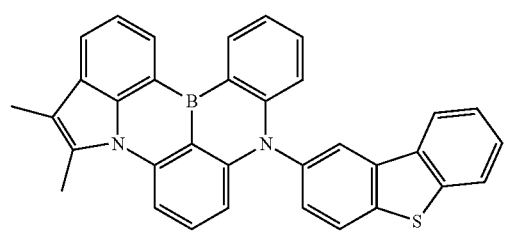
<D 331>
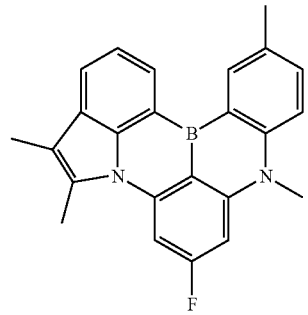
<D 332>
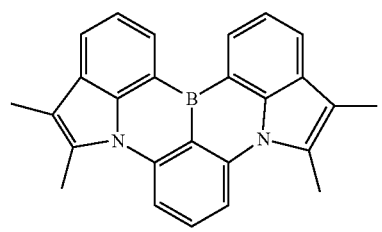
<D 333>
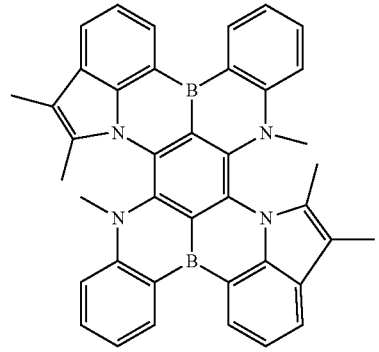

-continued
<D 334>
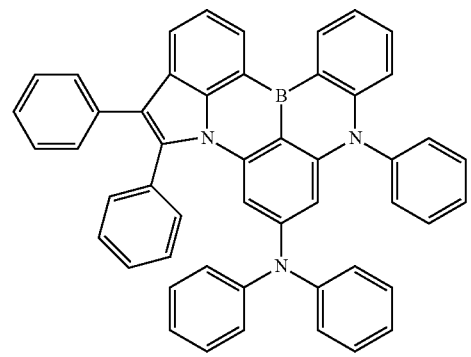
<D 335>
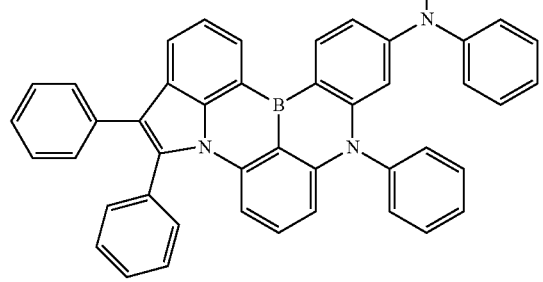
<D 336>
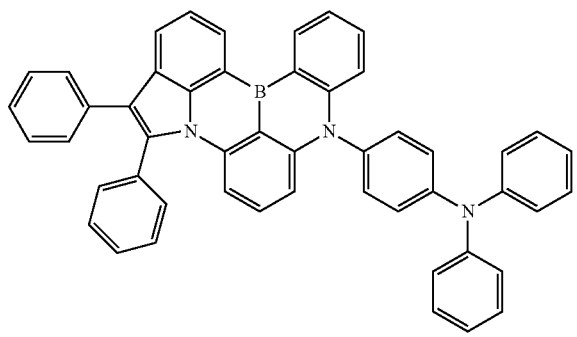
<D 337>
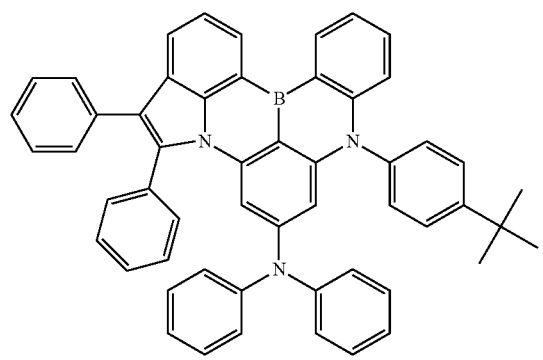
<D 338>
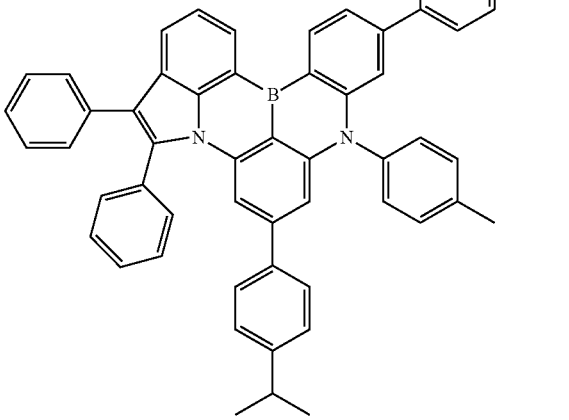
<D 339>
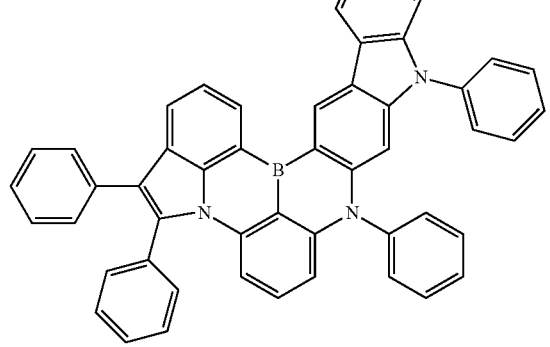
<D 340>
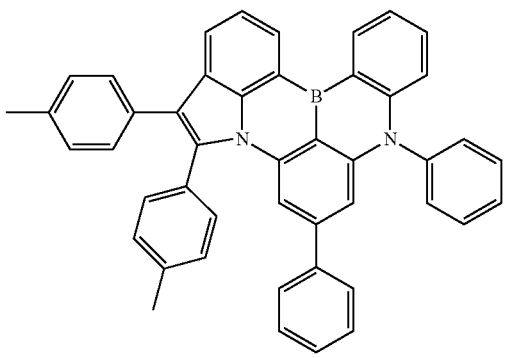

<D 341>
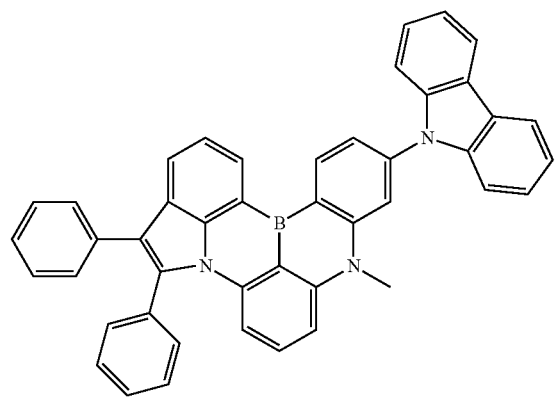
<D 342>
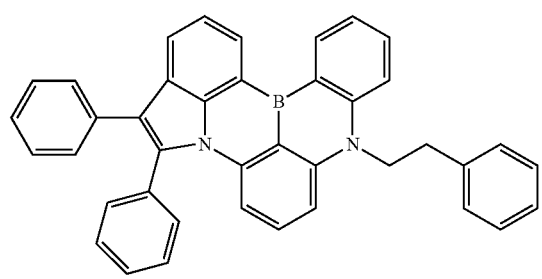
<D 343>
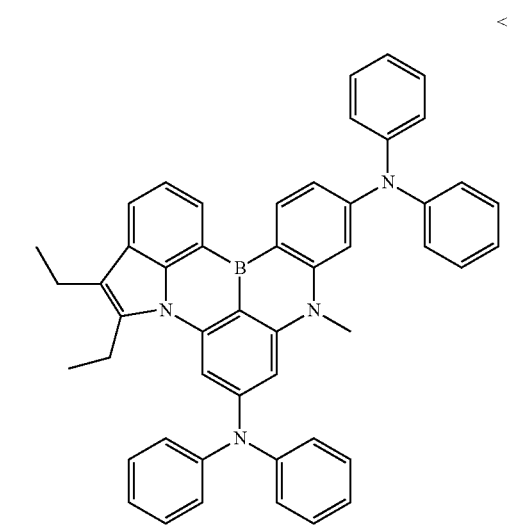
<D 344>
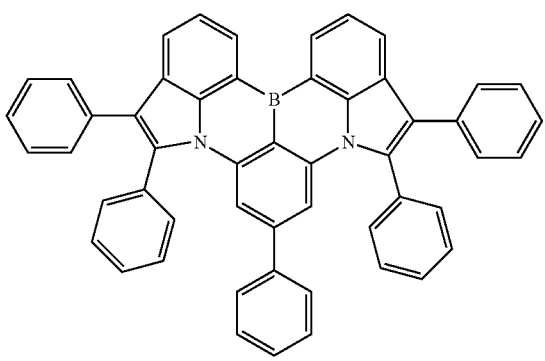
<D 345>
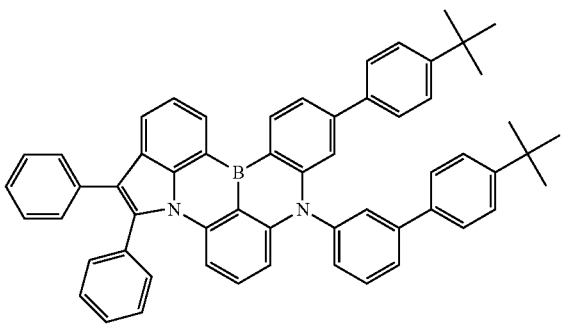
<D 346>
<D 347>
<D 348>
<D 349>

<D 350>
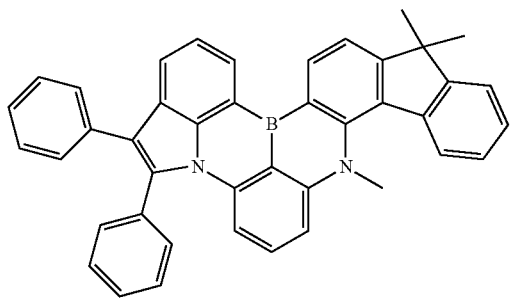
<D 351>
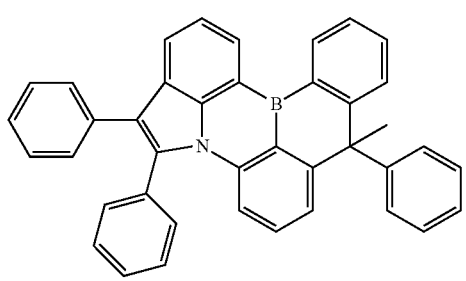
<D 352>
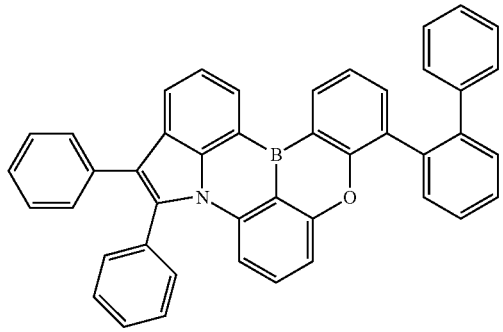
<D 353>
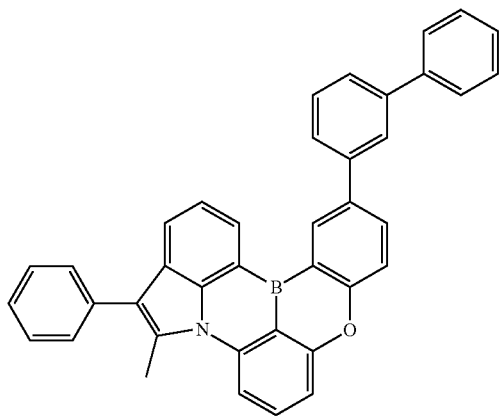
<D 354>
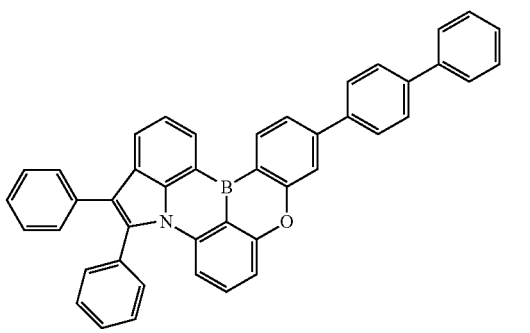
<D 355>
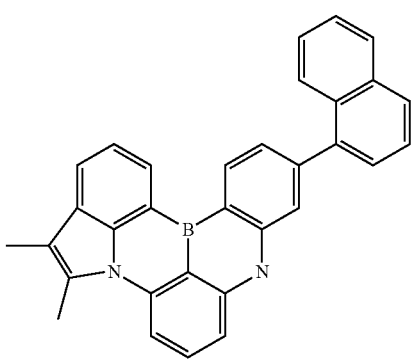
<D 356>
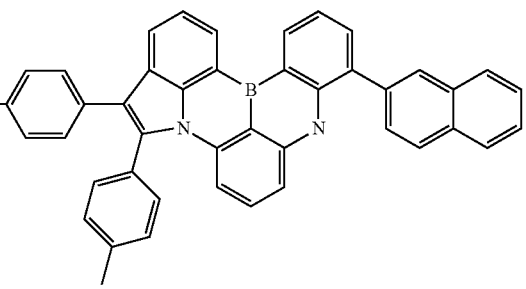
<D 357>
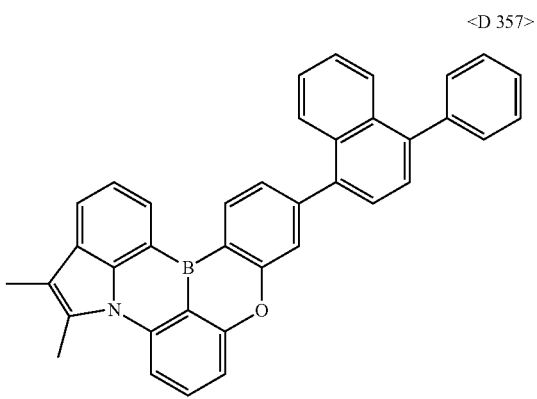

-continued
<D 358>
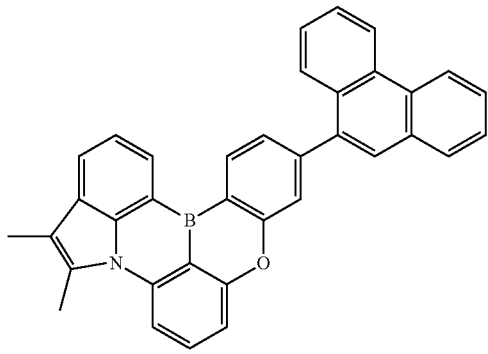
<D 359>
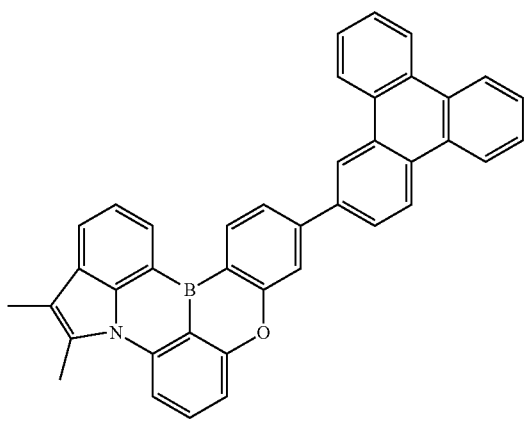
<D 360>
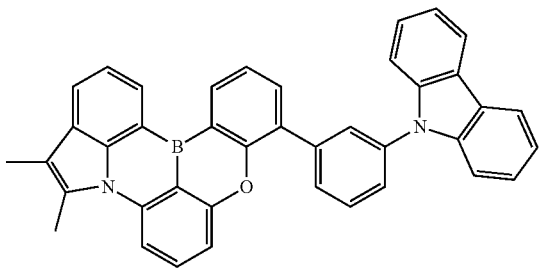
<D 361>
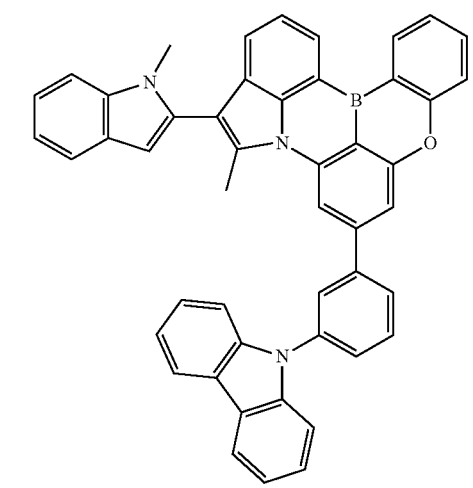
-continued
<D 362>
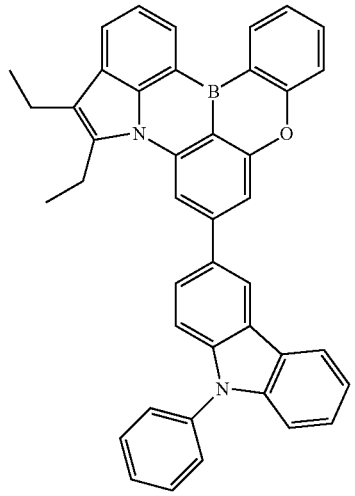
<D 363>
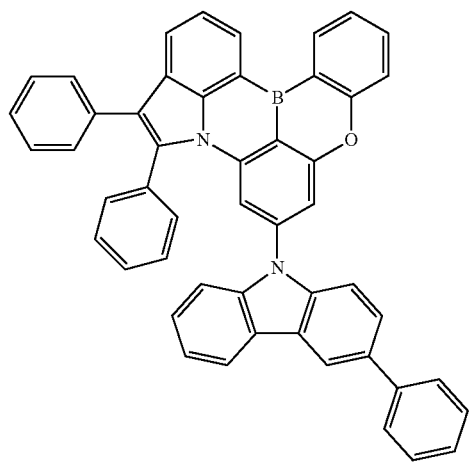
<D 364>
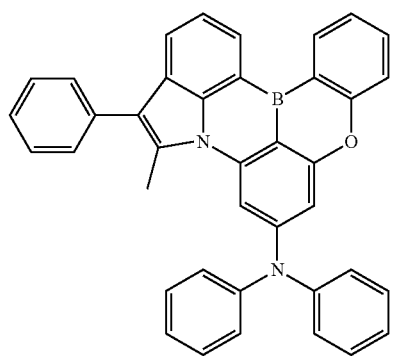

<D 365>
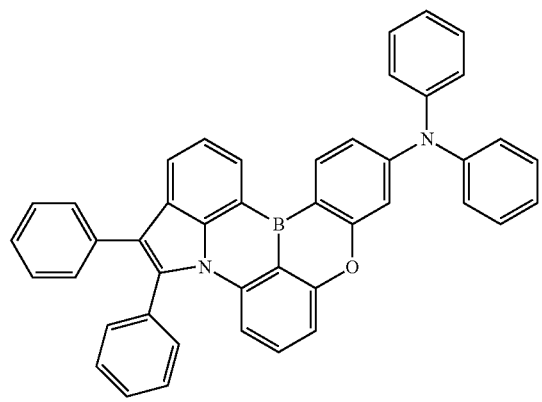
<D 366>
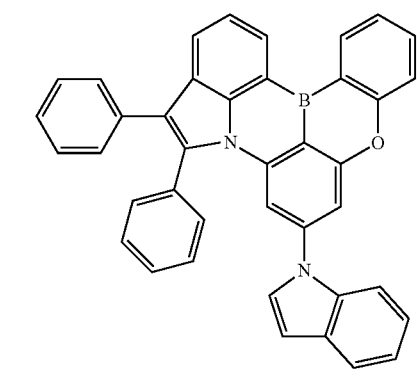
<D 367>
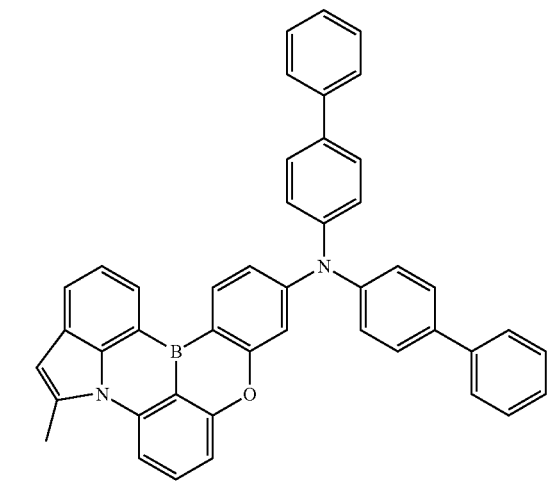
<D 368>
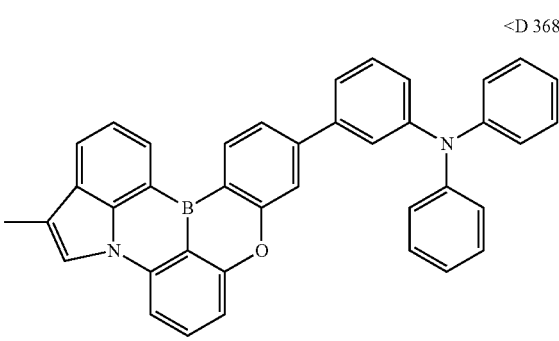
<D 368>
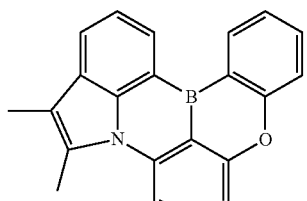
<D 369>
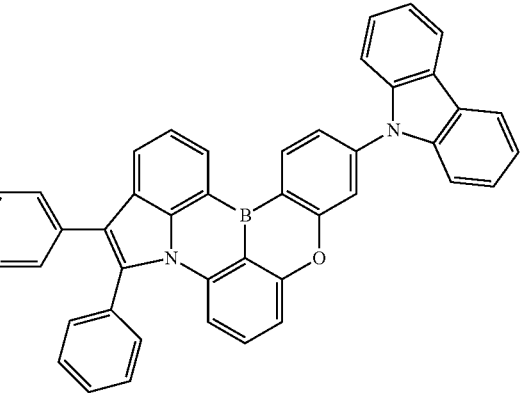
<D 370>
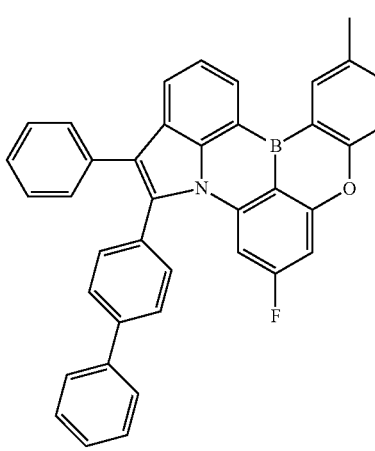
<D 371>
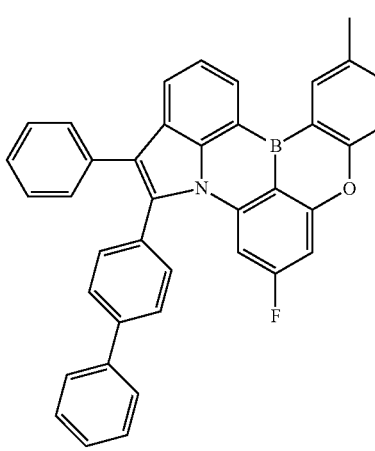

<D 372>
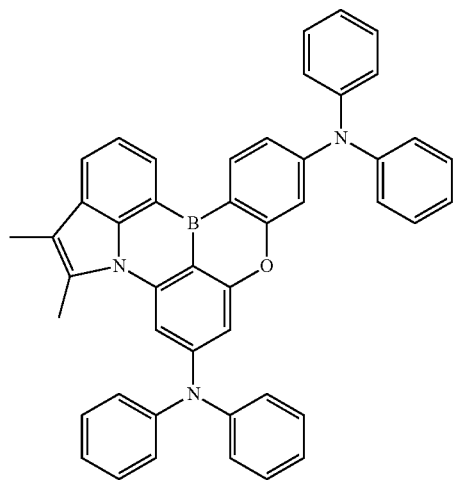
<D 373>
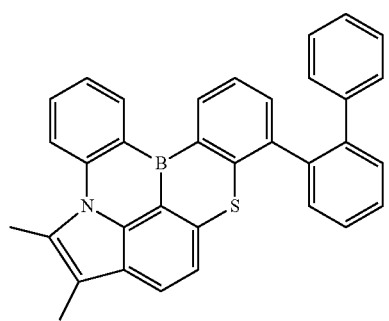
<D 374>
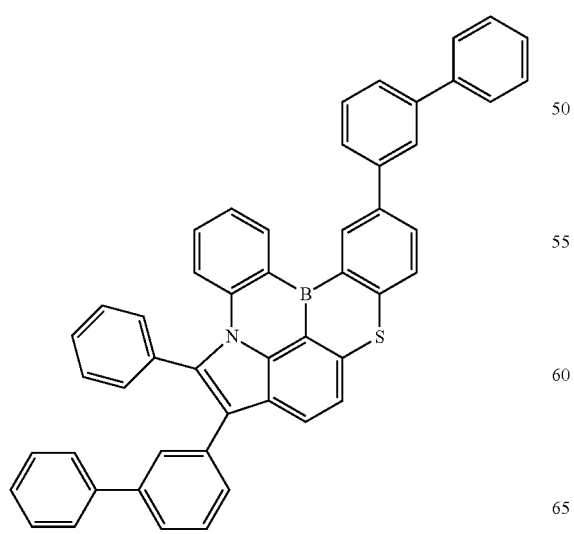
<D 375>
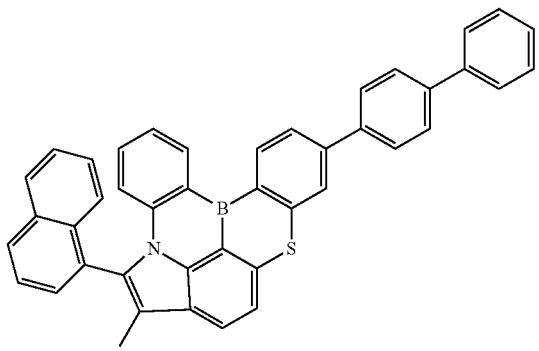
<D 376>
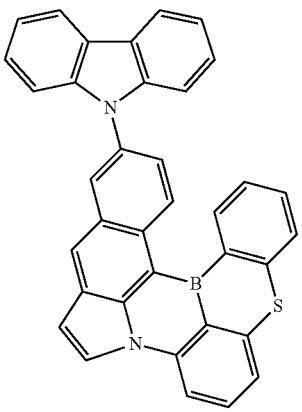
<D 377>
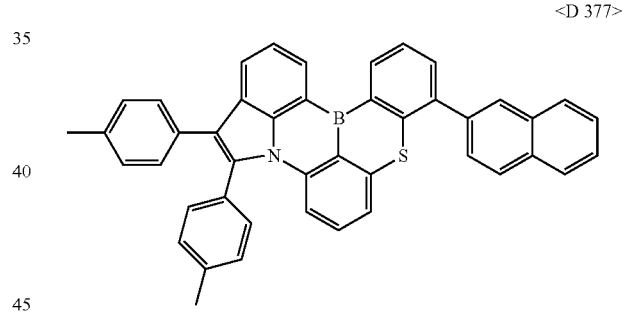
<D 378>
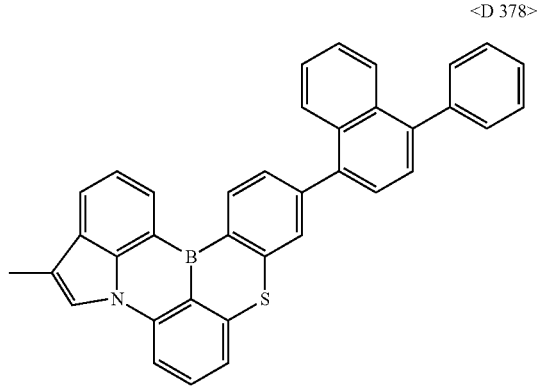

<D 379>
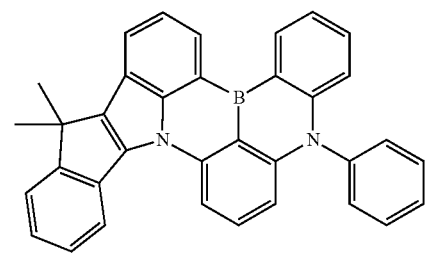
<D 380>
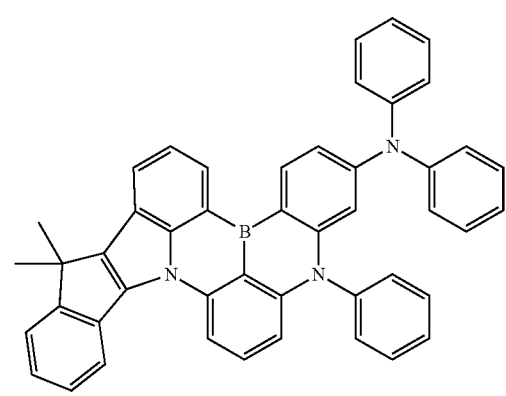
<D 381>
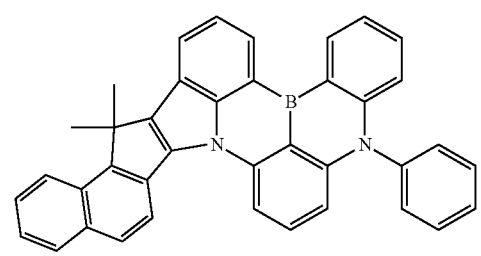
<D 382>
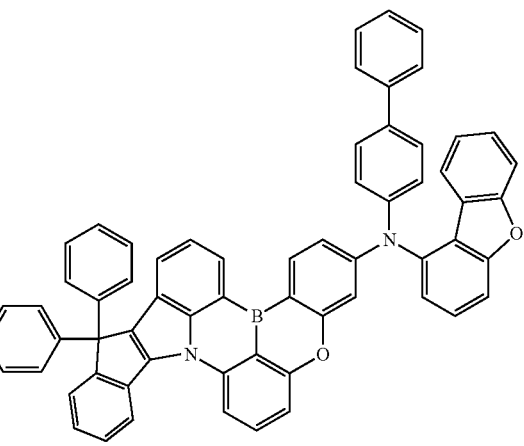
<D 383>
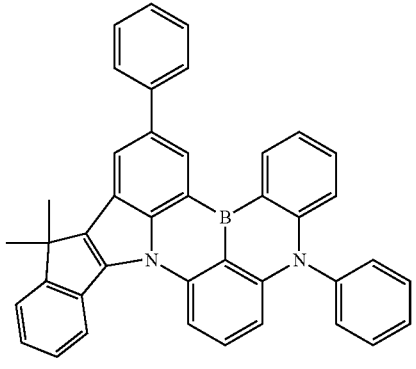
<D 384>
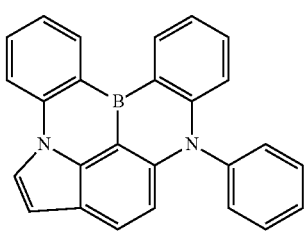
<D 385>
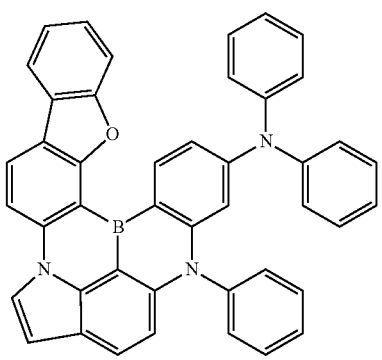
<D 386>
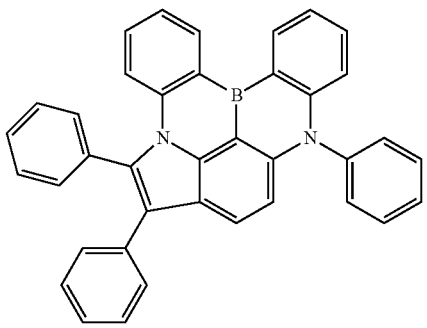
<D 387>
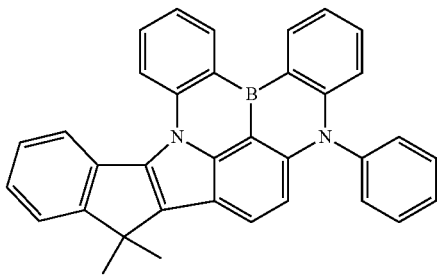
After being deposited on the light-emitting layer by deposition in a vacuum and spin coating, the electron transport layer 60 is covered with the electron injection layer 70. A cathode metal is deposited on the electron injection layer 70 by thermal vacuum deposition to form the cathode 80, thus obtaining an organic light-emitting diode.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum (Alq$_3$), Liq, TAZ, BAlq, beryllium bis(benzoquinolin-10-olate) (Bebq$_2$), AND, Compound 201, Compound 202, BCP, and oxadiazole derivatives such as PBD, BMD, and BND, but are not limited thereto:

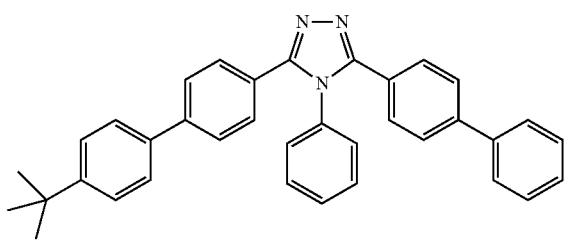

TAZ

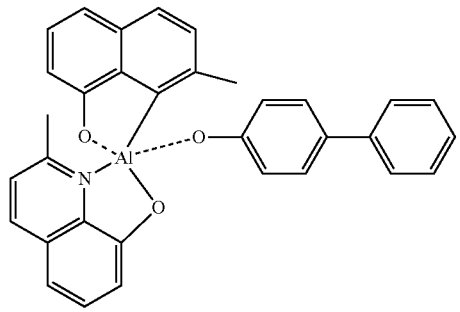

BAlq

<Compound 201>

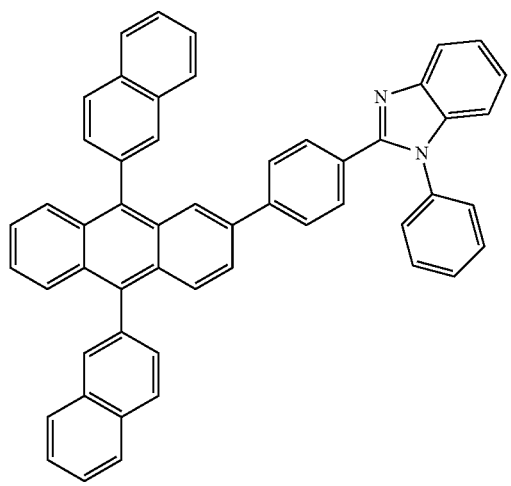

<Compound 202>

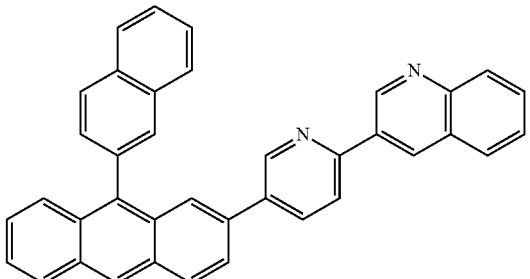

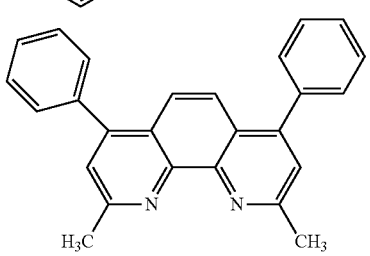

BCP

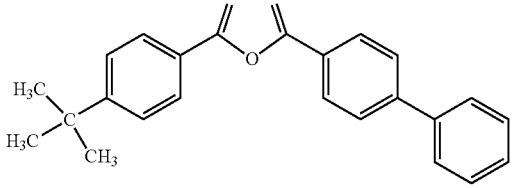

PBD

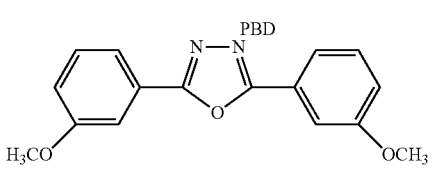

BMD

BND

In addition, the organic metal compound represented by Chemical Formula F may be used, either alone or in combination with the aforementioned electron transport layer material in the present disclosure:

$$Y_{m11}\text{-}M\text{-}(OA)_{n11} \quad \text{[Chemical Formula F]}$$

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond;

M is an alkali metal, an alkaline earth metal, an aluminum (Al) atom, or a boron (B) atom, with a proviso that:

when M is an alkali metal, m11=1 and n11=0;

when M is an alkaline earth metal, m11=1 and n11=1, or m11=2 and n11=0; or when M is aluminum or a boron, m is an integer of 1 to 3 and n is an integer of 0 to 2, satisfying the relationship m11+n11=3; and OA is a monodentate ligand capable of forming a single bond or a coordinate bond with M, is oxygen, and A is any one selected from a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing at least one of O, N, S, and Si as a heteroatom, wherein the term 'substituted' in the expression "a substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

In the present disclosure, Y's, are each one selected from among, but not limited to, the following [Structural Formula C1] to [Structural Formula C39]:

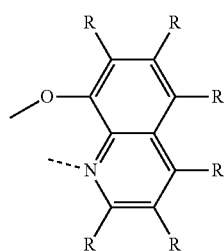

[Structural Formula C1]

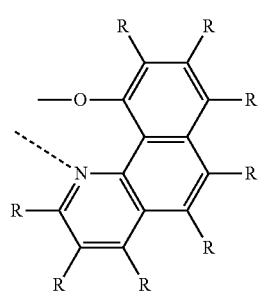

[Structural Formula C2]

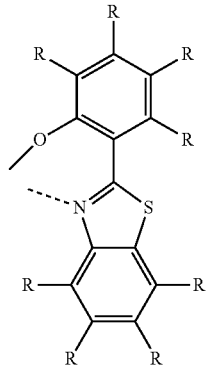

[Structural Formula C3]

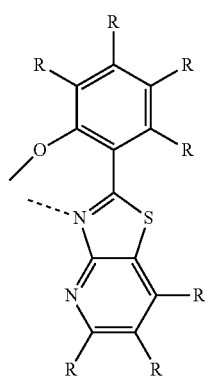

[Structural Formula C4]

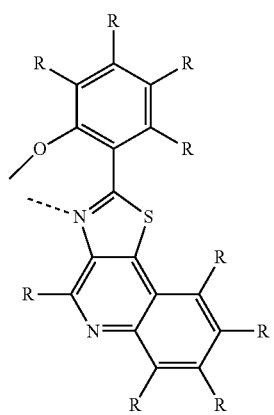

[Structual Formula C5]

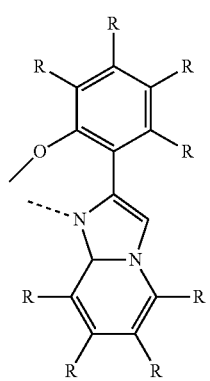

[Structural Formula C6]

[Structural Formula C7]
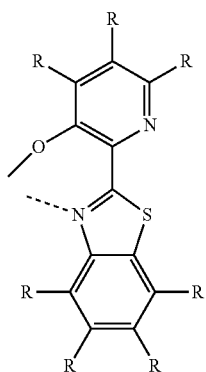
[Structural Formula C8]
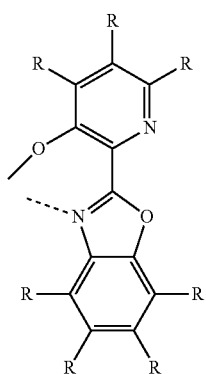
[Structural Formula C9]
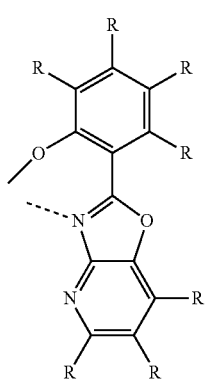
[Structural Formula C10]
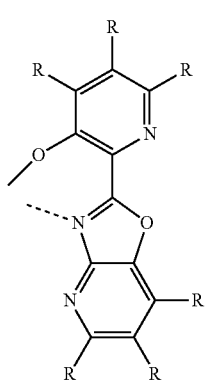
[Structural Formula C11]
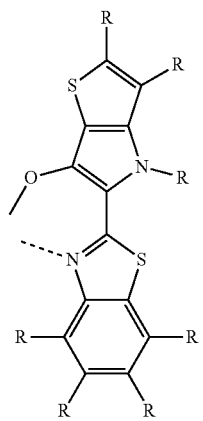
[Structural Formula C12]
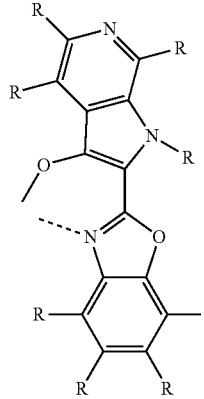
[Structural Formula C13]
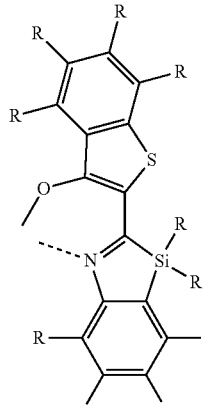
[Structural Formula C14]
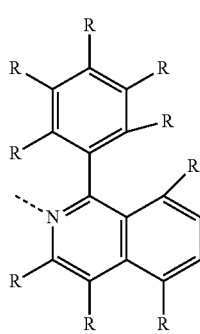

[Structural Formula C15]
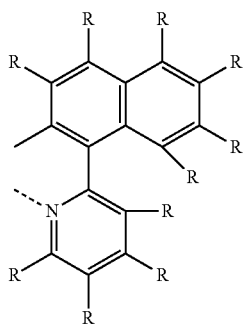
[Structural Formula C16]
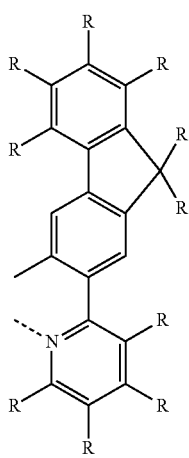
[Structural Formula C17]
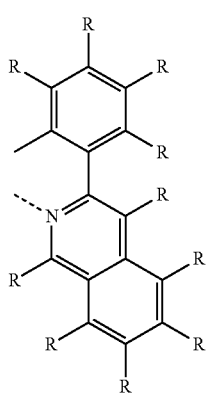
[Structural Formula C18]
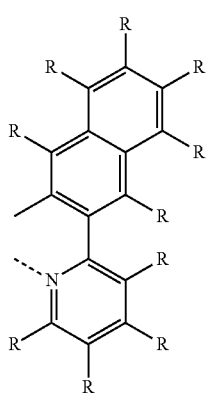
[Structural Formula C19]
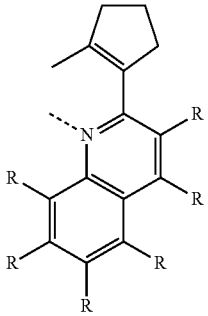
[Structural Formula C20]
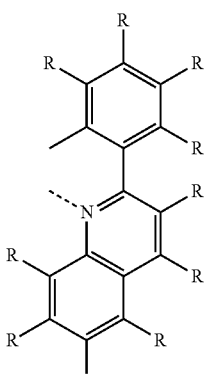
[Structural Formula C21]
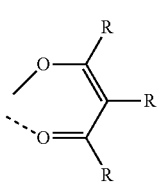
[Structural Formula C22]
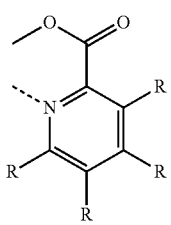
[Structural Formula C23]
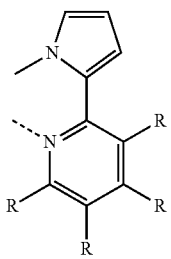
[Structural Formula C24]
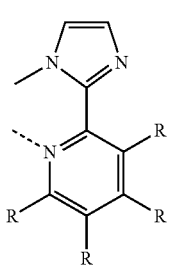

-continued
[Structural Formula C25]
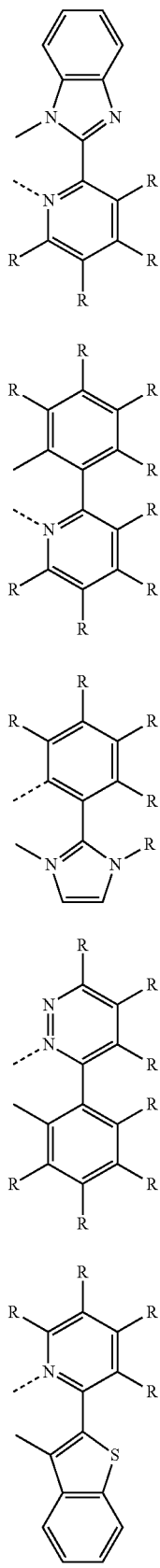
[Structural Formula C26]
[Structural Formula C27]
[Structural Formula C28]
[Structural Formula C29]
-continued
[Structural Formula C30]
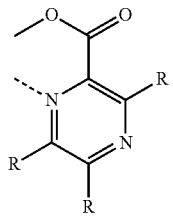
[Structural Formula C31]
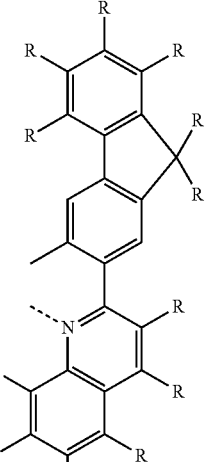
[Structural Formula C32]
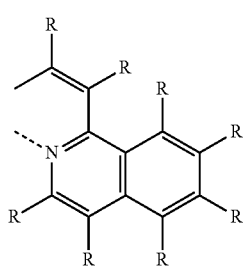
[Structural Formula C33]
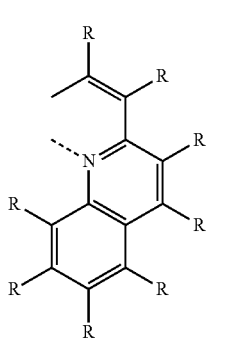
[Structural Formula C34]
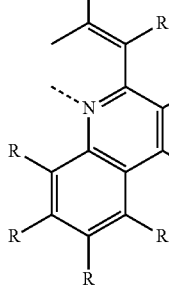

[Structural Formula C35]

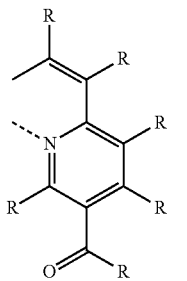

[Structural Formula C36]

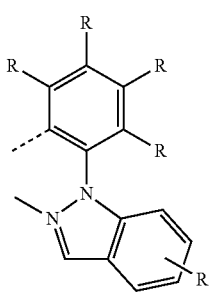

[Structural Formula C37]

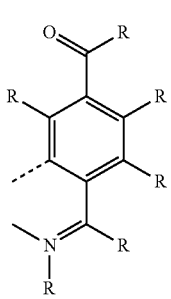

[Structural Formula C38]

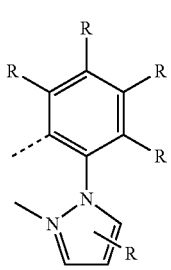

[Structural Formula C39]

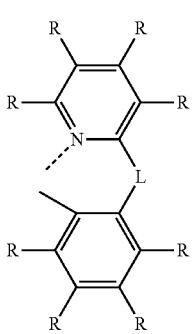

wherein,

R's, which may be the same or different, are each independently selected from a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker.

In the organic light emitting diode of the present disclosure, an electron injection layer (EIL) that functions to facilitate electron injection from the cathode may be deposited on the electron transport layer. The material for the EIL is not particularly limited.

So long as it is conventionally used in the art, any material can be available for the electron injection layer without particular limitations. Examples include CsF, NaF, LiF, NaCl, $Li_2O$, and BaO. Deposition conditions for the electron injection layer may vary, depending on compounds used, but may be generally selected from condition scopes that are almost the same as for the formation of hole injection layers.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting device of the present disclosure may have a multilayer structure in which the additional blue, green, and/or red light-emitting layer may be made of a fluorescent or phosphorescent material.

Further, one or more layers selected from among a hole injection layer, a hole transport layer, a light emitting layer, an electron transport layer, and an electron injection layer may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present invention.

EXAMPLES

Synthesis Example 1: Synthesis of Compound 3

Synthesis Example 1-(1): Synthesis of Intermediate 1-a

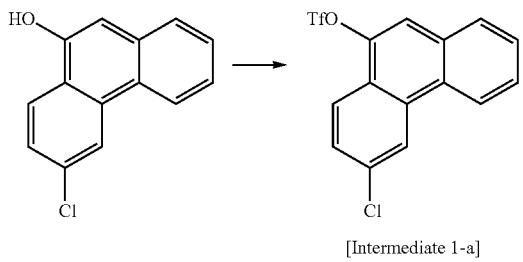 [SMILES: Oc1cc2ccccc2c2cc(Cl)ccc12 ; O=S(=O)(Oc1cc2ccccc2c2cc(Cl)ccc12)C(F)(F)F]

[Intermediate 1-a]

In a dried reactor filled with nitrogen, a mixture of 3-chloro-10-hydroxyphenanthrene (30 g, 131 mmol), pyridine (31.1 g, 393 mmol), and methylene chloride (300 ml) was cooled to 0° C. Then, drops of trifluoromethanesulfonic anhydride (44.42 g, 157 mmol) was slowly added, followed by stirring for one hour.

After completion of the reaction, 5° C. distilled water (200 ml) was slowly added. Extraction was conducted with methylene chloride and distilled water. Recrystallization in methylene chloride and hexane afforded [Intermediate 1-a] (33.0 g, 70%).

Synthesis Example 1-(2): Synthesis of Intermediate 1-b

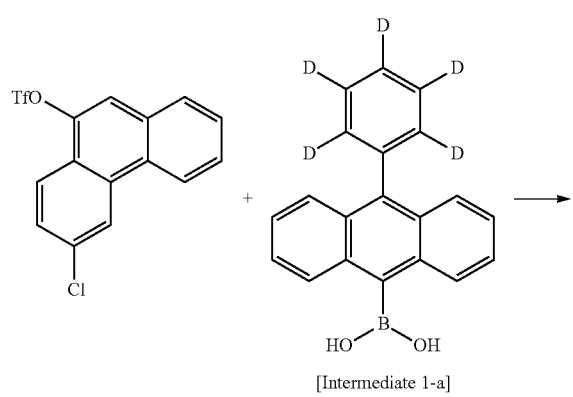

[Intermediate 1-a]

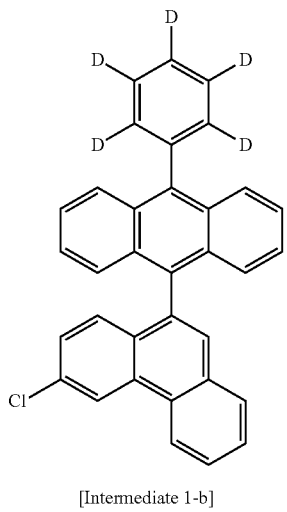

[Intermediate 1-b]

Into a 250-ml round-bottom flask, [Intermediate 1-a] (33 g, 91 mmol), 10-phenyl(d5)-anthracene-9-boronic acid (30.5 g, 101 mmol), tetrakis(triphenylphosphine)palladium (2.11 g, 2 mmol), and potassium carbonate (25.29 g, 183 mmol) were introduced, followed by toluene (270 ml), ethanol (90 ml), and water (60 ml). The temperature of the reaction was elevated to 80° C. and the mixture was stirred for 12 hours. After completion of the reaction, the reaction mixture was cooled to room temperature, added with methanol, and stirred. The organic layer thus formed was separated and concentrated in a vacuum. Recrystallization in toluene and acetone afforded [Intermediate 1-b] (27 g, 63%).

Synthesis Example 1-(3): Synthesis of Intermediate 1-c

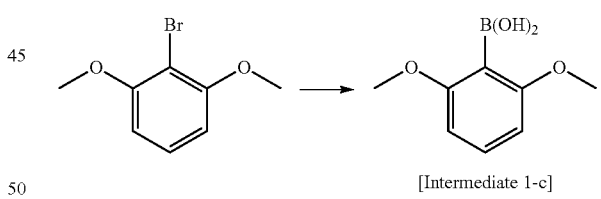

[Intermediate 1-c]

In a 1 L round-bottom flask, a solution of 2-bromo-1,3-dimethoxybenzene (50 g, 230 mmol) in tetrahydrofuran (400 ml) was chilled to −78° C. under a nitrogen atmosphere and added with drops of n-butyl lithium (167 ml, 280 mmol). The solution was stirred for 2 hours at the same temperature, mixed with trimethyl borate (36 ml, 320 mmol), and then stirred overnight at room temperature. After completion of the reaction, drops of 2N—HCl were slowly added for acidification. Extraction was conducted with water and ethyl acetate, and the organic layer thus formed was separated and dried over magnesium sulfate. The residue was concentrated at a reduced pressure and recrystallized in heptane and toluene to afford Intermediate 1-c (20.8 g, 50%).

Synthesis Example 1-(4): Synthesis of Intermediate 1-d

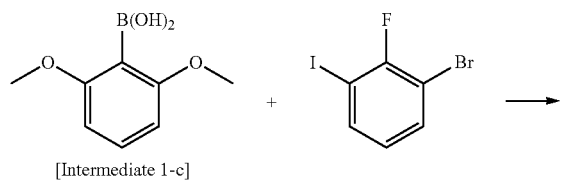

[Intermediate 1-c]

[Intermediate 1-d]

In a 500-ml reactor, Intermediate 1-a (20.8 g, 110 mmol), 1-bromo-2-fluoro-3-iodobenzene (28.7 g, 95 mmol), tetrakis (triphenylphosphine)palladium (33 g, 29 mmol), and sodium carbonate (30.3 g, 290 mmol) were put, followed by toluene (200 ml), ethanol (60 ml), and water (60 ml). The reactor was heated to 80° C. before solution was stirred for 12 hours. After completion of the reaction, the temperature of the reactor was lowered to room temperature and the reaction mixture was extracted with ethyl acetate. The organic layer thus formed was isolated by column chromatography afforded Intermediate 1-d (22.3 g, 63%)

Synthesis Example 1-(5): Synthesis of Intermediate 1-e

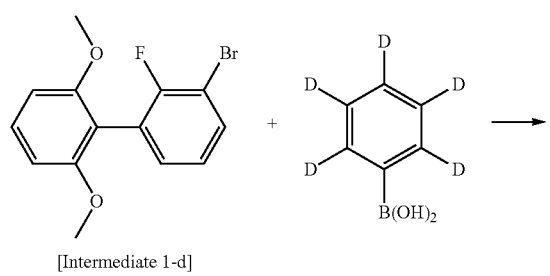

[Intermediate 1-d]

[Intermediate 1-e]

The same procedure as in Synthesis Example 1-(2) was carried out, with the exception of using phenyld5-boronic acid and [Intermediate 1-d] instead of 10-phenyl(d5)-anthracene-9-boronic acid and [Intermediate 1-a], respectively, to afford [Intermediate 1-e] (16.6 g, 72%).

Synthesis Example 1-(6): Synthesis of Intermediate 1-f

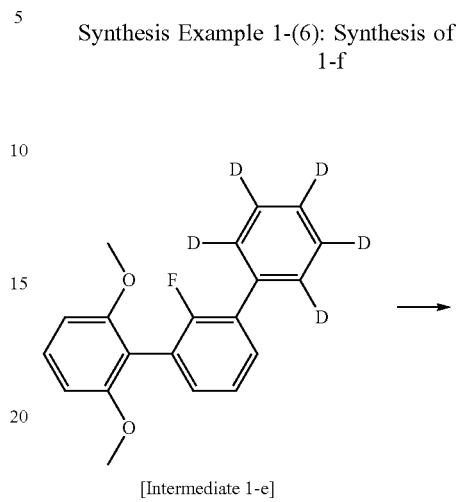

[Intermediate 1-e]

[Intermediate 1-f]

In a 500-ml round-bottom flask, Intermediate 1-e (16.6 g, 53 mmol), hydrogen bromic acid (48 ml, 260 mmol), and acetic acid (100 ml) were stirred together for 12 hours. After completion of the reaction, the reaction mixture was cooled to room temperature and stirred while water was added thereto. The reaction mixture was subjected to extraction with water and ethyl acetate. The organic layer thus formed was separated, concentrated in a vacuum, and recrystallized in heptane. Filtration and drying afforded Intermediate 1-f (17.6 g, 95%).

Synthesis Example 1-(7): Synthesis of Intermediate 1-g

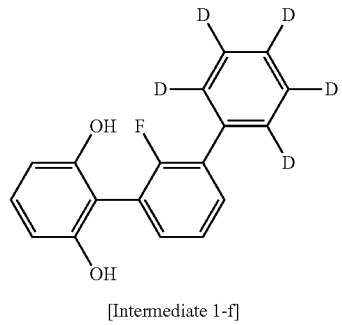

[Intermediate 1-f]

-continued

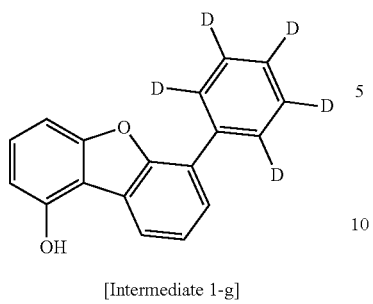

[Intermediate 1-g]

In a 500-ml round-bottom flask, Intermediate 1-f (14.3 g, 50 mmol), potassium carbonate (20.7 g, 150 mmol), and N-methyl-2-pyrrolidone (112 ml) were stirred together for 12 hours. After completion of the reaction, extraction was made and the organic layer thus formed was isolated. Concentration in a vacuum and recrystallization in heptane afforded Intermediate 1-g (10.6 g, 80%).

Synthesis Example 1-(8): Synthesis of Intermediate 1-h

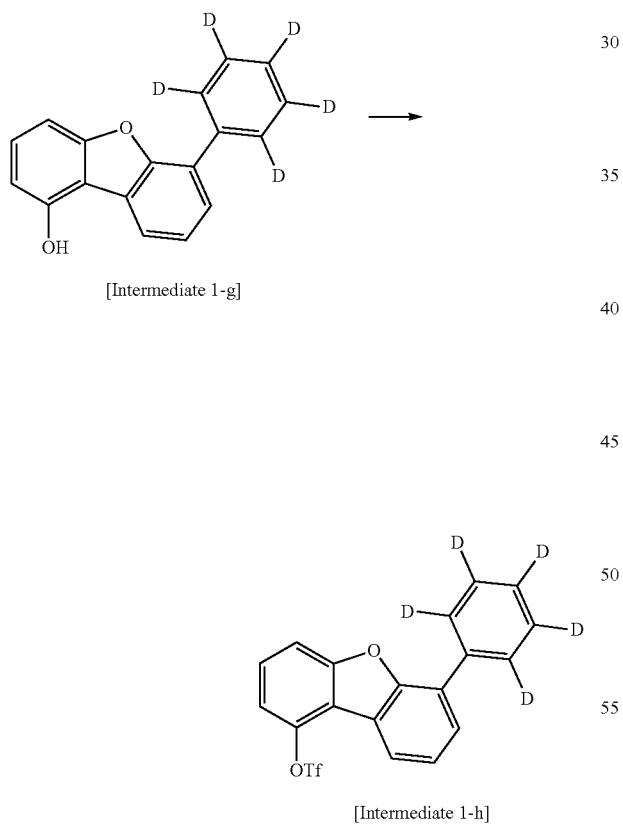

[Intermediate 1-g]

[Intermediate 1-h]

The same procedure as in Synthesis Example 1-(1) was carried out, with the exception of using [Intermediate 1-g] instead of 3-chloro10-hydroxyphenanthrene, to afford [Intermediate 1-h] (7 g, 80%).

Synthesis Example 1-(9): Synthesis of Intermediate 1-i

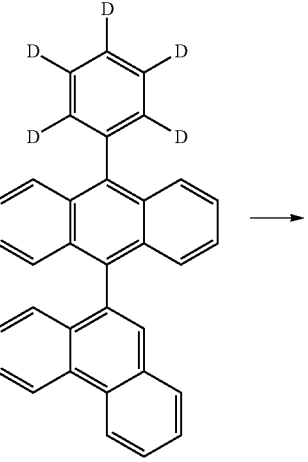

[Intermediate 1-b]

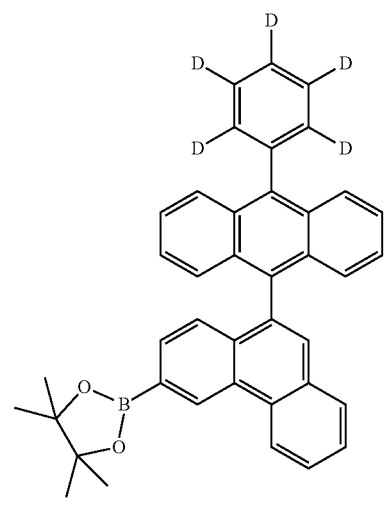

[Intermediate 1-i]

A mixture of [Intermediate 1-b] (27 g, 57 mmol), bis(pinacolato)diboron (19 g, 75 mmol), 1,1'-bis(diphenylphosphino)ferrocene palladium (II) chloride (1.7 g, 3 mmol), potassium acetate (16.9 g, 172 mmol), and toluene (270 ml) was stirred for 10 hours under reflux. After completion of the reaction, solid matter was filtered off and the filtrate was concentrated in a vacuum. Isolation by column chromatography with methylene chloride and heptane afforded [Intermediate 1-i] (20 g, 63%).

Synthesis Example 1-(10): Synthesis of Compound 3

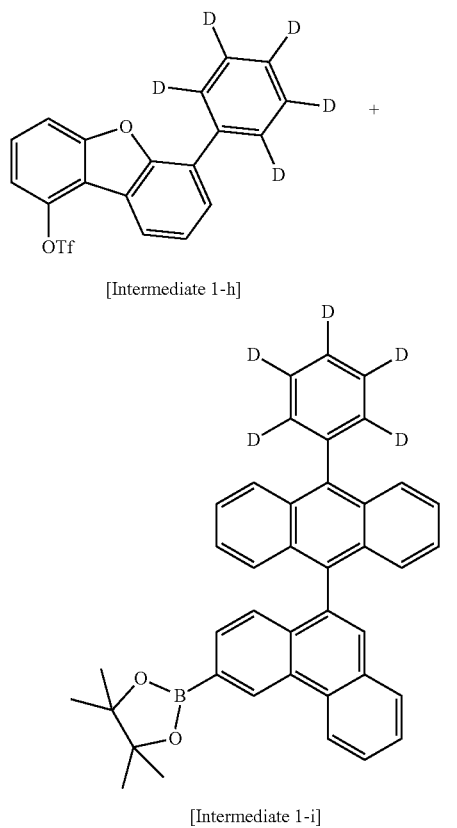

[Intermediate 1-h]

[Intermediate 1-i]

[Compound 3]

In a 250-ml round-bottom flask, Intermediate 1-h (7 g, 18 mmol), Intermediate 1-I (10.4 g, 19 mmol), tetrakis(triphenylphosphine)palladium (0.41 g, 0.3 mmol), and potassium carbonate (4.9 g, 35 mmol) were put, followed by toluene (49 ml), ethanol (21 ml), and water (14 ml). The solution was heated to 80° C. and stirred for 12 hours under reflux. After completion of the reaction, the reaction mixture was cooled to room temperature and added with methanol before stirring. The organic layer thus formed was isolated, concentrated in a vacuum, and recrystallized in acetone to afford Compound 3 (3.0 g, 25%).

MS (MALDI-TOF): m/z 682.31 [M$^+$]

Synthesis Example 2: Synthesis of Compound 4

Synthesis Example 2-(1): Synthesis of Intermediate 2-a

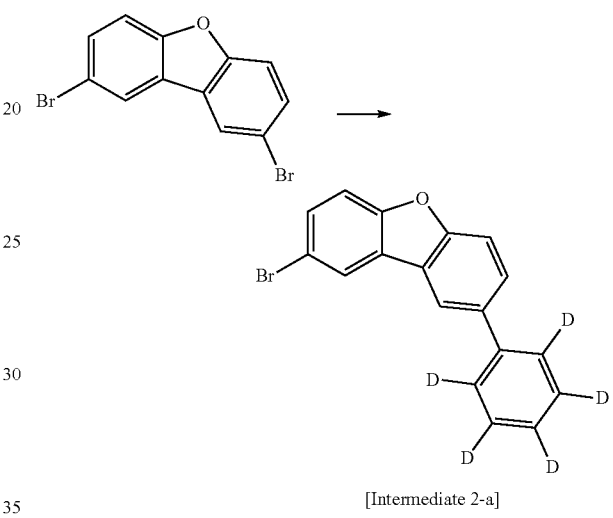

[Intermediate 2-a]

In a 2-L round-bottom flask, phenyl-d5-boronic acid (13 g, 0.08 mol) and 2,7-dibromobenzofuran (32.6 g, 0.1 mol) were dissolved in toluene (700 mL) and ethanol (150 mL). An aqueous potassium carbonate solution (150 mL) and tetrakis(triphenyl phosphine)palladium (2.3 g, 0.002 mol) were added to the reactor which was then heated to 110° C., followed by stirring for 12 hours.

The reaction mixture was adsorbed to active carbon and filtered in a vacuum. The filtrate was recrystallized in toluene and ethanol to afford Intermediate 2-a (23.6 g, 90%).

Synthesis Example 2-(2): Synthesis of Compound 4

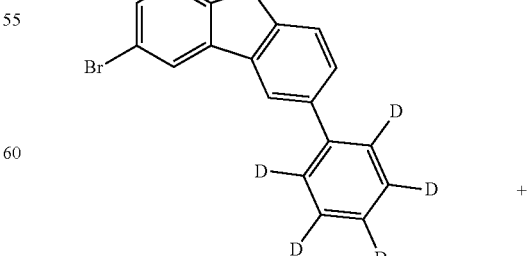

[Intermediate 2-a]

-continued

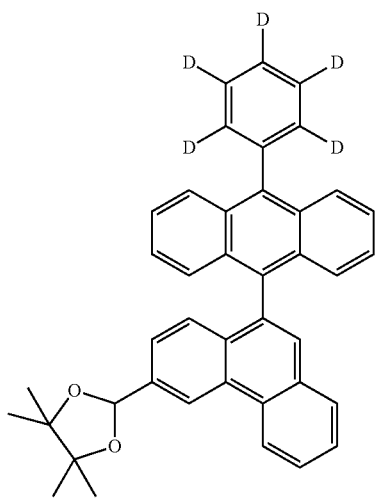

[Intermediate 1-i]

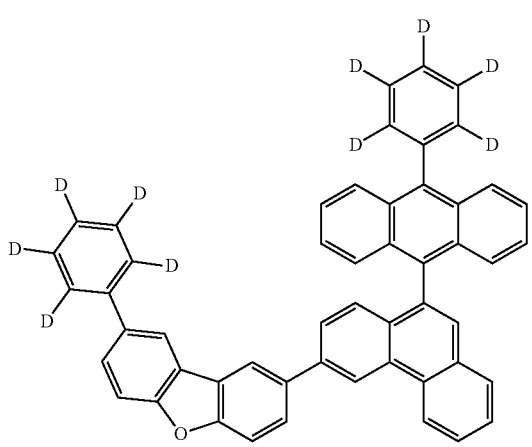

[Compound 4]

The same procedure as in Synthesis Example 1-(10) was carried out, with the exception of using [Intermediate 1-h] instead of [Intermediate 2-a], to afford [Compound 4] (12 g, 23%).

MS (MALDI-TOF): m/z 682.31 [M⁺]

Synthesis Example 3: Synthesis of Compound 8

Synthesis Example 3-(1): Synthesis of Intermediate 3-a

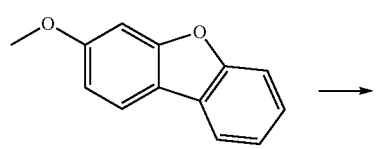

-continued

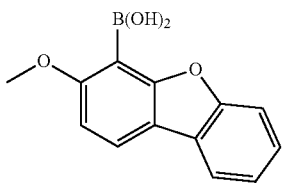

[Intermediate 3-a]

In a 1-L round-bottom flask, 3-methoxydibenzofuran (50 g, 252 mmol), was dissolved in tetrahydrofuran (500 ml) under a hydrogen condition. The solution was chilled to −78° C. and slowly added with drops of n-butyl lithium (173 ml, 277 mmol). The resulting solution was stirred for 6 hours at room temperature, chilled to −78°, and added with trimethyl borate (36 ml, 320 mmol) before being stirred overnight at room temperature. After completion of the reaction, 2N HCl was dropwise added for acidification. Extraction with water and ethyl acetate formed an organic layer which was then dried over magnesium sulfate. The residue was concentrated in a vacuum. The concentrate was recrystallized in heptane and toluene to afford [Intermediate 3-a] (45 g, 74%).

Synthesis Example 3-(2): Synthesis of Intermediate 3-b

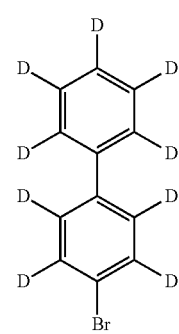

[Intermediate 3-b]

The same procedure as in Synthesis Example 2-(1) was carried out, with the exception of using 1,4-benzene(d4) instead of 2,7-dibromodibenzofuran, to afford [Intermediate 3-b].

Synthesis Example 3-(3): Synthesis of Intermediate 3-c

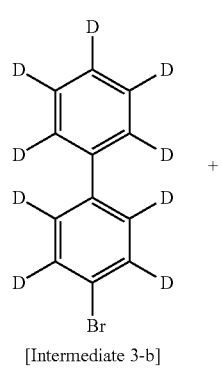

[Intermediate 3-b]

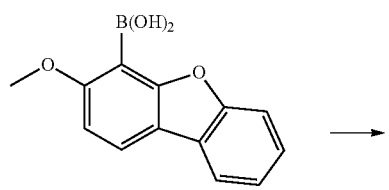

[Intermediate 3-a]

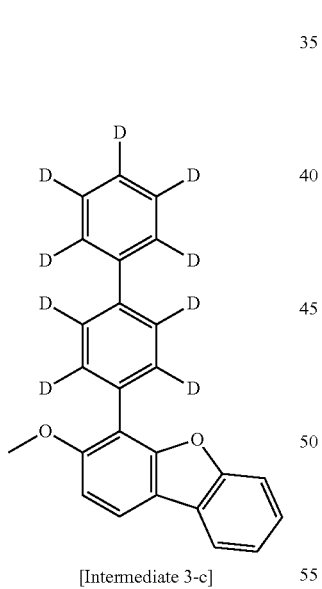

[Intermediate 3-c]

The same procedure as in Synthesis Example 2-(1) was carried out, with the exception of using [Intermediate 3-b] and [Intermediate 3-a] instead of 2,7-dibromodibenzofuran and phenyl-d5-boronic acid, respectively, to afford [Intermediate 3-c]

Synthesis Example 3-(4): Synthesis of Intermediate 3-d

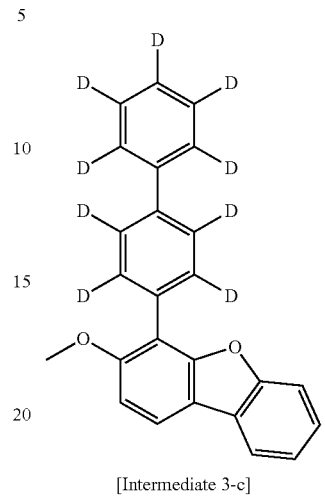

[Intermediate 3-c]

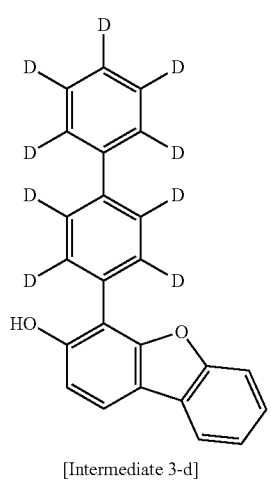

[Intermediate 3-d]

In a 500-ml round-bottom flask, a mixture of [Intermediate 3-c](25 g, 70 mmol), hydrobromic acid (8.4 ml, 104 mmol), and acetic acid (150 ml) was stirred for 12 hours. After completion of the reaction, the reaction mixture was cooled to room temperature and added with water before being stirred. Extraction was conducted with water and ethyl acetate to form an organic layer which was then concentrated in a vacuum. The concentrate was recrystallized in heptane, filtered, and dried to afford [Intermediate 3-d] (17 g, 71%).

Synthesis Example 3-(5): Synthesis of Intermediate 3-e

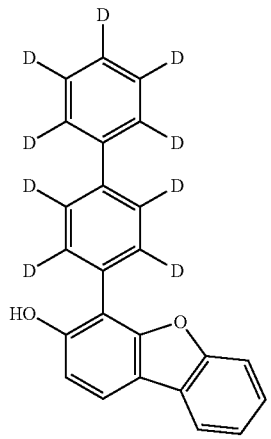

[Intermediate 3-d]

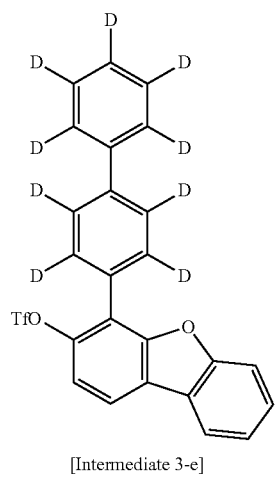

[Intermediate 3-e]

The same procedure as in Synthesis Example 1-(1) was carried out, with the exception of using [Intermediate 3-d] instead of 3-chloro10-hydroxyphenanthrene instead of, to afford [Intermediate 3-e].

Synthesis Example 3-(6): Synthesis of Intermediate 3-f

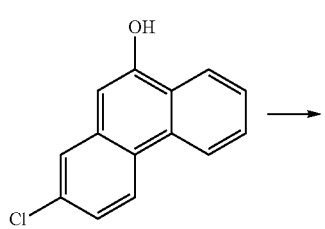

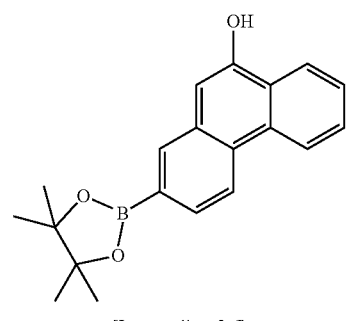

[Intermediate 3-f]

The same procedure as in Synthesis Example 1-(9) was carried out, with the exception of using 2-chloro 9-hydroxyphenanthrene instead of [Intermediate 1-b], to afford [Intermediate 3-f].

Synthesis Example 3-(7): Synthesis of Intermediate 3-g

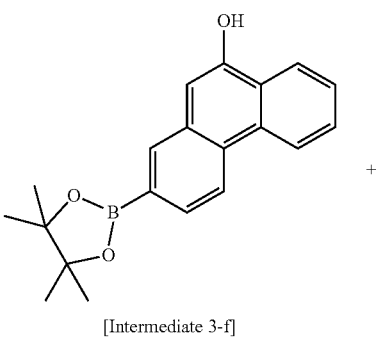

[Intermediate 3-f]

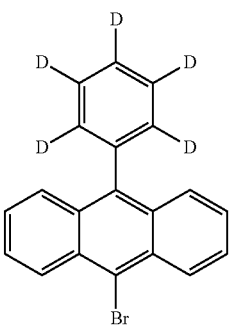

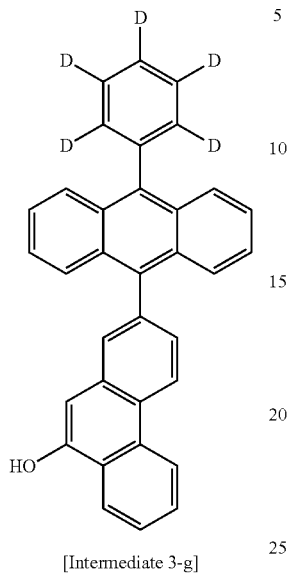

[Intermediate 3-g]

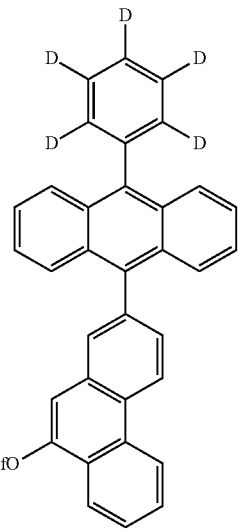

[Intermediate 3-h]

The same procedure as in Synthesis Example 2-(1) was carried out, with the exception of using 9-bromo-10-phenyl (d5)-anthracene and [Intermediate 3-f] instead of 2,7-dibromodibenzofuran and phenyl-d5-boronic acid, respectively, to afford [Intermediate 3-g].

Synthesis Example 3-(8): Synthesis of Intermediate 3-h

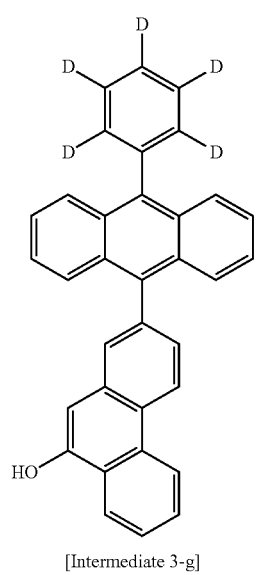

[Intermediate 3-g]

상 The same procedure as in Synthesis Example 1-(1) was carried out, with the exception of using [Intermediate 3-g] instead of 3-chloro10-hydroxyphenanthrene, to afford [Intermediate 3-h].

Synthesis Example 3-(9): Synthesis of Intermediate 3-i

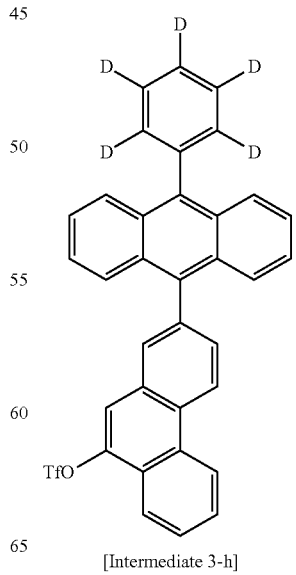

[Intermediate 3-h]

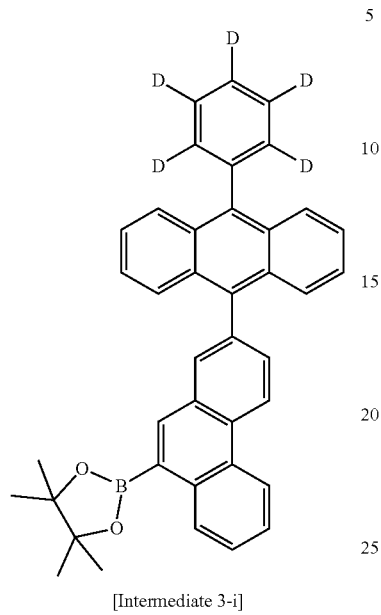

[Intermediate 3-i]

The same procedure as in Synthesis Example 1-(9) was carried out, with the exception of using [Intermediate 1-b] instead of [Intermediate 3-h], to afford [Intermediate 3-i].

Synthesis Example 3-(10): Synthesis of Compound 8

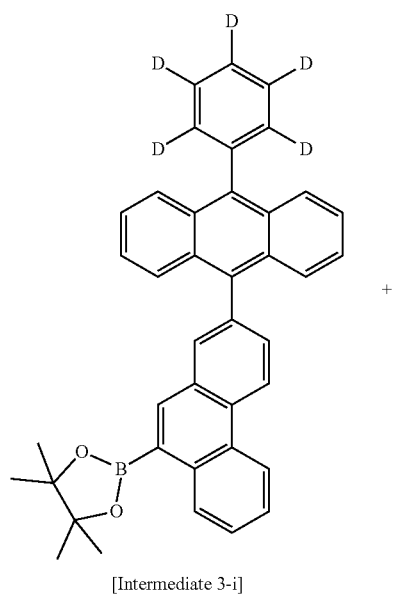

[Intermediate 3-i]

+

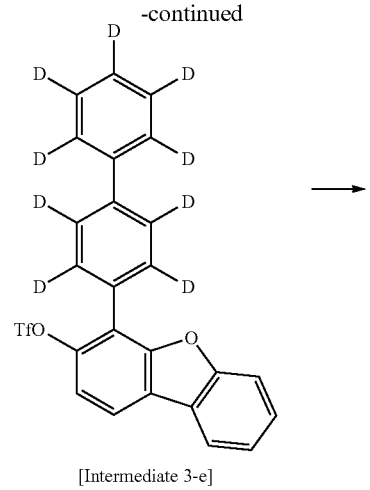

[Intermediate 3-e]

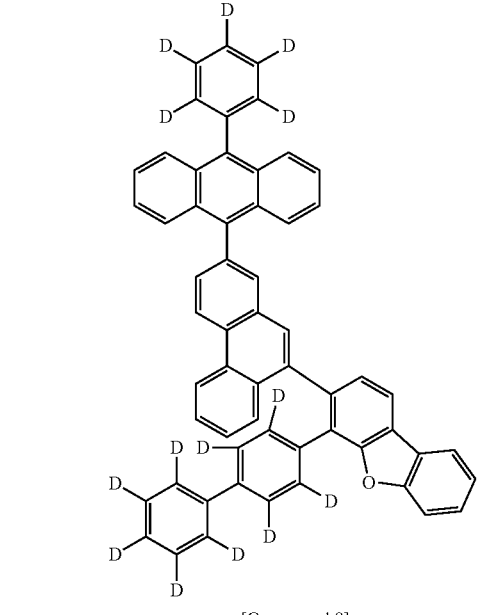

[Compound 8]

The same procedure as in Synthesis Example 1-(10) was carried out, with the exception of using [Intermediate 3-e] and [Intermediate 3-i] instead of [Intermediate 1-h] and [Intermediate 1-i], respectively, to afford [Compound 8].

MS (MALDI-TOF): m/z 762.36 [M⁺]

Synthesis Example 4: Synthesis of Compound 25

Synthesis Example 4-(1): Synthesis of Intermediate 4-a

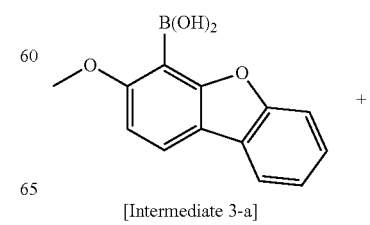

[Intermediate 3-a]

+

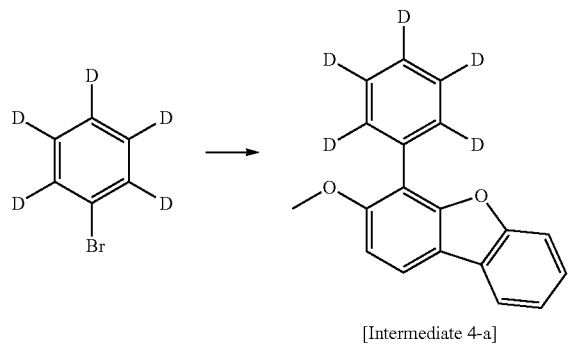

[Intermediate 4-a]

The same procedure as in Synthesis Example 2-(1) was carried out, with the exception of using bromophenyl(d5) and [Intermediate 3-a] instead of 2,7-dibromodibenzofuran and phenyl-d5-boronic acid, to afford [Intermediate 4-a].

Synthesis Example 4-(2): Synthesis of Intermediate 4-b

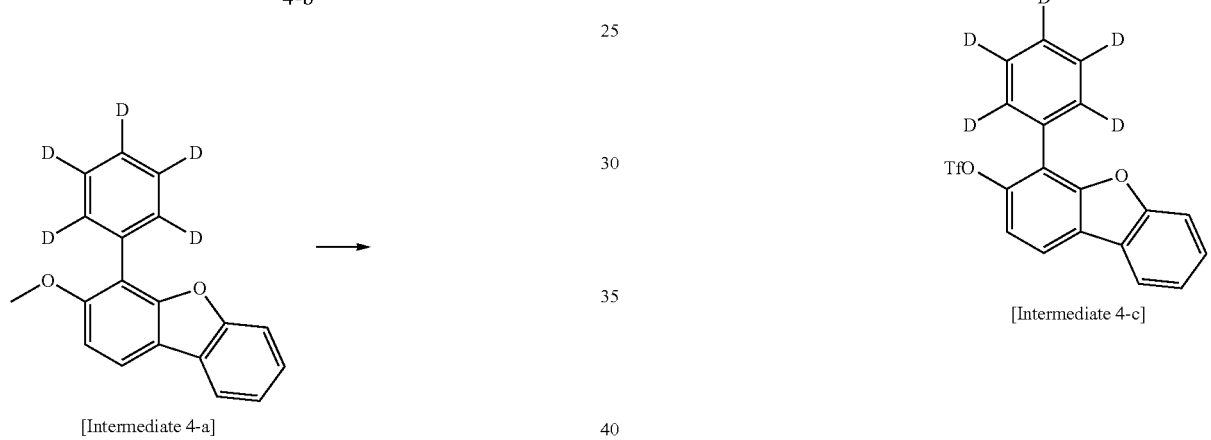

[Intermediate 4-a]

[Intermediate 4-b]

The same procedure as in Synthesis Example 3-(4) was carried out, with the exception of using [Intermediate 3-c] instead of [Intermediate 4-a], to afford [Intermediate 4-b].

Synthesis Example 4-(3): Synthesis of Intermediate 4-c

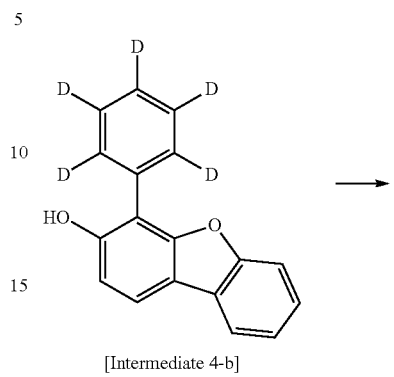

[Intermediate 4-b]

[Intermediate 4-c]

The same procedure as in Synthesis Example 1-(1) was carried out, with the exception of using [Intermediate 4-b] instead of 3-chloro-10-hydroxyphenanthrene, to afford [Intermediate 4-c].

Synthesis Example 4-(4): Synthesis of Intermediate 4-d

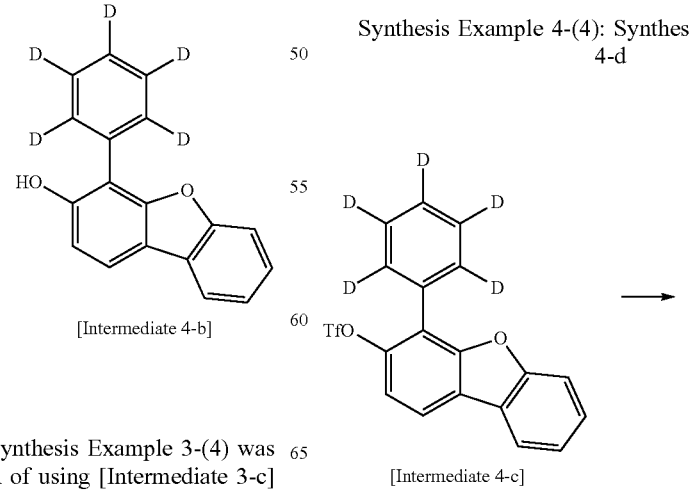

[Intermediate 4-c]

-continued

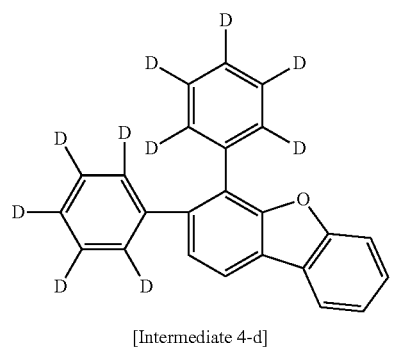

[Intermediate 4-d]

The same procedure as in Synthesis Example 2-(1) was carried out, with the exception of using [Intermediate 4-c] instead of 2,7-dibromodibenzofuran to afford [Intermediate 4-d].

Synthesis Example 4-(5): Synthesis of Intermediate 4-e

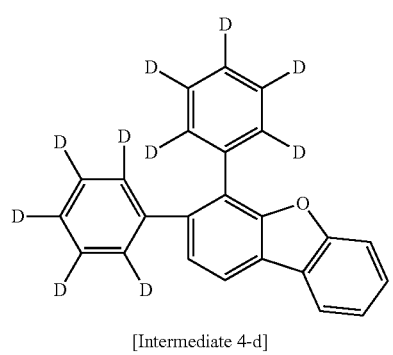

[Intermediate 4-d]

↓

[Intermediate 4-e]

The same procedure as in Synthesis Example 3-(1) was carried out, with the exception of using [Intermediate 4-d] instead of 3-methoxydibenzofuran, to afford [Intermediate 4-e].

Synthesis Example 4-(6): Synthesis of Compound 25

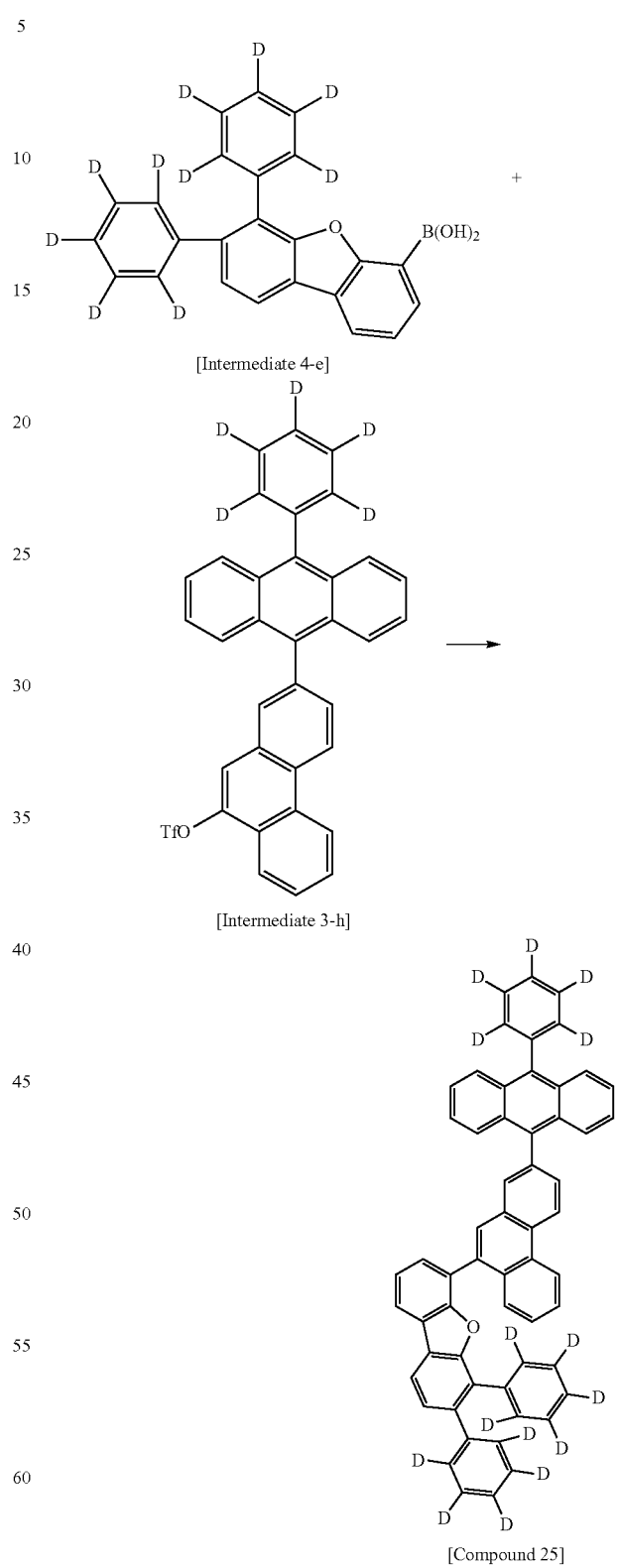

The same procedure as in Synthesis Example 1-(10) was carried out, with the exception of using [Intermediate 3-h]

and [Intermediate 4-e] instead of [Intermediate 1-h] and [Intermediate 1-i], respectively, to afford [Compound 25].

MS (MALDI-TOF): m/z 763.37 [M⁺]

Synthesis Example 5: Synthesis of Compound 1

Synthesis Example 5-(1): Synthesis of Intermediate 5-a

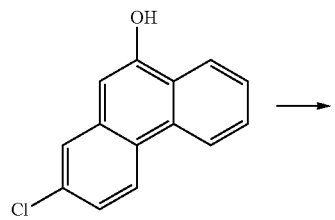

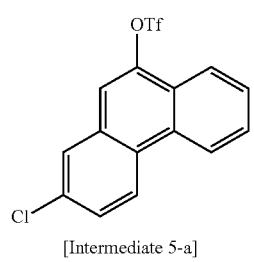

[Intermediate 5-a]

In a dried reactor filled with nitrogen, a mixture of 2-chloro9-hydroxyphenanthrene (30 g, 131 mmol), pyridine (31.1 g, 393 mmol), and methylene chloride (300 ml) was cooled to 0° C. Then, drops of trifluoromethanesulfonic anhydride (44.42 g, 157 mmol) was slowly added, followed by stirring for one hour. After completion of the reaction, 5° C. distilled water (200 ml) was slowly added. Extraction was conducted with methylene chloride and distilled water. Recrystallization in methylene chloride and hexane afforded [Intermediate 5-a] (33.0 g, 70%).

Synthesis Example 5-(2): Synthesis of Intermediate 5-b

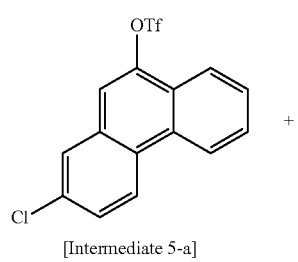

[Intermediate 5-a]

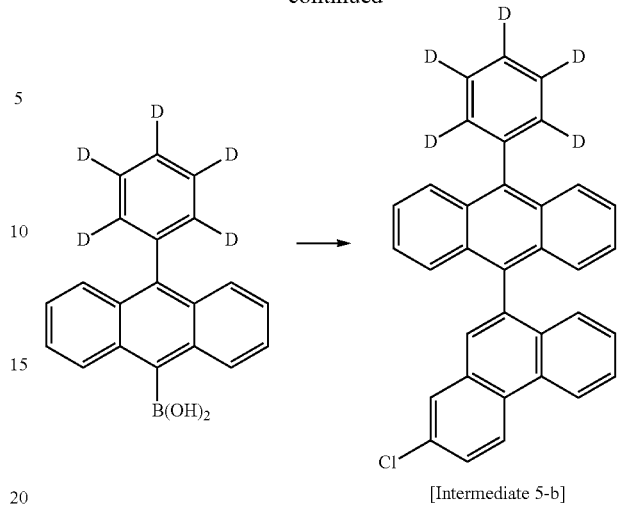

[Intermediate 5-b]

Into a 250-ml round-bottom flask, [Intermediate 5-a] (33 g, 91 mmol), 10-phenyl(d5)-anthracene-9-boronic acid (30.5 g, 101 mmol), tetrakis(triphenylphosphine)palladium (2.11 g, 2 mmol), and potassium carbonate (25.29 g, 183 mmol) were introduced, followed by toluene (270 ml), ethanol (90 ml), and water (60 ml). The temperature of the reaction was elevated to 80° C. and the mixture was stirred for 12 hours. After completion of the reaction, the reaction mixture was cooled to room temperature, added with methanol, and stirred. The organic layer thus formed was separated and concentrated in a vacuum. Recrystallization in toluene and acetone afforded [Intermediate 5-b] (30 g, 69%).

Synthesis Example 5-(3): Synthesis of Intermediate 5-c

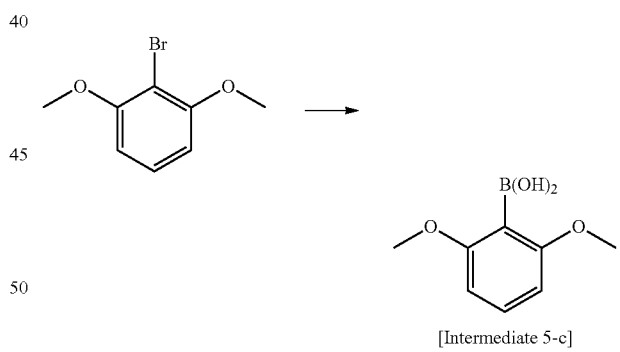

[Intermediate 5-c]

In a 1 L round-bottom flask, a solution of 2-bromo-1,3-dimethoxybenzene (50 g, 230 mmol) in tetrahydrofuran (400 ml) was chilled to −78° C. under a nitrogen atmosphere and added with drops of n-butyl lithium (167 ml, 280 mmol). The solution was stirred for 2 hours at the same temperature, mixed with trimethyl borate (36 ml, 320 mmol), and then stirred overnight at room temperature. After completion of the reaction, drops of 2N—HCl were slowly added for acidification. Extraction was conducted with water and ethyl acetate, and the organic layer thus formed was separated and dried over magnesium sulfate. The residue was concentrated at a reduced pressure and recrystallized in heptane and toluene to afford [Intermediate 5-c] (20.8 g, 50%).

Synthesis Example 5-(4): Synthesis of Intermediate 5-d

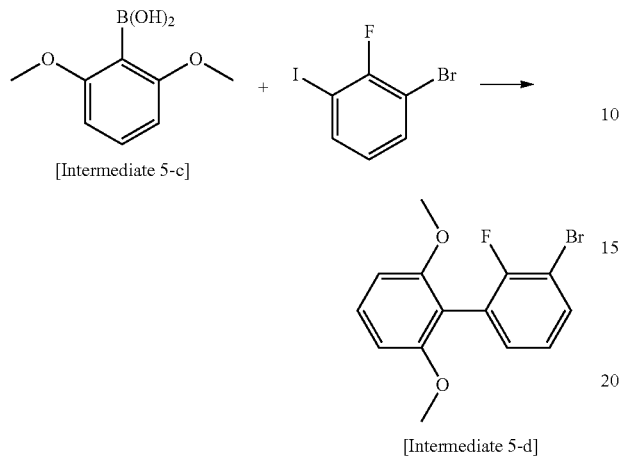

[Intermediate 5-c]

[Intermediate 5-d]

In a 500-ml reactor, [Intermediate 5-a] (20.8 g, 110 mmol), 1-bromo-2-fluoro-3-iodobenzene (28.7 g, 95 mmol), tetrakis(triphenylphosphine)palladium (33 g, 29 mmol), and sodium carbonate (30.3 g, 290 mmol) were put, followed by toluene (200 ml), ethanol (60 ml), and water (60 ml). The reactor was heated to 80° C. before solution was stirred for 12 hours. After completion of the reaction, the temperature of the reactor was lowered to room temperature and the reaction mixture was extracted with ethyl acetate. The organic layer thus formed was isolated by column chromatography afforded [Intermediate 5-d] (22.3 g, 63%)

Synthesis Example 5-(5): Synthesis of Intermediate 5-e

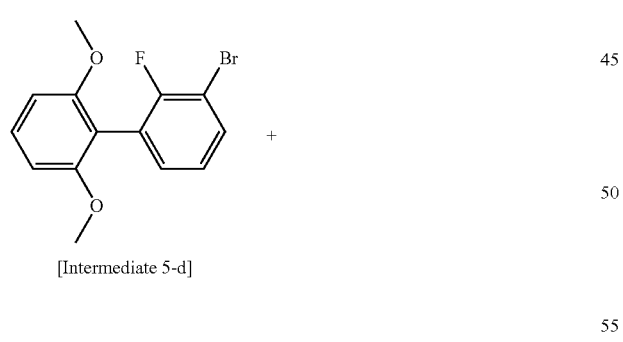

[Intermediate 5-d]

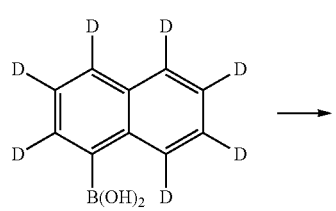

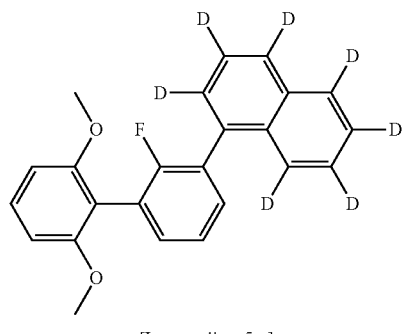

[Intermediate 5-e]

The same procedure as in Synthesis Example 1-(2) was carried out, with the exception of using 1-naphthalene d7-boronic acid and [Intermediate 5-d] instead of 10-phenyl (d5)-anthracene-9-boronic acid and [Intermediate 1-a], to afford [Intermediate 5-e] (16.6 g, 72%).

Synthesis Example 5-(6): Synthesis of Intermediate 5-f

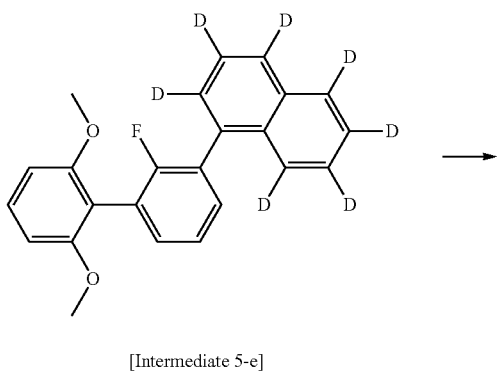

[Intermediate 5-e]

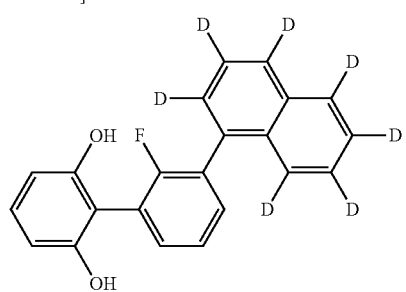

[Intermediate 5-f]

In a 500-ml round-bottom flask, [Intermediate 5-e] (19 g, 52 mmol), hydrogen bromic acid (48 ml, 260 mmol), and acetic acid (100 ml) were stirred together for 12 hours. After completion of the reaction, the reaction mixture was cooled to room temperature and stirred while water was added thereto. The reaction mixture was subjected to extraction with water and ethyl acetate. The organic layer thus formed was separated, concentrated in a vacuum, and recrystallized in heptane. Filtration and drying afforded [Intermediate 5-f] (16 g, 91%).

Synthesis Example 5-(7): Synthesis of Intermediate 5-g

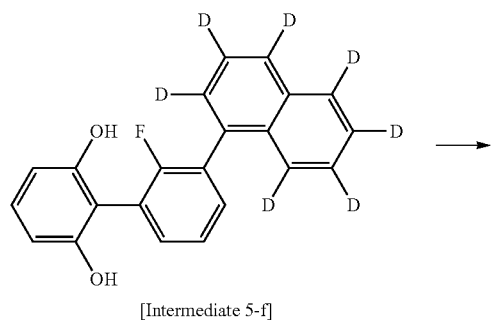

[Intermediate 5-f]

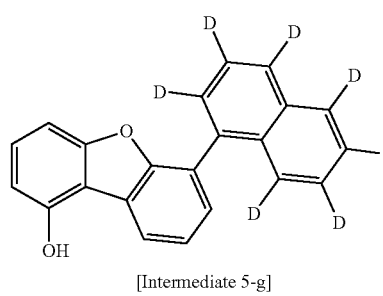

[Intermediate 5-g]

In a 500-ml round-bottom flask, [Intermediate 5-f] (16 g, 47 mmol), potassium carbonate (19.5 g, 141 mmol), and N-methyl-2-pyrrolidone (112 ml) were stirred together for 12 hours. After completion of the reaction, extraction was made and the organic layer thus formed was isolated. Concentration in a vacuum and recrystallization in heptane afforded [Intermediate 5-g] (13 g, 86%).

Synthesis Example 5-(8): Synthesis of Intermediate 5-h

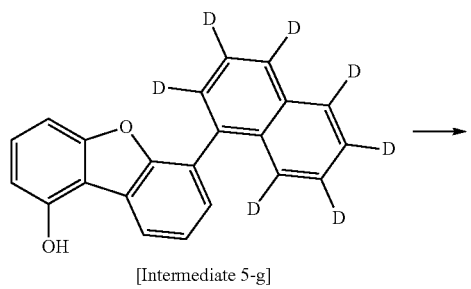

[Intermediate 5-g]

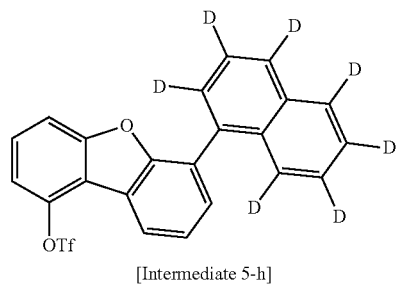

[Intermediate 5-h]

The same procedure as in Synthesis Example 1-(1) was carried out, with the exception of using [Intermediate 5-g] instead of 2-chloro-9-hydroxyphenanthrene, to afford [Intermediate 5-h] (15 g, 81.5%).

Synthesis Example 5-(9): Synthesis of Intermediate 5-i

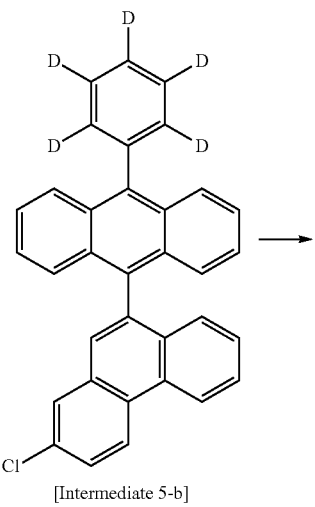

[Intermediate 5-b]

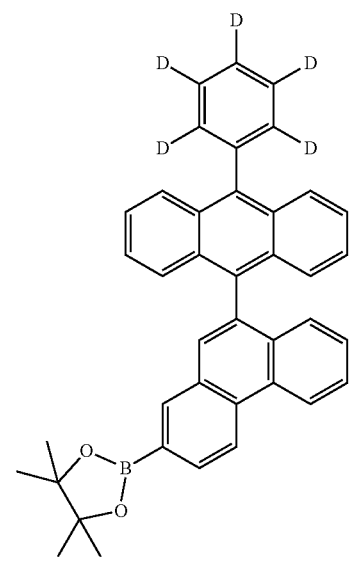

[Intermediate 5-i]

[Intermediate 5-b] (30 g, 64 mmol), bis(pinacolato)diboron (21.1 g, 83 mmol), 1,1'-bis(diphenylphosphino)ferrocene palladium (II) chloride (1.8 g, 3 mmol), potassium acetate (18.8 g, 191 mmol), and toluene 300 ml were stirred together for 10 hours under reflux. After completion of the reaction, solid matter was filtered off and the filtrate was concentrated in a vacuum. Isolation by column chromatography with methylene chloride and heptane afforded [Intermediate 5-i] (22 g, 61%).

Synthesis Example 5-(10): Synthesis of Compound 1

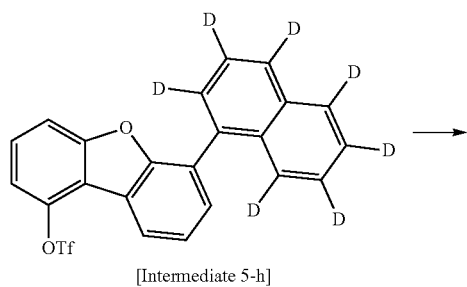

[Intermediate 5-h]

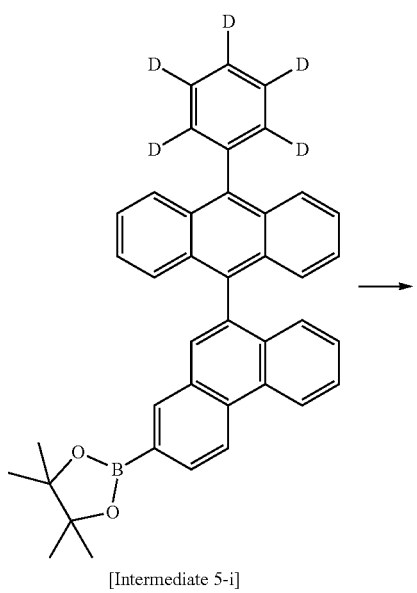

[Intermediate 5-i]

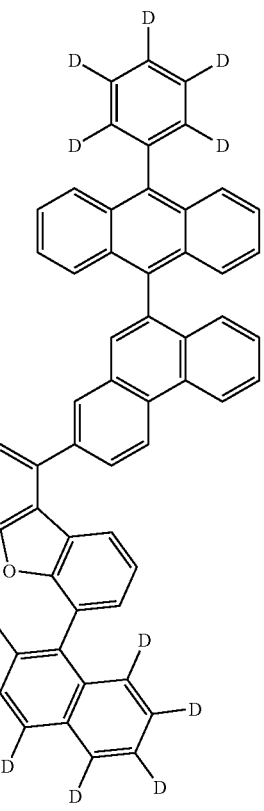

[Compound 1]

In a 250-ml round-bottom flask, [Intermediate 5-h] (13 g, 29 mmol), [Intermediate 5-i] (17.8 g, 32 mmol), tetrakis(triphenylphosphine)palladium (0.67 g, 0.6 mmol), and potassium carbonate (8 g, 58 mmol) were put, followed by toluene (91 ml), ethanol (39 ml), and water (26 ml). The solution was heated to 80° C. and stirred for 12 hours under reflux. After completion of the reaction, the reaction mixture was cooled to room temperature and added with methanol before stirring. The organic layer thus formed was isolated, concentrated in a vacuum, and recrystallized in acetone to afford [Compound 1] (7.3 g, 34.3%).

<Dopant Preparation>

Compound represented by any one of [Chemical Formula D1] and Chemical Formula D2]: dopant materials were synthesized referring to Examples disclosed in PCT/KR2015/004552.

Compound represented by any one of [Chemical Formula D3] to Chemical Formula D5]: prepared according to Synthesis Examples 6 to 8.

Synthesis Example 6: Synthesis of BD 2

Synthesis Example 6-(1): Synthesis of Intermediate 6-a

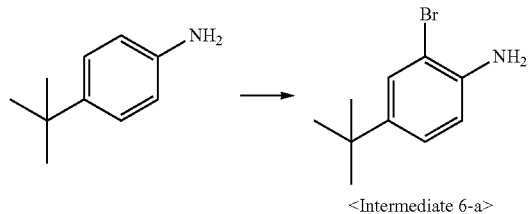

<Intermediate 6-a>

In a 1-L reactor, a solution of 4-tert-butylaniline (40 g, 236 mmol) in methylene chloride (400 mL) was stirred at 0° C. and then slowly added with N-bromosuccinimide (42 g, 236 mmol) before stirring at room temperature for 4 hours. After completion of the reaction, $H_2O$ was dropwise added and then extraction was conducted with methylene chloride. The organic layer thus formed was concentrated and isolated by column chromatography to afford <Intermediate 6-a> (48 g, yield 80%).

Synthesis Example 6-2: Synthesis of <Intermediate 6-b>

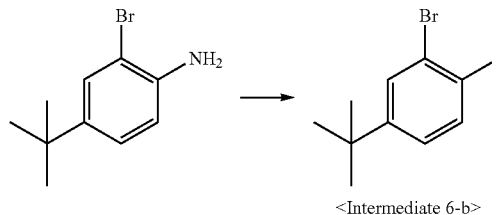

<Intermediate 6-b>

In a 2-L reactor, Intermediate 5-a (80 g, 351 mmol) and water (450 mL) were stirred together, followed by adding sulfuric acid (104 mL). At 0° C., a solution of sodium nitrite (31.5 g, 456 mmol) in water (240 mL) was dropwise added and then stirred for 2 hours at 0° C. A solution of potassium iodide (116.4 g, 701 mmol) in water (450 mL) was dropwise added at 0° C. and then stirred at room temperature for 6 hours. After completion of the reaction, an aqueous sodium thiosulfate solution was added and stirred at room temperature. Extraction was conducted with ethylacetate and the organic layer thus formed was isolated by column chromatography to afford <Intermediate 6-b> (58 g, yield 51%).

Synthesis Example 6-3: Synthesis of <Intermediate 6-c>

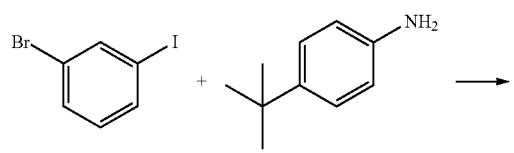

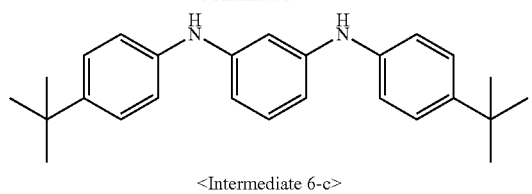

<Intermediate 6-c>

In a 1-L reactor, 1-bromo-5-iodobenzene (50.1 g, 177 mmol), 4-tert-butylaniline (58 g, 389 mmol), palladium acetate (1.6 g, 7 mmol), sodium tert-butoxide (51 g, 530 mmol), bis(diphenylphosphino)-1,1'-binaphthyl (4.4 g, 7 mmol), and toluene (500 mL) were stirred under reflux for 24 hours. After completion of the reaction, separation by filtration, concentration, and column chromatography afforded <Intermediate 6-c> (52.8 g, yield 80%).

Synthesis Example 6-4: Synthesis of <Intermediate 6-d>

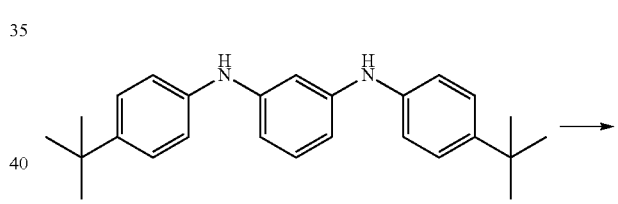

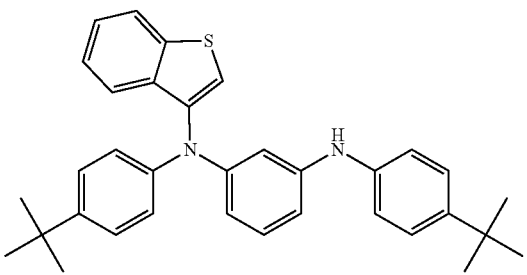

<Intermediate 6-d>

In a 250-mL reactor, Intermediate 5-c (36.5 g, 98 mmol), 3-bromobenzothiophene (20.9 g, 98 mmol), palladium acetate (0.5 g, 2 mmol), sodium tert-butoxide (18.9 g, 196 mmol), tri-tert-butylphosphine (0.8 g, 4 mmol), and toluene (200 mL) were stirred together under reflux for 5 hours. After completion of the reaction, separation by filtration, concentration, and column chromatography afforded <Intermediate 6-d> (35.6 g, yield 72%).

Synthesis Example 6-5: Synthesis of <Intermediate 6-e>

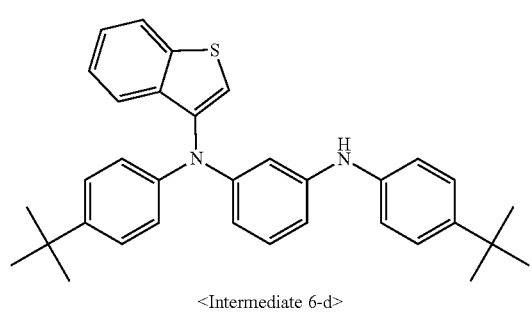

<Intermediate 6-d>

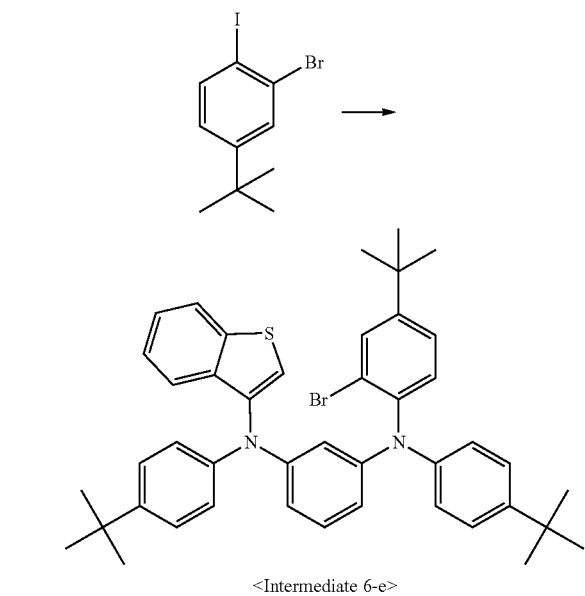

<Intermediate 6-e>

The same procedure as in Synthesis Example 6-(4) was carried out, with the exception of using <Intermediate 6-d> and 2-bromo-4-tert-butyl-1-iodobenzene instead of <Intermediate 6-c> and 3-bromobenzothiophene, respectively, to afford <Intermediate 6-e>. (yield 67%)

Synthesis Example 6-6: Synthesis of BD 2

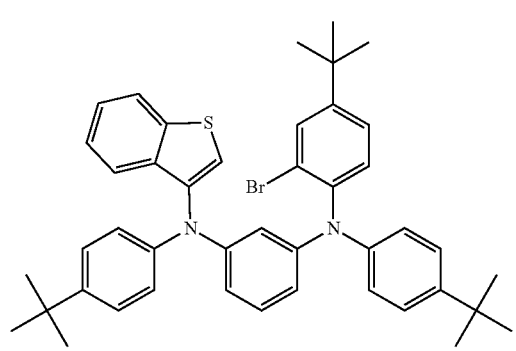

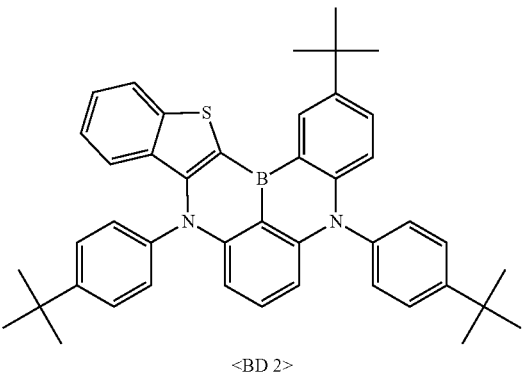

<BD 2>

To a 300-mL reactor were added <Intermediate 6-e> (16.5 g, 23 mmol) and tert-butyl benzene (120 mL). At −78° C., n-butyl lithium (42.5 mL, 68 mmol) was dropwise added. Then, the mixture was stirred at 60° C. for 3 hours. Subsequently, nitrogen was introduced at the same temperature into the reactor to remove heptane. Boron tribromide (11.3 g, 45 mmol) was dropwise added at −78° C. and then stirred for 1 hour at room temperature. N, N-Diisopropylethylamine (5.9 g, 45 mmol) was added at 0° C. and then stirred at 120° C. for 2 hours. After completion of the reaction, an aqueous sodium acetate solution was added at room temperature and stirred. Extraction was carried out with ethyl acetate. The organic layer was concentrated and separated by column chromatography to afford <BD 2> (2.2 g, yield 15%).

MS (MALDI-TOF): m/z 644.34 [M$^+$]

Synthesis Example 7: Synthesis of BD 3

Synthesis Example 7-(1): Synthesis of Intermediate 7-a

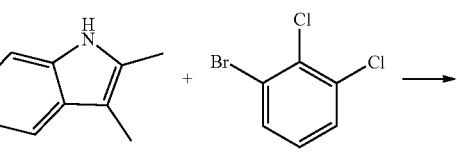

<Intermediate 7-a>

The same procedure as in Synthesis Example 6-(4) was carried out, with the exception of using 2,3-dimethylindole and 1-bromo-2,3-dichlorobenzene instead of <Intermediate 6-c> and 3-bromobenzothiophene, respectively, to afford <Intermediate 7-a>. (yield 47%)

Synthesis Example 7-(2): Synthesis of Intermediate 7-b

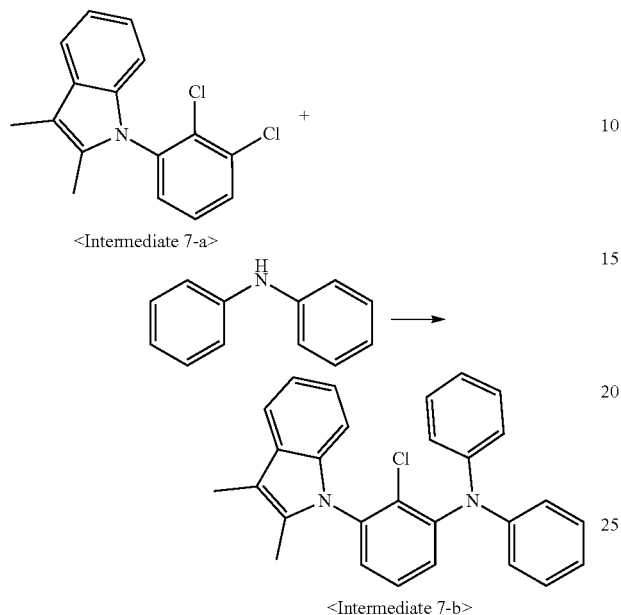

The same procedure as in Synthesis Example 6-(4) was carried out, with the exception of using diphenylamine and <Intermediate 7-a> instead of <Intermediate 6-c> and 3-bromobenzothiophene, respectively, to afford <Intermediate 7-b>. (yield 72%)

Synthesis Example 7-(3): Synthesis of BD 3

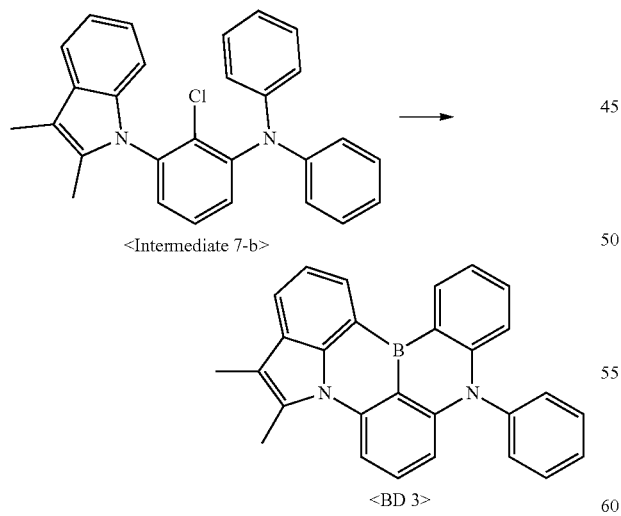

The same procedure as in Synthesis Example 6-(6) was carried out, with the exception of using <Intermediate 7-b> instead of <Intermediate 6-e>, to afford <BD 3>. (yield 72%)

MS (MALDI-TOF): m/z 369.18 [M⁺]

Synthesis Example 8: Synthesis of BD 4

Synthesis Example 8-(1): Intermediate 8-a

The same procedure as in Synthesis Example 6-(3) was carried out, with the exception of using N-3-bromophenyl-N,N-diphenylamine and 4-aminobiphenyl instead of 1-bromo-5-iodobenzene and 4-tert-butylaniline, to afford <Intermediate 8-a>. (yield 55%)

Synthesis Example 8-(2): Synthesis of Intermediate 8-b

-continued

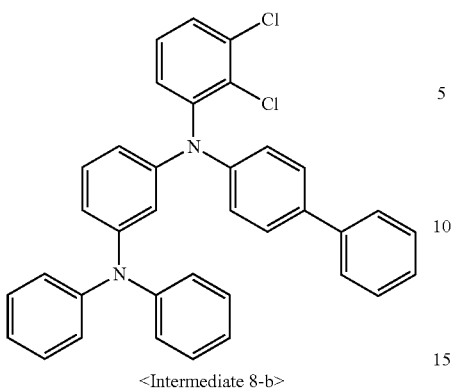
<Intermediate 8-b>

The same procedure as in Synthesis Example 6-(4) was carried out, with the exception of using <Intermediate 8-a> and 1-bromo-2,3-dichlorobenzene instead of <Intermediate 6-c> and 3-bromobenzothiophene, to afford <Intermediate 8-b>. (yield 53%) Synthesis Example 8-(3): Synthesis of Intermediate 8-c

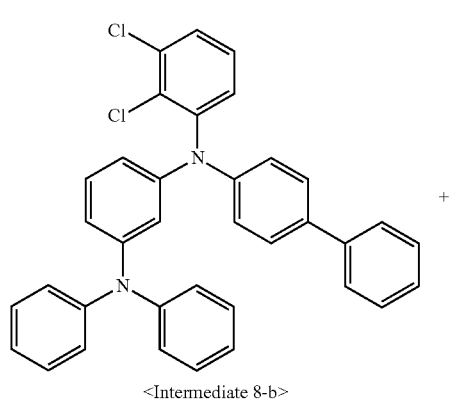
<Intermediate 8-b>

+

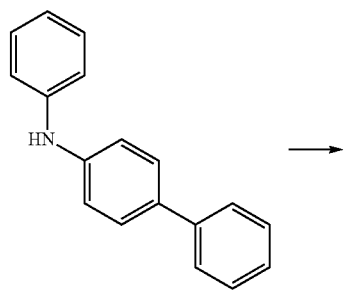

→

-continued

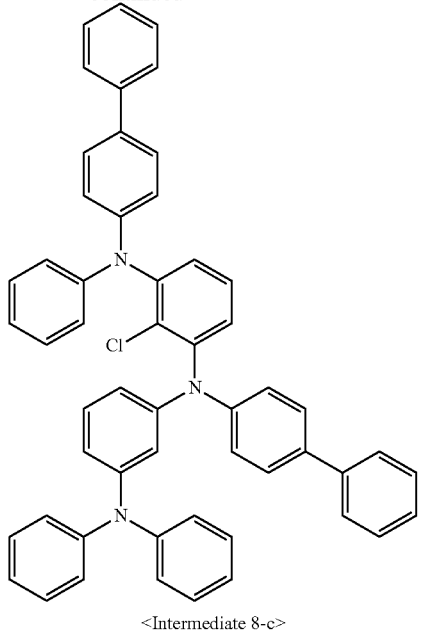
<Intermediate 8-c>

The same procedure as in Synthesis Example 6-(4) was carried out, with the exception of using 4-phenyldiphenylamine and <Intermediate 8-c> instead of <Intermediate 6-c> and 3-bromobenzothiophene, respectively, to afford <Intermediate 8-c>. (yield 57%)

Synthesis Example 8-(4): Synthesis of BD 4

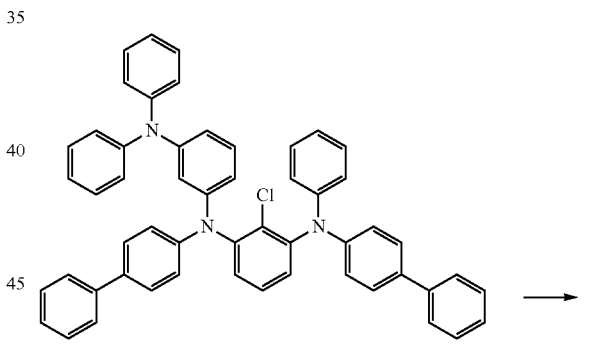
[Intermediate 8-c]

→

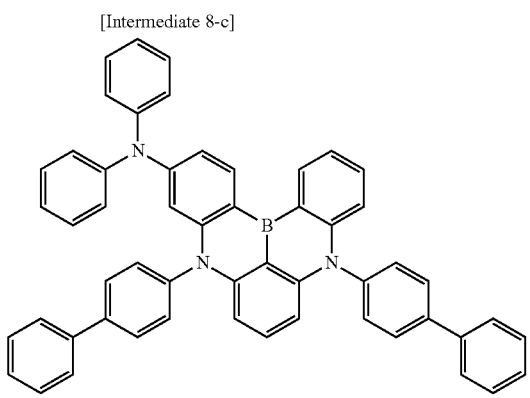
<BD 4>

The same procedure as in Synthesis Example 6-(6) was carried out, with the exception of using <Intermediate 8-c> instead of <Intermediate 6-e>, to afford <BD 4>. (yield 61%)

MS (MALDI-TOF): m/z 739.32 [M+]

Examples 1-17: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of $1\times10^7$ torr. On the ITO glass substrate, films were sequentially formed of 2-TNATA (400 Å) and HT (200 Å) in the order. Subsequently, a light-emitting layer (250 Å) was formed of a combination of host and dopant compounds (97:3 wt %) listed in Table 1, below. Then, [Chemical Formula E-1] was deposited to form an electron transport layer (300 Å) on which an electron injection layer of Liq (10 Å) was formed and then covered with an Al layer (1000 Å) to fabricate an organic light-emitting diode. The organic light-emitting diodes thus obtained were measured at 10 mA/cm² for luminescence properties

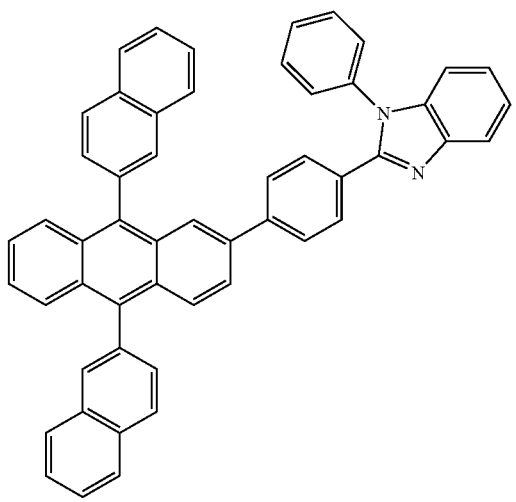

[Chemical Formula E-1]

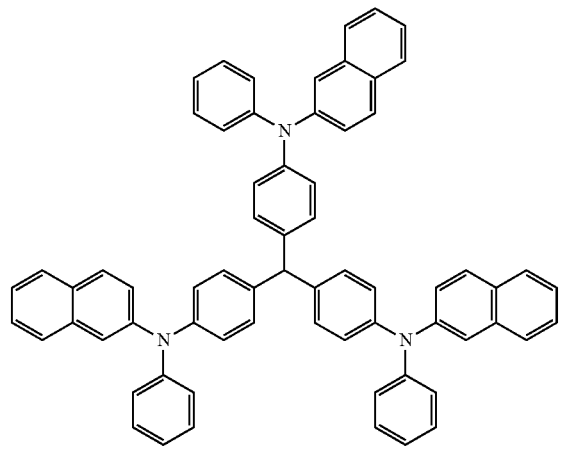

[DNTPD]

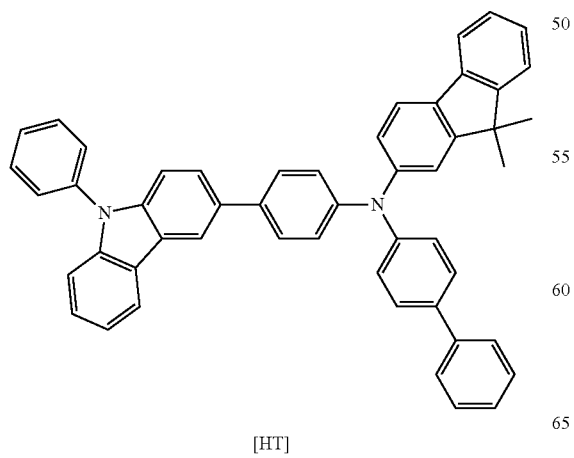

[HT]

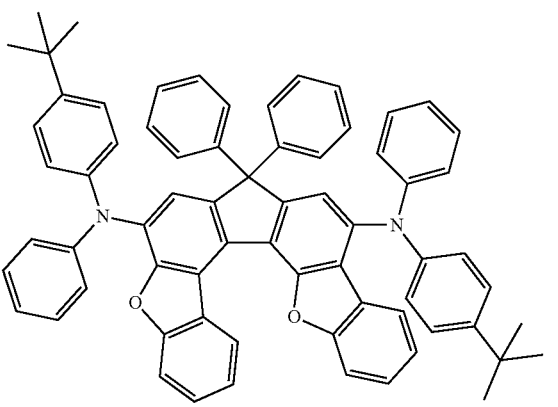

[BD 1]

[BD 2]

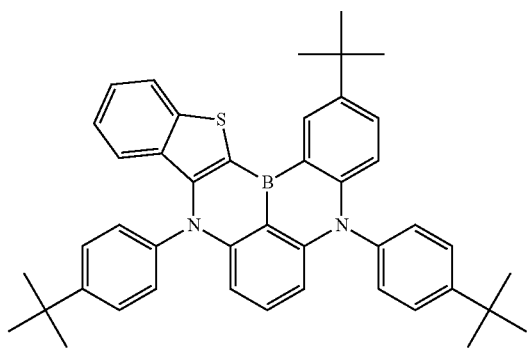

[BD 3]

[BD 4]

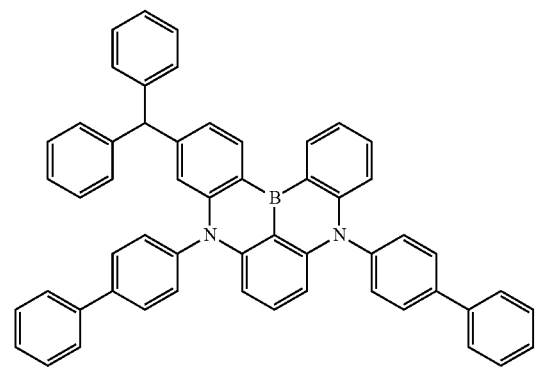

[BD 5]

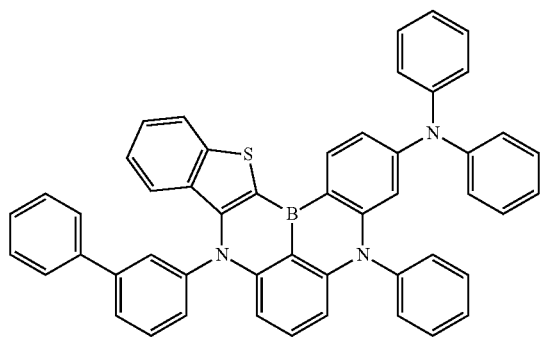

[BD 6]

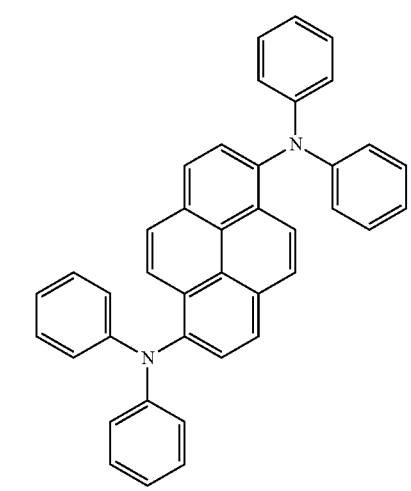

Comparative Examples 1 to 11

Organic light emitting diodes were fabricated in the same manner as in the Examples 1 to 17, with the exception of using [BH 1] to [BH 8] compounds instead of the host compounds of Examples 1 to 17. The luminescence of the organic light-emitting diodes thus obtained was measured at 10 mA/cm$^2$, and the measurements are summarized in Table 1, below.

[BH 1]

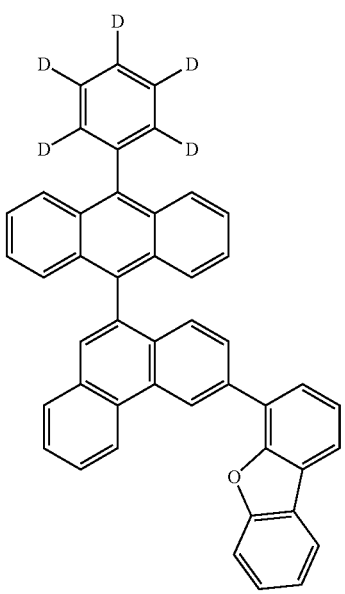

[BH 2]

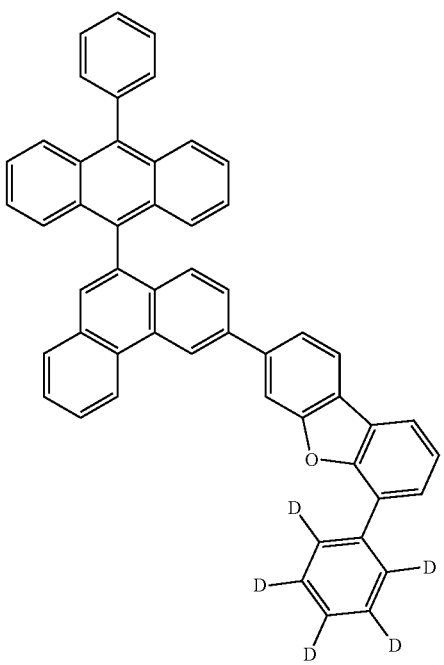

263
-continued
264
-continued
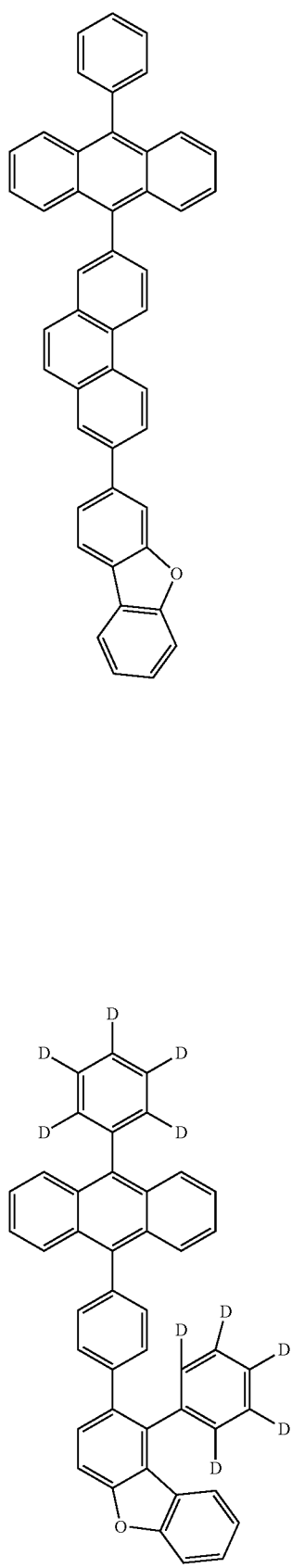
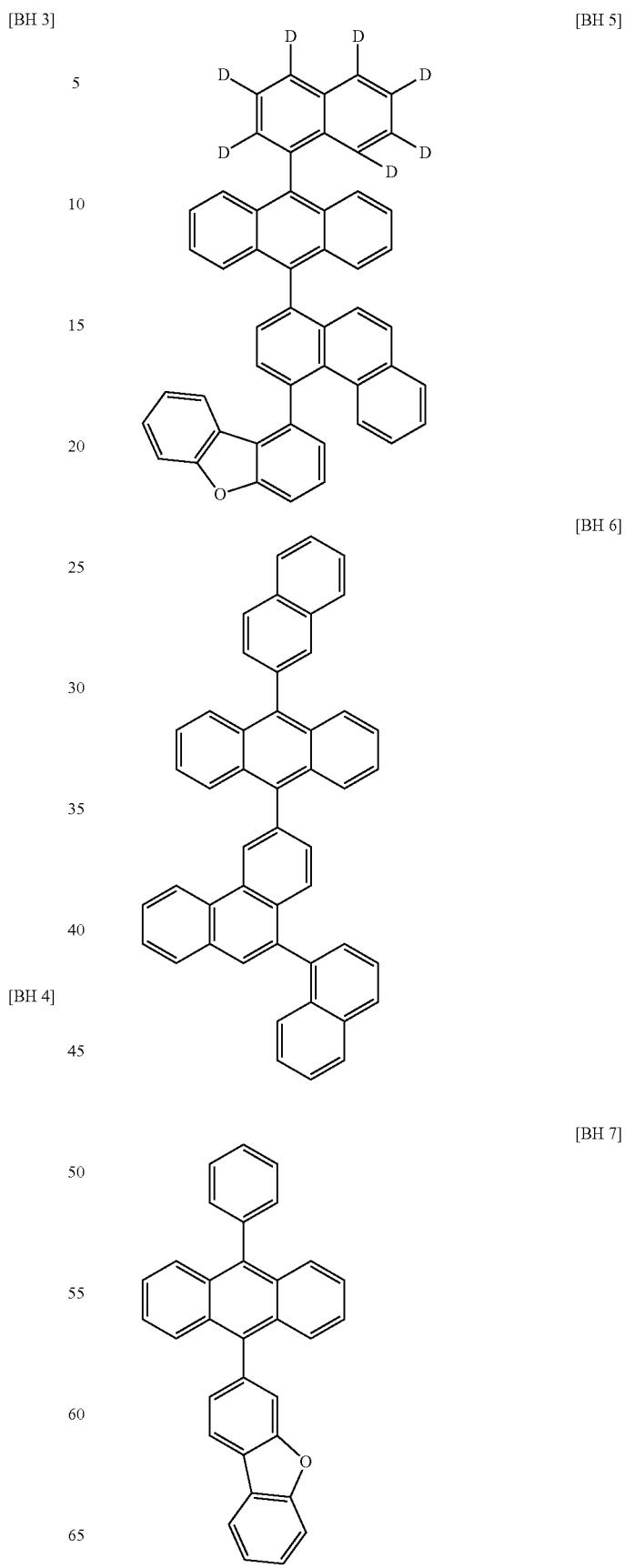
[BH 3]
[BH 4]
[BH 5]
[BH 6]
[BH 7]

-continued

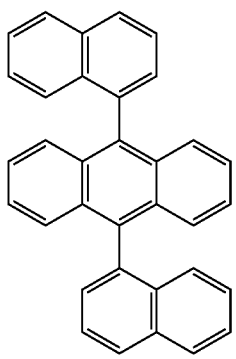

[BH 8]

TABLE 1

| | Host | Dopant | Driving Volt. | EQE | T97 |
|---|---|---|---|---|---|
| Ex. 1 | Compound 1 | BD 1 | 3.8 | 10.3 | 129 |
| Ex. 2 | Compound 4 | BD 1 | 3.6 | 10.1 | 132 |
| Ex. 3 | Compound 8 | BD 1 | 4.0 | 10.0 | 135 |
| Ex. 4 | Compound 12 | BD 1 | 3.7 | 9.8 | 126 |
| Ex. 5 | Compound 15 | BD 1 | 4.3 | 9.6 | 121 |
| Ex. 6 | Compound 25 | BD 1 | 3.6 | 9.5 | 118 |
| Ex. 7 | Compound 30 | BD 2 | 3.6 | 9.9 | 130 |
| Ex. 8 | Compound 1 | BD 2 | 3.8 | 10.5 | 141 |
| Ex. 9 | Compound 4 | BD 3 | 3.6 | 10.4 | 138 |
| Ex. 10 | Compound 8 | BD 3 | 4.0 | 10.1 | 139 |
| Ex. 11 | Compound 8 | BD 4 | 4.0 | 9.1 | 103 |
| Ex. 12 | Compound 12 | BD 3 | 3.6 | 10.2 | 143 |
| Ex. 13 | Compound 15 | BD 4 | 4.1 | 9.0 | 112 |
| Ex. 14 | Compound 25 | BD 4 | 3.7 | 9.3 | 107 |
| Ex. 15 | Compound 2 | BD 2 | 3.6 | 10.0 | 121 |
| Ex. 16 | Compound 3 | BD 5 | 3.8 | 10.1 | 136 |
| Ex. 17 | Compound 32 | BD 5 | 3.6 | 9.9 | 160 |
| C. Ex. 1 | BH 1 | BD 1 | 4.3 | 8.4 | 88 |
| C. Ex. 2 | BH 2 | BD 2 | 4.0 | 10.1 | 81 |
| C. Ex. 3 | BH 3 | BD 1 | 4.0 | 8.3 | 87 |
| C. Ex. 4 | BH 4 | BD 2 | 3.8 | 8.7 | 91 |
| C. Ex. 5 | BH 5 | BD 3 | 3.7 | 8.5 | 89 |
| C. Ex. 6 | BH 1 | BD 3 | 4.3 | 8.5 | 93 |
| C. Ex. 7 | BH 2 | BD 4 | 4.0 | 7.8 | 79 |
| C. Ex. 8 | BH 3 | BD 4 | 4.0 | 7.9 | 75 |
| C. Ex. 9 | BH 6 | BD 1 | 4.1 | 8.4 | 84 |
| C. Ex. 10 | BH 7 | BD 2 | 4.0 | 8.7 | 92 |
| C. Ex. 11 | BH 8 | BD 6 | 4.1 | 8.4 | 60 |

As is understood from data of Table 1, organic light-emitting diodes employing the organic light-emitting compounds according to the present disclosure as host materials exhibited longer lifespans and higher effeiciency properties, compared to those employing the compounds according to Comparative Examples 1 to 11 as host materials, thus finding high applicability in the organic light-emitting diode field.

INDUSTRIAL APPLICABILITY

When used as hosts in a light-emitting layer, the anthracene derivatives according to the present disclosure exhibit longer lifespan and higher efficiency properties than preexisting materials. Thus, the anthracene derivatives according to the present disclosure can impart improved properties to organic light-emitting diodes and thus are industrially applicable to organic light-emitting diodes and relevant industries.

The invention claimed is:
1. An organic light-emitting compound represented by the following Chemical Formula A:

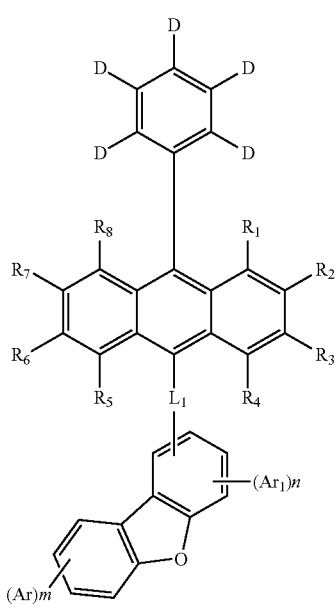

[Chemical Formula A]

wherein,
$R_1$ to $R_8$, which may be same or different, are each independently a hydrogen atom or a deuterium atom,
$Ar_1$ and $Ar_2$, which may be same or different, are each independently an at least partially deuterated aryl of 6 to 50 carbon atoms or an at least partially deuterated alkyl of 1 to 30 carbon atoms,
n is an integer of 0-3 wherein when n is 2 or larger, the $Ar_1$'s may each be same or different,
m is an integer of 0-4 wherein when m is 2 or larger, the $Ar_2$'s may each be same or different,
with a proviso that n+m is not 0,
the carbon atoms of the aromatic rings in the dibenzofuran moiety may be hydrogenated or deuterated when $Ar_1$ or $Ar_2$ is not bonded thereto,
$L_1$ is a linker represented by the following Structural Formula B,

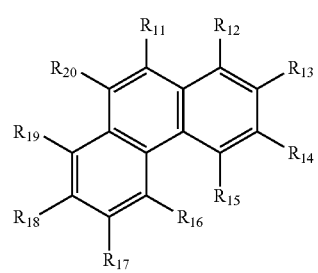

[Structural Formula B]

wherein,
two of substituents $R_{11}$ to $R_{20}$ are single bonds connected respectively to the anthracenyl moiety and the dibenzofuran moiety in the compound of Chemical Formula A,
the remaining eight, other than the two single bonds, among substituents $R_{11}$ to $R_{20}$, may be same or different and are each independently selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as a heteroatom, a cyano, a nitro, a halogen, a substituted or unsubstituted alkylsilyl of 1 to 30 carbon atoms, and a substituted or unsubstituted arylsilyl of 6 to 30 carbon atoms, wherein the term 'substituted' in the expression "a substituted or unsubstituted" means having at least one substituent selected from the group consisting of a deuterium atom, a cyano, a halogen, a nitro, an alkyl of 1 to 24 carbon atoms, a cycloalkyl of 3 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms, an alkoxy of 1 to 24 carbon atoms, an alkylsilyl of 1 to 24 carbon atoms, an arylsilyl of 6 to 24 carbon atoms, and an aryloxy of 6 to 24 carbon atoms.

2. The organic light-emitting compound of claim 1, wherein n is 0 and m is 1 or 2, and n is 1 or 2 and m is 0.

3. The organic light-emitting compound of claim 1, wherein $Ar_1$ and $Ar_2$, which are same or different, are each independently an at least partially deuterated aryl of 6 to 50 carbon atoms.

4. The organic light-emitting compound of claim 3, wherein $Ar_1$ and $Ar_2$, which are same or different, are each independently an at least partially deuterated aryl of 6 to 20 carbon atoms.

5. The organic light-emitting compound of claim 4, wherein $Ar_1$ and $Ar_2$, which are same or different, are each independently any one selected from among an at least partially deuterated phenyl, an at least partially deuterated naphthyl, an at least partially deuterated phenanthrenyl, and an at least partially deuterated biphenyl.

6. The organic light-emitting compound of claim 1, wherein among substituents $R_{11}$ to $R_{20}$, eight substituents other than the two single bonds, which are same or different, are each independently a hydrogen atom or a deuterium atom.

7. The organic light-emitting compound of claim 1, wherein the two single bonds of Structural Formula B, connected respectively to the anthracenyl moiety and the dibenzofuran moiety in the organic light-emitting compound represented by Chemical Formula A each are selected from among $R_{11}$, $R_{14}$, $R_{15}$, $R_{17}$, and $R_{18}$.

8. The organic light-emitting compound of claim 7, wherein the two single bonds of Structural Formula B, connected respectively to the anthracenyl moiety and the dibenzofuran moiety in the organic light-emitting compound represented by Chemical Formula A each are selected from among $R_{11}$, $R_{14}$, and $R_{18}$; or from among $R_{11}$ and $R_{17}$.

9. The organic light-emitting compound of claim 7, wherein Ru is a single bond connected to the anthracenyl moiety in the compound represented by Chemical Formula A and one of $R_{14}$ and $R_{18}$ is a single bond connected to the dibenzofuran moiety in the compound represented by Chemical Formula A.

10. The organic light-emitting compound of claim 1, wherein the compound represented by Chemical Formula A is an organic light-emitting compound represented by the following Chemical Formula A-1 or Chemical Formula A-2:

[Chemical Formula A-1]

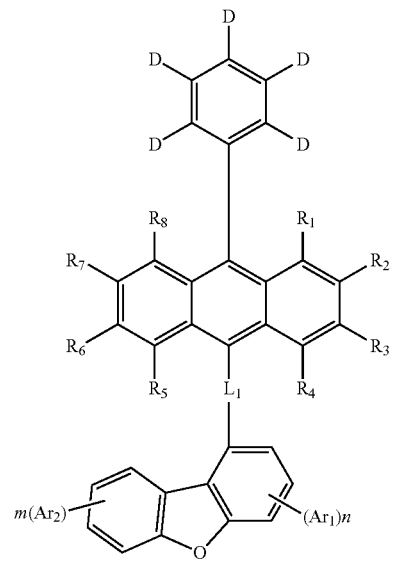

[Chemical Formula A-2]

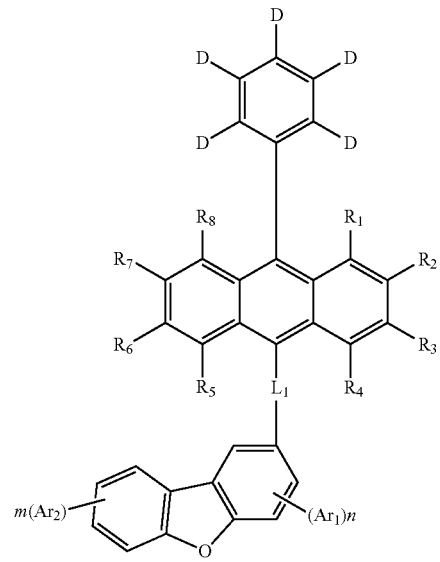

wherein $R_1$ to $R_8$, $L_1$, $Ar_1$, $Ar_2$, m, and n are as defined in Chemical Formula A.

11. The organic light-emitting compound of claim 1, wherein the organic light-emitting compound represented by Chemical Formula A is any one of <Compound 1> to <Compound 35>:
<Compound 1>
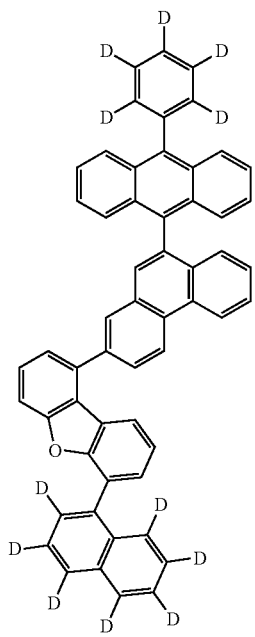
<Compound 2>
<Compound 3>
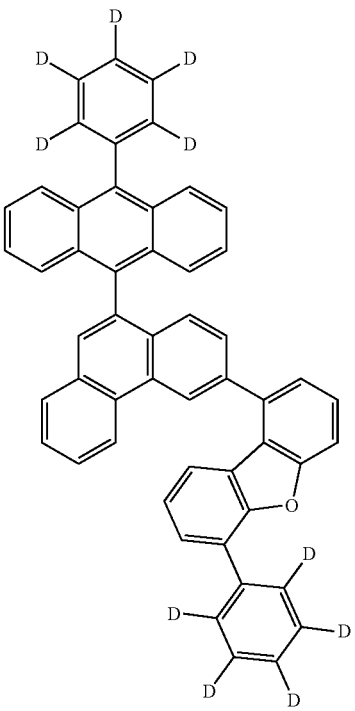
<Compound 4>
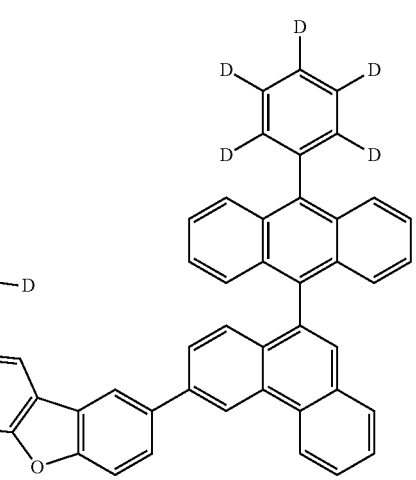

<Compound 5>
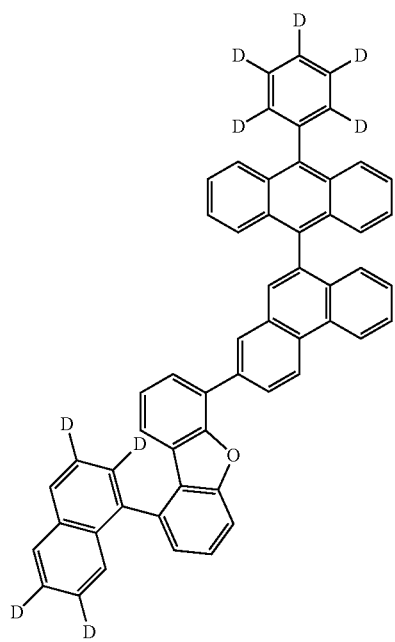
<Compound 7>
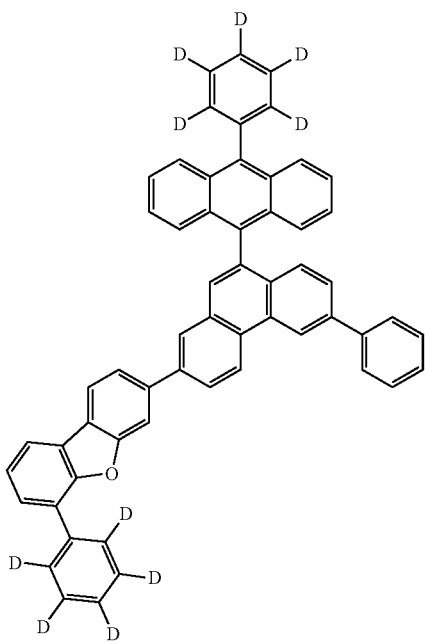
<Compound 6>
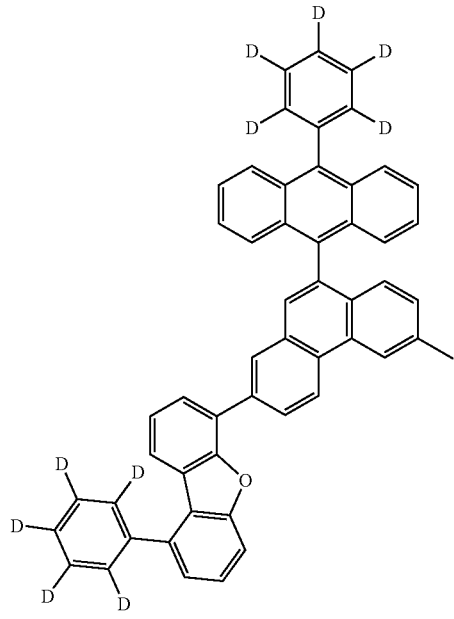
<Compound 8>

<Compound 9>
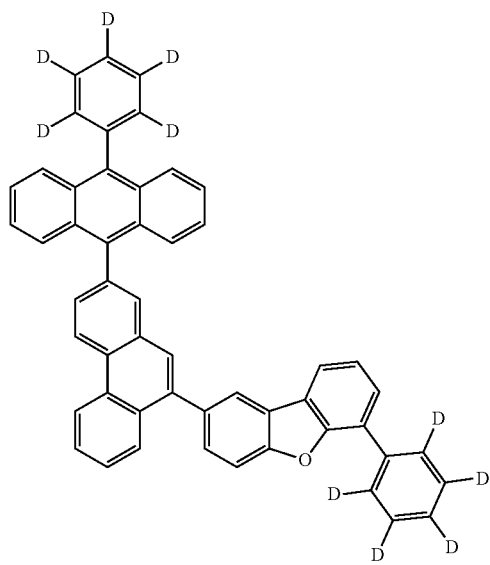
<Compound 10>
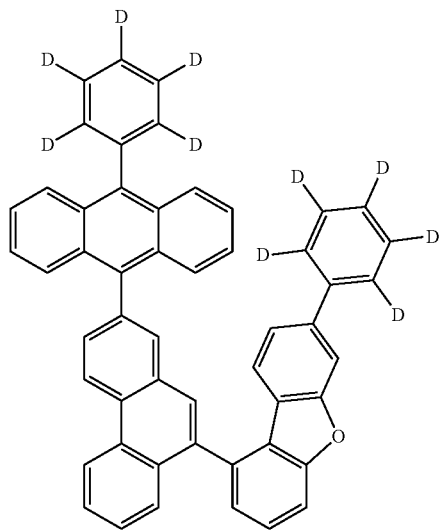
<Compound 11>
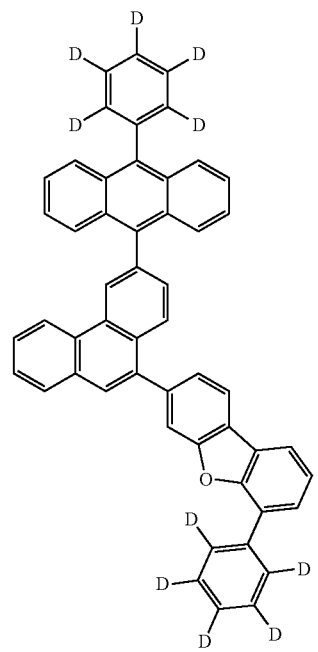
<Compound 12>
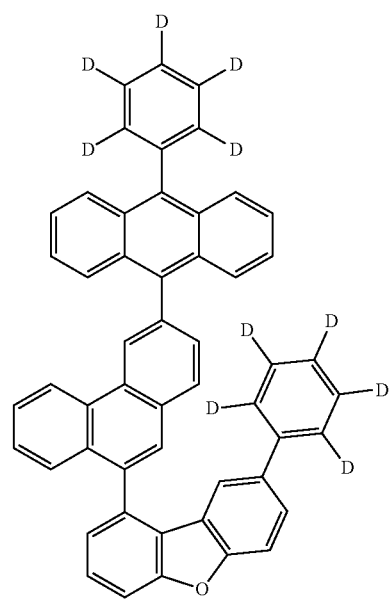

<Compound 13>
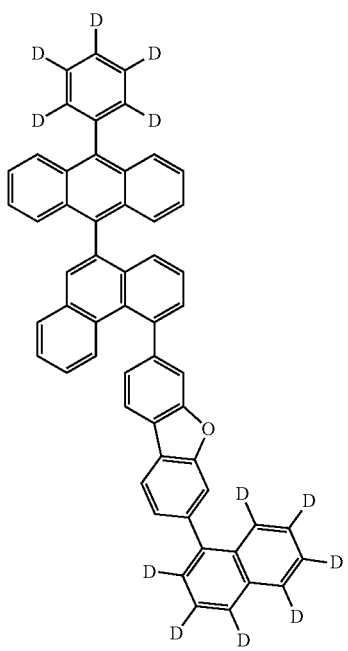
<Compound 14>
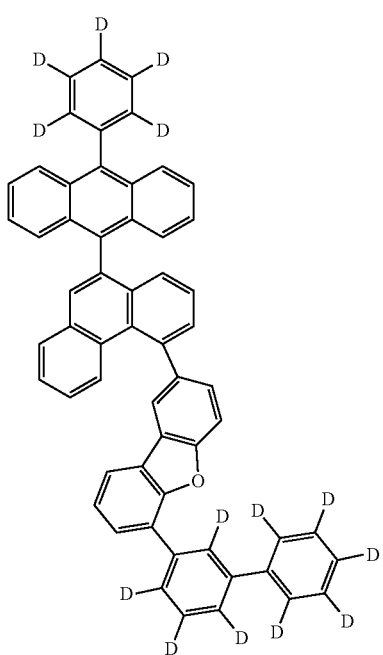
<Compound 15>
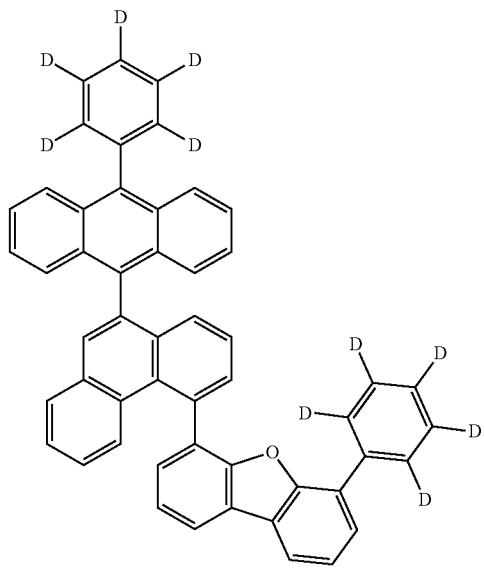
<Compound 16>
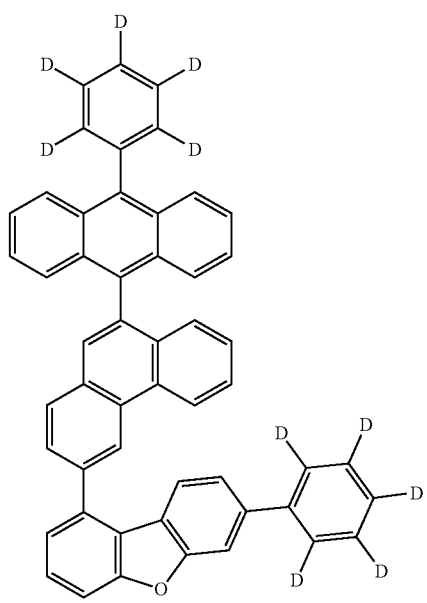

<Compound 17>
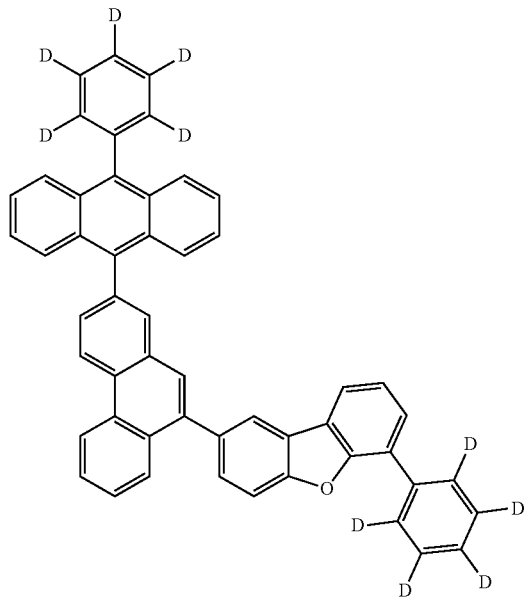
<Compound 18>
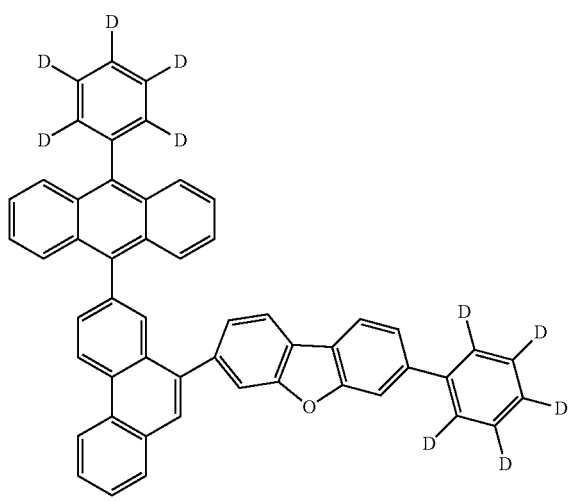
<Compound 19>
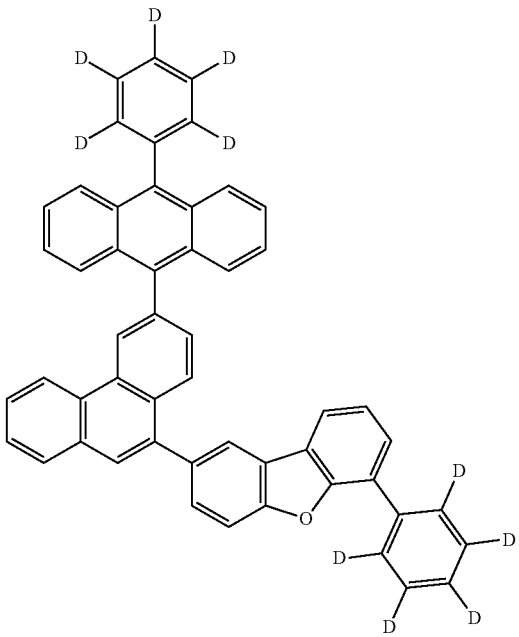
<Compound 20>
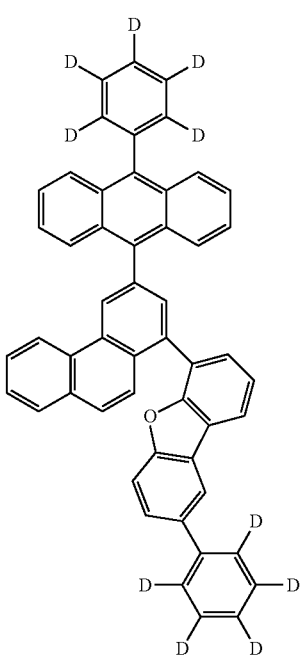

<Compound 21>
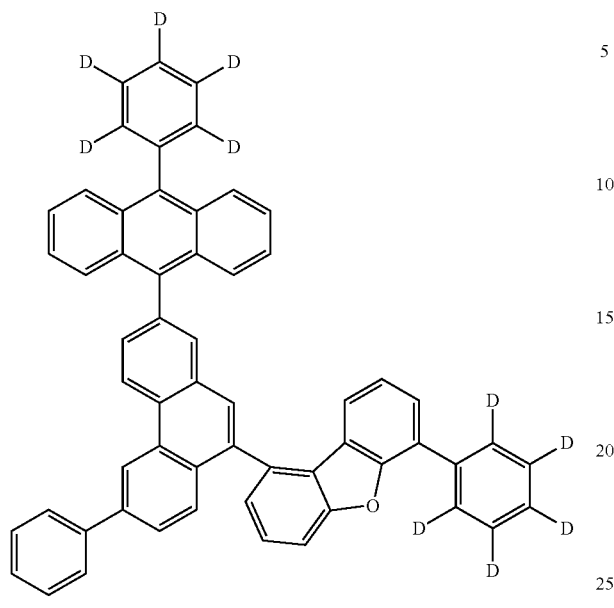
<Compound 23>
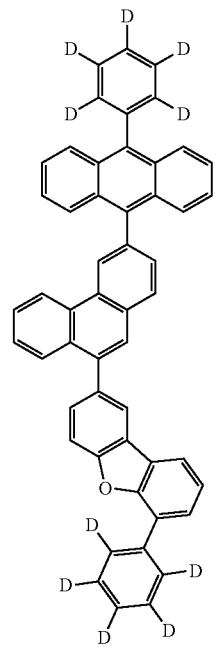
<Compound 22>
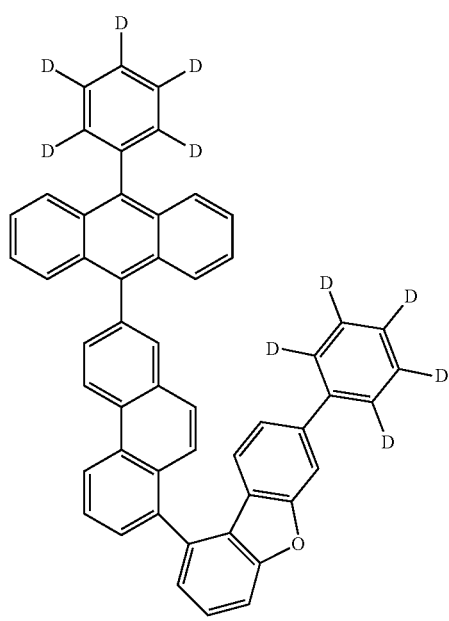
<Compound 24>
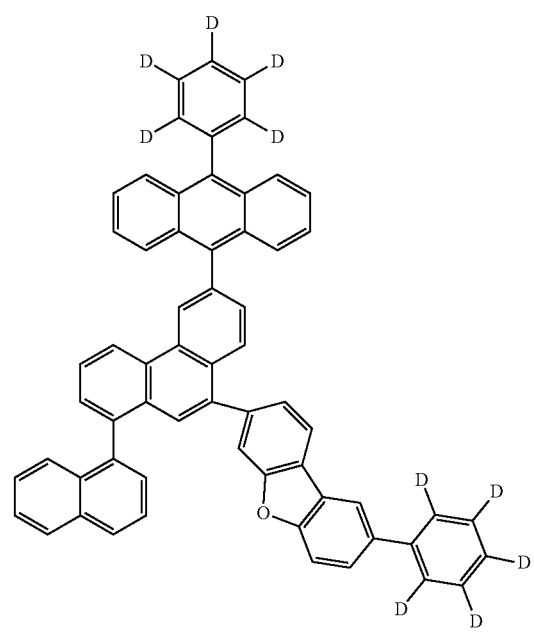

<Compound 25>
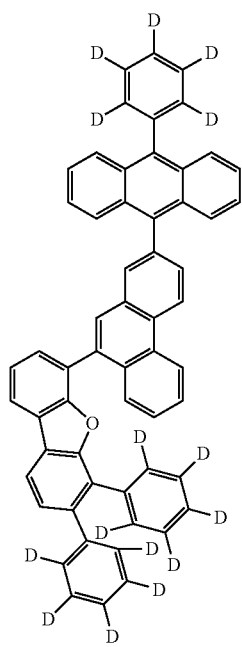
<Compound 26>
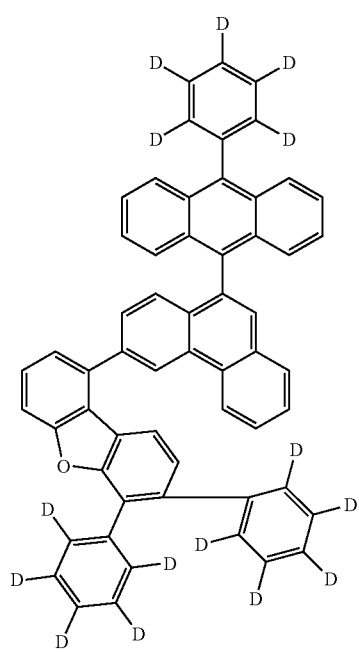
<Compound 27>
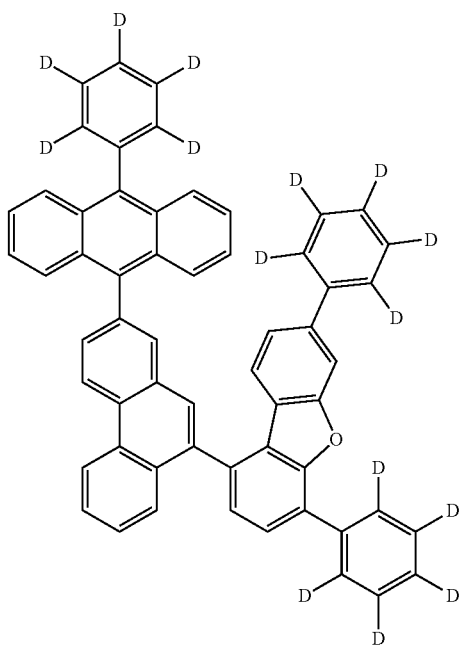
<Compound 28>
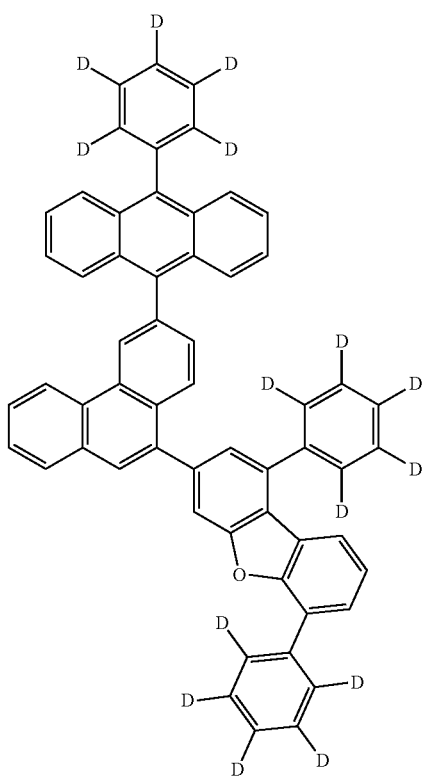

<Compound 29>
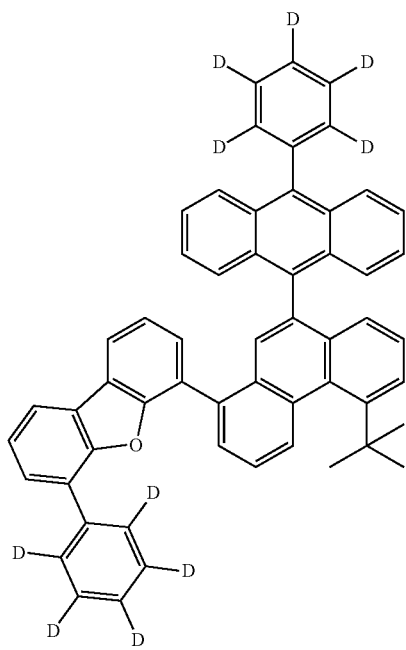
<Compound 30>
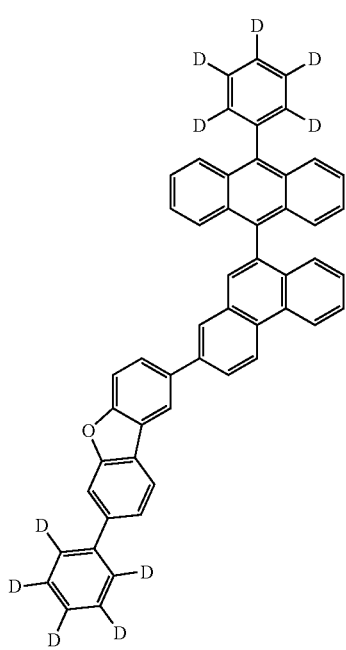
<Compound 31>
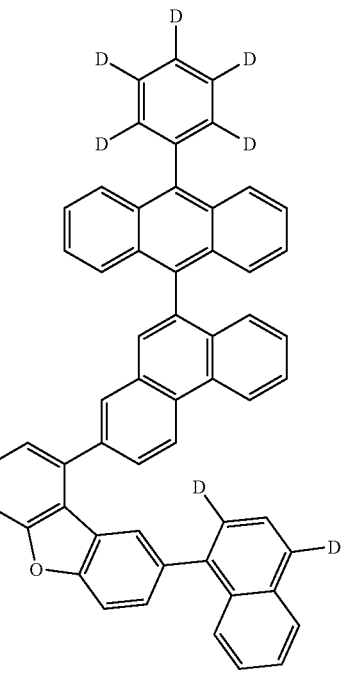
<Compound 32>
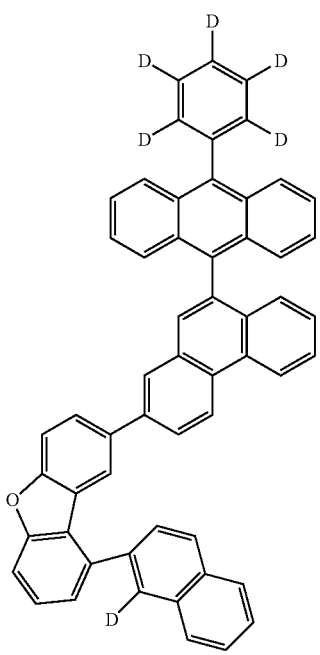

<Compound 33>

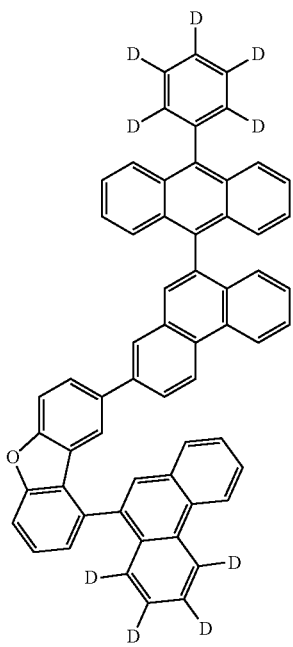

<Compound 35>

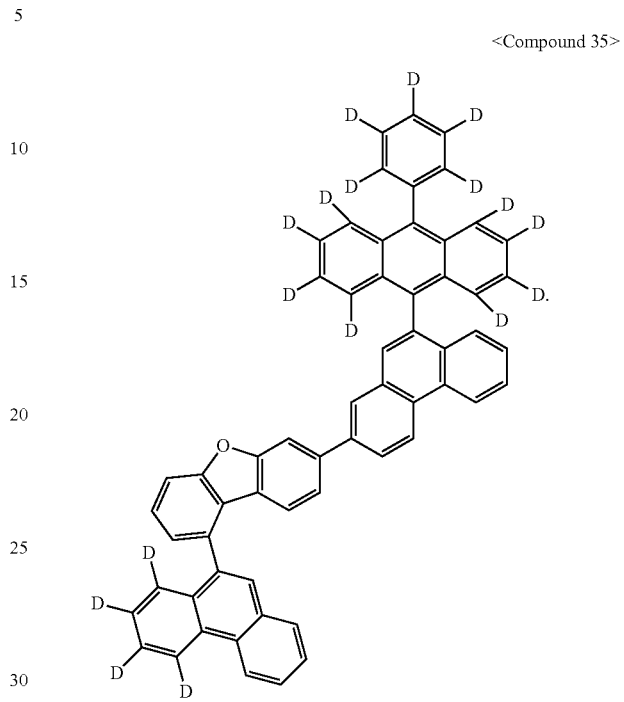

<Compound 34>

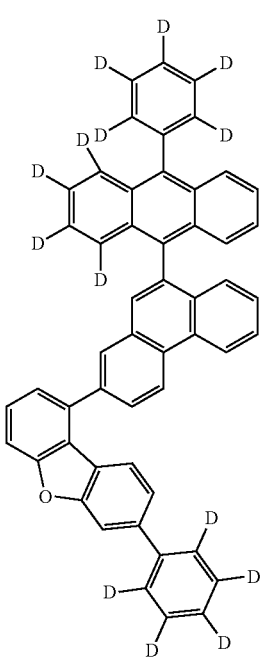

12. An organic light-emitting diode, comprising:
a first electrode;
a second electrode facing the first electrode; and
an organic layer interposed between the first electrode and the second electrode,
wherein the organic layer comprises at least one of the organic light-emitting compounds of claim 1.

13. The organic light-emitting diode of claim 12, wherein the organic layer within the organic light-emitting diode comprises at least one of a hole injection layer, a hole transport layer, a functional layer capable of both hole injection and hole transport, a light-emitting layer, an electron transport layer, and an electron injection layer.

14. The organic light-emitting diode of claim 13, wherein the organic layer interposed between the first electrode and the second electrode comprises a light-emitting layer wherein the light emitting layer comprises a host and a dopant, with the organic light-emitting compound serving as the host.

15. The organic light-emitting diode of claim 13, wherein at least one selected from among the layers is deposited using a deposition process or a solution process.

16. The organic light-emitting diode of claim 12, wherein the organic light-emitting diode is used for a device selected from among a flat display device; a flexible display device; a monochrome or grayscale flat illumination; and a monochrome or grayscale flexible illumination device.

17. The organic light-emitting diode of claim 14, wherein the dopant comprises at least one of the compounds represented by Chemical Formulas D1 to D7:

[Chemical Formula D1]

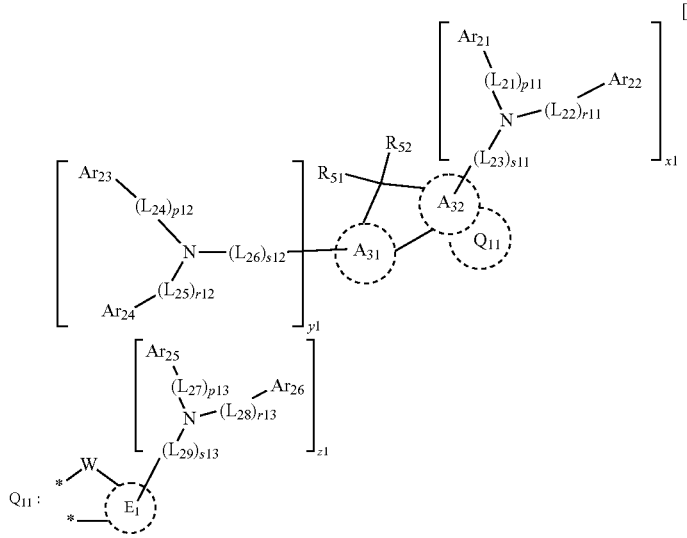

[Chemical Formula D2]

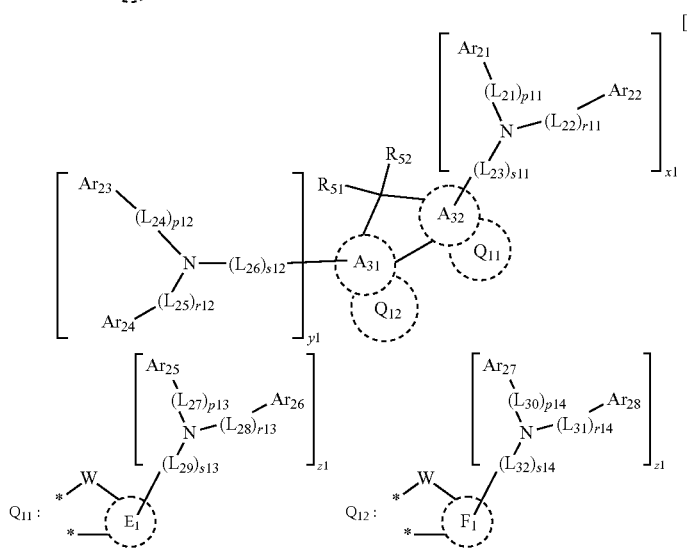

wherein, $A_{31}$, $A_{32}$, $E_1$, and $F_1$, which are same or different, are each independently a substituted or unsubstituted aromatic hydrocarbon ring of 6 to 50 carbon atoms, or a substituted or unsubstituted aromatic heterring of 2 to 40 carbon atoms wherein two adjacent carbon atoms of the aromatic ring $A_{31}$ and two adjacent carbon atoms of the aromatic ring $A_{32}$ form a 5-membered fused ring together with a carbon atom to which substituents $R_{51}$ and $R_{52}$ are bonded;

linkers $L_{21}$ to $L_{32}$, which are same or different, are each independently selected from a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is any one selected from N—$R_{53}$, $CR_{54}R_{55}$, $SiR_{56}R_{57}$, $GeR_{58}R_{59}$, O, S, and Se;

$R_{51}$ to $R_{59}$, and $Ar_{21}$ to $Ar_{28}$, which may be the same or different, are each independently any one of selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_{51}$ and $R_{52}$ together may form a mono- or polycyclic aliphatic or aromatic ring that may be a heterocyclic ring bearing a heteroatom selected from N, O, P, Si, S, Ge, Se, and Te as a ring member;

p11 to p14, r11 to r14, and s11 to s14 are each independently an integer of 1 to 3, wherein when any of them is 2 or greater, the corresponding $L_{21}$ to $L_{32}$ are same or different, x1 is an integer of 1 or 2, and y1 and z1 are same or different and are each independently an integer of 0 to 3;

$Ar_{21}$ may form a ring with $Ar_{22}$, $Ar_{23}$ may form a ring with $Ar_{24}$, $Ar_{25}$ may form a ring with $Ar_{26}$, and $Ar_{27}$ may form a ring with $Ar_{28}$;

two adjacent carbon atoms of the $A_{32}$ ring moiety of Chemical Formula D1 may occupy respective positions * of Structural Formula Qui to form a fused ring; and two adjacent carbon atoms of the $A_{31}$ ring moiety of Chemical Formula D2 may occupy respective positions * of structural Formula $Q_{12}$ to form a fused ring, and two adjacent carbon atoms of the $A_{32}$ ring moiety of Chemical Formula D2 may occupy respective positions * of Structural Formula $Q_{11}$ to form a fuse ring;

[Chemical Formula D3]

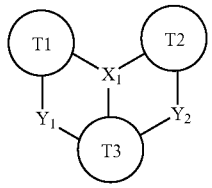

wherein, $X_1$ is any one selected from among B, P, and P=O, $T_1$ to $T_3$, which are same or different, are each independently a substituted or unsubstituted aromatic hydrocarbon ring of 6 to 50 carbon atoms, or a substituted or unsubstituted heteroaromatic ring of 2 to 40 carbon atoms;

$Y_1$ is any one selected from among N—$R_{61}$, $CR_{62}R_{63}$, O, S, and $SiR_{64}R_{65}$;

$Y_2$ is any one selected from among N—$R_{66}$, $CR_{67}R_{68}$, O, S, $SiR_{69}R_{70}$ wherein $R_{61}$ to $R_{70}$, which are same or different, are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen and wherein at least one of $R_{61}$ to $R_{70}$ may be connected to at least one of $T_1$ to $T_3$ to form an additional mono- or polycyclic aliphatic or aromatic ring;

[Chemical Formula D4]

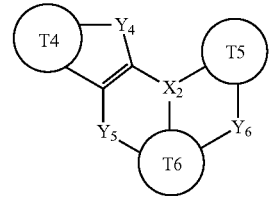

[Chemical Formula D5]

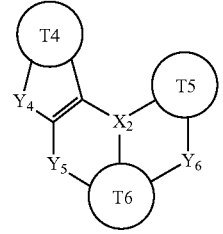

wherein, $X_2$ is any one selected from among B, P, and P=O, $T_4$ to $T_6$ are as defined for $T_1$ to $T_3$ in Chemical Formula D3, $Y_4$ to $Y_6$ are as defined for $Y_1$ to $Y_2$ in Chemical Formula D3;

[Chemical Formula D6]

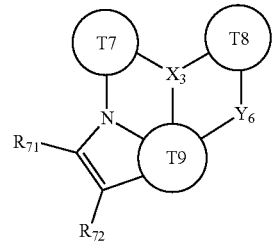

[Chemical Formula D7]

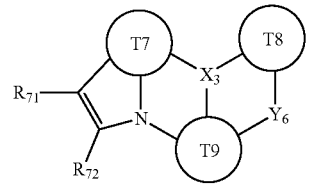

$X_3$ is any one selected from among B, P, and P=O, $T_7$ to $T_9$ are as defined for $T_1$ to $T_3$ in Chemical Formula D3, $Y_6$ is as defined for $Y_1$ to $Y_2$ in Chemical Formula D3, $R_{71}$ to $R_{72}$, which are same or different, are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen, wherein $R_{71}$ and $R_{72}$ may be connected to each other to form an additional mono- or polycyclic aliphatic or aromatic ring or connected to $T_7$ or $T_9$ ring moiety to form an additional mono- or polycyclic aliphatic or aromatic ring, wherein the term 'substituted' in the expression "a substituted or unsubstituted" means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

* * * * *